United States Patent

Fujita et al.

Patent Number: 5,976,408
Date of Patent: Nov. 2, 1999

[54] ACRYLONITRILE DERIVATIVE, LIQUID CRYSTAL COMPOSITION, AND LIQUID CRYSTAL DISPLAY DEVICE

[75] Inventors: Atsuko Fujita; Shuichi Matsui; Koichi Shibata; Kazutoshi Miyazawa; Yasuko Sekiguchi; Etsuo Nakagawa, all of Chiba, Japan

[73] Assignee: Chisso Corporation, Osaka, Japan

[21] Appl. No.: 08/930,986

[22] PCT Filed: Apr. 12, 1996

[86] PCT No.: PCT/JP96/01012

§ 371 Date: Dec. 19, 1997

§ 102(e) Date: Dec. 19, 1997

[87] PCT Pub. No.: WO96/32374

PCT Pub. Date: Oct. 17, 1996

[30] Foreign Application Priority Data

Apr. 14, 1995 [JP] Japan ................ 7-089747

[51] Int. Cl.$^6$ .......... C09K 19/30; C09K 19/12; C07C 255/00; C07C 69/76
[52] U.S. Cl. .............. 252/299.63; 252/299.01; 252/299.61; 252/299.66; 252/299.6; 558/416; 558/425; 560/60; 560/65; 560/102; 560/108; 549/369; 549/370; 544/298; 568/626; 568/455; 570/129
[58] Field of Search .......... 252/299.63, 299.01, 252/299.6, 299.61, 299.66; 558/416, 425; 570/129, 144; 544/298; 549/369, 370; 568/626, 455; 560/1, 60, 65, 102, 108

[56] References Cited

U.S. PATENT DOCUMENTS

| | | | |
|---|---|---|---|
| 4,363,767 | 12/1982 | Demus et al. | 252/299.63 |
| 5,449,810 | 9/1995 | Fujita et al. | 558/425 |
| 5,653,911 | 8/1997 | Kondo et al. | 252/299.01 |
| 5,662,830 | 9/1997 | Fujita et al. | 252/299.63 |
| 5,695,681 | 12/1997 | Siemensmeyer et al. | 252/299.01 |
| 5,783,114 | 7/1998 | Dyer et al. | 252/582 |

Primary Examiner—C H Kelly
Attorney, Agent, or Firm—Wenderoth, Lind & Ponack, L.L.P.

[57] ABSTRACT

An acrylonitrile derivative expressed by the following general formula I, a composition comprising the derivative and having an improved viscosity and optical anisotropy, and a liquid crystal display device:

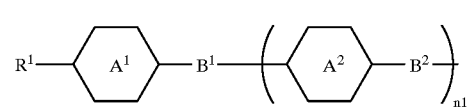

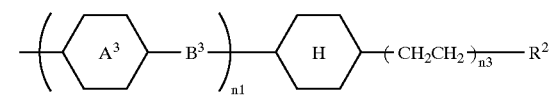

wherein rings $A^1$ to $A^3$ represent phenylene, cyclohexylene, dioxane, or pyrimidine, $R^1$ represents cyano group, halogen atom, an alkyl group, or an alkoxy group, and R2 represents

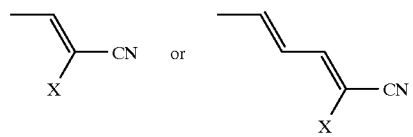

24 Claims, No Drawings

ACRYLONITRILE DERIVATIVE, LIQUID CRYSTAL COMPOSITION, AND LIQUID CRYSTAL DISPLAY DEVICE

TECHNICAL FIELD

The present invention relates to a novel liquid crystalline compound, a liquid crystal composition comprising the compound, and a liquid crystal display device comprising the composition.

BACKGROUND ART

Display devices which employ properties such as optical anisotropy and dielectric anisotropy of liquid crystal materials are widely used for watches, desktop calculators, and others. As liquid crystal phase, nematic liquid crystal phase, smectic liquid crystal phase, and cholesteric liquid crystal phase are known, and nematic phase is most general for practical purposes. As the display mode in this case, there exist TN (twisted nematic) mode, DS (dynamic scattering) mode, guest host mode, and DAP (deformation of aligned phases) mode. Whereas many compounds used for these types have heretofore been developed, there is no case in which a single compound is filled as it is in a display device and actually used. As liquid crystal materials used for display devices, it is necessary that the materials exhibit a liquid crystal phase at a wide temperature range with room temperature being its center, are stable against moisture, light, heat, air, electric field, and electromagnetic radiation under the atmosphere in which the materials are used, and have physical properties sufficient to drive display devices. However, these requirements can not be satisfied with a single compound. Then, a method has been adopted in which several kind of liquid crystalline compounds and furthermore non liquid-crystalline compounds are mixed to prepare a composition which meets the requirements, and then supplied for actual uses. Physical properties such as optical anisotropy, dielectric anisotropy, and electrical conductivity required of liquid crystal compositions depends on display mode and shape of devices. In STN mode which is used particularly in recent years for displays of liquid crystal display devices of a high quality, the ratio of elastic constants ($k_{33}/k_{11}$) of liquid crystal compositions must be enhanced to obtain a good display having a high steepness. Then, compounds which have a high elastic constant, wide range of liquid crystal temperature, and high miscibility with other liquid crystals, are stable, and have a low viscosity not to lose a high response speed have become an important question.

As examples of compounds having a high ratio of elastic constants, alkenyl compounds (Laid-open Japanese Patent Publication No. Sho 59-176,221) expressed by formula (1) are widely known. However, since the temperature range of nematic liquid crystal of the compounds is narrow, compounds having a high clearing point must be further added so that the narrow temperature range of nematic liquid crystal can be compensated when the compounds of formula (1) are mixed with a composition. However, since the compounds having a high clearing point generally exhibit a high viscosity, addition of the compounds increases viscosity of the whole of composition as the result. Derivatives of cynnamonitrile (Laid-open Japanese Patent Publication No. Sho 55-9,012) expressed by formula (2) are also known as liquid crystalline compound. However, since the compounds are chemically unstable, they can hardly be said to be ones of practical use. Whereas cyanocyclohexane derivatives in which cyano group substituted directly in cyclohexane ring (Journal of Molecular Crystal Liquid Crystal, No. 111, page 329, 1984) and which are expressed by formula (3) are also known, the compounds have a high viscosity and a narrow temperature range of liquid crystal. Further, new compounds such as difluorovinyl derivatives (Laid-open Japanese Patent Publication No. Hei 1-175,947) expressed by formula (4) and halogenized vinyl derivatives (WO 93/07,234) expressed by formula (5) have been developed. Whereas the former have a low viscosity, they are poor in reliability and have only a narrow liquid crystal range. The latter have a medium extent of the range of liquid crystal, but they are also poor in reliability and thus they have no practical uses. Then, discovery and development of new materials exhibiting a large elastic constants, and having a high clearing point, low viscosity, and high reliability have been expected.

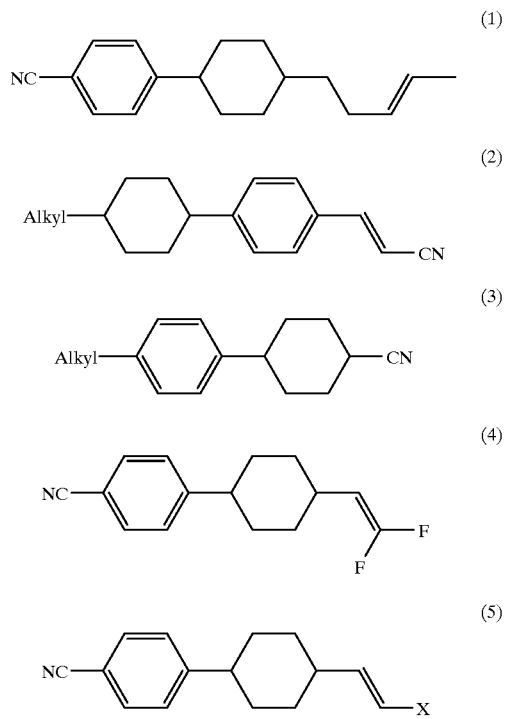

DISCLOSURE OF THE INVENTION

An object of the present invention is to solve the disadvantages in the prior art described above. Another object of the present invention is to provide novel crystalline compounds which maintain excellent properties as liquid crystal component, that is, a wide range of liquid crystal temperature, good miscibility with other liquid crystals, and low viscosity, and can impart large elastic constants to liquid crystals; compositions comprising the liquid crystalline compounds; and liquid crystal display devices comprising the composition.

In order to achieve the objects described above, the present invention has the following aspects:

(1) An acrylonitrile derivative expressed by general formula I

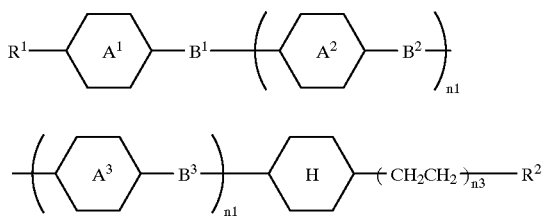

wherein ring $A^1$, ring $A^2$, and Ring $A^3$ independently represent 1,4-phenylene one or two hydrogen atoms of which may be replaced by fluorine atom, 1,4-cyclohexylene, 1,3-dioxane-2,5-diyl, or 1,3-pyrimidine-2,5-diyl, $R^1$ represents cyano group, halogen atom, an alkyl group, an alkoxy group, an alkyl group one or more hydrogen atoms of which are replaced by fluorine atom, an alkoxy group one or more hydrogen atoms of which are replaced by fluorine atom, or an alkoxyalkyl group when the ring $A^1$ represents 1,4-phenylene, but when the ring $A^1$ represents 1,4-cyclohexylene, 1,3-dioxane-2,5-diyl, or 1,3-pyrimidine-2,5-diyl, $R^1$ represents an alkyl group, an alkoxy group, or an alkoxyalkyl group, $B^1$, $B^2$, and $B^3$ represent a covalent bond, ethylene, ethenylene, ethynylene, oxymethylene, carbonyloxy, 1,4-butanediyl, or 1,4-butenediyl, n1, n2, and n3 are independently 0 or 1, $R^2$ represents a group expressed by formula II or formula III

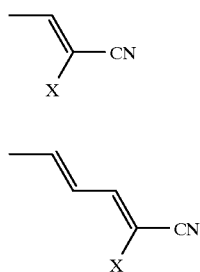

wherein X represents hydrogen atom or fluorine atom, and ring H represents 1,4-cyclohexylene, provided that in no case two or more hetero-rings are included in a molecule at the same time.

(2) The acrylonitrile derivative recited in (1) above wherein n1 and n2 are 0.

(3) The acrylonitrile derivative recited in (1) above wherein n1 is 0 and n2 is 1.

(4) The acrylonitrile derivative recited in (1) above wherein n1 and n2 are 1.

(5) The acrylonitrile derivative recited in (1) above wherein $R^1$ is an alkyl group, an alkoxy group, or an alkoxyalkyl group, ring $A^1$, ring $A^2$, and ring $A^3$ represent 1,4-phenylene one or two hydrogen atoms of which may be replaced by fluorine atom, or 1,4-cyclohexylene.

(6) The acrylonitrile derivative recited in (2) above wherein $R^1$ represents an alkyl group, an alkoxy group, or an alkoxyalkyl group, and ring $A^1$ represents 1,4-phenylene or 1,4-cyclohexylene.

(7) The acrylonitrile derivative recited in (5) above wherein either n1 or n2 is 0, and both $B^2$ and $B^3$ represent a covalent bond.

(8) The acrylonitrile derivative recited in (5) above wherein either n1 or n2 is 0, $B^2$ and $B^3$ independently represent a covalent bond or 1,2-ethylene, and $R^2$ represents a group expressed by the formula II.

(9) The acrylonitrile derivative recited in (5) above wherein either n1 or n2 is 0, $B^2$ and $B^3$ independently represent a covalent bond or 1,2-ethylene, and $R^2$ represents a group expressed by the formula III.

(10) The acrylonitrile derivative recited in (1) above wherein ring $A^1$ represents 1,4-phenylene one or two hydrogen atoms of which may be replaced by fluorine atom, and $R^1$ represents cyano group, halogen atom, an alkyl group one or more hydrogen atoms of which are replaced by fluorine atom, or an alkoxy group one or more hydrogen atoms of which are replaced by fluorine atom.

(11) The acrylonitrile derivative recited in (2) above wherein ring $A^1$ represents 1,4-phenylene one or more hydrogen atoms of which may be replaced by fluorine atom, and $R^1$ represents cyano group, halogen atom, an alkyl group one or more hydrogen atoms of which are replaced by fluorine atom, or an alkoxy group one or more hydrogen atoms of which are replaced by fluorine atom.

(12) The acrylonitrile derivative recited in (3) above wherein ring $A^1$ represents 1,4-phenylene one or more hydrogen atoms may be replaced by fluorine atom, and $R^1$ represents cyano group, halogen atom, an alkyl group one or more hydrogen atoms of which are replaced by fluorine atom, or an alkoxy group one or more hydrogen atoms of which are replaced by fluorine atom.

(13) The acrylonitrile derivative recited in (10) above wherein $R^1$ represents cyano group or halogen atom.

(14) The acrylonitrile derivative recited in (10) above wherein either n1 or n2 is 0, and both $B^2$ and $B^3$ represent a covalent bond.

(15) The acrylonitrile derivative recited in (13) wherein either n1 or n2 is 0, $B^2$ and $B^3$ represent a covalent bond, and $R^2$ represents a group expressed by the formula II.

(16) The acrylonitrile derivative recited in (13) above wherein either n1 or n2 is 0, both $B^2$ and $B^3$ represent a covalent bond, and $R^2$ represents a group expressed by the formula III.

(17) A liquid crystal composition comprising two or more components at least one of which is a liquid crystalline compound expressed by the general formula I.

(18) A liquid crystal composition comprising as a first component, at least one acrylonitrile derivative recited in any one of aspects (1) to (16), and comprising as a second component, at least one compound selected from the group consisting of the compounds expressed by any one of the general formulas IV, V, and VI

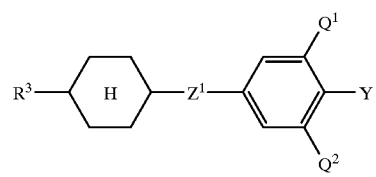

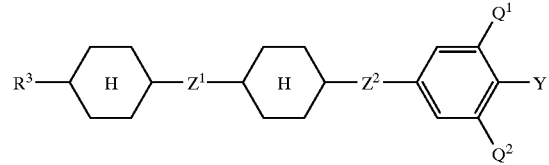

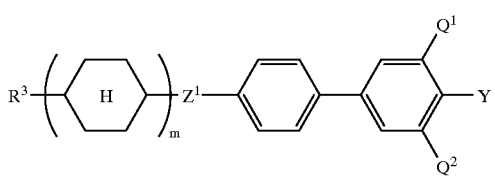

VI wherein $R^3$ represents an alkyl group having 1 to 10 carbon atoms, Y represents fluorine atom or chlorine atom, $Q^1$ and $Q^2$ independently represent hydrogen atom or fluorine atom, m is 1 or 2, and $Z^1$ and $Z^2$ independently represent —$CH_2CH_2$— or a covalent bond.

(19) A liquid crystal composition comprising as a first component, at least one acrylonitrile derivative recited in any one of aspects (1) to (16), and comprising as a second component, at least one compound selected from the group consisting of the compounds expressed by any one of the general formula VII, VIII, IX, X, and XI

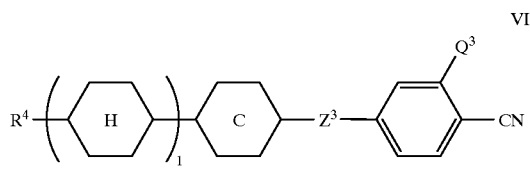

VII wherein $R^4$ represents an alkyl group having 1 to 10 carbon atoms or an alkenyl group having 2 to 10 carbon atoms, any methylene group (—$CH_2$—) in each of the alkyl group and alkenyl group may be replaced by oxygen atom (—O—), but in no case two or more methylene groups are continuously replaced by oxygen group, $Z^3$ represents —$CH_2CH_2$—, —COO—, or a covalent bond, $Q^3$ represents hydrogen atom or fluorine atom, ring C represents 1,4-cyclohexylene, 1,4-phenylene, or 1,3-dioxane-2,5-diyl, and l is 0 or 1,

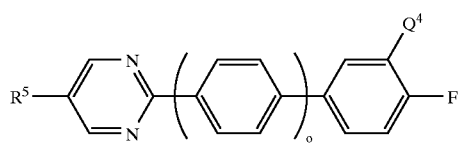

VIII wherein $R^5$ represents an alkyl group having 1 to 10 carbon atoms, $Q^4$ represents hydrogen atom or fluorine atom, and o is 0 or 1,

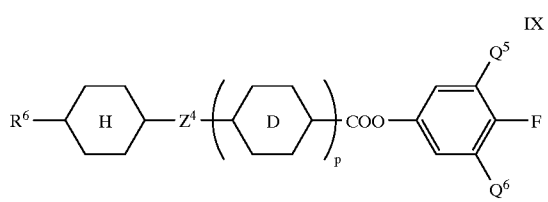

IX wherein $R^6$ represents an alkyl group having 1 to 10 carbon atoms, ring D represents 1,4-cyclohexylene or 1,4-phenylene, $Q^5$ and $Q^6$ represent hydrogen atom or fluorine atom, respectively, $Z^4$ represents —COO— or a covalent bond, and p is 0 or 1,

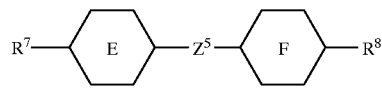

X wherein $R^7$ and $R^8$ independently represent an alkyl group having 1 to 10 carbon atoms or an alkenyl group having 2 to 10 carbon atoms, any methylene group (—$CH_2$—) in each of the alkyl group and alkenyl group may be replaced by oxygen atom, but in no case two or more methylene groups are continuously replaced by oxygen atom, ring E represents 1,4-cyclohexylene, 1,3-pyrimidine-2,5-diyl, or 1,4-phenylene, ring F represents 1,4-cyclohexylene or 1,4-phenylene, and $Z^5$ represents —C≡C—, —COO—, —$CH_2CH_2$—, or a covalent bond

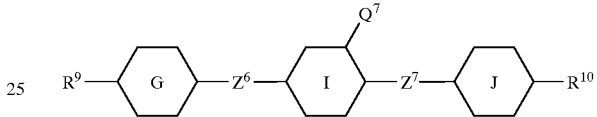

XI wherein $R^9$ represents an alkyl group or an alkoxy group having 1 to 10 carbon atoms, $R^{10}$ represents an alkyl, an alkoxy, or an alkoxymethyl group having 1 to 10 carbon atoms, ring G represents 1,4-cyclohexylene or 1,3-pyrimidine-2,5-diyl, ring I and ring J independently represent 1,4-cyclohexylene or 1,4-phenylene, $Z^6$ represents —COO—, —$CH_2CH_2$—, or a covalent bond, $Z^7$ represents —C≡C—, —COO—, or a covalent bond, and $Q^7$ represents hydrogen atom or fluorine atom.

(20) A liquid crystal composition comprising as a first component, at least one liquid crystalline compound recited in any one of aspects (1) to (16), comprising, as a part of a second component, at least one compound selected from the group consisting of the compounds expressed by any one of the general formulas IV, V, and VI, and comprising as other part of the second component, at least one compound selected from the group consisting of the compounds expressed by any one of the general formulas VII, VIII, IX, X, and XI.

(21) A liquid crystal display device comprising a liquid crystal composition recited in any one of aspects (17) to (20).

BEST MODE FOR CARRYING OUT THE INVENTION

Acrylonitrile derivatives of the present invention, expressed by general formula I, can also be expressed by any one of formulas XVII to XXIV when attention is paid to molecular terminal.

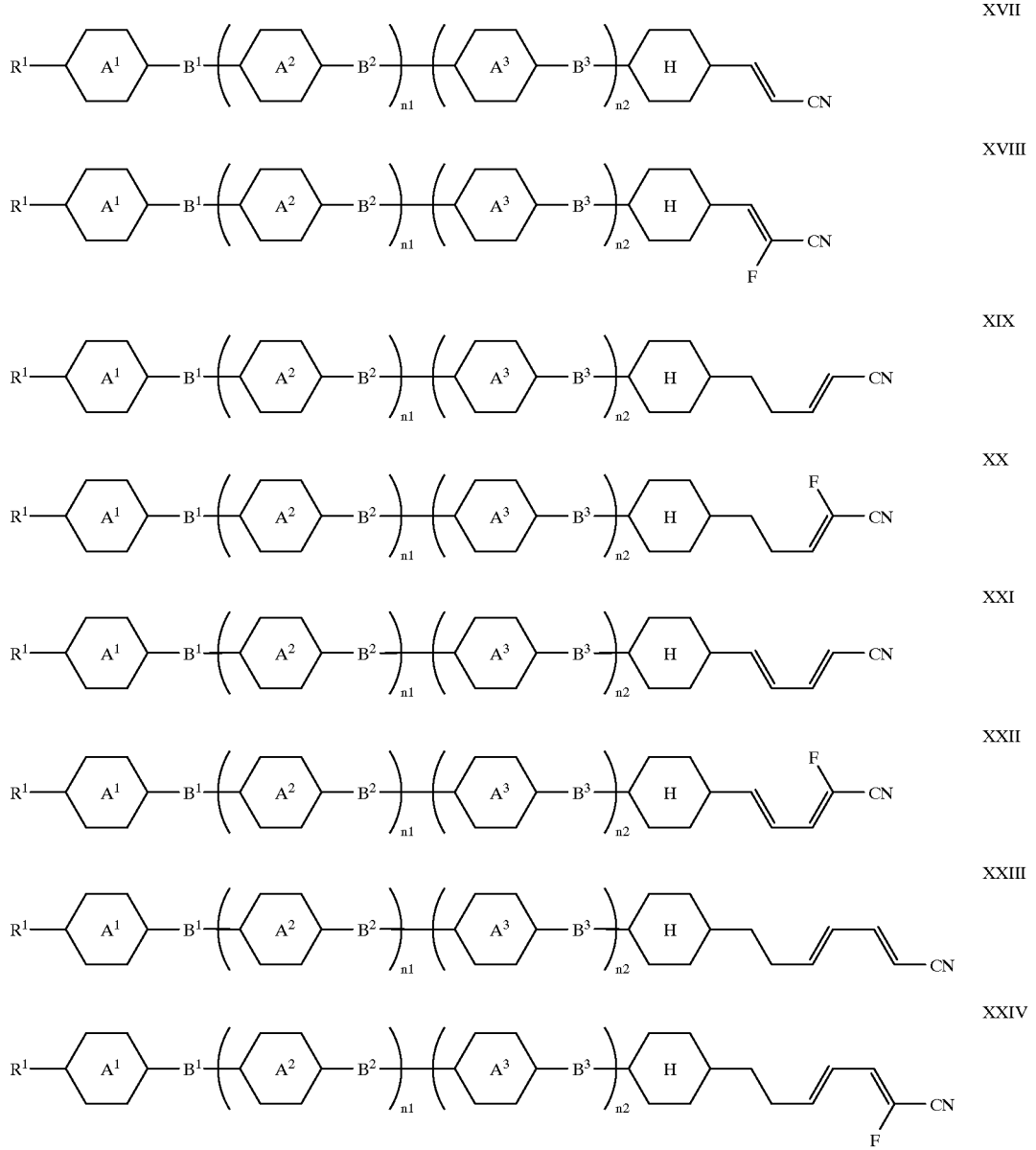

Among these, compounds having cyanoethylene group at a molecular terminal and expressed by formula XVII or XIX are stable against heat and ultraviolet irradiation, and thus they do not cause deterioration under ordinary conditions even when filled in liquid crystal panels. Compounds having a conjugated diene chain at a molecular terminal and expressed by formula XXI, XXII, XXIII, or XXIV have a large ratio of elastic constants, and are useful. Further, compounds containing fluorine atom and expressed by formula XVIII, XX, XXII, or XXIV have a wide range of liquid crystal temperature and a low viscosity in particular, and thus they are useful compounds.

On the other hand, when attention is paid to the number of ring in a molecule, compounds of the present invention can be developed into two-ring system compounds expressed by formula XXV, three-ring system compounds expressed by formula XXVI, or four-ring system compounds expressed by formula XXVII. Among these compounds of the present invention, so-called two-ring system compounds expressed by formula XXV are excellent materials because the range of liquid crystal can be adjusted around room temperature, and crystals are hardly precipitated even when they are used as component of liquid crystal compositions. Besides, since the two-ring system compounds have a low viscosity compared with the three-ring system compounds and four-ring system compounds, display of a high response speed can be obtained when the two-ring system compounds are filed in liquid crystal panels. So-called three-ring system compounds expressed by formula XXVI have a high clearing point, exhibit a good miscibility, and have a large ratio of elastic constants which is necessary for obtaining a good steepness. Further, any of compounds having the four-ring system structure and expressed by formula XXVII are important as component of liquid crystal compositions since they have a very high clearing point and a large ratio of elastic constants, and exhibit a comparatively large optical anisotropy.

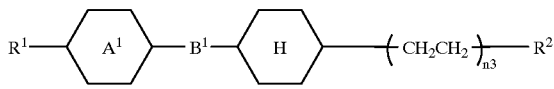

XXV

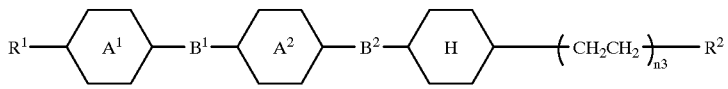

XXVI

XXVII

Among combinations of ring structures possible with the two-ring system compounds expressed by formula XXV, specific combinations exhibiting preferable properties are shown by formulas XXV-1 to XXV-4; among combinations of ring structures possible with the three-ring system compounds expressed by formula XXVI, specific combinations exhibiting preferable properties are shown by formulas XXVI-1 to XXVI-12; and among combinations of ring structures possible with the four-ring system compounds expressed by formula XXVII, specific combinations exhibiting preferable properties are shown by formulas XXVII-1 to XXVII-24.

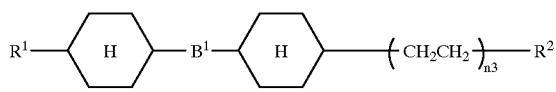

XXV-1

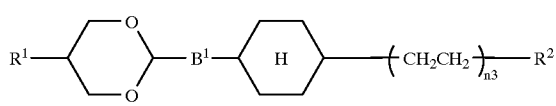

XXV-2

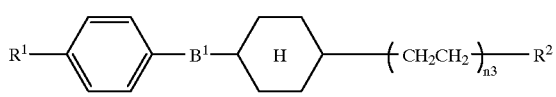

XXV-3

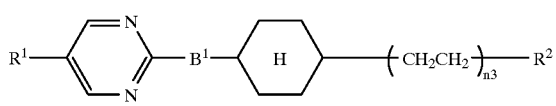

XXV-4

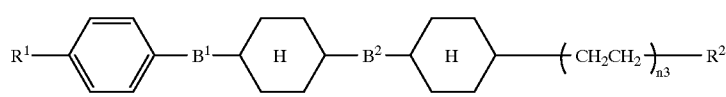

XXVI-1

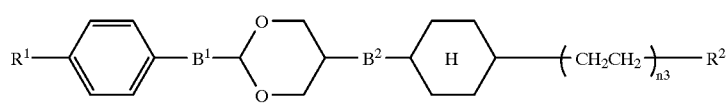

XXVI-2

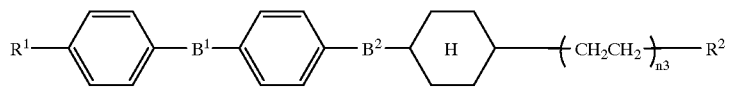
XXVI-3
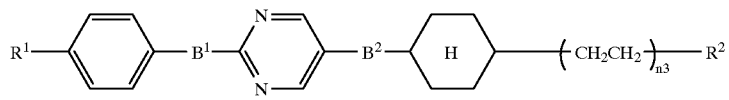
XXVI-4
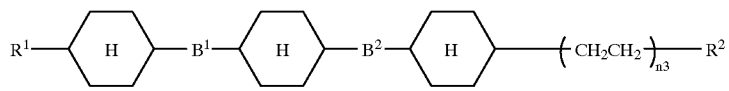
XXVI-5
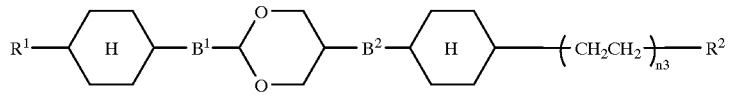
XXVI-6
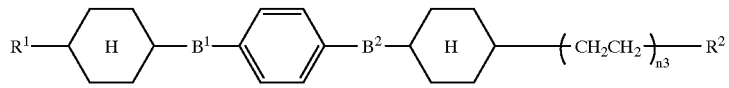
XXVI-7
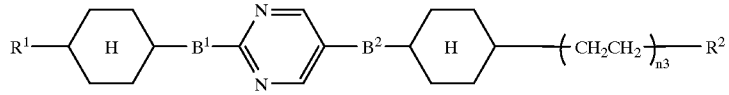
XXVI-8
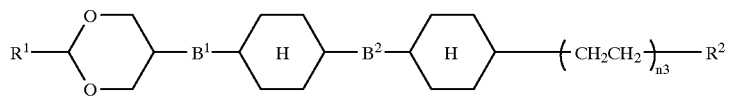
XXVI-9
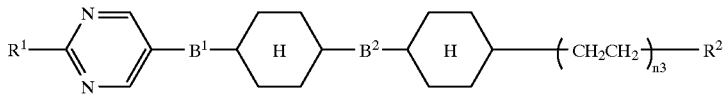
XXVI-10
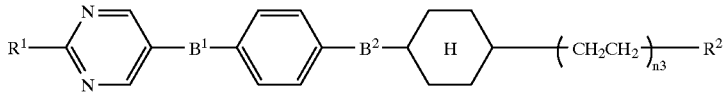
XXVI-11
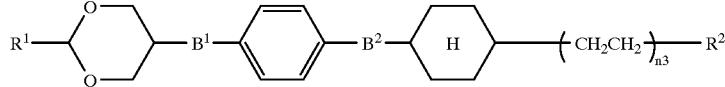
XXVI-12

XXVII-1
XXVII-2
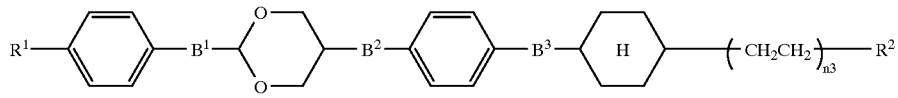
XXVII-3
XXVII-4
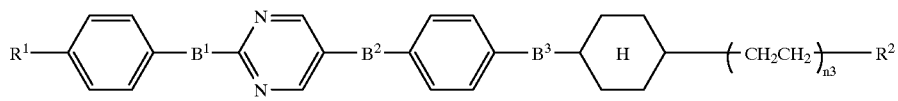
XXVII-5
XXVII-6
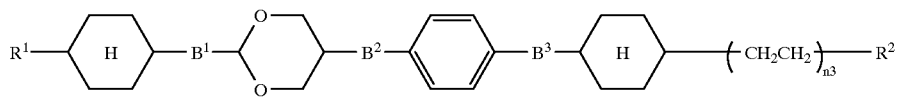
XXVII-7
XXVII-8
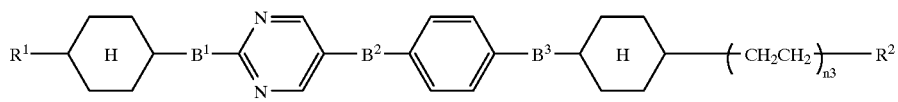
XXVII-9
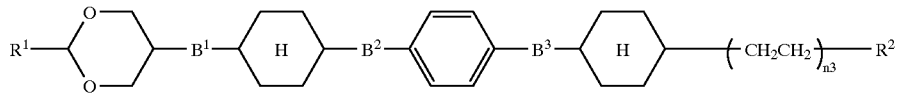
XXVII-10
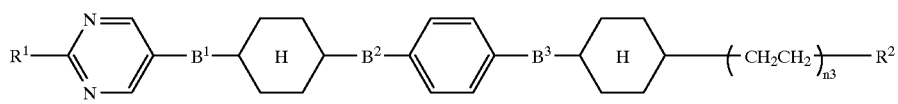
XXVII-11
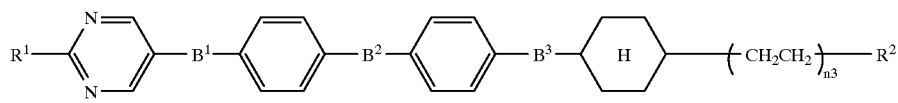

XXVII-12
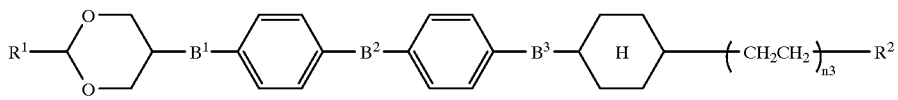
XXVII-13
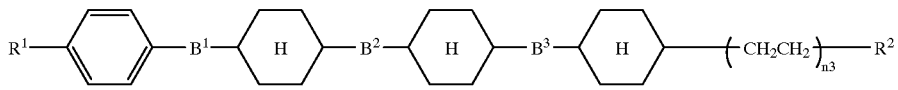
XXVII-14
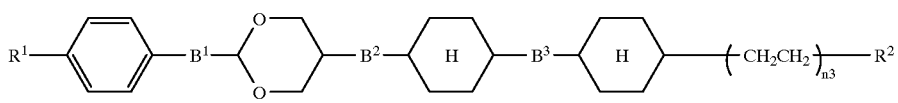
XXVII-15
XXVII-16
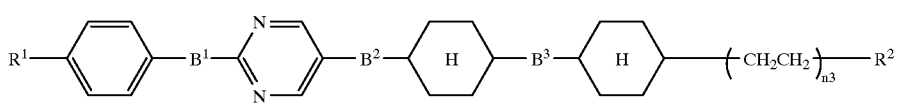
XXVII-17
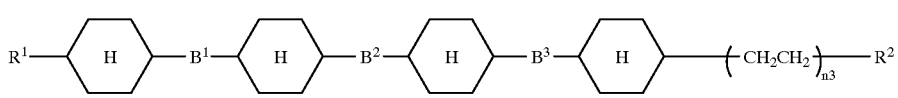
XXVII-18
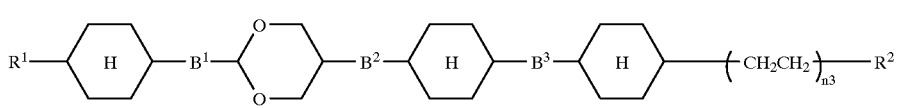
XXVII-19
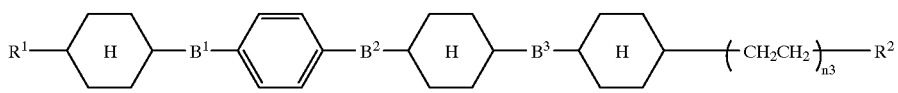
XXVII-20
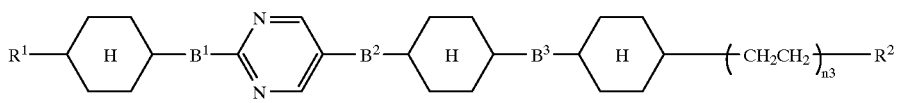
XXVII-21
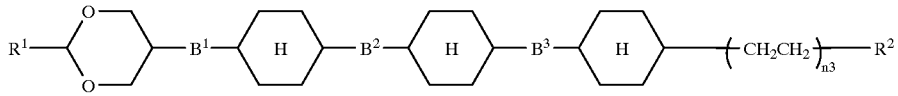

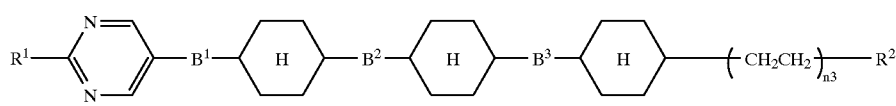

XXVII-22

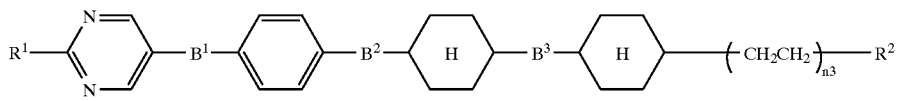

XXVII-23

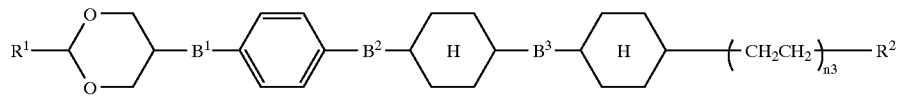

XXVII-24

Among these, compounds expressed by any one of formulas XXV-1, XXVI-1, 5, 6, 7, 8, 9, and 10, and XXVII-1, 5, 6, 7, 8, 9, 10, and 13 to 24, and having two or more cyclohexane rings in a molecule are useful since they have a wide temperature range of liquid crystal and a low viscosity. Any of the compounds expressed by any one of formulas XXV-2, XXV-4, XXV-2, 4, 6, 8, 9, 10, 11, and 12, and XXVII-2, 4, 6, 8, 9, 10, 11, 12, 14, 16, 18, 20, 21, 22, 23, and 24, and having a hetero ring exhibit a large dielectric anisotropy, and thus, they are important as component of liquid crystal compositions. Further, compounds expressed by any one of formulas XXV-3, XXVI-1, 2, 3, and 4, and XXVII-1, 2, 3, 4, 13, 14, 15, and 16 can be used for providing liquid crystal compositions satisfying their purposes by properly selecting substituents on the phenyl ring. In this connection, preferable examples of phenyl group to which the substituent is introduced are shown in formulas i to xxvii.

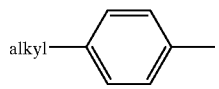

i

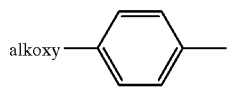

ii

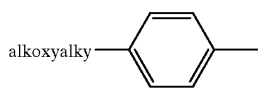

iii

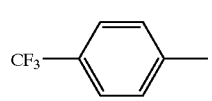

iv

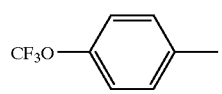

v

-continued

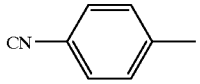

vi

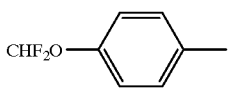

vii

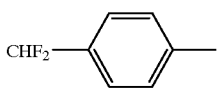

viii

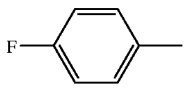

ix

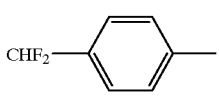

x

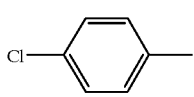

xi

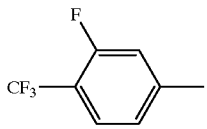

xii

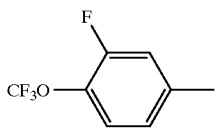

xiii

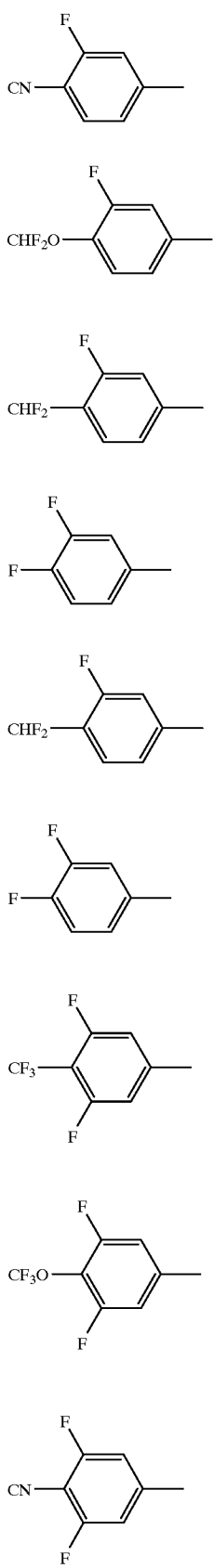

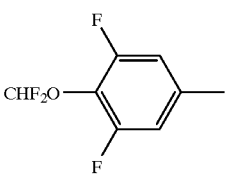

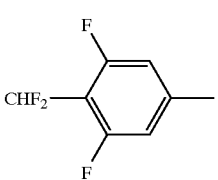

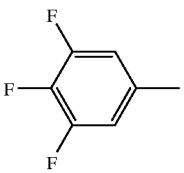

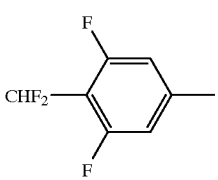

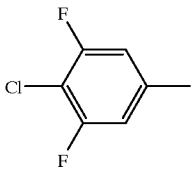

Any of the compounds of the present invention having, at a terminal, phenyl ring shown by any one of formulas iv, v, vi, vii, viii, ix, x, or xi in which fluorine atom, chlorine atom, methyl or methoxy group hydrogen atom of which is replaced by fluorine atom, or cyano group each having a strong electron atractivity, is introduced at para-position have a large dielectric anisotropy, low viscosity, and wide liquid crystal temperature range, and thus, they are important compounds for imparting dielectric property to liquid crystal compositions in particular. Further, compounds of the present invention having phenyl ring which has the electron attractive substituent described above and one or two fluorine atoms thereon and expressed by any one of formulas xxii to xxvii have a larger dielectric anisotropy, and thus, they are materials necessary for driving liquid crystal display devices at a low voltage. Compounds of the present invention having any one of phenyl rings (i to iii) in which an alkyl group, an alkoxy group, or an alkoxyalkyl group all of which are a weak electron-donating group do not have a large dipole moment. These compounds are characterized by their low viscosity and good miscibility, and are useful in the aspect that they can be used for the purpose of controlling physical properties of the whole liquid crystal compositions to required values.

Next, among compounds of the present invention expressed by formula XXV, XXVI, or XXVII in which a bonding group or groups $B^1$, $B^1$ and $B^2$, or $B^1$, $B^2$, and $B^3$ at internal positions are also included, specific examples of compounds which impart preferable properties are expressed by any one of formulas XXV-a to h, XXVI-a to p, and XXVII-a to s.

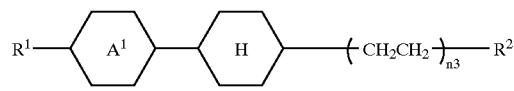

XXV-a

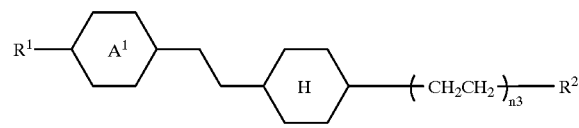

XXV-b

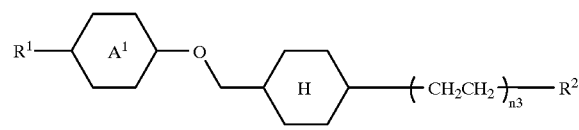

XXV-c

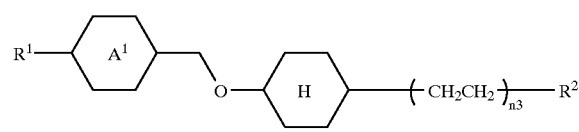

XXV-d

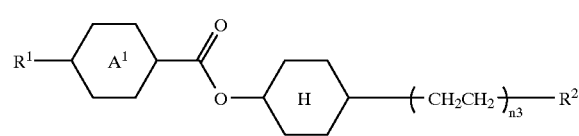

XXV-e

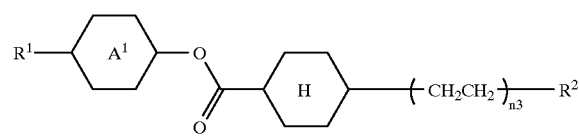

XXV-f

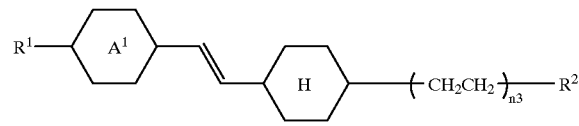

XXV-g

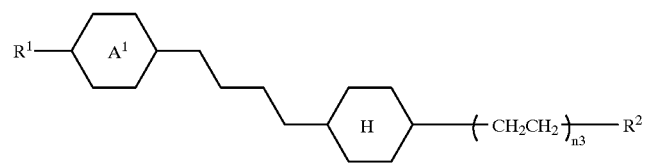

XXV-h

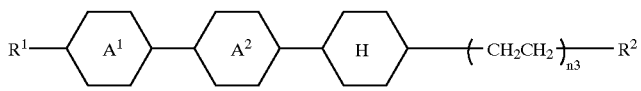
XXVI-a
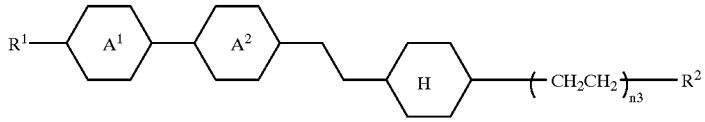
XXVI-b
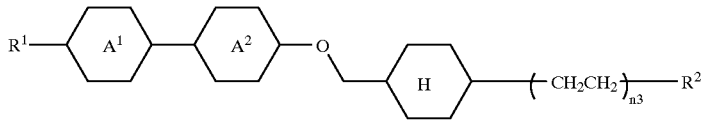
XXVI-c
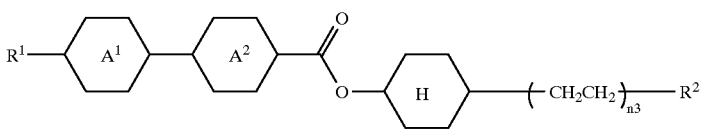
XXVI-d
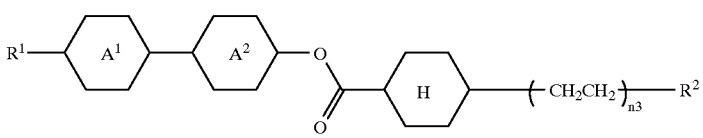
XXVI-e
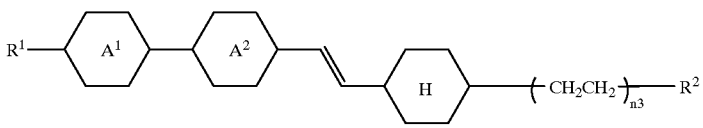
XXVI-f
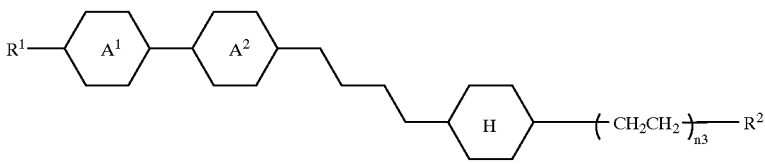
XXVI-g
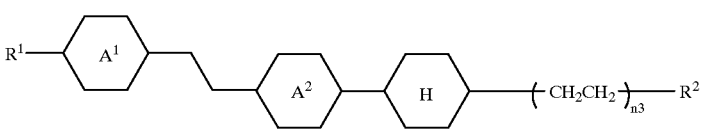
XXVI-h
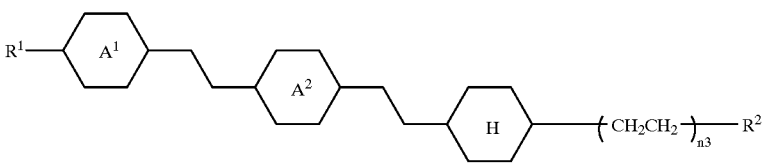
XXVI-i XXVI-j
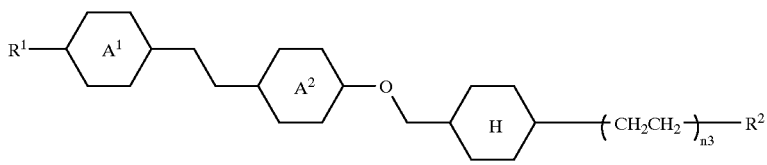
XXVI-k
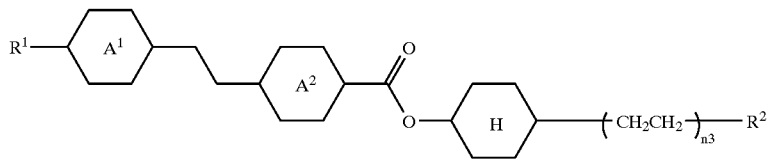
XXVI-l
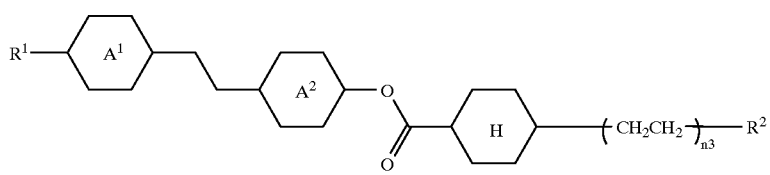
XXVI-m
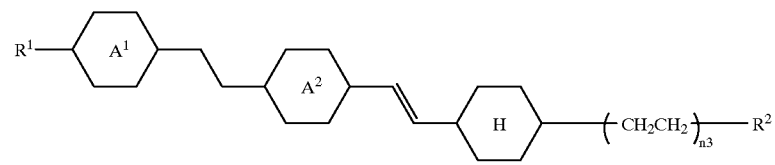
XXVI-n
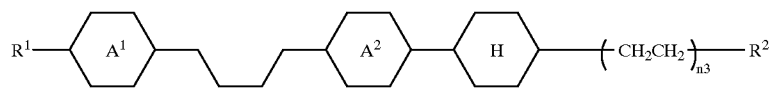
XXVI-o
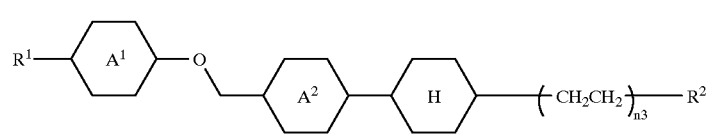
XXVI-p
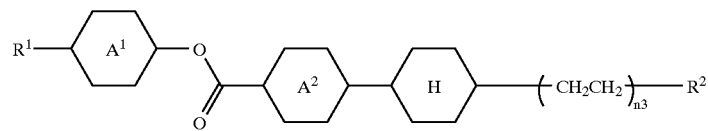
XXVII-a
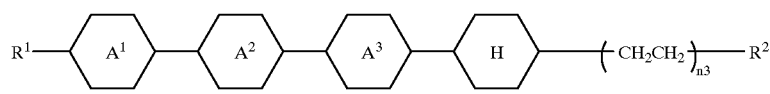
XXVII-b
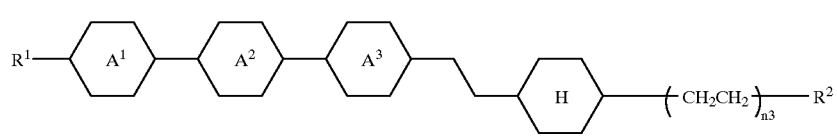

XXVII-c
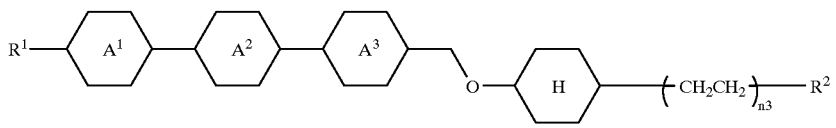
XXVII-d
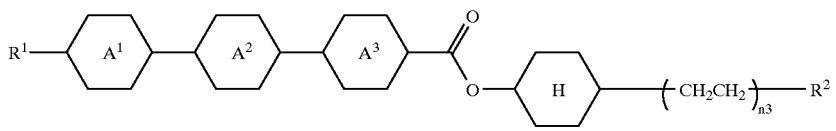
XXVII-e
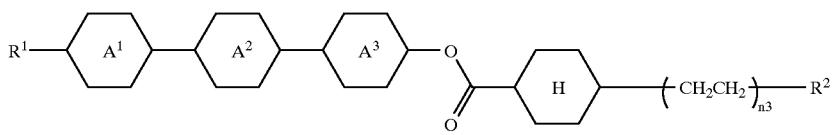
XXVII-f
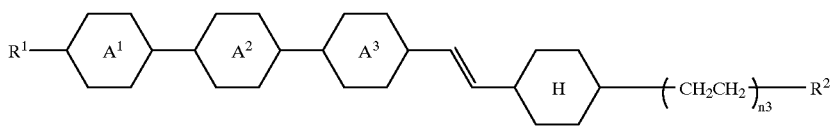
XXVII-g
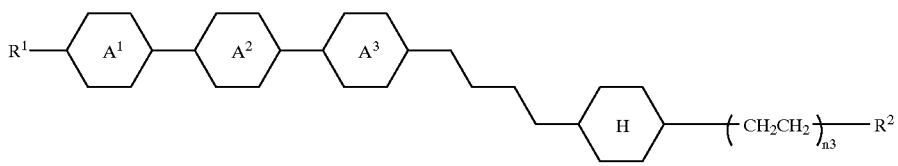
XXVII-h
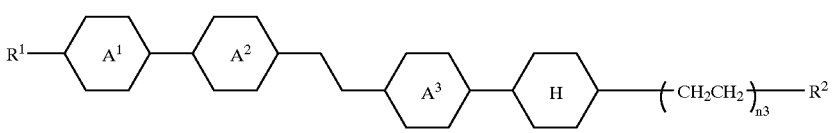
XXVII-i
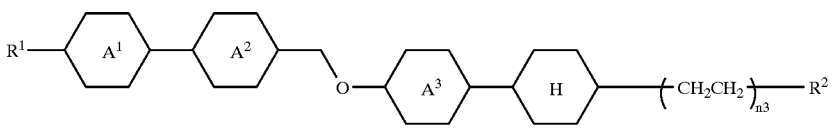
XXVII-j
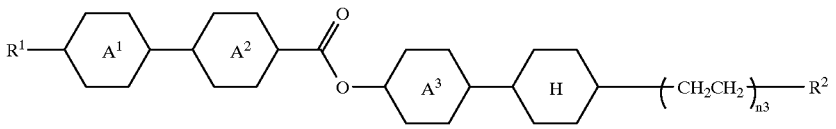
XXVII-k
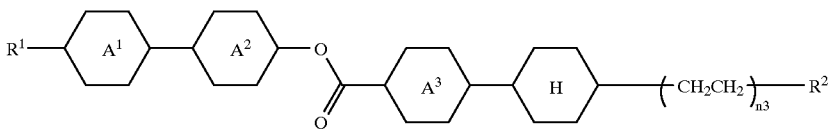

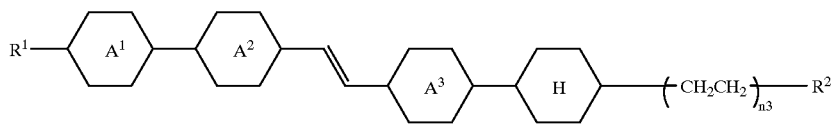
XXVII-l
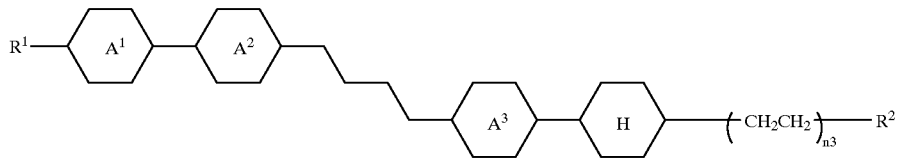
XXVII-m
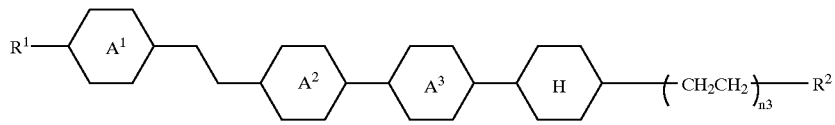
XXVII-n
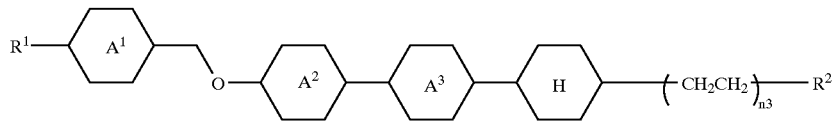
XXVII-o
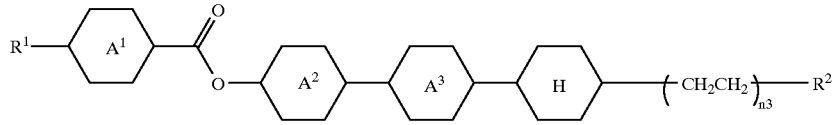
XXVII-p
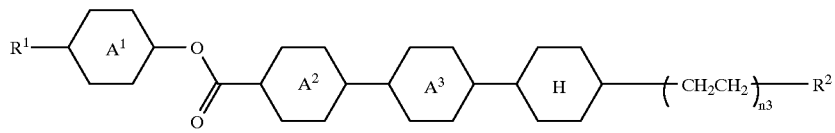
XXVII-q
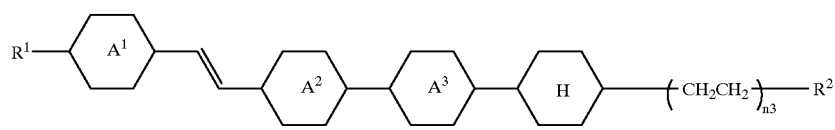
XXVII-r

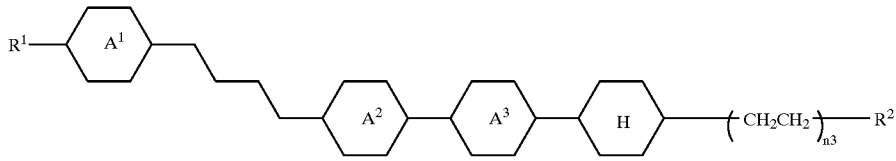

XXVII-s

Among these specific compounds, compounds expressed by any one of formulas XXV-a, XXVI-a to h, XXVI-o and p, and XXVII-a to s have at least one covalent bond as internal group, and exhibit a low viscosity and good miscibility. Compounds expressed by XXV-b, XXVI-b, and h to m, and XXVII-b, h, and n, and having ethylene chain or ethylene chain and other bond together as internal group exhibit a good liquid crystallinity and low viscosity, and have a good miscibility. Compounds expressed by any one of formulas XXV-c and d, XXVI-c, j, and o, and XXVII-c, l, and o, and having oxymethylene chain or oxymethylene chain and other bond together as internal group exhibit a medium extent of dielectric anisotropy and wide range of liquid crystal temperature, and are stable. Thus those compounds are useful. Compounds expressed by any one of formulas XXV-e and f, XXVI-d, e, k, Q, and p, and XXVII-d, e, j, k, p, and q, and having an ester group such as oxycarbonyl or carbonyloxy group, or the ester group and other group together as internal group exhibit a large dielectric anisotropy and sufficiently wide range of liquid crystal temperEthenyland thus they are useful. Ethenylene derivatives expressed by any one of formulas XXV-g, XXVI-f and m, and XXVII-f and Q have a particularly wide range of liquid crystal temperature and low viscosity. Also, these compounds have such an advantage that when they are used as a component of liquid crystal compositions, the compositions hardly exhibit a smectic phase. Further, butenyl derivatives expressed by any one of formulas XXV-h, XXVI-g and n, and XXVII-g, m, and s exhibit a good miscibility and low viscosity, and thus they are preferable compounds.

Method of preparation

Compounds of the present invention expressed by general formula I can be synthesized, for instance, by the method described below.

Compounds expressed by general formula I wherein $R^2$ represents a group expressed by formula II and X represents hydrogen atom:

The compounds can be obtained in a good yield by reacting a reaction agent prepared from diethylcyanomethyl phosphonate and a base with an aldehyde derivative expressed by formula XXVIII

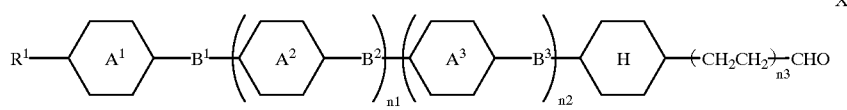

XXVIII wherein $R^1$, $A^1$, $B^1$, $A^2$, n1, $B^2$, $A^3$, n2, $B^3$, and n3 have the same meaning as defined above, in a non-protic polar solvent under a low temperature condition. While the product in this reaction is sometimes obtained as a mixture of two isomers, that is, E-isomer and Z-isomer, derived from the portion of double bond, only E-isomer having better properties as liquid crystal material can be isolated by a purification and separation procedure such as recrystallization and distillation, if necessary.

The compounds can also be obtained by the following method:

Halogenized vinyl derivative expressed by formula XXIX

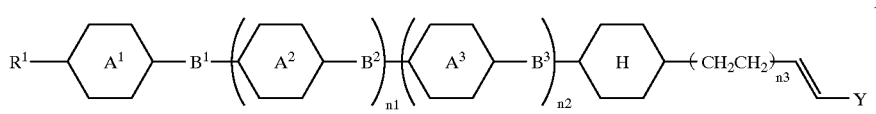

XXIX wherein $R^1$, $A^1$, $B^1$, $A^2$, n1, $B^2$, $A^3$, n2, $B^3$, and n3 have the same meaning as defined above, and Y represents iodine or bromine atom, is reacted with a metal cyanide in a non-protic polar solvent. In this case, copper cyanide and sodium cyanide can be mentioned as the metal cyanide. Further, this reaction can preferably be carried out under reflux conditions of the solvent to be used. As preferable solvent, acetone, dioxane, dimethylformamide, N-methylpyrrolidone, pyridine, and tetrahydrofuran can be mentioned.

Compounds expressed by general formula I wherein $R^2$ represent a group expressed by formula III and X represents hydrogen atom:

The compounds can be obtained in a good yield by reacting an α-β unsaturated aldehyde expressed by formula XXX

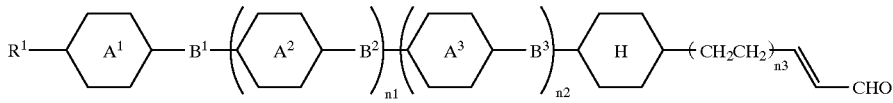

XXX wherein $R^1$, $A^1$, $B^1$, $A^2$, n1, $B^2$, $A^3$, n2, $B^3$, and n3 indicate the same meaning as defined above,
in a non-protic polar solvent under a low temperature with a reagent prepared from diethylcyano-methyl phosphonate and a base. Since this reaction proceeds retaining the steric conformation of reactants, the α-β unsaturated aldehyde which is a starting material must be a mixture of steric isomers, or E-isomer. While the product of this reaction is sometimes a mixture of two isomers, that is, E-isomer and Z-isomer, derived from the portion of double bond, only E-isomer having properties as better liquid crystal material can be isolated by a purification and separation procedure such as recrystallization and distillation, if necessary.

Compounds expressed by general formula I wherein $R^2$ represents a group expressed by formula II, and X represents fluorine atom:
Dihalide expressed by formula XXXI mixture containing an EE-isomer or EE-isomer only. As the metal cyanide used in the cyanization reaction, copper cyanide and sodium cyanide are preferable. Also, this reaction is preferably carried out under reflux conditions of the solvent to be used in the aspect that the yield is good.

Among the starting materials used in each of the reactions described above, compounds expressed by formula XXVIII can be produced by oxidizing a corresponding alcohol derivative by using, for example, an oxidizing agent such as PCC, or produced through such a synthesis rout as described in Laid-open Japanese Patent Publication No. Hei 01-175, 947 or WO 93/07,234. Halogenized vinyl derivatives expressed by formula XXIX can be produced by a method described in WO 93/07,234.

α-β unsaturated aldehydes expressed by formula XXX can be synthesized by, when n3 is 0, reacting a ketone derivative expressed by formula XXXIII

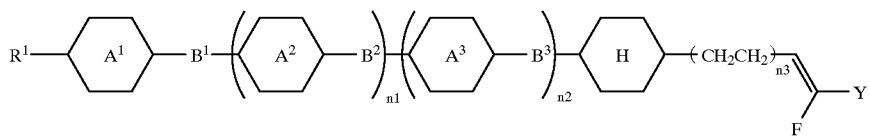

XXXI wherein $R^1$, $A^1$, $B^1$, $A^2$, n1, $B^2$, $A^3$, n2, $B^3$, and n3 have the same meaning as defined above, and Y represents iodine or bromine atom,
is converted into a cyanide in a non-protic solvent such as N-methylpyrrolidone by using a metal cyanide. Since this reaction proceeds while retaining the steric conformation of reactants, the dihalide which is a starting material must be a mixture of isomers or E-isomer only. As the metal cyanide used in the cyanization reaction, copper cyanide and sodium cyanide are preferable. Also, this reaction is preferably carried out under reflux conditions of the solvent to be used in particular.

Compounds expressed by general formula I wherein $R^2$ represents a group expressed by formula III, and X represents fluorine atom:
Dihalide expressed by formula XXXII

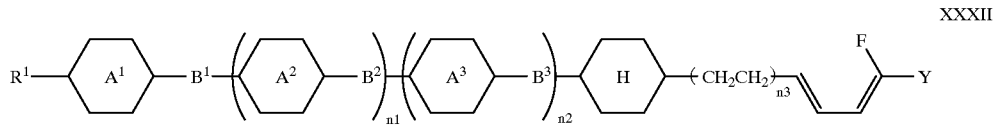

XXXII wherein $R^1$, $A^1$, $B^1$, $A^2$, n1, $B^2$, $A^3$, n2, $B^3$, and n3 have the same meaning as defined above, and Y represents iodine or bromine atom,
is converted into a cyanide in a non-protic solvent such as N-methylpyrrolidone by using a metal cyanide. Since this reaction proceeds retaining the steric conformation of reactants, the dihalide which is a starting material must be a

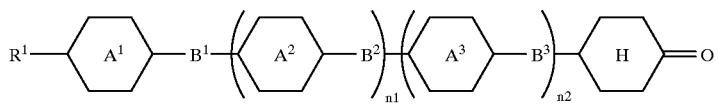

XXXIII wherein $R^1$, $A^1$, $B^1$, $A^2$, n1, $B^2$, $A^3$, n2, $B^3$, and n3 have the same meaning as defined above,
on the other hand, when n3 is 1, by reacting an aldehyde derivative expressed by formula XXXIV

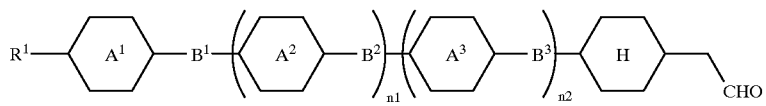

XXXIV wherein $R^1$, $A^1$, $B^1$, $A^2$, n1, $B^2$, $A^3$, n2, $B^3$, and n3 have the same meaning as defined above
with a Wittig's reagent prepared from 1,3-dioxane-2-ylethyltriphenyl phosphonium bromide and a base to once convert the ketone derivative or aldehyde derivative into compounds expressed by formula XXXV or XXXVI

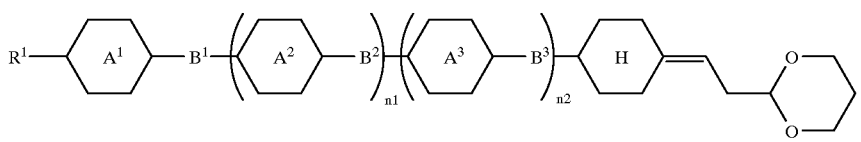

XXXV

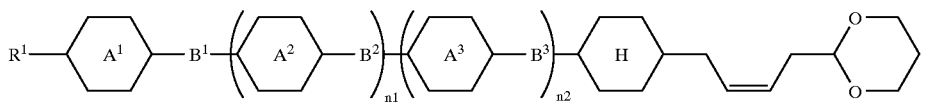

XXXVI wherein $R^1$, $A^1$, $B^1$, $A^2$, n1, $B^2$, $A^3$, n2, $B^3$, and n3 have the same meaning as defined above,
and then treating with an acid.

Further, the dihalides expressed by formula XXXI are obtained by treating an aldehyde derivative expressed by formula XXIII in a suitable solvent such as ethylene glycol dimethyl ether with a reaction agent prepared from tribromofluoromethane and triphenylphosphine. Products in this case usually become a mixture of E-isomer and Z-isomer derived from the steric conformation of olefin. While the products can be used as they are for a succeeding reaction, they can be used for a succeeding reaction after isolation of only Z-isomer by carrying out a purification procedure such as a column chromatography, if necessary.

Finally, the dihalides expressed by formula XXXII can be obtained by treating an α-β unsaturated aldehyde expressed by formula XXX in a suitable solvent such as ethylene glycol dimethyl ether with a reaction agent prepared from tribromofluoromethane and triphenyl phosphine. Products in this case usually become a mixture of E-isomer and Z-isomer derived from the steric conformation of olefin. While the products can be used as they are for a succeeding reaction, they can be used for a succeeding reaction after separation of only Z-isomer by carrying out a purification procedure such as chromatography, if necessary.

Any of the liquid crystalline compounds of the present invention obtained by such methods have a high clearing point and large ratio of elastic constants ($k_{33}/k_{11}$), and are remarkably excellent as component of nematic liquid crystal compositions including for TFT mode, particularly as component of liquid crystal compositions for STN display mode.

While the liquid crystal compositions provided by the present invention may be comprised only of a first component comprising at least one liquid crystalline compound expressed by general formula I, the compositions in which at least one compound (hereinafter referred to as a second A component) selected from the group consisting of the compounds expressed by any one of the general formulas IV, V, and VI described above and/or at least one compound (hereinafter referred to as second B component) selected from the group consisting of the compounds expressed by any one of the general formulas VII, VIII, IX, X, and XI described above is added in addition to the first component are preferable. Further, known compounds may be mixed as a third component for the purposes of adjusting threshold voltage, temperature range of liquid crystal, optical anisotropy (Δn), dielectric anisotropy (Δ∈), and viscosity.

Among the second A component, as preferable examples expressed by general formula IV, the compounds expressed by any one of formulas IV-1 to IV-12 can be mentioned, and as preferable compounds expressed by general formula V, compounds of formulas V-1 to V-18, and as preferable compounds expressed by general formula VI, compounds of formulas VI-1 to VI-18 can be mentioned, respectively.

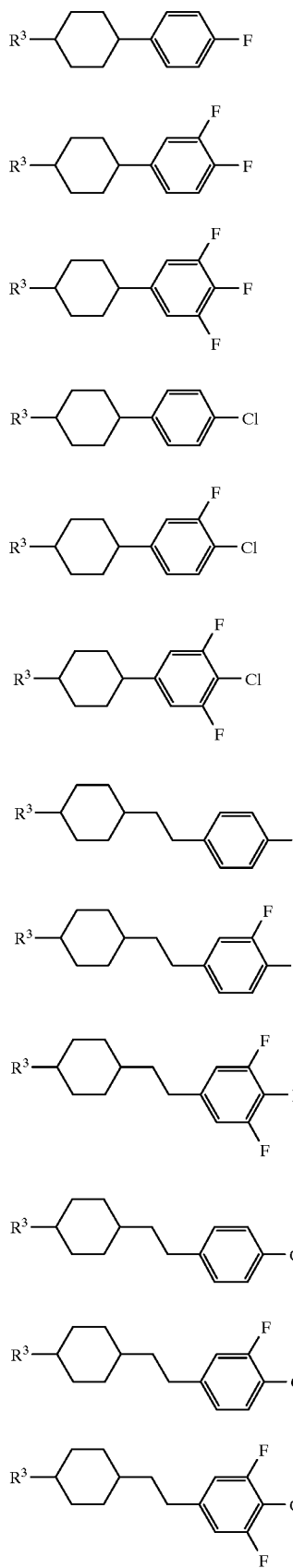

V-12
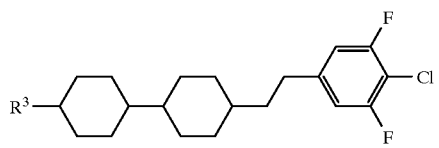
V-13
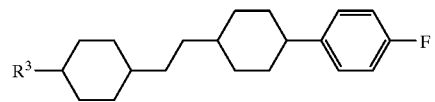
V-14
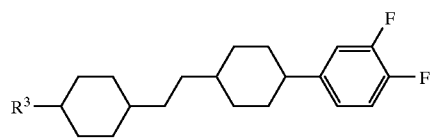
V-15
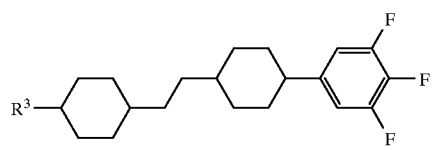
V-16
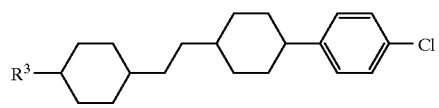
V-17
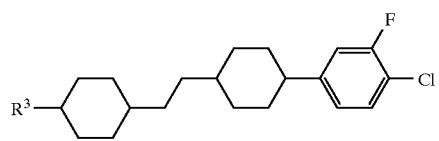
V-18
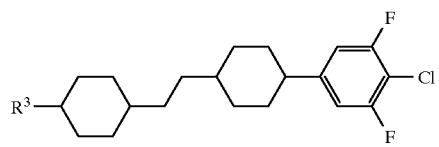
V1-1
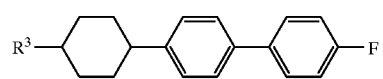
V1-2
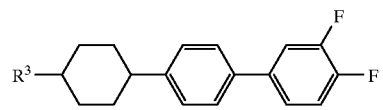
V1-3
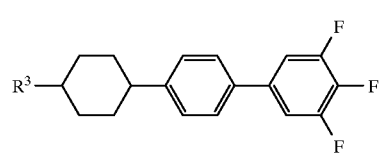
V1-4
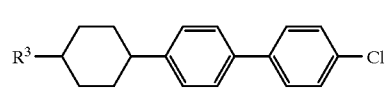
V1-5
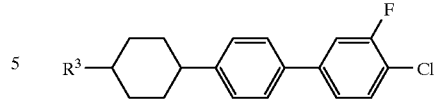
V1-6
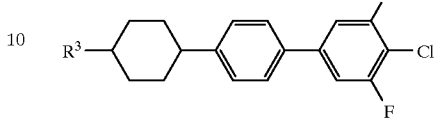
V1-7
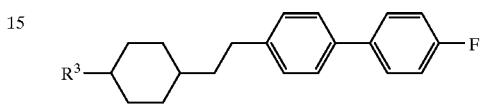
V1-8
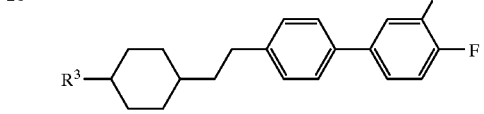
V1-9
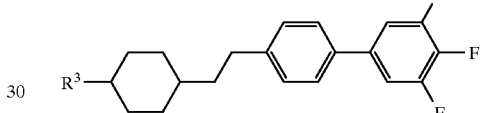
V1-10
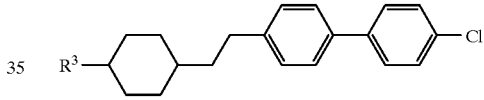
V1-11
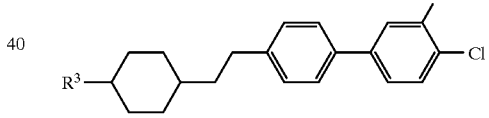
V1-12
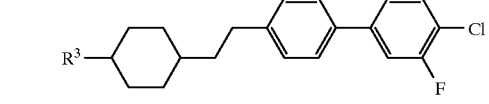
V1-13
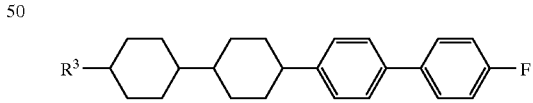
V1-14
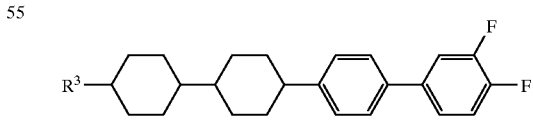
V1-15
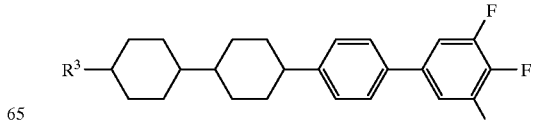

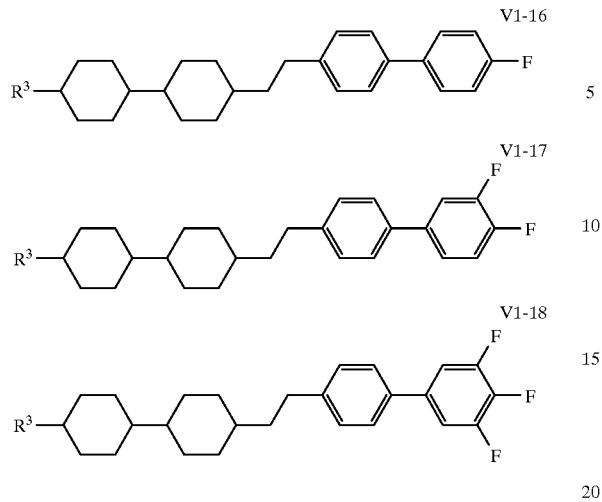

V1-16

V1-17

V1-18 wherein R³ represents an alkyl group.

Compounds expressed by any one of general formulas IV to VI have a positive dielectric anisotropy, and are remarkably excellent in heat stability and chemical stability, and thus, they are useful compounds when liquid crystal compositions for TFT (AM-LCD) of which a high reliability such as an especially high voltage holding ratio or a high specific resistance required are produced.

While the compounds can be used in any range of amount based on the total weight of liquid crystal composition when liquid crystal compositions for TFT are produced, the amount to be used is preferably 10 to 97% by weight, and more preferably 40 to 95 % by weight.

Among the second B component described above, as preferable examples of the compounds expressed by general formula VII, VIII, or IX, compounds expressed by any one of formulas VII-1 to VII-20, VIII-1 to VIII-3, and IX-1 to IX-11 can be mentioned, respectively.

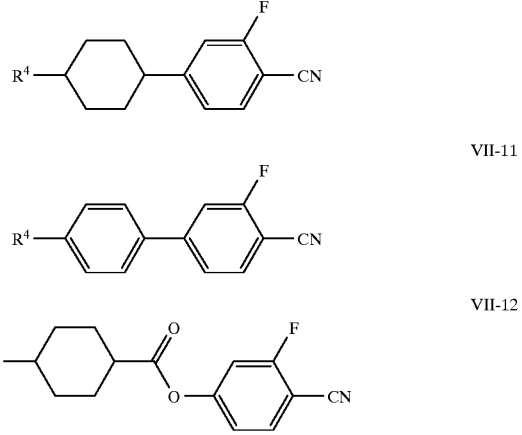

VII-1

VII-2

VII-3

VII-4

VII-5

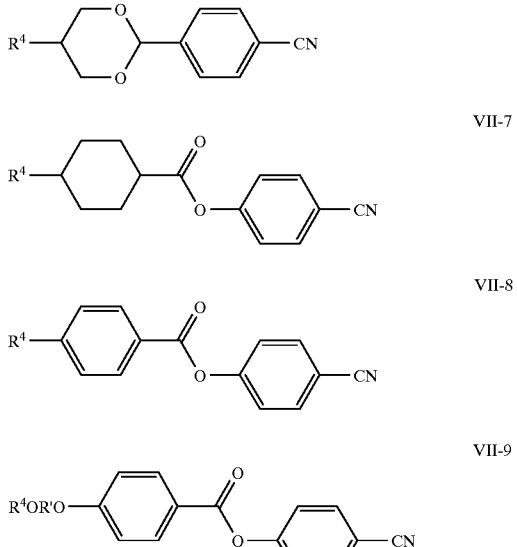

VII-6

VII-7

VII-8

VII-9

VII-10

VII-11

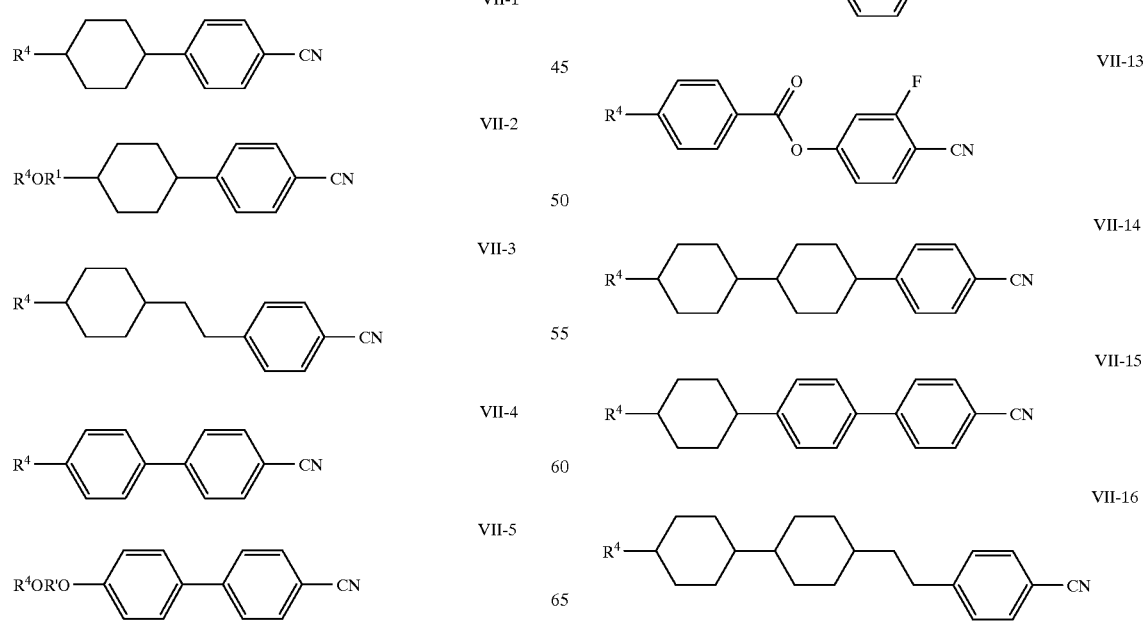

VII-12

VII-13

VII-14

VII-15

VII-16

VII-17
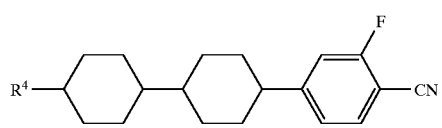

VII-18
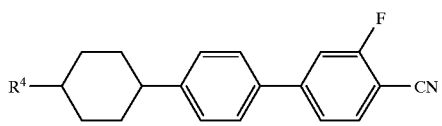

VII-19
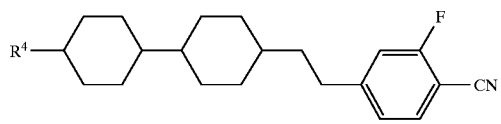

VII-20
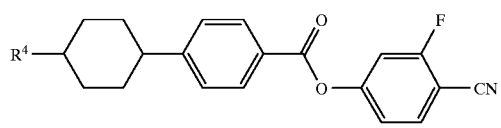

VIII-1
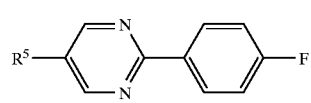

VIII-2
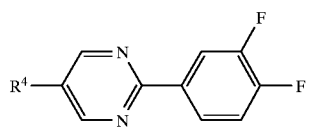

VIII-3
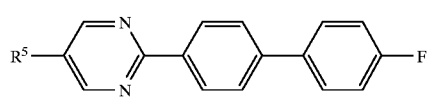

IX-1
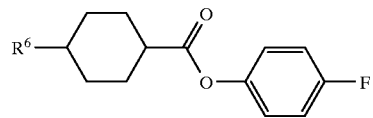

IX-2
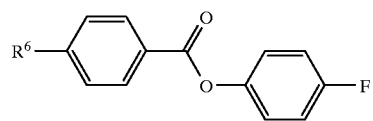

IX-3
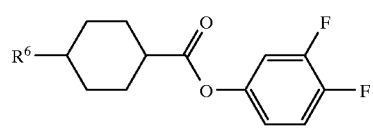

IX-4
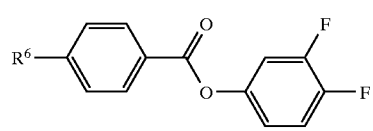

IX-5
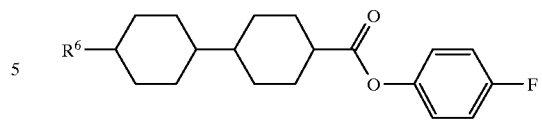

IX-6
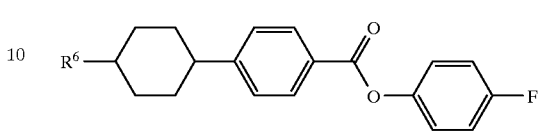

IX-7
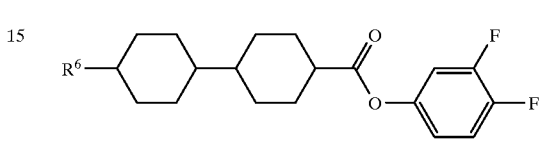

IX-8
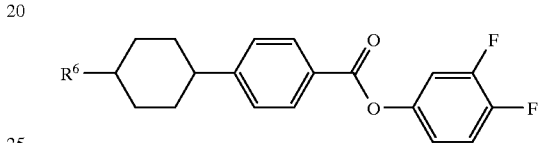

IX-9
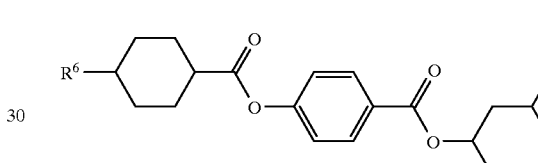

IX-10
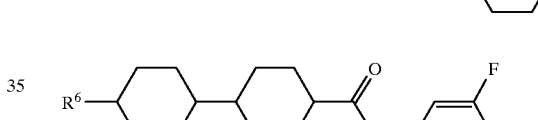

IX-11

wherein $R^4$, $R^5$, and $R^6$ represent an alkyl group or alkenyl group, and R' represents an alkylene.

Compounds expressed by these general formulas VII to IX have a large positive dielectric anisotropy, and are used as component of liquid crystal compositions for the purpose of particularly reducing threshold voltage. Also, the compounds are used for the purpose of adjusting viscosity and optical anisotropy (Δn), and widening the range of nematic temperature such as raising clearing point, as well as for the purpose of improving steepness.

Further, among the second B component, as preferable examples of compounds expressed by general formula X or XI, compounds expressed by any one of formulas X-1 to X-15, and XI-1 to XI-13 can be mentioned, respectively.

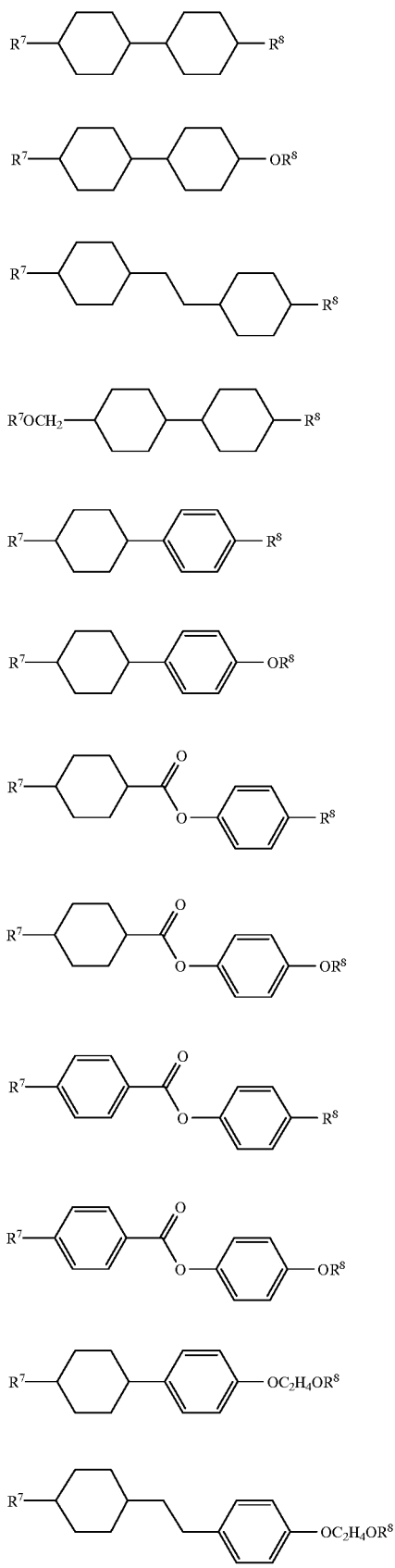
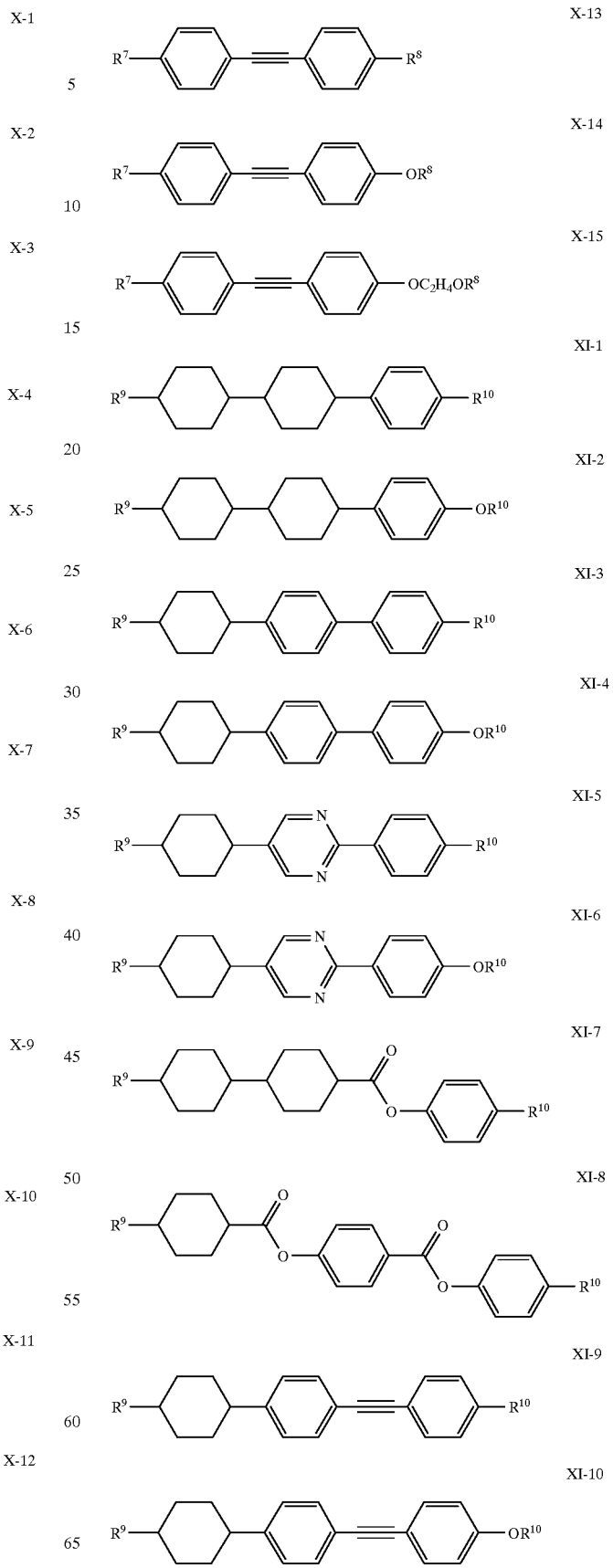

XI-11

XI-12

XI-13 wherein $R^7$, $R^8$, $R^9$, and $R^{10}$ represent an alkyl group.

Compounds expressed by general formula X or XI have a negative or small positive dielectric anisotropy. Among them, the compounds expressed by general formula X are used for the purposes of mainly reducing the viscosity of the compositions and adjusting Δn. Compounds expressed by general formula XI are used for the purpose of enhancing the range of nematic temperature such as raising the clearing point of compositions and/or the purpose of adjusting Δn. Accordingly, the compounds expressed by any one of general formulas VII to XI are useful when liquid crystal compositions particularly for STN display mode or TN display mode are produced.

While the compounds can be used in any range of amount depending on their purposes when liquid crystal compositions for TN display mode or STN display mode are produced, the amount to be used is preferably 10 to 97% by weight and preferably 40 to 95% by weight.

As described above, while the liquid crystal compositions for TFT may be composed of the first component and the second A component, the compositions may partially comprise the second B component. While the liquid crystal compositions for STN and TN may be composed of the first component and the second B component, the compositions may partially comprise the second component A.

Further, these liquid crystal compositions may further be added with the third component described above, and the compounds expressed by any one of formulas XII-1 to XII-35 can be mentioned as preferable examples.

XII-1

XII-2

XII-3

XII-4

XII-5

XII-6

XII-7

-continued
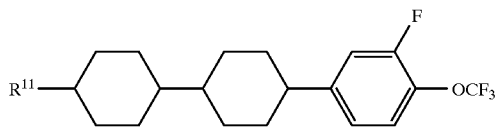
XII-8
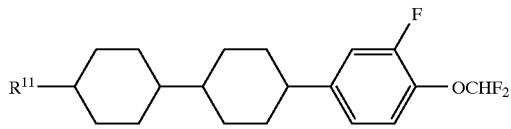
XII-9
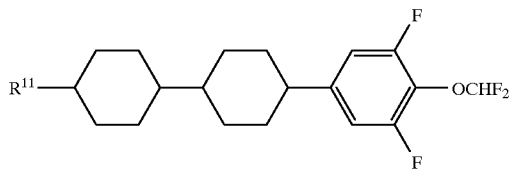
XII-10
XII-11
XII-12
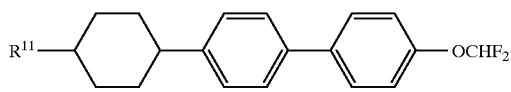
XII-13
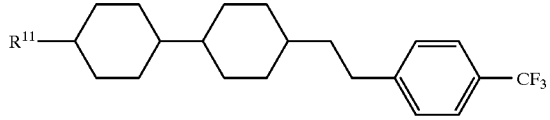
XII-14
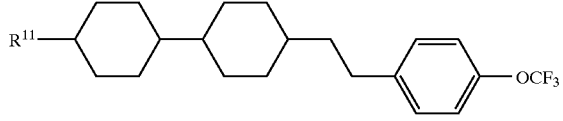
XII-15
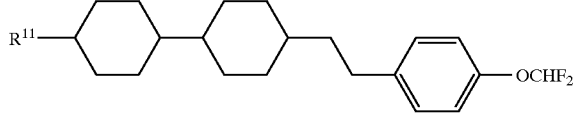
XII-16
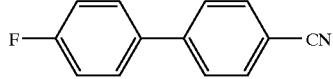
XII-17
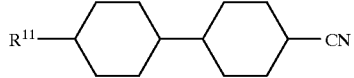
XII-18

-continued
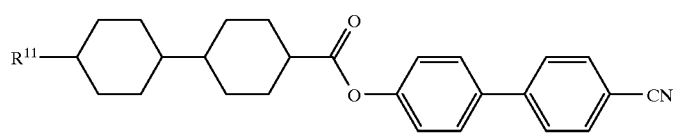
XII-19
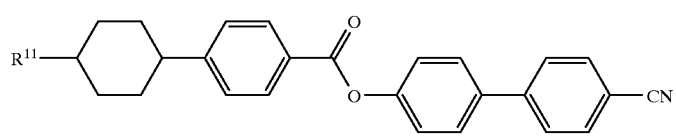
XII-20
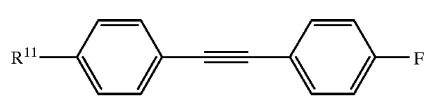
XII-21
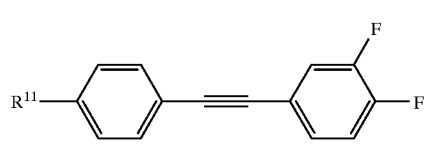
XII-22
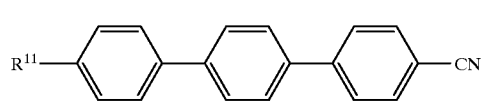
XII-23
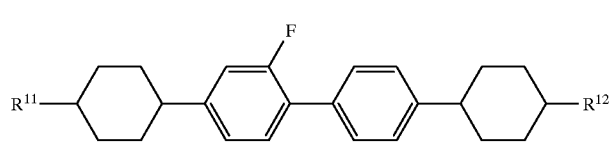
XII-24
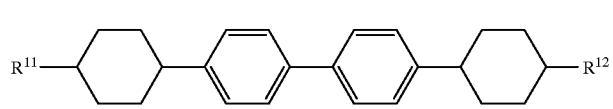
XII-25
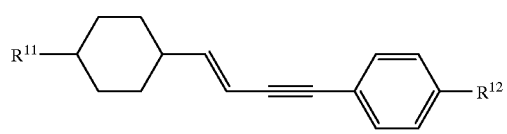
XII-26
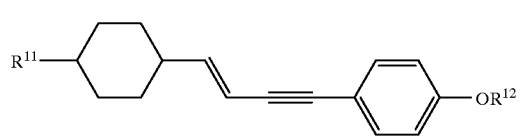
XII-27
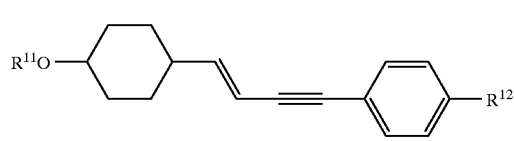
XII-28

-continued

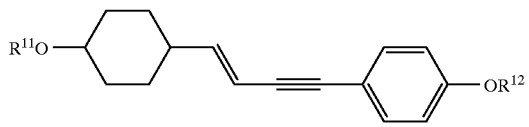
XII-29

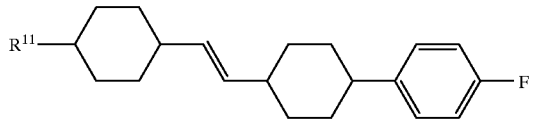
XII-30

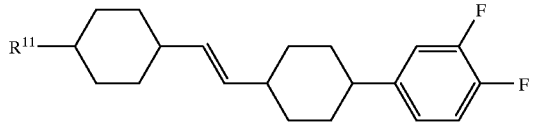
XII-31

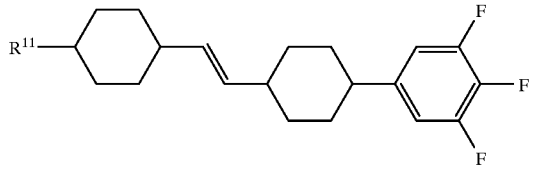
XII-32

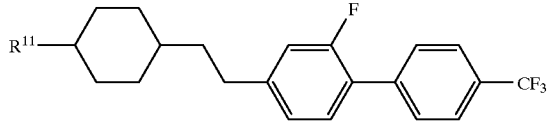
XII-33

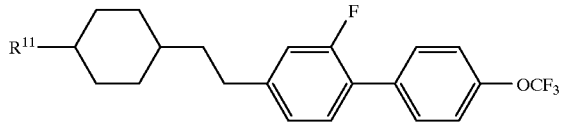
XII-34

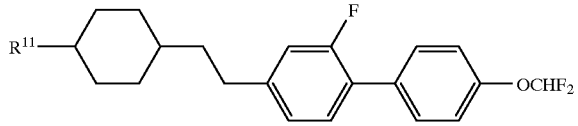
XII-35

Liquid crystal compositions provided by the present invention preferably contain at least one liquid crystalline compound expressed by general formula I in the range of 0.1 to 99% by weight to develop excellent properties.

Liquid crystal compositions of the present invention can be further optimized by adding a suitable additive depending on intended uses. As such additive, for example, some compounds are described as chiral additive in the literature. Such additive is added to cause the helical structure of liquid crystal and adjusting necessary twist angle, and to prevent reverse twisting. Liquid crystal compositions of the present invention optimized by such method can be produced by methods which are conventional by themselves, for instance, by a method in which several liquid crystalline compounds to be contained in the liquid crystal composition are dissolved with each other at a temperature higher than room temperature. The composition thus produced is filled in a liquid crystal cell to obtain a liquid crystal display device having a wide range of driving temperature and a high response speed.

Examples of the liquid crystal compositions comprising the compounds of the present invention are shown below, in which the number of compound is the same as that shown in Examples described below.

Further, the compounds are designated according to the definition shown in Table 1 below, and specifically, left side terminal groups are indicated by n-, nO-, nOm-, V-, Vn-, nVm-, nVmVk-, or C- (wherein n, m, and k are an integer of 1 or greater), bonding groups are indicated by 2, 4, E, T, V, CP2O, or OCP2, ring structures are indicated by B, B(F), B(F,F), H, Py, D, or Ch, and right side terminal groups are indicated by -F, -CL, -C, -CF3, -OCF3, -OCF2H, -n, -On, -EMe, -nV, -mVn, -mVn, -VFF, -V2F, -nVC, -VVC, or -VCF (wherein n and m are an integer of 1 or greater), respectively.

TABLE 1

| | Symbol |
|---|---|
| Left side terminal group | |
| C_nH_{2n+1}— | n— |
| C_nH_{2n+1}O— | nO— |
| C_nH_{2n+1}OC_mH_{2m}— | nOm— |
| CH_2=CH— | V— |
| CH_2=CHC_nH_{2n}— | Vn— |
| C_nH_{2n+1}CH=CHC_mH_{2m}— | nVm— |
| C_nH_{2n+1}CH=CHC_mH_{2m}CH=CHC_kH_{2k}— | nVmVk— |
| NC— | C— |
| Bonding group | |
| —C_2H_4— | 2 |
| —C_4H_8— | 4 |
| —COO— | E |
| —C≡C— | T |
| —CH=CH— | V |
| —CF_2O— | CF2O |
| —OCF_2— | OCF2 |
| Ring structure | |
|  | B |
| 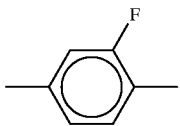 | B(F) |
| 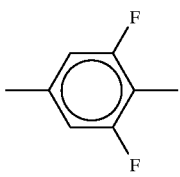 | B(F,F) |
|  | H |
| 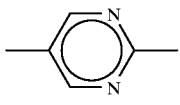 | Py |
| 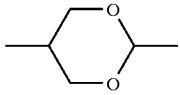 | D |
| 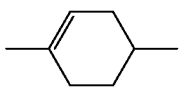 | Ch |
| Right side terminal group | |
| —F | —F |
| —Cl | —CL |
| —CN | —C |
| —CF_3 | —CF3 |
| —OCF_3 | —OCF3 |
| —OCF_2H | —OCF2H |

TABLE 1-continued

| | Symbol |
|---|---|
| —C_nH_{2n+1} | —n |
| —OC_nH_{2n+1} | —On |
| —COOCH_3 | —EMe |
| —C_nH_{2n}CH=CH_2 | —nV |
| —C_mH_{2m}CH=CHC_nH_{2n+1} | —mVn |
| —CH=CF_2 | —VFF |
| —CH=CHC_2H_4—F | —V2F |
| —C_nH_{2n}CH=CH—CN | —nVC |
| —CH=CH—CN | —VC |
| —CH=CHCH=CH—CN | —VVC |
| —CH=CF—CN | —VCF |

Percent (%) showing the content of each compound in the Composition Examples below means % by weight.

Composition Example 1

| | | |
|---|---|---|
| 2-HH—VC | (No. 1) | 4% |
| 3-HH—VC | (No. 2) | 3% |
| 4-HH—VC | (No. 3) | 3% |
| 5-HH—VC | (No. 4) | 3% |
| 7-HB(F)—F | | 4% |
| 5-H2B(F)—F | | 4% |
| 2-HHB(F)—F | | 12% |
| 3-HHB(F)—F | | 12% |
| 5-HHB(F)—F | | 12% |
| 2-H2HB(F)—F | | 4% |
| 3-H2HB(F)—F | | 2% |
| 5-H2HB(F)—F | | 4% |
| 2-HBB(F)—F | | 4% |
| 3-HBB(F)—F | | 4% |
| 5-HBB(F)—F | | 8% |
| 2-HBB—F | | 3% |
| 3-HBB—F | | 3% |
| 5-HBB—F | | 2% |
| 3-HHB—F | | 4% |
| 3-HHB-1 | | 5% |

Composition Example 2

| | | |
|---|---|---|
| 2-HH—VVC | (No. 201) | 4% |
| 3-HH—VVC | (No. 202) | 4% |
| 5-HH—VVC | (No. 204) | 5% |
| 3-HB—CL | | 4% |
| 5-HB—CL | | 4% |
| 7-HB—CL | | 4% |
| 2-HHB—CL | | 6% |
| 3-HHB—CL | | 6% |
| 5-HHB—CL | | 6% |
| 2-HBB(F)—F | | 6% |
| 3-HBB(F)—F | | 6% |
| 5-HBB(F)—F | | 12% |
| 3-HBB(F,F)—F | | 12% |
| 5-HBB(F,F)—F | | 12% |
| 3-H-2-HB(F)—CL | | 3% |
| 3-HB(F)TB-2 | | 3% |
| 3-HB(F)VB-2 | | 3% |

Composition Example 3

| | | |
|---|---|---|
| 3-H2H—VC | (No. 7) | 7% |
| 3-HH-2VC | (No. 102) | 7% |
| 7-HB(F,F)—F | | 7% |
| 3-HHB(F,F)—F | | 7% |
| 4-HHB(F,F)—F | | 5% |
| 3-H2HB(F,F)—F | | 10% |
| 4-H2HB(F,F)—F | | 8% |
| 5-H2HB(F,F)—F | | 8% |
| 3-HH2B(F,F)—F | | 12% |
| 5-HH2B(F,F)—F | | 7% |
| 3-HBB(F,F)—F | | 8% |
| 5-HBB(F,F)—F | | 8% |
| 3-HHBB(F,F)—F | | 3% |
| 3-HH2BB(F,F)—F | | 3% |

Composition Example 4

| | | |
|---|---|---|
| 5-BH—VC | (No. 13) | 7% |
| F—BH—VC | (No. 802) | 7% |
| 7-HB(F)—F | | 7% |
| 2-HHB(F)—F | | 8% |
| 3-HHB(F)—F | | 8% |
| 5-HHB(F)—F | | 8% |
| 2-H2HB(F)—F | | 6% |
| 3-H2HB(F)—F | | 3% |
| 5-H2HB(F)—F | | 6% |
| 2-HHB(F,F)—F | | 5% |
| 3-HHB(F,F)—F | | 5% |
| 3-HHEB(F,F)—F | | 5% |
| 3-HBEB(F,F)—F | | 3% |
| 3-HHB—CL | | 5% |
| 3-HHEB—F | | 3% |
| 5-HHEB—F | | 3% |
| 3-HBEB—F | | 3% |
| 3-HHB-1 | | 4% |
| 3-HHB-O1 | | 4% |

Composition Example 5

| | | |
|---|---|---|
| C—BH—VC | (No. 801) | 5% |
| 5-BH—VC | (No. 13) | 5% |
| 4-HH—VC | (No. 3) | 6% |
| 3-HH—VVC | (No. 202) | 6% |
| 7-HB(F)—F | | 10% |
| 2-HHB(F)—F | | 12% |
| 3-HHB(F)—F | | 12% |
| 5-HHB(F)—F | | 12% |
| 2-HBB(F)—F | | 3% |
| 3-HBB(F)—F | | 3% |
| 5-HBB(F)—F | | 6% |
| 3-HHB—F | | 5% |
| 3-HHEBB—F | | 3% |
| 5-HHEBB—F | | 3% |
| 3-HB—O2 | | 3% |
| 3-HHB-1 | | 3% |
| 3-HHB-3 | | 3% |

Composition Example 6

| | | |
|---|---|---|
| 3-HH—VCF | (No. 402) | 6% |
| 4-HH—VCF | (No. 403) | 6% |
| 5-HH—VCF | (No. 404) | 6% |
| 3O1-BEB(F)—CN | | 5% |
| 2-HB—CN | | 5% |
| 3-HB—CN | | 15% |
| 2-HHB—CN | | 5% |
| 3-HHB—CN | | 5% |
| 4-HHB—CN | | 5% |
| 3-PyBB—F | | 10% |
| 3-HH-4 | | 7% |
| 3-HH-5 | | 2% |
| 2-BTB—O1 | | 3% |
| 3-BTB—O1 | | 3% |
| 4-BTB—O1 | | 3% |
| 4-BTB—O2 | | 3% |
| 5-BTB—O1 | | 3% |
| 3-HHB-1 | | 5% |
| 3-HHB—O1 | | 3% |

Composition Example 7

| | | |
|---|---|---|
| 3-BHH—VC | (No. 21) | 10% |
| 3-HH—VC | (No. 2) | 10% |
| V2-HB—C | | 10% |
| 1V2-HB—CN | | 10% |
| 3-HB—CN | | 5% |
| 3-HHB—CN | | 5% |
| 3-PyBB—F | | 7% |
| 2-PyBH-3 | | 4% |
| 3-PyBH-3 | | 4% |
| 4-PyBH-3 | | 4% |
| 3-HH-4 | | 8% |
| 1O1-HH-3 | | 4% |
| 2-BTB-1 | | 4% |
| 1-BTB-6 | | 8% |
| 4-BTB-4 | | 4% |
| 3-HHB-1 | | 3% |

Composition Example 8

| | | |
|---|---|---|
| 4-HH—VC | (No. 3) | 6% |
| 4-HH—VVC | (No. 203) | 6% |
| 4-HH—VCF | (No. 403) | 7% |
| 2-BB—C | | 7% |
| 1O1-HB—C | | 8% |
| 2O1-HB—C | | 8% |
| 2-BEB—C | | 3% |
| 3-DB—C | | 3% |
| 5-PyB—F | | 6% |
| 3-PyBB—F | | 6% |
| 2-PyB-2 | | 3% |
| 3-PyB-2 | | 3% |
| 4-PyB-2 | | 3% |
| 2-PyBH-3 | | 4% |
| 3-PyBH-3 | | 4% |
| 4-PyBH-3 | | 4% |
| 3-PyB—O2 | | 3% |
| 2-HHB-1 | | 4% |
| 3-HHB-1 | | 5% |
| 3-HHB-3 | | 7% |

Composition Example 9

| | | |
|---|---|---|
| 3-H2H—VC | (No. 7) | 8% |
| 5-BH—VC | (No. 13) | 8% |
| 5-HH—VCF | (No. 404) | 8% |
| 3-PyB(F)—F | | 7% |
| 3-PyBB—F | | 4% |
| 4-PyBB—F | | 4% |
| 5-PyBB—F | | 4% |
| 2-PyB-2 | | 5% |
| 3-PyB-2 | | 5% |
| 4-PyB-2 | | 5% |
| 3-HEB—O4 | | 5% |
| 4-HEB—O2 | | 5% |
| 5-HEB—O2 | | 5% |
| 2-H2BTB-4 | | 4% |
| 3-H2BTB-4 | | 4% |
| 3-HHB-1 | | 5% |
| 3-HHB-3 | | 5% |
| 3-HHEBB—C | | 3% |
| 5-HHEBB—C | | 3% |
| 3-HBEBB—C | | 3% |

Composition Example 10

| | | |
|---|---|---|
| 2-HH—VVC | (No. 201) | 7% |
| C—BH—VC | (No. 801) | 7% |
| 3-HH-2VC | (No. 102) | 7% |
| 2O1-BEB(F)—C | | 3% |
| 3O1-BEB(F)—C | | 10% |
| 2-HB(F)—C | | 8% |
| 3-HB(F)—C | | 9% |
| 3-HHB(F)—C | | 3% |
| 2-HHB(F)—F | | 5% |
| 3-HHB(F)—F | | 5% |
| 5-HHB(F)—F | | 5% |
| 3-HHB-1 | | 5% |
| 3-HHB-3 | | 4% |
| 3-HHB—O1 | | 4% |
| 3-H2BTB-2 | | 3% |
| 3-H2BTB-3 | | 3% |
| 3-H2BTB-4 | | 3% |
| 3-HB(F)TB-2 | | 3% |
| 3-HB(F)TB-3 | | 3% |
| 3-HB(F)TB-4 | | 3% |

Composition Example 11

| | | |
|---|---|---|
| 3-HH—VVC | (No. 202) | 5% |
| 3-BHH—VC | (No. 21) | 9% |
| F—BH—VC | (No. 802) | 5% |
| 2V—HB—C | | 9% |
| 1V2-HB—C | | 9% |
| 3-HB—C | | 13% |
| 5-HB—C | | 7% |
| 1O1-HB—C | | 5% |
| 2O1-HB—C | | 5% |
| 3-HHB—F | | 4% |
| 3-HH-4 | | 4% |
| 2-BTB—O1 | | 6% |

-continued

| | | |
|---|---|---|
| 3-HHB—O1 | | 4% |
| 3-HHB-1 | | 4% |
| 3-HHB-3 | | 7% |
| 3-HB(F)TB-2 | | 4% |
| Composition Example 12 | | |
| 5-HH—VC | (No. 4) | 5% |
| 3-H2H—VC | (No. 7) | 6% |
| C—BH—VC | (No. 801) | 5% |
| 3-BHH—VC | (No. 21) | 6% |
| 1V2-BEB(F,F)—C | | 15% |
| 3O1-BEB(F)—C | | 15% |
| 3-HB—C | | 12% |
| 3-HB(F)—C | | 10% |
| 3-HHB(F)—C | | 8% |
| 3-PyBB—F | | 6% |
| 4-PyBB—F | | 6% |
| 5-PyBB—F | | 6% |
| Composition Example 13 | | |
| 4-HH—VVC | (No. 203) | 5% |
| 5-BH—VC | (No. 13) | 5% |
| 5-HH—VCF | (No. 404) | 5% |
| F—BH—VC | (No. 802) | 5% |
| 3O1-BEB(F)—C | | 8% |
| 4O1-BEB(F)—C | | 5% |
| 2-HHB(F)—F | | 4% |
| 3-HHB(F)—F | | 4% |
| 5-HHB(F)—F | | 4% |
| 3-HHEB—F | | 3% |
| 5-HHEB—F | | 3% |
| 3-HEB—F | | 3% |
| 3-HH-EMe | | 8% |
| 3-HEB—O4 | | 4% |
| 3-HEB-3 | | 4% |
| 3-HEB-4 | | 4% |
| 2-PyBH-3 | | 4% |
| 3-PyBH-3 | | 4% |
| 4-PyBH-3 | | 4% |
| 3-HB—O2 | | 10% |
| 3-HHB-1 | | 4% |
| Composition Example 14 | | |
| 3-HH—VC | (No. 2) | 7% |
| 3-H2H—VC | (No. 7) | 7% |
| 3-HH-2VC | (No. 102) | 7% |
| 5-HB—F | | 8% |
| 7-HB—F | | 8% |
| 2-HHB—OCF3 | | 5% |
| 3-HHB—OCF3 | | 5% |
| 5-HHB—OCF3 | | 5% |
| 3-HHB(F,F)—OCF2H | | 15% |
| 5-HHB(F,F)—OCF2H | | 15% |
| 3-HB(F,F)B(F)—F | | 6% |
| 5-HB(F,F)B(F)—F | | 6% |
| 3-HHEB—OCF3 | | 3% |
| 5-HHEB—OCF3 | | 3% |
| Composition Example 15 | | |
| C—BH—VC | (No. 801) | 5% |
| 3-HH—VCF | (No. 402) | 5% |
| 5-HH—VCF | (No. 404) | 5% |
| 3-BHH—VC | (No. 21) | 5% |
| 5-HB—F | | 8% |
| 6-HB—F | | 8% |
| 7-HB—F | | 8% |
| 2-HHB—OCF3 | | 6% |
| 3-HHB—OCF3 | | 6% |
| 4-HHB—OCF3 | | 6% |
| 5-HHB—OCF3 | | 6% |
| 3-HH2B—OCF3 | | 5% |
| 5-HH2B—OCF3 | | 5% |
| 3-HBB(F)—F | | 8% |
| 5-HBB(F)—F | | 8% |
| 3-HB(F)BH-3 | | 3% |
| 5-HB(F)BH-3 | | 3% |
| Composition Example 16 | | |
| 2-HH—VC | (No. 1) | 9% |
| 3-BHH—VC | (No. 21) | 8% |
| 4-HH—VCF | (No. 403) | 8% |
| V1-HB—C | | 3% |
| 4-BB-2 | | 3% |
| 3-BB—C | | 5% |
| 5-BB—C | | 5% |
| 2-HB(F)—C | | 5% |
| 3-H2B—O2 | | 4% |
| 5-H2B—O3 | | 8% |
| 3-BEB—C | | 5% |
| 5-HEB—O1 | | 6% |
| 5-HEB—O3 | | 6% |
| 5-BBB—C | | 3% |
| 4-BPyB—C | | 3% |
| 4-BPyB-5 | | 3% |
| 5-HB2B-4 | | 3% |
| 5-HBB2B-3 | | 3% |
| 1V-HH-1O1 | | 5% |
| 1V2-HBB-3 | | 5% |
| Composition Example 17 | | |
| 5-BH—VC | (No. 13) | 10% |
| F—BH—VC | (No. 802) | 10% |
| 4-HEB(F)—F | | 5% |
| 5-HEB(F)—F | | 5% |
| 2-BEB(F)—C | | 4% |
| 3-BEB(F)—C | | 4% |
| 4-BFB(F)—C | | 6% |
| 5-BEB(F)—C | | 6% |
| 1O3-HB(F)—C | | 6% |
| 3-HHEB(F)—F | | 4% |
| 5-HHEB(F)—F | | 4% |
| 2-HBEB(F)—F | | 5% |
| 3-HBEB(F)—F | | 5% |
| 4-HBEB(F)—F | | 5% |
| 5-HBEB(F)—F | | 5% |
| 3-HBTB-2 | | 10% |
| V2-HH-3 | | 3% |
| V2-HHB-1 | | 3% |

Now, the present invention will be described in more detail with reference to Examples. However, it should be understood that the present invention is by no means restricted by such specific Examples. In the Examples, symbols C, N, $S_A$, $S_B$, $S_E$, and I indicate crystal phase, nematic phase, Smectic A phase, Smectic B phase, Smectic E phase, and isotropic liquid phase, respectively, and combined symbols means the phase transition temperature between the combined phases. In this connection, CC' show a transition temperature of crystal-crystal.

EXAMPLE 1

Preparation of 1-cyano-2-(trans-4-(trans-4-ethylcyclohexyl)cyclohexyl)ethene [Compound expressed by general formula I wherein $R^1$ represents ethyl group, $A^1$ represents 1,4-cyclohexylene, $B^1$ represents a covalent bond, n1 is 0, n2 is 0, n3 is 0, $R^2$ represents a group expressed by formula II, and X represents hydrogen atom (Compound No. 1)]

To a solution prepared by dissolving 17.5 g of diethyl cyanomethyl phosphonate in 200 ml of tetrahydrofuran, was added 4.0 g of an oil dispersion of sodium hydride (60%) at −50° C., and then the solution was stirred for 30 min. To this solution was added a tetrahydrofuran solution containing 12 g of trans-4-(trans-4-ethylcyclohexyl)cyclohexane carbaldehyde. Reaction solution was stirred at −50° C. for 15 min, its temperature was gradually raised up to room temperature, a dilute hydrochloric acid was added to the solution, and the solution was extracted with toluene. After the organic layer was washed with water, it was dried by using anhydrous magnesium sulfate, and concentrated under a reduced pressure to obtain a brown oily product. The product was purified by using a silica gel column chromatography, and then recrystallized from heptane to obtain 5.1 g of the subject compound.

NI 132.0° C.

$S_BN$ 75.0 to 76.1° C.

$CS_B$ 46.5° C.

By the procedures similar to those described above, the following compounds (Compound Nos. 2 to 9) are synthesized.

Compound No.

2  1-cyano-2-(trans-4-(trans-4-propylcyclohexyl)cyclohexyl)ethene

NI 161.3 to 162.2° C.

$S_AN$ 65.1 to 65.5° C.

$S_BS_A$ 58.2 to 59.3° C.

$S_ES_B$ 56.7 to 57.4° C.

$CS_E$ 38.9 to 39.3° C.

3  1-cyano-2-(trans-4-(trans-4-butylcyclohexyl)cyclohexyl)ethene

NI 174.4 to 175.3° C.

$S_AN$ 84.9 to 85.8° C.

$S_BS_A$ 83.9 to 84.5° C.

$CS_B$ Lower than 15° C.

4  1-cyano-2-(trans-4-(trans-4-pentylcyclohexyl)cyclohexyl)ethene

NI 154.4° C.

$S_BN$ 83.4 to 84.4° C.

$CS_B$ Lower than 15° C.

5  1-cyano-2-(trans-4-(trans-4-heptylcyclohexyl)cyclohexyl)ethene 6  1-cyano-2-(trans-4-(2-(trans-4-ethylcyclohexyl)ethyl)cyclohexyl)ethene 7  1-cyano-2-(trans-4-(2-(trans-4-propylcyclohexyl)ethyl)cyclohexyl)ethene

NI 131.6° C.

($S_AN$ 50.6° C. $S_BS_A$ 44.1° C.)

CN 50.7° C.

8  1-cyano-2-(trans-4-(2-(trans-4-pentylcyclohexyl)ethyl)cyclohexyl)ethene 9  1-cyano-2-(trans-4-(2-(trans-4-heptylcyclohexyl)ethyl)cyclohexyl)ethene

EXAMPLE 2

Preparation of 1-cyano-2-(trans-4-(4-ethylphenyl)cyclohexyl)ethene [Compound expressed by general formula I wherein $R^1$ represents ethyl group, $A^1$ represents 1,4-phenylene, $B^1$ represents a covalent bond, n1 is 0, n2 is 0, n3 is 0, $R^2$ represents a group expressed by formula II, and X represents hydrogen atom (Compound No. 10)]

Subject compound was synthesized by the same procedures as in Example 1 with the exception that trans-4-(4-ethylphenyl)cyclohexane carboaldehyde was used as starting material instead of trans-4-(trans-4-ethylcyclohexyl)cyclohexane carboaldehyde.

By the procedures similar to those described above, the following compounds (Compound Nos. 11 to 29) are synthesized.

11  1-cyano-2-(trans-4-(4-propylphenyl)cyclohexyl)ethene 12  1-cyano-2-(trans-4-(4-butylphenyl)cyclohexyl)ethene 13  1-cyano-2-(trans-4-(4-pentylphenyl)cyclohexyl)ethene (NI 60.2 to 60.6° C.)

CI 67.3 to 67.8° C.

14  1-cyano-2-(trans-4-(4-heptylphenyl)cyclohexyl)ethene 15  1-cyano-2-(trans-4-(2-(4-ethylphenyl)ethyl)cyclohexyl)ethene 16  1-cyano-2-(trans-4-(2-(4-propylphenyl)ethyl)cyclohexyl)ethene 17  1-cyano-2-(trans-4-(2-(4-butylphenyl)ethyl)cyclohexyl)ethene 18  1-cyano-2-(trans-4-(2-(4-pentylphenyl)ethyl)cyclohexyl)ethene 19  1-cyano-2-(trans-4-(2-(4-heptylphenyl)ethyl)cyclohexyl)ethene 20  1-cyano-2-(trans-4-(trans-4-(4-methylphenyl)cyclohexyl)cyclohexyl)ethene

NI 297° C.

CN 97.3 to 98.4° C.

21  1-cyano-2-(trans-4-(trans-4-(4-propylphenyl)cyclohexyl)cyclohexyl)ethene 22  1-cyano-2-(trans-4-(trans-4-(4-butylphenyl)cyclohexyl)cyclohexyl)ethene 23  1-cyano-2-(trans-4-(trans-4-(4-pentylphenyl)cyclohexyl)cyclohexyl)ethene 24  1-cyano-2-(trans-4-(trans-4-(4-heptylphenyl)cyclohexyl)cyclohexyl)ethene 25  1-cyano-2-(trans-4-(2-(trans-4-(4-ethylphenyl)cyclohexyl)ethyl)cyclohexyl)ethene 26  1-cyano-2-(trans-4-(2-(trans-4-(4-propylphenyl)cyclohexyl)ethyl)cyclohexyl)ethene 27  1-cyano-2-(trans-4-(2-(trans-4-(4-butylphenyl)cyclohexyl)ethyl)cyclohexyl)ethene 28  1-cyano-2-(trans-4-(2-(trans-4-(4-pentylphenyl)cyclohexyl)ethyl)cyclohexyl)ethene 29  1-cyano-2-(trans-4-(2-(trans-4-(4-heptylphenyl)cyclohexyl)ethyl)cyclohexyl)ethene

EXAMPLE 3

Preparation of 1-cyano-2-(trans-4-(2-(trans-4-ethylcyclohexyl)ethenyl)cyclohexyl)ethene [Compound expressed by general formula I wherein $R^1$ represents ethyl group, $A^1$ represents 1,4-cyclohexylene, $B^1$ represents 1,2-ethenylene, n1 is 0, n2 is 0, n3 is 0, $R^2$ represents a group expressed by formula II, and X represents hydrogen atom (Compound No. 30)]

Subject compound was synthesized by the same procedures as in Example 1 with the exception that trans-4-(2E-(trans-4-ethylcyclohexyl)ethenyl)cyclohexane carboaldehyde was used as starting material instead of trans-4-(trans-4-ethylcyclohexyl)cyclohexane carboaldehyde.

By the procedures similar to those described above, the following compounds (Compound Nos. 31 to 39) are synthesized.

31  1-cyano-2-(trans-4-(2E-(trans-4-propylcyclohexyl)ethenyl)cyclohexyl)ethene 32  1-cyano-2-(trans-4-(2E-(trans-4-butylcyclohexyl)ethenyl)cyclohexyl)ethene 33  1-cyano-2-(trans-4-(2E-(trans-4-pentylcyclohexyl)ethenyl)cyclohexyl)ethene 34  1-cyano-2-(trans-4-(2E-(trans-4-heptylcyclohexyl)ethenyl)cyclohexyl)ethene 35  1-cyano-2-(trans-4-(2E-(trans-4-(4-ethylphenyl)cyclohexyl)ethenyl)cyclohexyl)ethene 36  1-cyano-2-(trans-4-(2E-(trans-4-(4-propylphenyl)cyclohexyl)ethenyl)cyclohexyl)ethene 37  1-cyano-2-(trans-4-(2E-(trans-4-(4-butylphenyl)cyclohexyl)ethenyl)cyclohexyl)ethene 38  1-cyano-2-(trans-4-(2E-(trans-4-(4-pentylphenyl)cyclohexyl)ethenyl)cyclohexyl)ethene 39  1-cyano-2-(trans-4-(2E-(trans-4-(4-heptylphenyl)cyclohexyl)ethenyl)cyclohexyl)ethene

EXAMPLE 4

Preparation of trans-4-(2-cyanoethenyl)cyclohexyl trans-4-propylcyclohexane carboxylate [Compound expressed by general formula I wherein $R^1$ represents propyl group, $A^1$ represents 1,4-cyclohexylene, $B^1$ represents carbonyloxy, n1 is 0, n2 is 0, n3 is 0, $R^2$ represents a group expressed by formula II, and X represents hydrogen atom (Compound No. 40)]

Subject compound was synthesized by the same procedures as in Example 1 with the exception that trans-4-formylcyclohexyl trans-4-propylcyclohexane carboxylate was used as starting material instead of trans-4-(trans-4-ethylcyclohexyl)cyclohexane carboaldehyde.

By the procedures similar to those described above, the following compounds (Compound Nos. 41 to 70) are synthesized.

41 trans-4-(2-cyanoethenyl)cyclohexyl trans-4-ethylcyclohexane carboxylate
42 trans-4-(2-cyanoethenyl)cyclohexyl trans-4-butylcyclohexane carboxylate
43 trans-4-(2-cyanoethenyl)cyclohexyl trans-4-pentylcyclohexane carboxylate
44 trans-4-(2-cyanoethenyl)cyclohexyl trans-4-hexylcyclohexane carboxylate
45 trans-4-ethylcyclohexyl trans-4-(2-cyanoethenyl)cyclohexane carboxylate
46 trans-4-propylcyclohexyl trans-4-(2-cyanoethenyl)cyclohexane carboxylate
47 trans-4-butylcyclohexyl trans-4-(2-cyanoethenyl)cyclohexane carboxylate
48 trans-4-pentylcyclohexyl trans-4-(2-cyanoethenyl)cyclohexane carboxylate
49 trans-4-hexylcyclohexyl trans-4-(2-cyanoethenyl)cyclohexane carboxylate
50 trans-4-(2-cyanoethenyl)cyclohexyl 4-ethylbenzoate
51 trans-4-(2-cyanoethenyl)cyclohexyl 4-propylbenzoate
52 trans-4-(2-cyanoethenyl)cyclohexyl 4-butylbenzoate
53 trans-4-(2-cyanoethenyl)cyclohexyl 4-pentylbenzoate
54 trans-4-(2-cyanoethenyl)cyclohexyl 4-hexylbenzoate
55 4-ethylphenyl trans-4-(2-cyanoethenyl)cyclohexane carboxylate
56 4-propylphenyl trans-4-(2-cyanoethenyl)cyclohexane carboxylate
57 4-butylphenyl trans-4-(2-cyanoethenyl)cyclohexane carboxylate
58 4-pentylphenyl trans-4-(2-cyanoethenyl)cyclohexane carboxylate
59 4-hexylphenyl trans-4-(2-cyanoethenyl)cyclohexane carboxylate
60 4-heptylphenyl trans-4-(2-cyanoethenyl)cyclohexane carboxylate
61 trans-4-(4-ethylphenyl)cyclohexyl trans-4-(2-cyanoethenyl)cyclohexane carboxylate
62 trans-4-(4-propylphenyl)cyclohexyl trans-4-(2-cyanoethenyl)cyclohexane carboxylate
63 trans-4-(4-butylphenyl)cyclohexyl trans-4-(2-cyanoethenyl)cyclohexane carboxylate
64 trans-4-(4-pentylphenyl)cyclohexyl trans-4-(2-cyanoethenyl)cyclohexane carboxylate
65 trans-4-(4-hexylphenyl)cyclohexyl trans-4-(2-cyanoethenyl)cyclohexane carboxylate
66 trans-4-(2-cyanoethenyl)cyclohexyl trans-4-(4-ethylphenyl)cyclohexane carboxylate
67 trans-4-(2-cyanoethenyl)cyclohexyl trans-4-(4-propylphenyl)cyclohexane carboxylate
68 trans-4-(2-cyanoethenyl)cyclohexyl trans-4-(4-butylphenyl)cyclohexane carboxylate
69 trans-4-(2-cyanoethenyl)cyclohexyl trans-4-(4-pentylphenyl)cyclohexane carboxylate
70 trans-4-(2-cyanoethenyl)cyclohexyl trans-4-(4-hexylphenyl)cyclohexane carboxylate

EXAMPLE 5

Preparation of 1-cyano-2-(trans-4-(4-ethylphenyl)methoxycyclohexyl)ethene [Compound expressed by general formula I wherein $R^1$ represents ethyl group, $A^1$ represents 1,4-phenylene, $B^1$ represents methyleneoxy, n1 is 0, n2 is 0, n3 is 0, $R^2$ represents a group expressed by formula II, and X represents hydrogen atom (Compound No. 71)]

Subject compound was synthesized by the same procedures as in Example 1 with the exception that trans-4-(4-ethylphenyl)methoxycyclohexane carboaldehyde was used as starting material instead of trans-4-(trans-4-ethylcyclohexyl)cyclohexane carboaldehyde.

By the procedures similar to those described above, the following compounds (Compound Nos. 72 to 87) are synthesized.

72 1-cyano-2-(trans-4-(4-propylphenyl)methoxycyclohexyl)ethene
73 1-cyano-2-(trans-4-(4-butylphenyl)methoxycyclohexyl)ethene
74 1-cyano-2-(trans-4-(4-pentylphenyl)methoxycyclohexyl)ethene
75 1-cyano-2-(trans-4-(4-heptylphenyl)methoxycyclohexyl)ethene
76 1-cyano-2-(trans-4-(trans-4-propylcyclohexyl)methoxycyclohexyl)ethene
77 1-cyano-2-(trans-4-(trans-4-pentylcyclohexyl)methoxycyclohexyl)ethene
78 1-cyano-2-(trans-4-(trans-4-heptylcyclohexyl)methoxycyclohexyl)ethene
79 1-cyano-2-(trans-4-(trans-4-(4-ethylphenyl)cyclohexyl)methoxycyclohexyl)ethene
80 1-cyano-2-(trans-4-(trans-4-(4-propylphenyl)cyclohexyl)methoxycyclohexyl)ethene
81 1-cyano-2-(trans-4-(trans-4-(4-butylphenyl)cyclohexyl)methoxycyclohexyl)ethene
82 1-cyano-2-(trans-4-(trans-4-(4-pentylphenyl)cyclohexyl)methoxycyclohexyl)ethene
83 1-cyano-2-(trans-4-(trans-4-(4-heptylphenyl)cyclohexyl)methoxycyclohexyl)ethene
84 1-cyano-2-(trans-4-(trans-4-(4-ethylphenyl)cyclohexyl)oxymethylcyclohexyl)ethene
85 1-cyano-2-(trans-4-(trans-4-(4-propylphenyl)cyclohexyl)oxymethylcyclohexyl)ethene
86 1-cyano-2-(trans-4-(trans-4-(4-butylphenyl)cyclohexyl)oxymethylcyclohexyl)ethene
87 1-cyano-2-(trans-4-(trans-4-(4-pentylphenyl)cyclohexyl)oxymethylcyclohexyl)ethene

EXAMPLE 6

Preparation of 1-cyano-2-(trans-4-(4-(4-propylphenyl)butyl)cyclohexyl)ethene [Compound expressed by general formula I wherein $R^1$ represents propyl group, $A^1$ represents 1,4-phenylene, $B^1$ represents 1,4-butylene, n1 is 0, n2 is 0, n3 is 0, $R^2$ represents a group expressed by formula II, and X represents hydrogen atom (Compound No. 88)]

Subject compound was synthesized by the same procedures as in Example 1 with the exception that trans-4-(4-(4-propylphenyl)butyl)cyclohexane carboaldehyde was used as starting material instead of trans-4-(trans-4-ethylcyclohexyl)cyclohexane carboaldehyde.

By the procedures similar to those described above, the following compounds (Compound Nos. 89 to 100) are synthesized.

89 1-cyano-2-(trans-4-(4-(4-ethylphenyl)butyl)cyclohexyl)ethene
90 1-cyano-2-(trans-4-(4-(4-butylphenyl)butyl)cyclohexyl)ethene
91 1-cyano-2-(trans-4-(4-(4-pentylphenyl)butyl)cyclohexyl)ethene 92  1-cyano-2-(trans-4-(4-(4-heptylphenyl)butyl) cyclohexyl)ethene
93  1-cyano-2-(trans-4-(trans-4-(4-(4-ethylphenyl)butyl) cyclohexyl)cyclohexyl)ethene
94  1-cyano-2-(trans-4-(trans-4-(4-(4-propylphenyl)butyl) cyclohexyl)cyclohexyl)ethene
95  1-cyano-2-(trans-4-(trans-4-(4-(4-butylphenyl)butyl) cyclohexyl)cyclohexyl)ethene
96  1-cyano-2-(trans-4-(trans-4-(4-(4-pentylphenyl)butyl) cyclohexyl)cyclohexyl)ethene
97  1-cyano-2-(trans-4-(4-(trans-4-(4-ethylphenyl) cyclohexyl)butyl)cyclohexyl)ethene
98  1-cyano-2-(trans-4-(4-(trans-4-(4-propylphenyl) cyclohexyl)butyl)cyclohexyl)ethene
99  1-cyano-2-(trans-4-(4-(trans-4-(4-butylphenyl) cyclohexyl)butyl)cyclohexyl)ethene
100  1-cyano-2-(trans-4-(4-(trans-4-(4-pentylphenyl) cyclohexyl)butyl)cyclohexyl)ethene

EXAMPLE 7

Preparation of 1-cyano-4-(trans-4-(trans-4-ethylcyclohexyl) cyclohexyl)-1-butene [Compound expressed by general formula I wherein $R^1$ represents ethyl group, ring $A^1$ represents 1,4-cyclohexylene, $B^1$ represents a covalent bond, n1 is 0, n2 is 0, n3 is 1, $R^2$ represents a group expressed by formula II, and X represents hydrogen atom (Compound No. 101)]

Subject compound was synthesized by the same procedures as in Example 1 with the exception that 3-(trans-4-(trans-4-ethylcyclohexyl)cyclohexyl)propanal was used as starting material instead of trans-4-(trans-4-ethylcyclohexyl)cyclohexane carboaldehyde.

By the procedures similar to those described above, the following compounds (Compound Nos. 102 to 110) are synthesized.

102  1-cyano-4-(trans-4-(trans-4-propylcyclohexyl) cyclohexyl)-1-butene

NI 136.9° C.

$S_A$N 101.4° C.

$S_B S_A$ 101.2° C.

$CS_B$ 74.7° C.

103  1-cyano-4-(trans-4-(trans-4-butylcyclohexyl) cyclohexyl)-1-butene
104  1-cyano-4-(trans-4-(trans-4-pentylcyclohexyl) cyclohexyl)-1-butene
105  1-cyano-4-(trans-4-(trans-4-heptylcyclohexyl) cyclohexyl)-1-butene
106  1-cyano-4-(trans-4-(2-(trans-4-ethylcyclohexyl)ethyl) cyclohexyl)-1-butene
107  1-cyano-4-(trans-4-(2-(trans-4-propylcyclohexyl)ethyl) cyclohexyl)-1-butene
108  1-cyano-4-(trans-4-(2-(trans-4-butylcyclohexyl)ethyl) cyclohexyl)-1-butene
109  1-cyano-4-(trans-4-(2-(trans-4-pentylcyclohexyl)ethyl) cyclohexyl)-1-butene
110  1-cyano-4-(trans-4-(2-(trans-4-heptylcyclohexyl)ethyl) cyclohexyl)-1-butene

EXAMPLE 8

Preparation of 1-cyano-4-(trans-4-(4-propylphenyl) cyclohexyl)-1-butene [Compound expressed by general formula I wherein $R^1$ represents propyl group, ring $A^1$ represents 1,4-phenylene, $B^1$ represents a covalent bond, n1 is 0, n2 is 0, n3 is 1, $R^2$ represents a group expressed by formula II, and X represents hydrogen atom (Compound No. 111)]

Subject compound was synthesized by the same procedures as in Example 1 with the exception that 3-(trans-4-(4-propylphenyl)cyclohexyl)propanal was used as starting material instead of trans-4-(trans-4-ethylcyclohexyl) cyclohexane carboaldehyde.

By the procedures similar to those described above, the following compounds (Compound Nos. 112 to 130) are synthesized.

112  1-cyano-4-(trans-4-(4-ethylphenyl)cyclohexyl)-1-butene
113  1-cyano-4-(trans-4-(4-butylphenyl)cyclohexyl)-1-butene
114  1-cyano-4-(trans-4-(4-pentylphenyl)cyclohexyl)-1-butene
115  1-cyano-4-(trans-4-(4-heptylphenyl)cyclohexyl)-1-butene
116  1-cyano-4-(trans-4-(2-(4-ethylphenyl)ethyl) cyclohexyl)-1-butene
117  1-cyano-4-(trans-4-(2-(4-propylphenyl)ethyl) cyclohexyl)-1-butene
118  1-cyano-4-(trans-4-(2-(4-butylphenyl)ethyl) cyclohexyl)-1-butene
119  1-cyano-4-(trans-4-(2-(4-pentylphenyl)ethyl) cyclohexyl)-1-butene
120  1-cyano-4-(trans-4-(2-(4-heptylphenyl)ethyl) cyclohexyl)-1-butene
121  1-cyano-4-(trans-4-(trans-4-(4-ethylphenyl)cyclohexyl) cyclohexyl)-1-butene
122  1-cyano-4-(trans-4-(trans-4-(4-propylphenyl) cyclohexyl)cyclohexyl)-1-butene
123  1-cyano-4-(trans-4-(trans-4-(4-butylphenyl)cyclohexyl) cyclohexyl)-1-butene
124  1-cyano-4-(trans-4-(trans-4-(4-pentylphenyl) cyclohexyl)cyclohexyl)-1-butene
125  1-cyano-4-(trans-4-(trans-4-(4-heptylphenyl) cyclohexyl)cyclohexyl)-1-butene
126  1-cyano-4-(trans-4-(2-(trans-4-(4-ethylphenyl) cyclohexyl)ethyl)cyclohexyl)-1-butene
127  1-cyano-4-(trans-4-(2-(trans-4-(4-propylphenyl) cyclohexyl)ethyl)cyclohexyl)-1-butene
128  1-cyano-4-(trans-4-(2-(trans-4-(4-butylphenyl) cyclohexyl)ethyl)cyclohexyl)-1-butene
129  1-cyano-4-(trans-4-(2-(trans-4-(4-pentylphenyl) cyclohexyl)ethyl)cyclohexyl)-1-butene
130  1-cyano-4-(trans-4-(2-(trans-4-(4-heptylphenyl) cyclohexyl)ethyl)cyclohexyl)-1-butene

EXAMPLE 9

Preparation of 1-cyano-4-(trans-4-(2-(trans-4-ethylcyclohexyl)ethenyl)cyclohexyl)-1-butene [Compound expressed by general formula I wherein $R^1$ represents ethyl group, ring $A^1$ represents 1,4-cyclohexylene, $B^1$ represents 1,2-ethenylene, n1 is 0, n2 is 0, n3 is 1, $R^2$ represents a group expressed by formula II, and X represents hydrogen atom (Compound No. 131)]

Subject compound was synthesized by the same procedures as in Example 1 with the exception that 3-(trans-4-(2E-(trans-4-ethylcyclohexyl)ethenyl)cyclohexyl)propanal was used as starting material instead of trans-4-(trans-4-ethylcyclohexyl)cyclohexane carboaldehyde.

By the procedures similar to those described above, the following compounds (Compound Nos. 132 to 140) are synthesized.

132  1-cyano-4-(trans-4-(2E-(trans-4-propylcyclohexyl) ethenyl)cyclohexyl)-1-butene
133  1-cyano-4-(trans-4-(2E-(trans-4-butylcyclohexyl) ethenyl)cyclohexyl)-1-butene
134  1-cyano-4-(trans-4-(2E-(trans-4-pentylcyclohexyl) ethenyl)cyclohexyl)-1-butene
135  1-cyano-4-(trans-4-(2E-(trans-4-heptylcyclohexyl) ethenyl)cyclohexyl)-1-butene 136 1-cyano-4-(trans-4-(2E-(trans-4-(4-ethylphenyl) cyclohexyl)ethenyl)cyclohexyl)-1-butene
137 1-cyano-4-(trans-4-(2E-(trans-4-(4-propylphenyl) cyclohexyl)ethenyl)cyclohexyl)-1-butene
138 1-cyano-4-(trans-4-(2E-(trans-4-(4-butylphenyl) cyclohexyl)ethenyl)cyclohexyl)-1-butene
139 1-cyano-4-(trans-4-(2E-(trans-4-(4-pentylphenyl) cyclohexyl)ethenyl)cyclohexyl)-1-butene
140 1-cyano-4-(trans-4-(2E-(trans-4-(4-heptylphenyl) cyclohexyl)ethenyl)cyclohexyl)-1-butene

EXAMPLE 10

Preparation of trans-4-(4-cyano-3-butenyl)cyclohexyl trans-4-ethylcyclohexane carboxylate [Compound expressed by general formula I wherein $R^1$ represents ethyl group, ring $A^1$ represents 1,4-cyclohexylene, $B^1$ represents carbonyloxy, n1 is 0, n2 is 0, n3 is 1, $R^2$ represents a group expressed by formula II, and X represents hydrogen atom (Compound No. 141)]

Subject compound was synthesized by the same procedures as in Example 1 with the exception that trans-4-(2-formylethyl)cyclohexyl trans-4-ethylcyclohexane carboxylate was used as starting material instead of trans-4-(trans-4-ethylcyclohexyl)cyclohexane carboaldehyde.

By the procedures similar to those described above, the following compounds (Compound Nos. 142 to 171) are synthesized.

142 trans-4-(4-cyano-3-butenyl)cyclohexyl trans-4-propylcyclohexane carboxylate
143 trans-4-(4-cyano-3-butenyl)cyclohexyl trans-4-butylcyclohexane carboxylate
144 trans-4-(4-cyano-3-butenyl)cyclohexyl trans-4-pentylcyclohexane carboxylate
145 trans-4-(4-cyano-3-butenyl)cyclohexyl trans-4-hexylcyclohexane carboxylate
146 trans-4-ethylcyclohexyl trans-4-(4-cyano-3-butenyl) cyclohexane carboxylate
147 trans-4-propylcyclohexyl trans-4-(4-cyano-3-butenyl) cyclohexane carboxylate
148 trans-4-butylcyclohexyl trans-4-(4-cyano-3-butenyl) cyclohexane carboxylate
149 trans-4-pentylcyclohexyl trans-4-(4-cyano-3-butenyl) cyclohexane carboxylate
150 trans-4-hexylcyclohexyl trans-4-(4-cyano-3-butenyl) cyclohexane carboxylate
151 trans-4-(4-cyano-3-butenyl)cyclohexyl 4-ethyl benzoate
152 trans-4-(4-cyano-3-butenyl)cyclohexyl 4-propyl benzoate
153 trans-4-(4-cyano-3-butenyl)cyclohexyl 4-butyl benzoate
154 trans-4-(4-cyano-3-butenyl)cyclohexyl 4-pentyl benzoate
155 trans-4-(4-cyano-3-butenyl)cyclohexyl 4-hexyl benzoate
156 4-ethylphenyl trans-4-(4-cyano-3-butenyl)cyclohexane carboxylate
157 4-propylphenyl trans-4-(4-cyano-3-butenyl) cyclohexane carboxylate
158 4-butylphenyl trans-4-(4-cyano-3-butenyl)cyclohexane carboxylate
159 4-pentylphenyl trans-4-(4-cyano-3-butenyl) cyclohexane carboxylate
160 4-hexylphenyl trans-4-(4-cyano-3-butenyl)cyclohexane carboxylate
161 4-heptylphenyl trans-4-(4-cyano-3-butenyl) cyclohexane carboxylate
162 trans-4-(4-ethylphenyl)cyclohexyl trans-4-(4-cyano-3-butenyl)cyclohexane carboxylate
163 trans-4-(4-propylphenyl)cyclohexyl trans-4-(4-cyano-3-butenyl)cyclohexane carboxylate
164 trans-4-(4-butylphenyl)cyclohexyl trans-4-(4-cyano-3-butenyl)cyclohexane carboxylate
165 trans-4-(4-pentylphenyl)cyclohexyl trans-4-(4-cyano-3-butenyl)cyclohexane carboxylate
166 trans-4-(4-hexylphenyl)cyclohexyl trans-4-(4-cyano-3-butenyl)cyclohexane carboxylate
167 trans-4-(4-cyano-3-butenyl)cyclohexyl trans-4-(4-ethylphenyl)cyclohexane carboxylate
168 trans-4-(4-cyano-3-butenyl)cyclohexyl trans-4-(4-propylphenyl)cyclohexane carboxylate
169 trans-4-(4-cyano-3-butenyl)cyclohexyl trans-4-(4-butylphenyl)cyclohexane carboxylate
170 trans-4-(4-cyano-3-butenyl)cyclohexyl trans-4-(4-pentylphenyl)cyclohexane carboxylate
171 trans-4-(4-cyano-3-butenyl)cyclohexyl trans-4-(4-hexylphenyl)cyclohexane carboxylate

EXAMPLE 11

Preparation of 1-cyano-4-(trans-4-(4-ethylphenyl) methoxycyclohexyl)-1-butene [Compound expressed by general formula I wherein $R^1$ represents ethyl group, ring $A^1$ represents 1,4-phenylene, $B^1$ represents methyleneoxy, n1 is 0, n2 is 0, n3 is 1, $R^2$ represents a group expressed by formula II, and X represents hydrogen atom (Compound No. 172)]

Subject compound was synthesized by the same procedures as in Example 1 with the exception that 3-(trans-4-(4-ethylphenyl)methoxycyclohexyl)propanal was used as starting material instead of trans-4-(trans-4-ethylcyclohexyl)cyclohexane carboaldehyde.

By the procedures similar to those described above, the following compounds (Compound Nos. 173 to 188) are synthesized.

173 1-cyano-4-(trans-4-(4-propylphenyl) methoxycyclohexyl)-1-butene
174 1-cyano-4-(trans-4-(4-butylphenyl) methoxycyclohexyl)-1-butene
175 1-cyano-4-(trans-4-(4-pentylphenyl) methoxycyclohexyl)-1-butene
176 1-cyano-4-(trans-4-(trans-4-propylcyclohexyl) methoxycyclohexyl)-1-butene
177 1-cyano-4-(trans-4-(trans-4-butylcyclohexyl) methoxycyclohexyl)-1-butene
178 1-cyano-4-(trans-4-(trans-4-pentylcyclohexyl) methoxycyclohexyl)-1-butene
179 1-cyano-4-(trans-4-(trans-4-heptylcyclohexyl) methoxycyclohexyl)-1-butene
180 1-cyano-4-(trans-4-(trans-4-(4-ethylphenyl)cyclohexyl) methoxycyclohexyl)-1-butene
181 1-cyano-4-(trans-4-(trans-4-(4-propylphenyl) cyclohexyl)methoxycyclohexyl)-1-butene
182 1-cyano-4-(trans-4-(trans-4-(4-butylphenyl)cyclohexyl) methoxycyclohexyl)-1-butene
183 1-cyano-4-(trans-4-(trans-4-(4-pentylphenyl) cyclohexyl)methoxycyclohexyl)-1-butene
184 1-cyano-4-(trans-4-(trans-4-(4-ethylphenyl)cyclohexyl) oxymethylcyclohexyl)-1-butene
185 1-cyano-4-(trans-4-(trans-4-(4-propylphenyl) cyclohexyl)oxymethylcyclohexyl)-1-butene
186 1-cyano-4-(trans-4-(trans-4-(4-butylphenyl)cyclohexyl) oxymethylcyclohexyl)-1-butene
187 1-cyano-4-(trans-4-(trans-4-(4-pentylphenyl) cyclohexyl)oxymethylcyclohexyl)-1-butene
188 1-cyano-4-(trans-4-(trans-4-(4-heptylphenyl) cyclohexyl)oxymethylcyclohexyl)-1-butene

EXAMPLE 12

Preparation of 1-cyano-4-(trans-4-(4-(4-ethylphenyl)butyl) cyclohexyl)-1-butene [Compound expressed by general formula I wherein $R^1$ represents ethyl group, ring $A^1$ represents 1,4-phenylene, $B^1$ represents 1,4-butylene, n1 is 0, n2 is 0, n3 is 1, $R^2$ represents a group expressed by formula II, and X represents hydrogen atom (Compound No. 189)]

Subject compound was synthesized by the same procedures as in Example 1 with the exception that 3-(trans-4-(4-(4-ethylphenyl)butyl)cyclohexyl)propanal was used as starting material instead of trans-4-(trans-4-ethylcyclohexyl)cyclohexane carboaldehyde.

By the procedures similar to those described above, the following compounds (Compound Nos. 190 to 200) are synthesized.

190 1-cyano-4-(trans-4-(4-(4-propylphenyl)butyl) cyclohexyl)-1-butene
191 1-cyano-4-(trans-4-(4-(4-butylphenyl)butyl) cyclohexyl)-1-butene
192 1-cyano-4-(trans-4-(4-(4-pentylphenyl)butyl) cyclohexyl)-1-butene
193 1-cyano-4-(trans-4-(trans-4-(4-(4-ethylphenyl)butyl) cyclohexyl)cyclohexyl)-1-butene
194 1-cyano-4-(trans-4-(trans-4-(4-(4-propylphenyl)butyl) cyclohexyl)cyclohexyl)- 1-butene
195 1-cyano-4-(trans-4-(trans-4-(4-(4-butylphenyl)butyl) cyclohexyl)cyclohexyl)-1-butene
196 1-cyano-4-(trans-4-(trans-4-(4-(4-pentylphenyl)butyl) cyclohexyl)cyclohexyl)-1-butene
197 1-cyano-4-(trans-4-(4-(trans-4-(4-ethylphenyl) cyclohexyl)butyl)cyclohexyl)-1-butene
198 1-cyano-4-(trans-4-(4-(trans-4-(4-propylphenyl) cyclohexyl)butyl)cyclohexyl)-1-butene
199 1-cyano-4-(trans-4-(4-(trans-4-(4-butylphenyl) cyclohexyl)butyl)cyclohexyl)-1-butene
200 1-cyano-4-(trans-4-(4-(trans-4-(4-pentylphenyl) cyclohexyl)butyl)cyclohexyl)-1-butene

EXAMPLE 13

Preparation of 1-cyano-4-(trans-4-(trans-4-ethylcyclohexyl) cyclohexyl)-1,3-butadiene [Compound expressed by general formula I wherein $R^1$ represents ethyl group, ring $A^1$ represents 1,4-cyclohexylene, $B^1$ represents a covalent bond, n1 is 0, n2 is 0, n3 is 0, $R^2$ represents a group expressed by formula III, and X represents hydrogen atom (Compound No. 201)]

Subject compound was synthesized by the same procedures as in Example 1 with the exception that 3-(trans-4-(trans-4-ethylcyclohexyl)cyclohexyl)-2-propenal was used as starting material instead of trans-4-(trans-4-ethylcyclohexyl)cyclohexane carboaldehyde.

NI 191.7° C.

CN 45.3 to 45.9° C.

The starting material was prepared by the following method:

In 20 ml of THF (tetrahydrofuran), was suspended 5.0 g of 1,3-dioxane-2-ylethyltriphenyl phosphonium bromide, and then 1.2 g of potassium butoxide was added portionwise thereto while stirring under a cooled condition with ice. After the yellow suspension thus obtained was stirred for 30 min, a solution prepared by dissolving 1.5 g of trans-4-(trans-4-ethylcyclohexyl)cyclohexanone in 10 ml of THF was added dropwise thereto. The reaction solution was stirred for 30 min under a cooled condition with ice, the temperature of the solution was raised up to room temperature, and then the solution was passed through a short column filled with a silica gel, and concentrated under a reduced pressure. The yellow oily product thus obtained was purified by using a silica gel column chromatography to obtain 1.3 g of colorless crystal. As a result of analysis by various methods, this product was confirmed to be 1,3-dioxane-2-ylethylidene-trans-4-(trans-4-ethylcyclohexyl) cyclohexane.

In a mixed solution comprising 50 ml of THF and 5 ml of 1N hydrochloric acid, was dissolved 1.3 of the compound, and the solution was stirred under a reflux for 2 hours. After finishing of the reaction, the solution was extracted with ether, and the organic layer was washed with water, dried, and concentrated under a reduced pressure to obtain a light-yellow oily product. As a result of analysis by various methods, this product was confirmed to be 3-(trans-4-(trans-4-ethylcyclohexyl)cyclohexyl-2-propenal. This product was used, without any purification, in the succeeding reaction.

By the procedures similar to those described above, the following compounds (Compound Nos. 202 to 210) are synthesized.

202 1-cyano-4-(trans-4-(trans-4-propylcyclohexyl) cyclohexyl)-1,3-butadiene

NI 213.7° C.

CN 75.2 to 74.9° C.

203 1-cyano-4-(trans-4-(trans-4-butylcyclohexyl) cyclohexyl)-1,3-butadiene
204 1-cyano-4-(trans-4-(trans-4-pentylcyclohexyl) cyclohexyl)-1,3-butadiene

NI 209.7° C.

$S_BN$ 67.8 to 68.3° C.

$CS_B$ 64.1 to 64.7° C.

205 1-cyano-4-(trans-4-(trans-4-heptylcyclohexyl) cyclohexyl)-1,3-butadiene
206 1-cyano-4-(trans-4-(2-(trans-4-ethylcyclohexyl)ethyl) cyclohexyl)-1,3-butadiene
207 1-cyano-4-(trans-4-(2-(trans-4-propylcyclohexyl)ethyl) cyclohexyl)-1,3-butadiene
208 1-cyano-4-(trans-4-(2-(trans-4-butylcyclohexyl)ethyl) cyclohexyl)-1,3-butadiene
209 1-cyano-4-(trans-4-(2-(trans-4-pentylcyclohexyl)ethyl) cyclohexyl)-1,3-butadiene
210 1-cyano-4-(trans-4-(2-(trans-4-heptylcyclohexyl)ethyl) cyclohexyl)-1,3-butadiene

EXAMPLE 14

Preparation of 1-cyano-4-(trans-4-(4-ethylphenyl) cyclohexyl)-1,3-butadiene [Compound expressed by general formula I wherein $R^1$ represents ethyl group, ring $A^1$ represents 1,4 -phenylene, $B^1$ represents a covalent bond, n1 is 0, n2 is 0, n3 is 0, $R^2$ represents a group expressed by formula III, and X represents hydrogen atom (Compound No. 211)]

Subject compound was synthesized by the same procedures as in Example 13 with the exception that 3-(trans-4-(4-ethylphenyl)cyclohexyl)-2-propenal synthesized from trans-4-(4-ethylphenyl)cyclohexanone was used as starting material instead of 3-(trans-4-(trans-4-ethylcyclohexyl) cyclohexyl)-2-propenal.

By the procedures similar to those described above, the following compounds (Compound Nos. 212 to 230) are synthesized.

212 1-cyano-4-(trans-4-(4-propylphenyl)cyclohexyl)-1,3-butadiene
213 1-cyano-4-(trans-4-(4-butylphenyl)cyclohexyl)-1,3-butadiene
214 1-cyano-4-(trans-4-(4-pentylphenyl)cyclohexyl)-1,3-butadiene
215 1-cyano-4-(trans-4-(4-heptylphenyl)cyclohexyl)-1,3-butadiene
216 1-cyano-4-(trans-4-(2-(4-ethylphenyl)ethyl) cyclohexyl)-1,3-butadiene 217 1-cyano-4-(trans-4-(2-(4-propylphenyl)ethyl) cyclohexyl)-1,3-butadiene 218 1-cyano-4-(trans-4-(2-(4-butylphenyl)ethyl) cyclohexyl)-1,3-butadiene 219 1-cyano-4-(trans-4-(2-(4-pentylphenyl)ethyl) cyclohexyl)-1,3-butadiene 220 1-cyano-4-(trans-4-(2-(4-heptylphenyl)ethyl) cyclohexyl)-1,3-butadiene 221 1-cyano-4-(trans-4-(trans-4-(4-methylphenyl) cyclohexyl)cyclohexyl)-1,3-butadiene

NI >300° C.

CN 104.2° C.

222 1-cyano-4-(trans-4-(trans-4-(4-propylphenyl) cyclohexyl)cyclohexyl)-1,3-butadiene 223 1-cyano-4-(trans-4-(trans-4-(4-butylphenyl)cyclohexyl) cyclohexyl)-1,3-butadiene 224 1-cyano-4-(trans-4-(trans-4-(4-pentylphenyl) cyclohexyl)cyclohexyl)-1,3-butadiene 225 1-cyano-4-(trans-4-(trans-4-(4-heptylphenyl) cyclohexyl)cyclohexyl)-1,3-butadiene 226 1-cyano-4-(trans-4-(2-(trans-4-(4-ethylphenyl) cyclohexyl)ethyl)cyclohexyl)-1,3-butadiene 227 1-cyano-4-(trans-4-(2-(trans-4-(4-propylphenyl) cyclohexyl)ethyl)cyclohexyl)-1,3-butadiene 228 1-cyano-4-(trans-4-(2-(trans-4-(4-butylphenyl) cyclohexyl)ethyl)cyclohexyl)-1,3-butadiene 229 1-cyano-4-(trans-4-(2-(trans-4-(4-pentylphenyl) cyclohexyl)ethyl)cyclohexyl)-1,3-butadiene 230 1-cyano-4-(trans-4-(2-(trans-4-(4-heptylphenyl) cyclohexyl)ethyl)cyclohexyl)-1,3-butadiene

EXAMPLE 15

Preparation of 1-cyano-4-(trans-4-(2-(4-ethylcyclohexyl) ethenyl)cyclohexyl)-1,3-butadiene [Compound expressed by general formula I wherein $R^1$ represents ethyl group, ring $A^1$ represents 1,4-cyclohexylene, $B^1$ represents ethenylene, n1 is 0, n2 is 0, n3 is 0, $R^2$ represents a group expressed by formula III, and X represents hydrogen atom (Compound No. 231)]

Subject compound was synthesized by the same procedures as in Example 13 with the exception that 3-(trans-4-(2E-(trans-4-ethylcyclohexyl)ethenyl)cyclohexyl)-2-propenal synthesized from (trans-4-(2E-(trans-4-ethylcyclohexyl)ethenyl)cyclohexanone was used as starting material instead of 3-(trans-4-(trans-4-ethylcyclohexyl)cyclohexyl)-2-propenal.

By the procedures similar to those described above, the following compounds (Compound Nos. 232 to 240) are synthesized.

232 1-cyano-4-(trans-4-(2E-(trans-4-propylcyclohexyl) ethenyl)cyclohexyl)-1,3-butadiene 233 1-cyano-4-(trans-4-(2E-(trans-4-butylcyclohexyl) ethenyl)cyclohexyl)-1,3-butadiene 234 1-cyano-4-(trans-4-(2E-(trans-4-pentylcyclohexyl) ethenyl)cyclohexyl)-1,3-butadiene 235 1-cyano-4-(trans-4-(2E-(trans-4-heptylcyclohexyl) ethenyl)cyclohexyl)-1,3-butadiene 236 1-cyano-4-(trans-4-(2E-(trans-4-(4-ethylphenyl) cyclohexyl)ethenyl)cyclohexyl)-1,3-butadiene 237 1-cyano-4-(trans-4-(2E-(trans-4-(4-propylphenyl) cyclohexyl)ethenyl)cyclohexyl)-1,3-butadiene 238 1-cyano-4-(trans-4-(2E-(trans-4-(4-butylphenyl) cyclohexyl)ethenyl)cyclohexyl)-1,3-butadiene 239 1-cyano-4-(trans-4-(2E-(trans-4-(4-pentylphenyl) cyclohexyl)ethenyl)cyclohexyl)-1,3-butadiene 240 1-cyano-4-(trans-4-(2E-(trans-4-(4-heptylphenyl) cyclohexyl)ethenyl)cyclohexyl)- 1,3-butadiene

EXAMPLE 16

Preparation of trans-4-(4-cyano-1,3-butadienyl)cyclohexyl trans-4-ethylcyclohexane carboxylate [Compound expressed by general formula I wherein $R^1$ represents ethyl group, ring $A^1$ represents 1,4-cyclohexylene, $B^1$ represents carbonyloxy, n1 is 0, n2 is 0, n3 is 0, $R^2$ represents a group expressed by formula III, and X represents hydrogen atom (Compound No. 241)]

Subject compound was synthesized by the same procedures as in Example 13 with the exception that trans-4-(2-formylethenyl)cyclohexyl trans-4-ethylcyclohexane carboxylate synthesized from 4-oxocyclohexyl trans-4-ethylcyclohexane carboxylate was used as starting material instead of 3-(trans-4-(trans-4-ethylcyclohexyl)cyclohexyl)-2-propenal.

By the procedures similar to those described above, the following compounds (Compound Nos. 242 to 271) are synthesized.

242 trans-4-(4-cyano-1,3-butadienyl)cyclohexyl trans-4-propylcyclohexane carboxylate 243 trans-4-(4-cyano-1,3-butadienyl)cyclohexyl trans-4-butylcyclohexane carboxylate 244 trans-4-(4-cyano-1,3-butadienyl)cyclohexyl trans-4-pentylcyclohexane carboxylate 245 trans-4-(4-cyano-1,3-butadienyl)cyclohexyl trans-4-hexylcyclohexane carboxylate 246 trans-4-ethylcyclohexyl trans-4-(4-cyano-1,3-butadienyl)cyclohexane carboxylate 247 trans-4-propylcyclohexyl trans-4-(4-cyano-1,3-butadienyl)cyclohexane carboxylate 248 trans-4-butylcyclohexyl trans-4-(4-cyano-1,3-butadienyl)cyclohexane carboxylate 249 trans-4-pentylcyclohexyl trans-4-(4-cyano-1,3-butadienyl)cyclohexane carboxylate 250 trans-4-hexylcyclohexyl trans-4-(4-cyano-1,3-butadienyl)cyclohexane carboxylate 251 trans-4-(4-cyano-1,3-butadienyl)cyclohexyl 4-ethyl benzoate 252 trans-4-(4-cyano-1,3-butadienyl)cyclohexyl 4-propyl benzoate 253 trans-4-(4-cyano-1,3-butadienyl)cyclohexyl 4-butyl benzoate 254 trans-4-(4-cyano-1,3-butadienyl)cyclohexyl 4-pentyl benzoate 255 trans-4-(4-cyano-1,3-butadienyl)cyclohexyl 4-hexyl benzoate 256 4-ethylphenyl trans-4-(4-cyano-1,3-butadienyl) cyclohexane carboxylate 257 4-propylphenyl trans-4-(4-cyano-1,3-butadienyl) cyclohexane carboxylate 258 4-butylphenyl trans-4-(4-cyano-1,3-butadienyl) cyclohexane carboxylate 259 4-pentylphenyl trans-4-(4-cyano-1,3-butadienyl) cyclohexane carboxylate 260 4-hexylphenyl trans-4-(4-cyano-1,3-butadienyl) cyclohexane carboxylate 261 4-heptylphenyl trans-4-(4-cyano-1,3-butadienyl) cyclohexane carboxylate 262 trans-4-(4-ethylphenyl)cyclohexyl trans-4-(4-cyano-1,3-butadienyl)cyclohexane carboxylate 263 trans-4-(4-propylphenyl)cyclohexyl trans-4-(4-cyano-1,3-butadienyl)cyclohexane carboxylate 264 trans-4-(4-butylphenyl)cyclohexyl trans-4-(4-cyano-1,3-butadienyl)cyclohexane carboxylate 265 trans-4-(4-pentylphenyl)cyclohexyl trans-4-(4-cyano-1,3-butadienyl)cyclohexane carboxylate 266 trans-4-(4-hexylphenyl)cyclohexyl trans-4-(4-cyano-1,3-butadienyl)cyclohexane carboxylate 267 trans-4-(4-cyano-1,3-butadienyl)cyclohexyl trans-4-(4-ethylphenyl)cyclohexane carboxylate 268 trans-4-(4-cyano-1,3-butadienyl)cyclohexyl trans-4-(4-propylphenyl)cyclohexane carboxylate 269 trans-4-(4-cyano-1,3-butadienyl)cyclohexyl trans-4-(4-butylphenyl)cyclohexane carboxylate 270 trans-4-(4-cyano-1,3-butadienyl)cyclohexyl trans-4-(4-pentylphenyl)cyclohexane carboxylate 271 trans-4-(4-cyano-1,3-butadienyl)cyclohexyl trans-4-(4-hexylphenyl)cyclohexane carboxylate

EXAMPLE 17

Preparation of 1-cyano-4-(trans-4-(4-ethylphenyl)methoxycyclohexyl)-1,3-butadiene [Compound expressed by general formula I wherein $R^1$ represents ethyl group, ring $A^1$ represents 1,4-phenylene, $B^1$ represents methyleneoxy, n1 is 0, n2 is 0, n3 is 0, $R^2$ represents a group expressed by formula III, and X represents hydrogen atom (Compound No. 272)]

Subject compound was synthesized by the same procedures as in Example 13 with the exception that 3-(trans-4-(4-ethylphenyl)methoxycyclohexyl)-2-propenal synthesized from (trans-4-(4-ethylphenyl)methoxycyclohexanone was used as starting material instead of 3-(trans-4-(trans-4-ethylcyclohexyl)cyclohexyl)-2-propenal.

By the procedures similar to those described above, the following compounds (Compound Nos. 273 to 287) are synthesized.

273 1-cyano-4-(trans-4-(4-propylphenyl)methoxycyclohexyl)-1,3-butadiene 274 1-cyano-4-(trans-4-(4-butylphenyl)methoxycyclohexyl)-1,3-butadiene 275 1-cyano-4-(trans-4-(4-pentylphenyl)methoxycyclohexyl)-1,3-butadiene 276 1-cyano-4-(trans-4-(4-heptylphenyl)methoxycyclohexyl)-1,3-butadiene 277 1-cyano-4-(trans-4-(trans-4-propylcyclohexyl)methoxycyclohexyl)-1,3-butadiene 278 1-cyano-4-(trans-4-(trans-4-butylcyclohexyl)methoxycyclohexyl)-1,3-butadiene 279 1-cyano-4-(trans-4-(trans-4-pentylcyclohexyl)methoxycyclohexyl)-1,3-butadiene 280 1-cyano-4-(trans-4-(trans-4-(4-ethylphenyl)cyclohexyl)methoxycyclohexyl)-1,3-butadiene 281 1-cyano-4-(trans-4-(trans-4-(4-propylphenyl)cyclohexyl)methoxycyclohexyl)-1,3-butadiene 282 1-cyano-4-(trans-4-(trans-4-(4-pentylphenyl)cyclohexyl)methoxycyclohexyl)-1,3-butadiene 283 1-cyano-4-(trans-4-(trans-4-(4-heptylphenyl)cyclohexyl)methoxycyclohexyl)-1,3-butadiene 284 1-cyano-4-(trans-4-(trans-4-(4-ethylphenyl)cyclohexyl)oxymethylcyclohexyl)-1,3-butadiene 285 1-cyano-4-(trans-4-(trans-4-(4-propylphenyl)cyclohexyl)oxymethylcyclohexyl)-1,3-butadiene 286 1-cyano-4-(trans-4-(trans-4-(4-butylphenyl)cyclohexyl)oxymethylcyclohexyl)-1,3-butadiene 287 1-cyano-4-(trans-4-(trans-4-(4-pentylphenyl)cyclohexyl)oxymethylcyclohexyl)-1,3-butadiene

EXAMPLE 18

Preparation of 1-cyano-4-(trans-4-(4-(4-ethylphenyl)butyl)cyclohexyl)-1,3-butadiene [Compound expressed by general formula I wherein $R^1$ represents ethyl group, ring $A^1$ represents 1,4-phenylene, $B^1$ represents butenylene, n1 is 0, n2 is 0, n3 is 0, $R^2$ represents a group expressed by formula III, and X represents hydrogen atom (Compound No. 288)]

Subject compound was synthesized by the same procedures as in Example 13 with the exception that 3-(trans-4-(4-(4-ethylphenyl)butyl)cyclohexyl)-2-propenal synthesized from trans-4-(4-(4-ethylphenyl)butyl)cyclohexanone was used as starting material instead of 3-(trans-4-(trans-4-ethylcyclohexyl)cyclohexyl)-2-propenal.

By the procedures similar to those described above, the following compounds (Compound Nos. 289 to 300) are synthesized.

289 1-cyano-4-(trans-4-(4-(4-propylphenyl)butyl)cyclohexyl)-1,3-butadiene 290 1-cyano-4-(trans-4-(4-(4-butylphenyl)butyl)cyclohexyl)-1,3-butadiene 291 1-cyano-4-(trans-4-(4-(4-pentylphenyl)butyl)cyclohexyl)-1,3-butadiene 292 1-cyano-4-(trans-4-(4-(4-heptylphenyl)butyl)cyclohexyl)-1,3-butadiene 293 1-cyano-4-(trans-4-(trans-4-(4-(4-ethylphenyl)butyl)cyclohexyl)cyclohexyl)-1,3-butadiene 294 1-cyano-4-(trans-4-(trans-4-(4-(4-propylphenyl)butyl)cyclohexyl)cyclohexyl)-1,3-butadiene 295 1-cyano-4-(trans-4-(trans-4-(4-(4-butylphenyl)butyl)cyclohexyl)cyclohexyl)-1,3-butadiene 296 1-cyano-4-(trans-4-(trans-4-(4-(4-pentylphenyl)butyl)cyclohexyl)cyclohexyl)-1,3-butadiene 297 1-cyano-4-(trans-4-(4-(trans-4-(4-ethylphenyl)cyclohexyl)butyl)cyclohexyl)-1,3-butadiene 298 1-cyano-4-(trans-4-(4-(trans-4-(4-propylphenyl)cyclohexyl)butyl)cyclohexyl)-1,3-butadiene 299 1-cyano-4-(trans-4-(4-(trans-4-pentylcyclohexyl)butyl)cyclohexyl)-1,3-butadiene 300 1-cyano-4-(trans-4-(4-(trans-4-heptylcyclohexyl)butyl)cyclohexyl)-1,3-butadiene

EXAMPLE 19

Preparation of 1-cyano-6-(trans-4-(trans-4-ethylcyclohexyl)cyclohexyl)-1,3-hexadiene [Compound expressed by general formula I wherein $R^1$ represents ethyl group, ring $A^1$ represents 1,4-cyclohexylene, $B^1$ represents a covalent bond, n1 is 0, n2 is 0, n3 is 1, $R^2$ represents a group expressed by formula III, and X represents hydrogen atom (Compound No. 301)]

Subject compound was synthesized by the same procedures as in Example 1 with the exception that 5-(trans-4-(trans-4-ethylcyclohexyl)cyclohexyl)-2-pentene-1-al was used as starting material instead of trans-4-(trans-4-ethylcyclohexyl)cyclohexane carboaldehyde.

NI 191.7° C.

CN 45.3 to 45.9° C.

By the procedures similar to those described above, the following compounds (Compound Nos. 302 to 310) are synthesized.

302 1-cyano-6-(trans-4-(trans-4-propylcyclohexyl)cyclohexyl)-1,3-hexadiene 303 1-cyano-6-(trans-4-(trans-4-butylcyclohexyl)cyclohexyl)-1,3-hexadiene 304 1-cyano-6-(trans-4-(trans-4-pentylcyclohexyl)cyclohexyl)-1,3-hexadiene 305 1-cyano-6-(trans-4-(trans-4-heptylcyclohexyl)cyclohexyl)-1,3-hexadiene 306 1-cyano-6-(trans-4-(2-(trans-4-ethylcyclohexyl)ethyl)cyclohexyl)-1,3-hexadiene 307 1-cyano-6-(trans-4-(2-(trans-4-propylcyclohexyl)ethyl)cyclohexyl)-1,3-hexadiene 308 1-cyano-6-(trans-4-(2-(trans-4-butylcyclohexyl)ethyl)cyclohexyl)-1,3-hexadiene 309 1-cyano-6-(trans-4-(2-(trans-4-pentylcyclohexyl)ethyl)cyclohexyl)-1,3-hexadiene 310 1-cyano-6-(trans-4-(2-(trans-4-heptylcyclohexyl)ethyl)cyclohexyl)- 1,3-hexadiene

EXAMPLE 20

Preparation of 1-cyano-6-(trans-4-(4-ethylphenyl) cyclohexyl)-1,3-hexadiene [Compound expressed by general formula I wherein $R^1$ represents ethyl group, ring $A^1$ represents 1,4-phenylene, $B^1$ represents a covalent bond, n1 is 0, n2 is 0, n3 is 1, $R^2$ represents a group expressed by formula III, and X represents hydrogen atom (Compound No. 311)]

Subject compound was synthesized by the same procedures as in Example 13 with the exception that 5-(trans-4-(4-ethylphenyl)cyclohexyl)-2-pentene-1-al synthesized from trans-4-(4-ethylphenyl)cyclohexanone was used as starting material instead of 3-(trans-4-(trans-4-ethylcyclohexyl)cyclohexyl)-2-propenal.

By the procedures similar to those described above, the following compounds (Compound Nos. 312 to 330) are synthesized.

312 1-cyano-6-(trans-4-(4-propylphenyl)cyclohexyl)-1,3-hexadiene
313 1-cyano-6-(trans-4-(4-butylphenyl)cyclohexyl)-1,3-hexadiene
314 1-cyano-6-(trans-4-(4-pentylphenyl)cyclohexyl)-1,3-hexadiene
315 1-cyano-6-(trans-4-(4-heptylphenyl)cyclohexyl)-1,3-hexadiene
316 1-cyano-6-(trans-4-(2-(4-ethylphenyl)ethyl) cyclohexyl)-1,3-hexadiene
317 1-cyano-6-(trans-4-(2-(4-propylphenyl)ethyl) cyclohexyl)-1,3-hexadiene
318 1-cyano-6-(trans-4-(2-(4-butylphenyl)ethyl) cyclohexyl)-1,3-hexadiene
319 1-cyano-6-(trans-4-(2-(4-pentylphenyl)ethyl) cyclohexyl)-1,3-hexadiene
320 1-cyano-6-(trans-4-(2-(4-heptylphenyl)ethyl) cyclohexyl)-1,3-hexadiene
321 1-cyano-6-(trans-4-(trans-4-(4-ethylphenyl)cyclohexyl) cyclohexyl)-1,3-hexadiene
322 1-cyano-6-(trans-4-(trans-4-(4-propylphenyl) cyclohexyl)cyclohexyl)-1,3-hexadiene
323 1-cyano-6-(trans-4-(trans-4-(4-butylphenyl)cyclohexyl) cyclohexyl)-1,3-hexadiene
324 1-cyano-6-(trans-4-(trans-4-(4-pentylphenyl) cyclohexyl)cyclohexyl)-1,3-hexadiene
325 1-cyano-6-(trans-4-(trans-4-(4-heptylphenyl) cyclohexyl)cyclohexyl)-1,3-hexadiene
326 1-cyano-6-(trans-4-(2-(trans-4-(4-ethylphenyl) cyclohexyl)ethyl)cyclohexyl)-1,3-hexadiene
327 1-cyano-6-(trans-4-(2-(trans-4-(4-propylphenyl) cyclohexyl)ethyl)cyclohexyl)-1,3-hexadiene
328 1-cyano-6-(trans-4-(2-(trans-4-(4-butylphenyl) cyclohexyl)ethyl)cyclohexyl)-1,3-hexadiene
329 1-cyano-6-(trans-4-(2-(trans-4-(4-pentylphenyl) cyclohexyl)ethyl)cyclohexyl)-1,3-hexadiene
330 1-cyano-6-(trans-4-(2-(trans-4-(4-heptylphenyl) cyclohexyl)ethyl)cyclohexyl)-1,3-hexadiene

EXAMPLE 21

Preparation of 1-cyano-6-(trans-4-(2-(trans-4-ethylcyclohexyl)ethenyl)cyclohexyl)-1,3-hexadiene [Compound expressed by general formula I wherein $R^1$ represents ethyl group, ring $A^1$ represents 1,4-cyclohexylene, $B^1$ represents ethenylene, n1 is 0, n2 is 0, n3 is 1, $R^2$ represents a group expressed by formula III, and X represents hydrogen atom (Compound No. 331)]

Subject compound was synthesized by the same procedures as in Example 13 with the exception that 5-(trans-4-(2E-(trans-4-ethylcyclohexyl)ethenyl)cyclohexyl)-2-pentene-1-al synthesized from trans-4-(2E-(trans-4-ethylcyclohexyl)ethenyl)cyclohexanone was used as starting material instead of 3-(trans-4-(trans-4-ethylcyclohexyl)cyclohexyl)-2-propenal.

By the procedures similar to those described above, the following compounds (Compound Nos. 332 to 340) are synthesized.

332 1-cyano-6-(trans-4-(2E-(trans-4-propylcyclohexyl) ethenyl)cyclohexyl)-1,3-hexadiene
333 1-cyano-6-(trans-4-(2E-(trans-4-butylcyclohexyl) ethenyl)cyclohexyl)-1,3-hexadiene
334 1-cyano-6-(trans-4-(2E-(trans-4-pentylcyclohexyl) ethenyl)cyclohexyl)-1,3-hexadiene
335 1-cyano-6-(trans-4-(2E-(trans-4-heptylcyclohexyl) ethenyl)cyclohexyl)-1,3-hexadiene
336 1-cyano-6-(trans-4-(2E-(trans-4-(4-ethylphenyl) cyclohexyl)ethenyl)cyclohexyl)-1,3-hexadiene
337 1-cyano-6-(trans-4-(2E-(trans-4-(4-propylphenyl) cyclohexyl)ethenyl)cyclohexyl)-1,3-hexadiene
338 1-cyano-6-(trans-4-(2E-(trans-4-(4-butylphenyl) cyclohexyl)ethenyl)cyclohexyl)- 1,3-hexadiene
339 1-cyano-6-(trans-4-(2E-(trans-4-(4-pentylphenyl) cyclohexyl)ethenyl)cyclohexyl)-1,3-hexadiene
340 1-cyano-6-(trans-4-(2E-(trans-4-(4-heptylphenyl) cyclohexyl)ethenyl)cyclohexyl)-1,3-hexadiene

EXAMPLE 22

Preparation of trans-4-(6-cyano-3,5-hexadienyl)cyclohexyl trans-4-ethylcyclohexane carboxylate [Compound expressed by general formula I wherein $R^1$ represents ethyl group, ring $A^1$ represents 1,4-cyclohexylene, $B^1$ represents carbonyloxy, n1 is 0, n2 is 0, n3 is 1, $R^2$ represents a group expressed by formula III, and X represents hydrogen atom (Compound No. 341)]

Subject compound was synthesized by the same procedures as in Example 13 with the exception that trans-4-(4-formyl-3-butenyl)cyclohexyl trans-4-ethylcyclohexane carboxylate was used as starting material instead of 3-(trans-4-(trans-4-ethylcyclohexyl)cyclohexyl)-2-propenal.

By the procedures similar to those described above, the following compounds (Compound Nos. 342 to 371) are synthesized.

342 trans-4-(6-cyano-3,5-hexadienyl)cyclohexyl trans-4-propylcyclohexane carboxylate
343 trans-4-(6-cyano-3,5-hexadienyl)cyclohexyl trans-4-butylcyclohexane carboxylate
344 trans-4-(6-cyano-3,5-hexadienyl)cyclohexyl trans-4-pentylcyclohexane carboxylate
345 trans-4-(6-cyano-3,5-hexadienyl)cyclohexyl trans-4-hexylcyclohexane carboxylate
346 trans-4-ethylcyclohexyl trans-4-(6-cyano-3,5-hexadienyl)cyclohexane carboxylate
347 trans-4-propylcyclohexyl trans-4-(6-cyano-3,5-hexadienyl)cyclohexane carboxylate
348 trans-4-butylcyclohexyl trans-4-(6-cyano-3,5-hexadienyl)cyclohexane carboxylate
349 trans-4-pentylcyclohexyl trans-4-(6-cyano-3,5-hexadienyl)cyclohexane carboxylate
350 trans-4-hexylcyclohexyl trans-4-(6-cyano-3,5-hexadienyl)cyclohexane carboxylate
351 trans-4-(6-cyano-3,5-hexadienyl)cyclohexyl 4-ethyl benzoate
352 trans-4-(6-cyano-3,5-hexadienyl)cyclohexyl 4-propyl benzoate
353 trans-4-(6-cyano-3,5-hexadienyl)cyclohexyl 4-butyl benzoate
354 trans-4-(6-cyano-3,5-hexadienyl)cyclohexyl 4-pentyl benzoate
355 trans-4-(6-cyano-3,5-hexadienyl)cyclohexyl 4-hexyl benzoate 356 4-ethylphenyl trans-4-(6-cyano-3,5-hexadienyl) cyclohexane carboxylate
357 4-propylphenyl trans-4-(6-cyano-3,5-hexadienyl) cyclohexane carboxylate
358 4-butylphenyl trans-4-(6-cyano-3,5-hexadienyl) cyclohexane carboxylate
359 4-pentylphenyl trans-4-(6-cyano-3,5-hexadienyl) cyclohexane carboxylate
360 4-hexylphenyl trans-4-(6-cyano-3,5-hexadienyl) cyclohexane carboxylate
361 4-heptylphenyl trans-4-(6-cyano-3,5-hexadienyl) cyclohexane carboxylate
362 trans-4-(4-ethylphenyl)cyclohexyl trans-4-(6-cyano-3,5-hexadienyl)cyclohexane carboxylate
363 trans-4-(4-propylphenyl)cyclohexyl trans-4-(6-cyano-3,5-hexadienyl)cyclohexane carboxylate
364 trans-4-(4-butylphenyl)cyclohexyl trans-4-(6-cyano-3,5-hexadienyl)cyclohexane carboxylate
365 trans-4-(4-pentylphenyl)cyclohexyl trans-4-(6-cyano-3,5-hexadienyl)cyclohexane carboxylate
366 trans-4-(4-hexylphenyl)cyclohexyl trans-4-(6-cyano-3,5-hexadienyl)cyclohexane carboxylate
367 trans-4-(6-cyano-3,5-hexadienyl)cyclohexyl trans-4-(4-ethylphenyl)cyclohexane carboxylate
368 trans-4-(6-cyano-3,5-hexadienyl)cyclohexyl trans-4-(4-propylphenyl)cyclohexane carboxylate
369 trans-4-(6-cyano-3,5-hexadienyl)cyclohexyl trans-4-(4-butylphenyl)cyclohexane carboxylate
370 trans-4-(6-cyano-3,5-hexadienyl)cyclohexyl trans-4-(4-pentylphenyl)cyclohexane carboxylate
371 trans-4-(6-cyano-3,5-hexadienyl)cyclohexyl trans-4-(4-hexylphenyl)cyclohexane carboxylate

EXAMPLE 23

Preparation of 1-cyano-6-(trans-4-(4-ethylphenyl) methoxycyclohexyl)-1,3-hexadiene [Compound expressed by general formula I wherein $R^1$ represents ethyl group, ring $A^1$ represents 1,4-phenylene, $B^1$ represents methyleneoxy, n1 is 0, n2 is 0, n3 is 1, $R^2$ represents a group expressed by formula III, and X represents hydrogen atom (Compound No. 372)]

Subject compound was synthesized by the same procedures as in Example 13 with the exception that 5-(trans-4-(4-ethylphenyl)methoxycylohexyl)-2-pentene-1-al synthesized from trans-4-(4-ethylphenyl)methoxycyclohexanone was used as starting material instead of 3-(trans-4-(trans-4-ethylcyclohexyl)cyclohexyl)-2-propenal.

By the procedures similar to those described above, the following compounds (Compound Nos. 373 to 387) are synthesized.

373 1-cyano-6-(trans-4-(4-propylphenyl) methoxycyclohexyl-1,3-hexadiene
374 1-cyano-6-(trans-4-(4-butylphenyl) methoxycyclohexyl-1,3-hexadiene
375 1-cyano-6-(trans-4-(4-pentylphenyl) methoxycyclohexyl-1,3-hexadiene
376 1-cyano-6-(trans-4-(4-heptylphenyl) methoxycyclohexyl-1,3-hexadiene
377 1-cyano-6-(trans-4-(trans-4-propylcyclohexyl) methoxycyclohexyl)-1,3-hexadiene
378 1-cyano-6-(trans-4-(trans-4-butylcyclohexyl) methoxycyclohexyl)-1,3-hexadiene
379 1-cyano-6-(trans-4-(trans-4-pentylcyclohexyl) methoxycyclohexyl)-1,3-hexadiene
380 1-cyano-6-(trans-4-(trans-4-(4-ethylphenyl)cyclohexyl) methoxycyclohexyl)-1,3-hexadiene
381 1-cyano-6-(trans-4-(trans-4-(4-propylphenyl) cyclohexyl)methoxycyclohexyl)- 1,3-hexadiene
382 1-cyano-6-(trans-4-(trans-4-(4-pentylphenyl) cyclohexyl)methoxycyclohexyl)-1,3-hexadiene
383 1-cyano-6-(trans-4-(trans-4-(4-heptylphenyl) cyclohexyl)methoxycyclohexyl)-1,3-hexadiene
384 1-cyano-6-(trans-4-(trans-4-(4-ethylphenyl)cyclohexyl) oxymethylcyclohexyl)-1,3-hexadiene
385 1-cyano-6-(trans-4-(trans-4-(4-propylphenyl) cyclohexyl)oxymethylcyclohexyl)-1,3-hexadiene
386 1-cyano-6-(trans-4-(trans-4-(4-butylphenyl)cyclohexyl) oxymethylcyclohexyl)-1,3-hexadiene
387 1-cyano-6-(trans-4-(trans-4-(4-pentylphenyl) cyclohexyl)oxymethylcyclohexyl)-1,3-hexadiene

EXAMPLE 24

Preparation of 1-cyano-6-(trans-4-(4-(4-ethylphenyl)butyl) cyclohexyl)-1,3-hexadiene [Compound expressed by general formula I wherein $R^1$ represents ethyl group, ring $A^1$ represents 1,4-phenylene, $B^1$ represents butenylene, n1 is 0, n2 is 0, n3 is 1, $R^2$ represents a group expressed by formula III, and X represents hydrogen atom (Compound No. 388)]

Subject compound was synthesized by the same procedures as in Example 13 with the exception that 5-(trans-4-(4-(4-ethylphenyl)butyl)cyclohexyl)-2-pentene-1-al synthesized from trans-4-(4-(4-ethylphenyl)butyl)cyclohexanone was used as starting material instead of 3-(trans-4-(trans-4-ethylcyclohexyl)cyclohexyl)-2-propenal.

By the procedures similar to those described above, the following compounds (Compound Nos. 389 to 400) are synthesized.

389 1-cyano-6-(trans-4-(4-(4-propylphenyl)butyl) cyclohexyl)-1,3-hexadiene
390 1-cyano-6-(trans-4-(4-(4-butylphenyl)butyl) cyclohexyl)-1,3-hexadiene
391 1-cyano-6-(trans-4-(4-(4-pentylphenyl)butyl) cyclohexyl)-1,3-hexadiene
392 1-cyano-6-(trans-4-(4-(4-heptylphenyl)butyl) cyclohexyl)-1,3-hexadiene
393 1-cyano-6-(trans-4-(trans-4-(4-(4-ethylphenyl)butyl) cyclohexyl)cyclohexyl)-1,3-hexadiene
394 1-cyano-6-(trans-4-(trans-4-(4-(4-propylphenyl)butyl) cyclohexyl)cyclohexyl)-1,3-hexadiene
395 1-cyano-6-(trans-4-(trans-4-(4-(4-butylphenyl)butyl) cyclohexyl)cyclohexyl)-1,3-hexadiene
396 1-cyano-6-(trans-4-(trans-4-(4-(4-pentylphenyl)butyl) cyclohexyl)cyclohexyl)-1,3-hexadiene
397 1-cyano-6-(trans-4-(4-(trans-4-(4-ethylphenyl) cyclohexyl)butyl)cyclohexyl)-1,3-hexadiene
398 1-cyano-6-(trans-4-(4-(trans-4-(4-propylphenyl) cyclohexyl)butyl)cyclohexyl)-1,3-hexadiene
399 1-cyano-6-(trans-4-(4-(trans-4-pentylcyclohexyl)butyl) cyclohexyl)-1,3-hexadiene
400 1-cyano-6-(trans-4-(4-(trans-4-heptylcyclohexyl)butyl) cyclohexyl)-1,3-hexadiene

EXAMPLE 25

Preparation of 1-fluoro-1-cyano-2-(trans-4-(trans-4-ethylcyclohexyl)cyclohexyl)ethene [Compound expressed by general formula I wherein $R^1$ represents ethyl group, $A^1$ represents 1,4-cyclohexylene, $B^1$ represents a covalent bond, n1 is 0, n2 is 0, n3 is 0, $R^2$ represents a group expressed by formula II, and X represents fluorine atom (Compound No. 401)]

A solution of tribromofluoromethane and triphenyl phosphine in ethylene glycol dimethyl ether was stirred at 70° C. for 1 hour. The reaction solution was cooled with ice, and a solution of trans-4-(trans-4-ethylcyclohexyl)cyclohexane carboaldehyde in tetrahydrofuran was added thereto. After the reaction solution was further stirred for 1 hour, the temperature of the solution was gradually raised up to room temperature, and insoluble substances were removed by filtration. Dilute hydrochloric acid was added to the filtrate, and it was extracted with toluene. After the organic layer was washed with water, it was dried by using anhydrous magnesium sulfate, and concentrated under a reduced pressure to obtain a brown oily product. After this product was purified by using a silica gel column chromatography, it was recrystallized from heptane to obtain trans-4-(trans-4-ethylcyclohexyl)cyclohexyl-2-fluoro-2-bromoethene.

The compound and copper cyanide were dissolved in 2-methylpyrrolidone, and refluxed for 3 hours. The reaction solution was cooled down to room temperature, a dilute hydrochloric acid solution of iron chloride was added thereto, and then the solution was extracted with ethyl acetate. The organic layer thus obtained was washed with water, dried over anhydrous magnesium sulfate, and concentrated under a reduced pressure to obtain brown oily product. After this product was purified by using a silica gel column chromatography, it was recrystallized from toluene to obtain the subject compound.

By the procedures similar to those described above, the following compounds (Compound Nos. 402 to 410) are synthesized.

402 1-fluoro-1-cyano-2-(trans-4-(trans-4-propylcyclohexyl) cyclohexyl)ethene
  NI 124.8° C.
  $S_B N$ 66.0° C.
  $CS_B$ lower than 15° C.
403 1-fluoro-1-cyano-2-(trans-4-(trans-4-butylcyclohexyl) cyclohexyl)ethene
  NI 121.9° C.
  $S_B N$ 74.8° C.
  $CS_B$ lower than 15° C.
404 1-fluoro-1-cyano-2-(trans-4-(trans-4-pentylcyclohexyl) cyclohexyl)ethene
  NI 119.3° C.
  $S_B N$ 68.5° C.
  $CS_B$ lower than 15° C.
405 1-fluoro-1-cyano-2-(trans-4-(trans-4-heptylcyclohexyl) cyclohexyl)ethene
406 1-fluoro-1-cyano-2-(trans-4-(2-(trans-4-ethylcyclohexyl)ethyl)cyclohexyl)ethene
407 1-fluoro-1-cyano-2-(trans-4-(2-(trans-4-propylcyclohexyl)ethyl)cyclohexyl)ethene
408 1-fluoro-1-cyano-2-(trans-4-(2-(trans-4-butylcyclohexyl)ethyl)cyclohexyl)ethene
409 1-fluoro-1-cyano-2-(trans-4-(2-(trans-4-pentylcyclohexyl)ethyl)cyclohexyl)ethene
410 1-fluoro-1-cyano-2-(trans-4-(2-(trans-4-heptylcyclohexyl)ethyl)cyclohexyl)ethene

EXAMPLE 26

Preparation of 1-fluoro-1-cyano-2-(trans-4-(4-ethylphenyl)cyclohexyl)ethene [Compound expressed by general formula I wherein $R^1$ represents ethyl group, $A^1$ represents 1,4-phenylene, $B^1$ represents a covalent bond, n1 is 0, n2 is 0, n3 is 0, $R^2$ represents a group expressed by formula II, and X represents fluorine atom (Compound No. 411)]

Subject compound was synthesized by the same procedures as in Example 25 with the exception that trans-4-(4-ethylphenyl)cyclohexane carboaldehyde was used as starting material instead of trans-4-(trans-4-ethylcyclohexyl)cyclohexane carboaldehyde.

By the procedures similar to those described above, the following compounds (Compound Nos. 412 to 430) are synthesized.

412 1-fluoro-1-cyano-2-(trans-4-(4-propylphenyl) cyclohexyl)ethene
413 1-fluoro-1-cyano-2-(trans-4-(4-butylphenyl) cyclohexyl)ethene
414 1-fluoro-1-cyano-2-(trans-4-(4-pentylphenyl) cyclohexyl)ethene
415 1-fluoro-1-cyano-2-(trans-4-(4-heptylphenyl) cyclohexyl)ethene
416 1-fluoro-1-cyano-2-(trans-4-(2-(4-ethylphenyl)ethyl) cyclohexyl)ethene
417 1-fluoro-1-cyano-2-(trans-4-(2-(4-propylphenyl)ethyl) cyclohexyl)ethene
418 1-fluoro-1-cyano-2-(trans-4-(2-(4-butylphenyl)ethyl) cyclohexyl)ethene
419 1-fluoro-1-cyano-2-(trans-4-(2-(4-pentylphenyl)ethyl) cyclohexyl)ethene
420 1-fluoro-1-cyano-2-(trans-4-(4-methylbiphenyl) cyclohexyl)ethene
  NI 251° C.
  $S_A N$ 171.3° C.
  $CS_A$ 134.7° C.
  CC' 111.7° C.
421 1-fluoro-1-cyano-2-(trans-4-(trans-4-(4-ethylphenyl) cyclohexyl)cyclohexyl)ethene
  NI 216.8° C.
  CN 115.0° C.
422 1-fluoro-1-cyano-2-(trans-4-(trans-4-(4-propylphenyl) cyclohexyl)cyclohexyl)ethene
423 1-fluoro-1-cyano-2-(trans-4-(trans-4-(4-butylphenyl) cyclohexyl)cyclohexyl)ethene
424 1-fluoro-1-cyano-2-(trans-4-(trans-4-(4-pentylphenyl) cyclohexyl)cyclohexyl)ethene
425 1-fluoro-1-cyano-2-(trans-4-(trans-4-(4-heptylphenyl) cyclohexyl)cyclohexyl)ethene
426 1-fluoro-1-cyano-2-(trans-4-(2-(trans-4-(4-ethylphenyl) cyclohexyl)ethyl)cyclohexyl)ethene
427 1-fluoro-1-cyano-2-(trans-4-(2-(trans-4-(4-propylphenyl)cyclohexyl)ethyl)cyclohexyl)ethene
428 1-fluoro-1-cyano-2-(trans-4-(2-(trans-4-(4-butylphenyl)cyclohexyl)ethyl)cyclohexyl)ethene
429 1-fluoro-1-cyano-2-(trans-4-(2-(trans-4-(4-pentylphenyl)cyclohexyl)ethyl)cyclohexyl)ethene
430 1-fluoro-1-cyano-2-(trans-4-(2-(trans-4-(4-heptylphenyl)cyclohexyl)ethyl)cyclohexyl)ethene

EXAMPLE 27

Preparation of 1-fluoro-1-cyano-2-(trans-4-(2-(trans-4-ethylcyclohexyl)ethenyl)cyclohexyl)ethene [Compound expressed by general formula I wherein $R^1$ represents ethyl group, $A^1$ represents 1,4-cyclohexylene, $B^1$ represents 1,2-ethenylene, n1 is 0, n2 is 0, n3 is 0, $R^2$ represents a group expressed by formula II, and X represents fluorine atom (Compound No. 431)]

Subject compound was synthesized by the same procedures as in Example 1 with the exception that trans-4-(2E-(trans-4-ethylcyclohexyl)ethenyl)cyclohexane carboaldehyde was used as starting material instead of trans-4-(trans-4-ethylcyclohexyl)cyclohexane carboaldehyde.

By the procedures similar to those described above, the following compounds (Compound Nos. 432 to 440) are synthesized.

432 1-fluoro-1-cyano-2-(trans-4-(2E-(trans-4-propylcyclohexyl)ethenyl)cyclohexyl)ethene
433 1-fluoro-1-cyano-2-(trans-4-(2E-(trans-4-butylcyclohexyl)ethenyl)cyclohexyl)ethene
434 1-fluoro-1-cyano-2-(trans-4-(2E-(trans-4-pentylcyclohexyl)ethenyl)cyclohexyl)ethene 435 1-fluoro-1-cyano-2-(trans-4-(2E-(trans-4-heptylcyclohexyl)ethenyl)cyclohexyl)ethene
436 1-fluoro-1-cyano-2-(trans-4-(2E-(trans-4-(4-ethylphenyl)cyclohexyl)ethenyl)cyclohexyl)ethene
437 1-fluoro-1-cyano-2-(trans-4-(2E-(trans-4-(4-propylphenyl)cyclohexyl)ethenyl)cyclohexyl)ethene
438 1-fluoro-1-cyano-2-(trans-4-(2E-(trans-4-(4-butylphenyl)cyclohexyl)ethenyl)cyclohexyl)ethene
439 1-fluoro-1-cyano-2-(trans-4-(2E-(trans-4-(4-pentylphenyl)cyclohexyl)ethenyl)cyclohexyl)ethene
440 1-fluoro-1-cyano-2-(trans-4-(2E-(trans-4-(4-heptylphenyl)cyclohexyl)ethenyl)cyclohexyl)ethene

EXAMPLE 28

Preparation of trans-4-(2-cyano-2-fluoroethenyl)cyclohexyl trans-4-ethylcyclohexane carboxylate [Compound expressed by general formula I wherein $R^1$ represents ethyl group, $A^1$ represents 1,4-cyclohexylene, $B^1$ represents carbonyloxy, n1 is 0, n2 is 0, n3 is 0, $R^2$ represents a group expressed by formula II, and X represents fluorine atom (Compound No. 441)]

Subject compound was synthesized by the same procedures as in Example 1 with the exception that trans-4-formylcyclohexyl trans-4-ethylcyclohexane carboxylate was used as starting material instead of trans-4-(trans-4-ethylcyclohexyl)cyclohexane carboaldehyde.

By the procedures similar to those described above, the following compounds (Compound Nos. 442 to 471) are synthesized.

442 trans-4-(2-cyano-2-fluoroethenyl)cyclohexyl trans-4-propylcyclohexane carboxylate
443 trans-4-(2-cyano-2-fluoroethenyl)cyclohexyl trans-4-butylcyclohexane carboxylate
444 trans-4-(2-cyano-2-fluoroethenyl)cyclohexyl trans-4-pentylcyclohexane carboxylate
445 trans-4-(2-cyano-2-fluoroethenyl)cyclohexyl trans-4-hexylcyclohexane carboxylate
446 trans-4-ethylcyclohexyl trans-4-(2-cyano-2-fluoroethenyl)cyclohexane carboxylate
447 trans-4-propylcyclohexyl trans-4-(2-cyano-2-fluoroethenyl)cyclohexane carboxylate
448 trans-4-butylcyclohexyl trans-4-(2-cyano-2-fluoroethenyl)cyclohexane carboxylate
449 trans-4-pentylcyclohexyl trans-4-(2-cyano-2-fluoroethenyl)cyclohexane carboxylate
450 trans-4-hexylcyclohexyl trans-4-(2-cyano-2-fluoroethenyl)cyclohexane carboxylate
451 trans-4-(2-cyano-2-fluoroethenyl)cyclohexyl 4-ethyl benzoate
452 trans-4-(2-cyano-2-fluoroethenyl)cyclohexyl 4-propyl benzoate
453 trans-4-(2-cyano-2-fluoroethenyl)cyclohexyl 4-butyl benzoate
454 trans-4-(2-cyano-2-fluoroethenyl)cyclohexyl 4-pentyl benzoate
455 trans-4-(2-cyano-2-fluoroethenyl)cyclohexyl 4-hexyl benzoate
456 4-ethylphenyl trans-4-(2-cyano-2-fluoroethenyl) cyclohexane carboxylate
457 4-propylphenyl trans-4-(2-cyano-2-fluoroethenyl) cyclohexane carboxylate
458 4-butylphenyl trans-4-(2-cyano-2-fluoroethenyl) cyclohexane carboxylate
459 4-pentylphenyl trans-4-(2-cyano-2-fluoroethenyl) cyclohexane carboxylate
460 4-hexylphenyl trans-4-(2-cyano-2-fluoroethenyl) cyclohexane carboxylate
461 4-heptylphenyl trans-4-(2-cyano-2-fluoroethenyl) cyclohexane carboxylate
462 trans-4-(4-ethylphenyl)cyclohexyl trans-4-(2-cyano-2-fluoroethenyl)cyclohexane carboxylate
463 trans-4-(4-propylphenyl)cyclohexyl trans-4-(2-cyano-2-fluoroethenyl)cyclohexane carboxylate
464 trans-4-(4-butylphenyl)cyclohexyl trans-4-(2-cyano-2-fluoroethenyl)cyclohexane carboxylate
465 trans-4-(4-pentylphenyl)cyclohexyl trans-4-(2-cyano-2-fluoroethenyl)cyclohexane carboxylate
466 trans-4-(4-hexylphenyl)cyclohexyl trans-4-(2-cyano-2-fluoroethenyl)cyclohexane carboxylate
467 trans-4-(2-cyano-2-fluoroethenyl)cyclohexyl trans-4-(4-ethylphenyl)cyclohexane carboxylate
468 trans-4-(2-cyano-2-fluoroethenyl)cyclohexyl trans-4-(4-propylphenyl)cyclohexane carboxylate
469 trans-4-(2-cyano-2-fluoroethenyl)cyclohexyl trans-4-(4-butylphenyl)cyclohexane carboxylate
470 trans-4-(2-cyano-2-fluoroethenyl)cyclohexyl trans-4-(4-pentylphenyl)cyclohexane carboxylate
471 trans-4-(2-cyano-2-fluoroethenyl)cyclohexyl trans-4-(4-hexylphenyl)cyclohexane carboxylate

EXAMPLE 29

Preparation of 1-fluoro-1-cyano-2-(trans-4-(4-ethylphenyl)methoxycyclohexyl)ethene [Compound expressed by general formula I wherein $R^1$ represents ethyl group, $A^1$ represents 1,4-phenylene, $B^1$ represents methyleneoxy, n1 is 0, n2 is 0, n3 is 0, $R^2$ represents a group expressed by formula II, and X represents fluorine atom (Compound No. 472)]

Subject compound was synthesized by the same procedures as in Example 1 with the exception that trans-4-(4-ethylphenyl)methoxycyclohexane carboaldehyde was used as starting material instead of trans-4-(trans-4-ethylcyclohexyl)cyclohexane carboaldehyde.

By the procedures similar to those described above, the following compounds (Compound Nos. 473 to 489) are synthesized.

473 1-fluoro-1-cyano-2-(trans-4-(4-propylphenyl) methoxycyclohexyl)ethene
474 1-fluoro-1-cyano-2-(trans-4-(4-butylphenyl) methoxycyclohexyl)ethene
475 1-fluoro-1-cyano-2-(trans-4-(4-pentylphenyl) methoxycyclohexyl)ethene
476 1-fluoro-1-cyano-2-(trans-4-(4-heptylphenyl) methoxycyclohexyl)ethene
477 1-fluoro-1-cyano-2-(trans-4-(trans-4-propylcyclohexyl) methoxycyclohexyl)ethene
478 1-fluoro-1-cyano-2-(trans-4-(trans-4-butylcyclohexyl) methoxycyclohexyl)ethene
479 1-fluoro-1-cyano-2-(trans-4-(trans-4-pentylcyclohexyl) methoxycyclohexyl)ethene
480 1-fluoro-1-cyano-2-(trans-4-(trans-4-heptylcyclohexyl) methoxycyclohexyl)ethene
481 1-fluoro-1-cyano-2-(trans-4-(trans-4-(4-ethylphenyl) cyclohexyl)methoxycyclohexyl)ethene
482 1-fluoro-1-cyano-2-(trans-4-(trans-4-(4-propylphenyl) cyclohexyl)methoxycyclohexyl)ethene
483 1-fluoro-1-cyano-2-(trans-4-(trans-4-(4-butylphenyl) cyclohexyl)methoxycyclohexyl)ethene
484 1-fluoro-1-cyano-2-(trans-4-(trans-4-(4-pentylphenyl) cyclohexyl)methoxycyclohexyl)ethene
485 1-fluoro-1-cyano-2-(trans-4-(trans-4-(4-heptylphenyl) cyclohexyl)methoxycyclohexyl)ethene
486 1-fluoro-1-cyano-2-(trans-4-(trans-4-(4-ethylphenyl) cyclohexyl)oxymethylcyclohexyl)ethene
487 1-fluoro-1-cyano-2-(trans-4-(trans-4-(4-propylphenyl) cyclohexyl)oxymethylcyclohexyl)ethene
488 1-fluoro-1-cyano-2-(trans-4-(trans-4-(4-butylphenyl) cyclohexyl)oxymethylcyclohexyl)ethene 489 1-fluoro-1-cyano-2-(trans-4-(trans-4-(4-pentylphenyl) cyclohexyl)oxymethylcyclohexyl)ethene

EXAMPLE 30

Preparation of 1-fluoro-1-cyano-2-(trans-4-(4-(4-ethylphenyl)butyl)cyclohexyl)ethene [Compound expressed by general formula I wherein $R^1$ represents ethyl group, $A^1$ represents 1,4-phenylene, $B^1$ represents 1,4-butylene, n1 is 0, n2 is 0, n3 is 0, $R^2$ represents a group expressed by formula II, and x represents fluorine atom (Compound No. 490)]

Subject compound was synthesized by the same procedures as in Example 1 with the exception that trans-4-(4-(4-ethylphenyl)butyl)cyclohexane carboaldehyde was used as starting material instead of trans-4-(trans-4-ethylcyclohexyl)cyclohexane carboaldehyde.

By the procedures similar to those described above, the following compounds (Compound Nos. 491 to 500) are synthesized.

491 1-fluoro-1-cyano-2-(trans-4-(4-(4-propylphenyl)butyl) cyclohexyl)ethene 492 1-fluoro-1-cyano-2-(trans-4-(4-(4-butylphenyl)butyl) cyclohexyl)ethene 493 1-fluoro-1-cyano-2-(trans-4-(4-(4-pentylphenyl)butyl) cyclohexyl)ethene 494 1-fluoro-1-cyano-2-(trans-4-(trans-4-(4-(4-ethylphenyl) butyl)cyclohexyl)cyclohexyl)ethene 495 1-fluoro-1-cyano-2-(trans-4-(trans-4-(4-(4-propylphenyl)butyl)cyclohexyl)cyclohexyl)ethene 496 1-fluoro-1-cyano-2-(trans-4-(trans-4-(4-(4-pentylphenyl)butyl)cyclohexyl)cyclohexyl)ethene 497 1-fluoro-1-cyano-2-(trans-4-(trans-4-(4-(4-heptylphenyl)butyl)cyclohexyl)cyclohexyl)ethene 498 1-fluoro-1-cyano-2-(trans-4-(4-(trans-4-(4-ethylphenyl) cyclohexyl)butyl)cyclohexyl)ethene 499 1-fluoro-1-cyano-2-(trans-4-(4-(trans-4-(4-propylphenyl)cyclohexyl)butyl)cyclohexyl)ethene 500 1-fluoro-1-cyano-2-(trans-4-(4-(trans-4-(4-butylphenyl)cyclohexyl)butyl)cyclohexyl)ethene

EXAMPLE 31

Preparation of 1-cyano-1-fluoro-4-(trans-4-(trans-4-ethylcyclohexyl)cyclohexyl)-1-butene [Compound expressed by general formula I wherein $R^1$ represents ethyl group, $A^1$ represents 1,4-cyclohexylene, $B^1$ represents a covalent bond, n1 is 0, n2 is 0, n3 is 1, $R^2$ represents a group expressed by formula II, and X represents fluorine atom (Compound No. 501)]

Subject compound was synthesized by the same procedures as in Example 25 with the exception that 3-(trans-4-(trans-4-ethylcyclohexyl)cyclohexyl)propanal was used as starting material instead of trans-4-(trans-4-ethylcyclohexyl)cyclohexane carboaldehyde.

By the procedures similar to those described above, the following compounds (Compound Nos. 502 to 510) are synthesized.

502 1-cyano-1-fluoro-4-(trans-4-(trans-4-propylcyclohexyl) cyclohexyl)-1-butene 503 1-cyano-1-fluoro-4-(trans-4-(trans-4-butylcyclohexyl) cyclohexyl)-1-butene 504 1-cyano-1-fluoro-4-(trans-4-(trans-4-pentylcyclohexyl) cyclohexyl)-1-butene 505 1-cyano-1-fluoro-4-(trans-4-(trans-4-heptylcyclohexyl) cyclohexyl)-1-butene 506 1-cyano-1-fluoro-4-(trans-4-(2-(trans-4-ethylcyclohexyl)ethyl)cyclohexyl)-1-butene 507 1-cyano-1-fluoro-4-(trans-4-(2-(trans-4-propylcyclohexyl)ethyl)cyclohexyl)-1-butene 508 1-cyano-1-fluoro-4-(trans-4-(2-(trans-4-butylcyclohexyl)ethyl)cyclohexyl)- 1-butene 509 1-cyano-1-fluoro-4-(trans-4-(2-(trans-4-pentylcyclohexyl)ethyl)cyclohexyl)-1-butene 510 1-cyano-1-fluoro-4-(trans-4-(2-(trans-4-heptylcyclohexyl)ethyl)cyclohexyl)-1-butene

EXAMPLE 32

Preparation of 1-cyano-1-fluoro-4-(trans-4-(4-ethylphenyl) cyclohexyl)-1-butene [Compound expressed by general formula I wherein $R^1$ represents ethyl group, $A^1$ represents 1,4-phenylene, $B^1$ represents a covalent bond, n1 is 0, n2 is 0, n3 is 1, $R^2$ represents a group expressed by formula II, and X represents fluorine atom (Compound No. 511)]

Subject compound was synthesized by the same procedures as in Example 25 with the exception that 3-(trans-4-(4-ethylphenyl)cyclohexyl)propanal was used as starting material instead of trans-4-(trans-4-ethylcyclohexyl) cyclohexane carboaldehyde.

By the procedures similar to those described above, the following compounds (Compound Nos. 512 to 530) are synthesized.

512 1-cyano-1-fluoro-4-(trans-4-(4-propylphenyl) cyclohexyl)-1-butene 513 1-cyano-1-fluoro-4-(trans-4-(4-butylphenyl) cyclohexyl)-1-butene 514 1-cyano-1-fluoro-4-(trans-4-(4-pentylphenyl) cyclohexyl)-1-butene 515 1-cyano-1-fluoro-4-(trans-4-(4-heptylphenyl) cyclohexyl)-1-butene 516 1-cyano-1-fluoro-4-(trans-4-(2-(4-ethylphenyl)ethyl) cyclohexyl)- 1-butene 517 1-cyano-1-fluoro-4-(trans-4-(2-(4-propylphenyl)ethyl) cyclohexyl)-1-butene 518 1-cyano-1-fluoro-4-(trans-4-(2-(4-butylphenyl)ethyl) cyclohexyl)-1-butene 519 1-cyano-1-fluoro-4-(trans-4-(2-(4-pentylphenyl)ethyl) cyclohexyl)-1-butene 520 1-cyano-1-fluoro-4-(trans-4-(2-(4-heptylphenyl)ethyl) cyclohexyl)-1-butene 521 1-cyano-1-fluoro-4-(trans-4-(trans-4-(4-ethylphenyl) cyclohexyl)cyclohexyl)-1-butene 522 1-cyano-1-fluoro-4-(trans-4-(trans-4-(4-propylphenyl) cyclohexyl)cyclohexyl)-1-butene 523 1-cyano-1-fluoro-4-(trans-4-(trans-4-(4-butylphenyl) cyclohexyl)cyclohexyl)-1-butene 524 1-cyano-1-fluoro-4-(trans-4-(trans-4-(4-pentylphenyl) cyclohexyl)cyclohexyl)-1-butene 525 1-cyano-1-fluoro-4-(trans-4-(trans-4-(4-heptylphenyl) cyclohexyl)cyclohexyl)-1-butene 526 1-cyano-1-fluoro-4-(trans-4-(2-(trans-4-(4-ethylphenyl) cyclohexyl)ethyl)cyclohexyl)-1-butene 527 1-cyano-1-fluoro-4-(trans-4-(2-(trans-4-(4-propylphenyl)cyclohexyl)ethyl)cyclohexyl)-1-butene 528 1-cyano-1-fluoro-4-(trans-4-(2-(trans-4-(4-butylphenyl)cyclohexyl)ethyl)cyclohexyl)-1-butene 529 1-cyano-1-fluoro-4-(trans-4-(2-(trans-4-(4-pentylphenyl)cyclohexyl)ethyl)cyclohexyl)-1-butene 530 1-cyano-1-fluoro-4-(trans-4-(2-(trans-4-(4-heptylphenyl)cyclohexyl)ethyl)cyclohexyl)-1-butene

EXAMPLE 33

Preparation of 1-cyano-1-fluoro-4-(trans-4-(2-(trans-4-ethylcyclohexyl)ethenyl)cyclohexyl)-1-butene [Compound expressed by general formula I wherein $R^1$ represents ethyl group, $A^1$ represents 1,4-cyclohexylene, $B^1$ represents 1,2-ethenylene, n1 is 0, n2 is 0, n3 is 1, $R^2$ represents a group expressed by formula II, and X represents fluorine atom (Compound No. 531)]

Subject compound was synthesized by the same procedures as in Example 25 with the exception that 3-(trans-4-(2E-(trans-4-ethylcyclohexyl)ethenyl)cyclohexyl)propanal was used as starting material instead of trans-4-(trans-4-ethylcyclohexyl)cyclohexane carboaldehyde.

By the procedures similar to those described above, the following compounds (Compound Nos. 532 to 540) are synthesized.

532 1-cyano-1-fluoro-4-(trans-4-(2E-(trans-4-propylcyclohexyl)ethenyl)cyclohexyl)-1-butene
533 1-cyano-1-fluoro-4-(trans-4-(2E-(trans-4-butylcyclohexyl)ethenyl)cyclohexyl)-1-butene
534 1-cyano-1-fluoro-4-(trans-4-(2E-(trans-4-pentylcyclohexyl)ethenyl)cyclohexyl)-1-butene
535 1-cyano-1-fluoro-4-(trans-4-(2E-(trans-4-heptylcyclohexyl)ethenyl)cyclohexyl)-1-butene
536 1-cyano-1-fluoro-4-(trans-4-(2E-(trans-4-(4-ethylphenyl)cyclohexyl)ethenyl)cyclohexyl)-1-butene
537 1-cyano-1-fluoro-4-(trans-4-(2E-(trans-4-(4-propylphenyl)cyclohexyl)ethenyl)cyclohexyl)-1-butene
538 1-cyano-1-fluoro-4-(trans-4-(2E-(trans-4-(4-butylphenyl)cyclohexyl)ethenyl)cyclohexyl)-1-butene
539 1-cyano-1-fluoro-4-(trans-4-(2E-(trans-4-(4-pentylphenyl)cyclohexyl)ethenyl)cyclohexyl)-1-butene
540 1-cyano-1-fluoro-4-(trans-4-(2E-(trans-4-(4-heptylphenyl)cyclohexyl)ethenyl)cyclohexyl)-1-butene

EXAMPLE 34

Preparation of trans-4-(4-cyano-4-fluoro-3-butenyl)cyclohexyl trans-4-ethylcyclohexane carboxylate [Compound expressed by general formula I wherein $R^1$ represents ethyl group, $A^1$ represents 1,4-cyclohexylene, $B^1$ represents carbonyloxy, n1 is 0, n2 is 0, n3 is 1, $R^2$ represents a group expressed by formula II, and X represents fluorine atom (Compound No. 541)]

Subject compound was synthesized by the same procedures as in Example 25 with the exception that trans-4-(2-formylethyl)cyclohexyl trans-4-ethylcyclohexane carboxylate was used as starting material instead of trans-4-(trans-4-ethylcyclohexyl)cyclohexane carboaldehyde.

By the procedures similar to those described above, the following compounds (Compound Nos. 542 to 571) are synthesized.

542 trans-4-(4-cyano-4-fluoro-3-butenyl)cyclohexyl trans-4-propylcyclohexane carboxylate
543 trans-4-(4-cyano-4-fluoro-3-butenyl)cyclohexyl trans-4-butylcyclohexane carboxylate
544 trans-4-(4-cyano-4-fluoro-3-butenyl)cyclohexyl trans-4-pentylcyclohexane carboxylate
545 trans-4-(4-cyano-4-fluoro-3-butenyl)cyclohexyl trans-4-hexylcyclohexane carboxylate
546 trans-4-ethylcyclohexyl trans-4-(4-cyano-4-fluoro-3-butenyl)cyclohexane carboxylate
547 trans-4-propylcyclohexyl trans-4-(4-cyano-4-fluoro-3-butenyl)cyclohexane carboxylate
548 trans-4-butylcyclohexyl trans-4-(4-cyano-4-fluoro-3-butenyl)cyclohexane carboxylate
549 trans-4-pentylcyclohexyl trans-4-(4-cyano-4-fluoro-3-butenyl)cyclohexane carboxylate
550 trans-4-hexylcyclohexyl trans-4-(4-cyano-4-fluoro-3-butenyl)cyclohexane carboxylate
551 trans-4-(4-cyano-4-fluoro-3-butenyl)cyclohexyl 4-ethyl benzoate
552 trans-4-(4-cyano-4-fluoro-3-butenyl)cyclohexyl 4-propyl benzoate
553 trans-4-(4-cyano-4-fluoro-3-butenyl)cyclohexyl 4-butyl benzoate
554 trans-4-(4-cyano-4-fluoro-3-butenyl)cyclohexyl 4-pentyl benzoate
555 trans-4-(4-cyano-4-fluoro-3-butenyl)cyclohexyl 4-hexyl benzoate
556 4-ethylphenyl trans-4-(4-cyano-4-fluoro-3-butenyl)cyclohexane carboxylate
557 4-propylphenyl trans-4-(4-cyano-4-fluoro-3-butenyl)cyclohexane carboxylate
558 4-butylphenyl trans-4-(4-cyano-4-fluoro-3-butenyl)cyclohexane carboxylate
559 4-pentylphenyl trans-4-(4-cyano-4-fluoro-3-butenyl)cyclohexane carboxylate
560 4-hexylphenyl trans-4-(4-cyano-4-fluoro-3-butenyl)cyclohexane carboxylate
561 4-heptylphenyl trans-4-(4-cyano-4-fluoro-3-butenyl)cyclohexane carboxylate
562 trans-4-(4-ethylphenyl)cyclohexyl trans-4-(4-cyano-4-fluoro-3-butenyl)cyclohexane carboxylate
563 trans-4-(4-propylphenyl)cyclohexyl trans-4-(4-cyano-4-fluoro-3-butenyl)cyclohexane carboxylate
564 trans-4-(4-butylphenyl)cyclohexyl trans-4-(4-cyano-4-fluoro-3-butenyl)cyclohexane carboxylate
565 trans-4-(4-pentylphenyl)cyclohexyl trans-4-(4-cyano-4-fluoro-3-butenyl)cyclohexane carboxylate
566 trans-4-(4-hexylphenyl)cyclohexyl trans-4-(4-cyano-4-fluoro-3-butenyl)cyclohexane carboxylate
567 trans-4-(4-cyano-4-fluoro-3-butenyl)cyclohexyl trans-4-(4-ethylphenyl)cyclohexane carboxylate
568 trans-4-(4-cyano-4-fluoro-3-butenyl)cyclohexyl trans-4-(4-propylphenyl)cyclohexane carboxylate
569 trans-4-(4-cyano-4-fluoro-3-butenyl)cyclohexyl trans-4-(4-butylphenyl)cyclohexane carboxylate
570 trans-4-(4-cyano-4-fluoro-3-butenyl)cyclohexyl trans-4-(4-pentylphenyl)cyclohexane carboxylate
571 trans-4-(4-cyano-4-fluoro-3-butenyl)cyclohexyl trans-4-(4-hexylphenyl)cyclohexane carboxylate

EXAMPLE 35

Preparation of 1-cyano-1-fluoro-4-(trans-4-(4-ethylphenyl)methoxycyclohexyl)-1-butene [Compound expressed by general formula I wherein $R^1$ represents ethyl group, $A^1$ represents 1,4-phenylene, $B^1$ represents methyleneoxy, n1 is 0, n2 is 0, n3 is 1, $R^2$ represents a group expressed by formula II, and X represents fluorine atom (Compound No. 572)]

Subject compound was synthesized by the same procedures as in Example 25 with the exception that 3-(trans-4-(4-ethylphenyl)methoxycyclohexyl)propanal was used as starting material instead of trans-4-(trans-4-ethylcyclohexyl)cyclohexane carboaldehyde.

By the procedures similar to those described above, the following compounds (Compound Nos. 573 to 589) are synthesized.

573 1-cyano-1-fluoro-4-(trans-4-(4-propylphenyl)methoxycyclohexyl)-1-butene
574 1-cyano-1-fluoro-4-(trans-4-(4-butylphenyl)methoxycyclohexyl)-1-butene
575 1-cyano-1-fluoro-4-(trans-4-(4-pentylphenyl)methoxycyclohexyl)-1-butene
576 1-cyano-1-fluoro-4-(trans-4-(4-heptylphenyl)methoxycyclohexyl)-1-butene
577 1-cyano-1-fluoro-4-(trans-4-(trans-4-propylcyclohexyl)methoxycyclohexyl)-1-butene
578 1-cyano-1-fluoro-4-(trans-4-(trans-4-butylcyclohexyl)methoxycyclohexyl)-1-butene
579 1-cyano-1-fluoro-4-(trans-4-(trans-4-pentylcyclohexyl)methoxycyclohexyl)-1-butene
580 1-cyano-1-fluoro-4-(trans-4-(trans-4-heptylcyclohexyl)methoxycyclohexyl)-1-butene
581 1-cyano-1-fluoro-4-(trans-4-(trans-4-(4-ethylphenyl)cyclohexyl)methoxycyclohexyl)-1-butene 582 1-cyano-1-fluoro-4-(trans-4-(trans-4-(4-propylphenyl)cyclohexyl)methoxycyclohexyl)-1-butene 583 1-cyano-1-fluoro-4-(trans-4-(trans-4-(4-butylphenyl)cyclohexyl)methoxycyclohexyl)-1-butene 584 1-cyano-1-fluoro-4-(trans-4-(trans-4-(4-pentylphenyl)cyclohexyl)methoxycyclohexyl)-1-butene 585 1-cyano-1-fluoro-4-(trans-4-(trans-4-(4-heptylphenyl)cyclohexyl)methoxycyclohexyl)-1-butene 586 1-cyano-1-fluoro-4-(trans-4-(trans-4-(4-ethylphenyl)cyclohexyl)oxymethylcyclohexyl)-1-butene 587 1-cyano-1-fluoro-4-(trans-4-(trans-4-(4-propylphenyl)cyclohexyl)oxymethylcyclohexyl)-1-butene 588 1-cyano-1-fluoro-4-(trans-4-(trans-4-(4-butylphenyl)cyclohexyl)oxymethylcyclohexyl)-1-butene 589 1-cyano-1-fluoro-4-(trans-4-(trans-4-(4-pentylphenyl)cyclohexyl)oxymethylcyclohexyl)-1-butene

EXAMPLE 36

Preparation of 1-cyano-1-fluoro-4-(trans-4-(4-(4-ethylphenyl)butyl)cyclohexyl)-1-butene [Compound expressed by general formula I wherein $R^1$ represents ethyl group, $A^1$ represents 1,4-phenylene, $B^1$ represents 1,4-butylene, n1 is 0, n2 is 0, n3 is 1, $R^2$ represents a group expressed by formula II, and X represents fluorine atom (Compound No. 590)]

Subject compound was synthesized by the same procedures as in Example 25 with the exception that 3-(trans-4-(4-(4-ethylphenyl)butyl)cyclohexyl)propanal was used as starting material instead of trans-4-(trans-4-ethylcyclohexyl)cyclohexane carboaldehyde.

By the procedures similar to those described above, the following compounds (Compound Nos. 591 to 600) are synthesized.

591 1-cyano-1-fluoro-4-(trans-4-(4-(4-propylphenyl)butyl)cyclohexyl)-1-butene 592 1-cyano-1-fluoro-4-(trans-4-(4-(4-pentylphenyl)butyl)cyclohexyl)-1-butene 593 1-cyano-1-fluoro-4-(trans-4-(trans-4-(4-(4-ethylphenyl)butyl)cyclohexyl)cyclohexyl)-1-butene 594 1-cyano-1-fluoro-4-(trans-4-(trans-4-(4-(4-propylphenyl)butyl)cyclohexyl)cyclohexyl)-1-butene 595 1-cyano-1-fluoro-4-(trans-4-(trans-4-(4-(4-butylphenyl)butyl)cyclohexyl)cyclohexyl)-1-butene 596 1-cyano-1-fluoro-4-(trans-4-(trans-4-(4-(4-pentylphenyl)butyl)cyclohexyl)cyclohexyl)-1-butene 597 1-cyano-1-fluoro-4-(trans-4-(4-(trans-4-(4-ethylphenyl)cyclohexyl)butyl)cyclohexyl)-1-butene 598 1-cyano-1-fluoro-4-(trans-4-(4-(trans-4-(4-propylphenyl)cyclohexyl)butyl)cyclohexyl)-1-butene 599 1-cyano-1-fluoro-4-(trans-4-(4-(trans-4-(4-butylphenyl)cyclohexyl)butyl)cyclohexyl)-1-butene 600 1-cyano-1-fluoro-4-(trans-4-(4-(trans-4-(4-pentylphenyl)cyclohexyl)butyl)cyclohexyl)-1-butene

EXAMPLE 37

Preparation of 1-cyano-1-fluoro-4-(trans-4-(trans-4-ethylcyclohexyl)cyclohexyl)-1,3-butadiene [Compound expressed by general formula I wherein $R^1$ represents ethyl group, $A^1$ represents 1,4-cyclohexylene, $B^1$ represents a covalent bond, n1 is 0, n2 is 0, n3 is 0, $R^2$ represents a group expressed by formula III, and X represents fluorine atom (Compound No. 601)]

Subject compound was synthesized by the same procedures as in Example 25 with the exception that 3-(trans-4-(trans-4-ethylcyclohexyl)cyclohexyl)-2-propenal obtained according to the method of Example 13 was used as starting material instead of trans-4-(trans-4-ethylcyclohexyl)cyclohexane carboaldehyde.

By the procedures similar to those described above, the following compounds (Compound Nos. 602 to 610) are synthesized.

602 1-cyano-1-fluoro-4-(trans-4-(trans-4-propylcyclohexyl)cyclohexyl)-1,3-butadiene 603 1-cyano-1-fluoro-4-(trans-4-(trans-4-butylcyclohexyl)cyclohexyl)-1,3-butadiene 604 1-cyano-1-fluoro-4-(trans-4-(trans-4-pentylcyclohexyl)cyclohexyl)-1,3-butadiene 605 1-cyano-1-fluoro-4-(trans-4-(trans-4-heptylcyclohexyl)cyclohexyl)-1,3-butadiene 606 1-cyano-1-fluoro-4-(trans-4-(2-(trans-4-ethylcyclohexyl)ethyl)cyclohexyl)-1,3-butadiene 607 1-cyano-1-fluoro-4-(trans-4-(2-(trans-4-propylcyclohexyl)ethyl)cyclohexyl)-1,3-butadiene 608 1-cyano-1-fluoro-4-(trans-4-(2-(trans-4-butylcyclohexyl)ethyl)cyclohexyl)- 1,3-butadiene 609 1-cyano-1-fluoro-4-(trans-4-(2-(trans-4-pentylcyclohexyl)ethyl)cyclohexyl)-1,3-butadiene 610 1-cyano-1-fluoro-4-(trans-4-(2-(trans-4-heptylcyclohexyl)ethyl)cyclohexyl)-1,3-butadiene

EXAMPLE 38

Preparation of 1-cyano-1-fluoro-4-(trans-4-(4-ethylphenyl)cyclohexyl)-1,3-butadiene [Compound expressed by general formula I wherein $R^1$ represents ethyl group, $A^1$ represents 1,4-phenylene, $B^1$ represents a covalent bond, n1 is 0, n2 is 0, n3 is 0, $R^2$ represents a group expressed by formula III, and X represents fluorine atom (Compound No. 611)]

Subject compound was synthesized by the same procedures as in Example 25 with the exception that 3-(trans-4-(4-ethylphenyl)cyclohexyl)-2-propenal synthesized from trans-4-(4-ethylphenyl)cyclohexanone was used as starting material instead of trans-4-(trans-4-ethylcyclohexyl)cyclohexane carboaldehyde.

By the procedures similar to those described above, the following compounds (Compound Nos. 612 to 630) are synthesized.

612 1-cyano-1-fluoro-4-(trans-4-(4-propylphenyl)cyclohexyl)-1,3-butadiene 613 1-cyano-1-fluoro-4-(trans-4-(4-butylphenyl)cyclohexyl)-1,3-butadiene 614 1-cyano-1-fluoro-4-(trans-4-(4-pentylphenyl)cyclohexyl)-1,3-butadiene 615 1-cyano-1-fluoro-4-(trans-4-(4-heptylphenyl)cyclohexyl)-1,3-butadiene 616 1-cyano-1-fluoro-4-(trans-4-(2-(4-ethylphenyl)ethyl)cyclohexyl)-1,3-butadiene 617 1-cyano-1-fluoro-4-(trans-4-(2-(4-propylphenyl)ethyl)cyclohexyl)-1,3-butadiene 618 1-cyano-1-fluoro-4-(trans-4-(2-(4-butylphenyl)ethyl)cyclohexyl)-1,3-butadiene 619 1-cyano-1-fluoro-4-(trans-4-(2-(4-pentylphenyl)ethyl)cyclohexyl)-1,3-butadiene 620 1-cyano-1-fluoro-4-(trans-4-(2-(4-heptylphenyl)ethyl)cyclohexyl)-1,3-butadiene 621 1-cyano-1-fluoro-4-(trans-4-(trans-4-(4-ethylphenyl)cyclohexyl)cyclohexyl)-1,3-butadiene 622 1-cyano-1-fluoro-4-(trans-4-(trans-4-(4-propylphenyl)cyclohexyl)cyclohexyl)-1,3-butadiene 623 1-cyano-1-fluoro-4-(trans-4-(trans-4-(4-butylphenyl)cyclohexyl)cyclohexyl)-1,3-butadiene 624 1-cyano-1-fluoro-4-(trans-4-(trans-4-(4-pentylphenyl)cyclohexyl)cyclohexyl)-1,3-butadiene 625 1-cyano-1-fluoro-4-(trans-4-(trans-4-(4-heptylphenyl)cyclohexyl)cyclohexyl)-1,3-butadiene 626 1-cyano-1-fluoro-4-(trans-4-(2-(trans-4-(4-ethylphenyl)cyclohexyl)ethyl)cyclohexyl)-1,3-butadiene 627 1-cyano-1-fluoro-4-(trans-4-(2-(trans-4-(4-propylphenyl)cyclohexyl)ethyl)cyclohexyl)-1,3-butadiene 628 1-cyano-1-fluoro-4-(trans-4-(2-(trans-4-(4-butylphenyl)cyclohexyl)ethyl)cyclohexyl)-1,3-butadiene 629 1-cyano-1-fluoro-4-(trans-4-(2-(trans-4-(4-pentylphenyl)cyclohexyl)ethyl)cyclohexyl)- 1,3-butadiene 630 1-cyano-1-fluoro-4-(trans-4-(2-(trans-4-(4-heptylphenyl)cyclohexyl)ethyl)cyclohexyl)-1,3-butadiene

EXAMPLE 39

Preparation of 1-cyano-1-fluoro-4-(trans-4-(2-(trans-4-ethylcyclohexyl)ethenyl)cyclohexyl)-1,3-butadiene [Compound expressed by general formula I wherein $R^1$ represents ethyl group, $A^1$ represents 1,4-cyclohexylene, $B^1$ represents 1,2-ethenylene, n1 is 0, n2 is 0, n3 is 0, $R^2$ represents a group expressed by formula III, and X represents fluorine atom (Compound No. 631)]

Subject compound was synthesized by the same procedures as in Example 25 with the exception that 3-(trans-4-(2E-(trans-4-ethylcyclohexyl)ethenyl)cyclohexyl)-2-propenal synthesized from trans-4-(2E-(trans-4-ethylcyclohexyl)ethenyl)cyclohexanone was used as starting material instead of trans-4-(trans-4-ethylcyclohexyl)cyclohexane carboaldehyde.

By the procedures similar to those described above, the following compounds (Compound Nos. 632 to 640) are synthesized.

632 1-cyano-1-fluoro-4-(trans-4-(2E-(trans-4-propylcyclohexyl)ethenyl)cyclohexyl)-1,3-butadiene 633 1-cyano-1-fluoro-4-(trans-4-(2E-(trans-4-butylcyclohexyl)ethenyl)cyclohexyl)-1,3-butadiene 634 1-cyano-1-fluoro-4-(trans-4-(2E-(trans-4-pentylcyclohexyl)ethenyl)cyclohexyl)-1,3-butadiene 635 1-cyano-1-fluoro-4-(trans-4-(2E-(trans-4-heptylcyclohexyl)ethenyl)cyclohexyl)-1,3-butadiene 636 1-cyano-1-fluoro-4-(trans-4-(2E-(trans-4-ethylphenyl)cyclohexyl)ethenyl)cyclohexyl)- 1,3-butadiene 637 1-cyano-1-fluoro-4-(trans-4-(2E-(trans-4-propylphenyl)cyclohexyl)ethenyl)cyclohexyl)-1,3-butadiene 638 1-cyano-1-fluoro-4-(trans-4-(2E-(trans-4-butylphenyl)cyclohexyl)ethenyl)cyclohexyl)-1,3-butadiene 639 1-cyano-1-fluoro-4-(trans-4-(2E-(trans-4-pentylphenyl)cyclohexyl)ethenyl)cyclohexyl)-1,3-butadiene 640 1-cyano-1-fluoro-4-(trans-4-(2E-(trans-4-heptylphenyl)cyclohexyl)ethenyl)cyclohexyl)-1,3-butadiene

EXAMPLE 40

Preparation of trans-4-(4-cyano-4-fluoro-1,3-butadienyl)cyclohexyl trans-4-ethylcyclohexane carboxylate [Compound expressed by general formula I wherein $R^1$ represents ethyl group, $A^1$ represents 1,4-cyclohexylene, $B^1$ represents carbonyloxy, n1 is 0, n2 is 0, n3 is 0, $R^2$ represents a group expressed by formula III, and X represents fluorine atom (Compound No. 641)]

Subject compound was synthesized by the same procedures as in Example 25 with the exception that trans-4-(2-formylethenyl)cyclohexyl)trans-4-ethylcyclohexane carboxylate obtained from 4-oxocyclohexyl trans-4-ethylcyclohexane carboxylate was used as starting material instead of trans-4-(trans-4-ethylcyclohexyl)cyclohexane carboaldehyde.

By the procedures similar to those described above, the following compounds (Compound Nos. 642 to 671) are synthesized.

642 trans-4-(4-cyano-4-fluoro-1,3-butadienyl)cyclohexyl trans-4-propylcyclohexane carboxylate 643 trans-4-(4-cyano-4-fluoro-1,3-butadienyl)cyclohexyl trans- 4-butylcyclohexane carboxylate 644 trans-4-(4-cyano-4-fluoro-1,3-butadienyl)cyclohexyl trans-4-pentylcyclohexane carboxylate 645 trans-4-(4-cyano-4-fluoro-1,3-butadienyl)cyclohexyl trans-4-hexylcyclohexane carboxylate 646 trans-4-ethylcyclohexyl trans-4-(4-cyano-4-fluoro-1,3-butadienyl)cyclohexane carboxylate 647 trans-4-propylcyclohexyl trans-4-(4-cyano-4-fluoro-1,3-butadienyl)cyclohexane carboxylate 648 trans-4-butylcyclohexyl trans-4-(4-cyano-4-fluoro-1,3-butadienyl)cyclohexane carboxylate 649 trans-4-pentylcyclohexyl trans-4-(4-cyano-4-fluoro-1,3-butadienyl)cyclohexane carboxylate 650 trans-4-hexylcyclohexyl trans-4-(4-cyano-4-fluoro-1,3-butadienyl)cyclohexane carboxylate 651 trans-4-(4-cyano-4-fluoro-1,3-butadienyl)cyclohexyl 4-ethyl benzoate 652 trans-4-(4-cyano-4-fluoro-1,3-butadienyl)cyclohexyl 4-propyl benzoate 653 trans-4-(4-cyano-4-fluoro-1,3-butadienyl)cyclohexyl 4-butyl benzoate 654 trans-4-(4-cyano-4-fluoro-1,3-butadienyl)cyclohexyl 4-pentyl benzoate 655 trans-4-(4-cyano-4-fluoro-1,3-butadienyl)cyclohexyl 4-hexyl benzoate 656 4-ethylphenyl trans-4-(4-cyano-4-fluoro-1,3-butadienyl)cyclohexane carboxylate 657 4-propylphenyl trans-4-(4-cyano-4-fluoro-1,3-butadienyl)cyclohexane carboxylate 658 4-butylphenyl trans-4-(4-cyano-4-fluoro-1,3-butadienyl)cyclohexane carboxylate 659 4-pentylphenyl trans-4-(4-cyano-4-fluoro-1,3-butadienyl)cyclohexane carboxylate 660 4-hexylphenyl trans-4-(4-cyano-4-fluoro-1,3-butadienyl)cyclohexane carboxylate 661 4-heptylphenyl trans-4-(4-cyano-4-fluoro-1,3-butadienyl)cyclohexane carboxylate 662 trans-4-(4-ethylphenyl)cyclohexyl trans-4-(4-cyano-4-fluoro-1,3-butadienyl)cyclohexane carboxylate 663 trans-4-(4-propylphenyl)cyclohexyl trans-4-(4-cyano-4-fluoro-1,3-butadienyl)cyclohexane carboxylate 664 trans-4-(4-butylphenyl)cyclohexyl trans-4-(4-cyano-4-fluoro-1,3-butadienyl)cyclohexane carboxylate 665 trans-4-(4-pentylphenyl)cyclohexyl trans-4-(4-cyano-4-fluoro-1,3-butadienyl)cyclohexane carboxylate 666 trans-4-(4-hexylphenyl)cyclohexyl trans-4-(4-cyano-4-fluoro-1,3-butadienyl)cyclohexane carboxylate 667 trans-4-(4-cyano-4-fluoro-1,3-butadienyl)cyclohexyl trans-4-(4-ethylphenyl)cyclohexane carboxylate 668 trans-4-(4-cyano-4-fluoro-1,3-butadienyl)cyclohexyl trans-4-(4-propylphenyl)cyclohexane carboxylate 669 trans-4-(4-cyano-4-fluoro-1,3-butadienyl)cyclohexyl trans-4-(4-butylphenyl)cyclohexane carboxylate 670 trans-4-(4-cyano-4-fluoro-1,3-butadienyl)cyclohexyl trans- 4-(4-pentylphenyl)cyclohexane carboxylate 671 trans-4-(4-cyano-4-fluoro-1,3-butadienyl)cyclohexyl trans-4-(4-hexylphenyl)cyclohexane carboxylate

EXAMPLE 41

Preparation of 1-cyano-1-fluoro-4-(trans-4-(4-ethylphenyl)methoxycyclohexyl)-1,3-butadiene [Compound expressed by general formula I wherein $R^1$ represents ethyl group, $A^1$ represents 1,4-phenylene, $B^1$ represents methyleneoxy, n1 is 0, n2 is 0, n3 is 0, $R^2$ represents a group expressed by formula III, and X represents fluorine atom (Compound No. 672)]

Subject compound was synthesized by the same procedures as in Example 25 with the exception that 3-(trans-4-(4-ethylphenyl)methoxycyclohexyl)-2-propenal synthesized from trans-4-(4-ethylphenyl)methoxycyclohexanone was used as starting material instead of trans-4-(trans-4-ethylcyclohexyl)cyclohexane carboaldehyde.

By the procedures similar to those described above, the following compounds (Compound Nos. 673 to 689) are synthesized.

673 1-cyano-1-fluoro-4-(trans-4-(4-propylphenyl) methoxycyclohexyl)-1,3-butadiene
674 1-cyano-1-fluoro-4-(trans-4-(4-butylphenyl) methoxycyclohexyl)-1,3-butadiene
675 1-cyano-1-fluoro-4-(trans-4-(4-pentylphenyl) methoxycyclohexyl)-1,3-butadiene
676 1-cyano-1-fluoro-4-(trans-4-(4-heptylphenyl) methoxycyclohexyl)-1,3-butadiene
677 1-cyano-1-fluoro-4-(trans-4-(trans-4-propylcyclohexyl) methoxycyclohexyl)- 1,3-butadiene
678 1-cyano-1-fluoro-4-(trans-4-(trans-4-butylcyclohexyl) methoxycyclohexyl)-1,3-butadiene
679 1-cyano-1-fluoro-4-(trans-4-(trans-4-pentylcyclohexyl) methoxycyclohexyl)-1,3-butadiene
680 1-cyano-1-fluoro-4-(trans-4-(trans-4-heptylcyclohexyl) methoxycyclohexyl)-1,3-butadiene
681 1-cyano-1-fluoro-4-(trans-4-(trans-4-(4-ethylphenyl) cyclohexyl)methoxycyclohexyl)-1,3-butadiene
682 1-cyano-1-fluoro-4-(trans-4-(trans-4-(4-propylphenyl) cyclohexyl)methoxycyclohexyl)-1,3-butadiene
683 1-cyano-1-fluoro-4-(trans-4-(trans-4-(4-butylphenyl) cyclohexyl)methoxycyclohexyl)-1,3-butadiene
684 1-cyano-1-fluoro-4-(trans-4-(trans-4-(4-pentylphenyl) cyclohexyl)methoxycyclohexyl)-1,3-butadiene
685 1-cyano-1-fluoro-4-(trans-4-(trans-4-(4-heptylphenyl) cyclohexyl)methoxycyclohexyl)-1,3-butadiene
686 1-cyano-1-fluoro-4-(trans-4-(trans-4-(4-ethylphenyl) cyclohexyl)oxymethylcyclohexyl)-1,3-butadiene
687 1-cyano-1-fluoro-4-(trans-4-(trans-4-(4-propylphenyl) cyclohexyl)oxymethylcyclohexyl)-1,3-butadiene
688 1-cyano-1-fluoro-4-(trans-4-(trans-4-(4-butylphenyl) cyclohexyl)oxymethylcyclohexyl)-1,3-butadiene
689 1-cyano-1-fluoro-4-(trans-4-(trans-4-(4-pentylphenyl) cyclohexyl)oxymethylcyclohexyl)-1,3-butadiene

EXAMPLE 42

Preparation of 1-cyano-1-fluoro-4-(trans-4-(4-(4-ethylphenyl)butyl)cyclohexyl)-1,3-butadiene [Compound expressed by general formula I wherein $R^1$ represents ethyl group, $A^1$ represents 1,4-phenylene, $B^1$ represents 1,4-butylene, n1 is 0, n2 is 0, n3 is 0, $R^2$ represents a group expressed by formula III, and X represents fluorine atom (Compound No. 690)]

Subject compound was synthesized by the same procedures as in Example 25 with the exception that 3-(trans-4-(4-(4-ethylphenyl)butyl)cyclohexyl)-2-propenal synthesized trans-4-(4-(4-ethylphenyl)butyl)cyclohexanone was used as starting material instead of trans-4-(trans-4-ethylcyclohexyl)cyclohexane carboaldehyde.

By the procedures similar to those described above, the following compounds (Compound Nos. 691 to 700) are synthesized.

691 1-cyano-1-fluoro-4-(trans-4-(4-(4-propylphenyl)butyl) cyclohexyl)-1,3-butadiene
692 1-cyano-1-fluoro-4-(trans-4-(4-(4-butylphenyl)butyl) cyclohexyl)-1,3-butadiene
693 1-cyano-1-fluoro-4-(trans-4-(4-(4-heptylphenyl)butyl) cyclohexyl)-1,3-butadiene
694 1-cyano-1-fluoro-4-(trans-4-(trans-4-(4-(4-ethylphenyl) butyl)cyclohexyl)cyclohexyl)-1,3-butadiene
695 1-cyano-1-fluoro-4-(trans-4-(trans-4-(4-(4-propylphenyl)butyl)cyclohexyl)cyclohexyl)-1,3-butadiene
696 1-cyano-1-fluoro-4-(trans-4-(trans-4-(4-(4-butylphenyl)butyl)cyclohexyl)cyclohexyl)-1,3-butadiene
697 1-cyano-1-fluoro-4-(trans-4-(trans-4-(4-(4-pentylphenyl)butyl)cyclohexyl)cyclohexyl)-1,3-butadiene
698 1-cyano-1-fluoro-4-(trans-4-(4-(trans-4-(4-ethylphenyl) cyclohexyl)butyl)cyclohexyl)-1,3-butadiene
699 1-cyano-1-fluoro-4-(trans-4-(4-(trans-4-(4-propylphenyl)cyclohexyl)butyl)cyclohexyl)-1,3-butadiene
700 1-cyano-1-fluoro-4-(trans-4-(4-(trans-4-(4-butylphenyl)cyclohexyl)butyl)cyclohexyl)-1,3-butadiene

EXAMPLE 43

Preparation of 1-cyano-1-fluoro-6-(trans-4-(trans-4-ethylcyclohexyl)cyclohexyl)-1,3-hexadiene [Compound expressed by general formula I wherein $R^1$ represents ethyl group, $A^1$ represents 1,4-cyclohexylene, $B^1$ represents a covalent bond, n1 is 0, n2 is 0, n3 is 1, $R^2$ represents a group expressed by formula III, and X represents fluorine atom (Compound No. 701)]

Subject compound was synthesized by the same procedures as in Example 25 with the exception that 5-(trans-4-(trans-4-ethylcyclohexyl)cyclohexyl)-2-pentene-1-al was used as starting material instead of trans-4-(trans-4-ethylcyclohexyl)cyclohexane carboaldehyde.

By the procedures similar to those described above, the following compounds (Compound Nos. 702 to 710) are synthesized.

702 1-cyano-1-fluoro-6-(trans-4-(trans-4-propylcyclohexyl) cyclohexyl)-1,3-hexadiene
703 1-cyano-1-fluoro-6-(trans-4-(trans-4-butylcyclohexyl) cyclohexyl)-1,3-hexadiene
704 1-cyano-1-fluoro-6-(trans-4-(trans-4-pentylcyclohexyl) cyclohexyl)-1,3-hexadiene
705 1-cyano-1-fluoro-6-(trans-4-(trans-4-heptylcyclohexyl) cyclohexyl)- 1,3-hexadiene
706 1-cyano-1-fluoro-6-(trans-4-(2-(trans-4-ethylcyclohexyl)ethyl)cyclohexyl)-1,3-hexadiene
707 1-cyano-1-fluoro-6-(trans-4-(2-(trans-4-propylcyclohexyl)ethyl)cyclohexyl)-1,3-hexadiene
708 1-cyano-1-fluoro-6-(trans-4-(2-(trans-4-butylcyclohexyl)ethyl)cyclohexyl)-1,3-hexadiene
709 1-cyano-1-fluoro-6-(trans-4-(2-(trans-4-pentylcyclohexyl)ethyl)cyclohexyl)-1,3-hexadiene
710 1-cyano-1-fluoro-6-(trans-4-(2-(trans-4-heptylcyclohexyl)ethyl)cyclohexyl)-1,3-hexadiene

EXAMPLE 44

Preparation of 1-cyano-1-fluoro-6-(trans-4-(4-ethylphenyl) cyclohexyl)-1,3-hexadiene [Compound expressed by general formula I wherein $R^1$ represents ethyl group, $A^1$ represents 1,4-phenylene, $B^1$ represents a covalent bond, n1 is 0, n2 is 0, n3 is 1, $R^2$ represents a group expressed by formula III, and X represents fluorine atom (Compound No. 711)]

Subject compound was synthesized by the same procedures as in Example 25 with the exception that 5-(trans-4-(4-ethylphenyl)cyclohexyl)-2-pentene-1-al was used as starting material instead of trans-4-(trans-4-ethylcyclohexyl)cyclohexane carboaldehyde.

By the procedures similar to those described above, the following compounds (Compound Nos. 712 to 730) are synthesized.

712 1-cyano-1-fluoro-6-(trans-4-(4-propylphenyl)cyclohexyl)-1,3-hexadiene
713 1-cyano-1-fluoro-6-(trans-4-(4-butylphenyl)cyclohexyl)-1,3-hexadiene
714 1-cyano-1-fluoro-6-(trans-4-(4-pentylphenyl)cyclohexyl)-1,3-hexadiene
715 1-cyano-1-fluoro-6-(trans-4-(4-heptylphenyl)cyclohexyl)-1,3-hexadiene
716 1-cyano-1-fluoro-6-(trans-4-(2-(4-ethylphenyl)ethyl)cyclohexyl)-1,3-hexadiene
717 1-cyano-1-fluoro-6-(trans-4-(2-(4-propylphenyl)ethyl)cyclohexyl)-1,3-hexadiene
718 1-cyano-1-fluoro-6-(trans-4-(2-(4-butylphenyl)ethyl)cyclohexyl)-1,3-hexadiene
719 1-cyano-1-fluoro-6-(trans-4-(2-(4-pentylphenyl)ethyl)cyclohexyl)-1,3-hexadiene
720 1-cyano-1-fluoro-6-(trans-4-(2-(4-heptylphenyl)ethyl)cyclohexyl)-1,3-hexadiene
721 1-cyano-1-fluoro-6-(trans-4-(trans-4-(4-ethylphenyl)cyclohexyl)cyclohexyl)-1,3-hexadiene
722 1-cyano-1-fluoro-6-(trans-4-(trans-4-(4-propylphenyl)cyclohexyl)cyclohexyl)-1,3-hexadiene
723 1-cyano-1-fluoro-6-(trans-4-(trans-4-(4-butylphenyl)cyclohexyl)cyclohexyl)-1,3-hexadiene
724 1-cyano-1-fluoro-6-(trans-4-(trans-4-(4-pentylphenyl)cyclohexyl)cyclohexyl)-1,3-hexadiene
725 1-cyano-1-fluoro-6-(trans-4-(trans-4-(4-heptylphenyl)cyclohexyl)cyclohexyl)-1,3-hexadiene
726 1-cyano-1-fluoro-6-(trans-4-(2-(trans-4-(4-ethylphenyl)cyclohexyl)ethyl)cyclohexyl)-1,3-hexadiene
727 1-cyano-1-fluoro-6-(trans-4-(2-(trans-4-(4-propylphenyl)cyclohexyl)ethyl)cyclohexyl)-1,3-hexadiene
728 1-cyano-1-fluoro-6-(trans-4-(2-(trans-4-(4-butylphenyl)cyclohexyl)ethyl)cyclohexyl)-1,3-hexadiene
729 1-cyano-1-fluoro-6-(trans-4-(2-(trans-4-(4-pentylphenyl)cyclohexyl)ethyl)cyclohexyl)-1,3-hexadiene
730 1-cyano-1-fluoro-6-(trans-4-(2-(trans-4-(4-heptylphenyl)cyclohexyl)ethyl)cyclohexyl)-1,3-hexadiene

EXAMPLE 45

Preparation of 1-cyano-1-fluoro-6-(trans-4-(2-(trans-4-ethylcyclohexyl)ethenyl)cyclohexyl)-1,3-hexadiene [Compound expressed by general formula I wherein $R^1$ represents ethyl group, $A^1$ represents 1,4-cyclohexylene, $B^1$ represents 1,2-ethenylene, n1 is 0, n2 is 0, n3 is 1, $R^2$ represents a group expressed by formula III, and X represents fluorine atom (Compound No. 731)]

Subject compound was synthesized by the same procedures as in Example 25 with the exception that 5-(trans-4-(2E-(trans-4-ethylcyclohexyl)ethenyl)cyclohexyl)-2-pentene-1-al was used as starting material instead of trans-4-(trans-4-ethylcyclohexyl)cyclohexane carboaldehyde.

By the procedures similar to those described above, the following compounds (Compound Nos. 732 to 740) are synthesized.

732 1-cyano-1-fluoro-6-(trans-4-(2E-(trans-4-propylcyclohexyl)ethenyl)cyclohexyl)-1,3-hexadiene
733 1-cyano-1-fluoro-6-(trans-4-(2E-(trans-4-butylcyclohexyl)ethenyl)cyclohexyl)-1,3-hexadiene
734 1-cyano-1-fluoro-6-(trans-4-(2E-(trans-4-pentylcyclohexyl)ethenyl)cyclohexyl)-1,3-hexadiene
735 1-cyano-1-fluoro-6-(trans-4-(2E-(trans-4-heptylcyclohexyl)ethenyl)cyclohexyl)-1,3-hexadiene
736 1-cyano-1-fluoro-6-(trans-4-(2E-(trans-4-(4-ethylphenyl)cyclohexyl)ethenyl)cyclohexyl)-1,3-hexadiene
737 1-cyano-1-fluoro-6-(trans-4-(2E-(trans-4-(4-propylphenyl)cyclohexyl)ethenyl)cyclohexyl)-1,3-hexadiene
738 1-cyano-1-fluoro-6-(trans-4-(2E-(trans-4-(4-butylphenyl)cyclohexyl)ethenyl)cyclohexyl)-1,3-hexadiene
739 1-cyano-1-fluoro-6-(trans-4-(2E-(trans-4-(4-pentylphenyl)cyclohexyl)ethenyl)cyclohexyl)-1,3-hexadiene
740 1-cyano-1-fluoro-6-(trans-4-(2E-(trans-4-(4-heptylphenyl)cyclohexyl)ethenyl)cyclohexyl)-1,3-hexadiene

EXAMPLE 46

Preparation of trans-4-(6-cyano-6-fluoro-3,5-hexadienyl)cyclohexyl trans-4-ethylcyclohexane carboxylate [Compound expressed by general formula I wherein $R^1$ represents ethyl group, $A^1$ represents 1,4-cyclohexylene, $B^1$ represents carbonyloxy, n1 is 0, n2 is 0, n3 is 1, $R^2$ represents a group expressed by formula III, and X represents fluorine atom (Compound No. 741)]

Subject compound was synthesized by the same procedures as in Example 25 with the exception that trans-4-(4-formyl-3-butenyl)cyclohexyl trans-4-ethylcyclohexane carboxylate was used as starting material instead of trans-4-(trans-4-ethylcyclohexyl)cyclohexane carboaldehyde.

By the procedures similar to those described above, the following compounds (Compound Nos. 742 to 771) are synthesized.

742 trans-4-(6-cyano-6-fluoro-3,5-hexadienyl)cyclohexyl trans-4-propylcyclohexane carboxylate
743 trans-4-(6-cyano-6-fluoro-3,5-hexadienyl)cyclohexyl trans-4-butylcyclohexane carboxylate
744 trans-4-(6-cyano-6-fluoro-3,5-hexadienyl)cyclohexyl trans-4-pentylcyclohexane carboxylate
745 trans-4-(6-cyano-6-fluoro-3,5-hexadienyl)cyclohexyl trans-4-hexylcyclohexane carboxylate
746 trans-4-ethylcyclohexyl trans-4-(6-cyano-6-fluoro-3,5-hexadienyl)cyclohexane carboxylate
747 trans-4-propylcyclohexyl trans-4-(6-cyano-6-fluoro-3,5-hexadienyl)cyclohexane carboxylate
748 trans-4-butylcyclohexyl trans-4-(6-cyano-6-fluoro-3,5-hexadienyl)cyclohexane carboxylate
749 trans-4-pentylcyclohexyl trans-4-(6-cyano-6-fluoro-3,5-hexadienyl)cyclohexane carboxylate
750 trans-4-hexylcyclohexyl trans-4-(6-cyano-6-fluoro-3,5-hexadienyl)cyclohexane carboxylate
751 trans-4-(6-cyano-6-fluoro-3,5-hexadienyl)cyclohexyl 4-ethyl benzoate
752 trans-4-(6-cyano-6-fluoro-3,5-hexadienyl)cyclohexyl 4-propyl benzoate
753 trans-4-(6-cyano-6-fluoro-3,5-hexadienyl)cyclohexyl 4-butyl benzoate
754 trans-4-(6-cyano-6-fluoro-3,5-hexadienyl)cyclohexyl 4-pentyl benzoate
755 trans-4-(6-cyano-6-fluoro-3,5-hexadienyl)cyclohexyl 4-hexyl benzoate
756 4-ethylphenyl trans-4-(6-cyano-6-fluoro-3,5-hexadienyl)cyclohexane carboxylate
757 4-propylphenyl trans-4-(6-cyano-6-fluoro-3,5-hexadienyl)cyclohexane carboxylate
758 4-butylphenyl trans-4-(6-cyano-6-fluoro-3,5-hexadienyl)cyclohexane carboxylate
759 4-pentylphenyl trans-4-(6-cyano-6-fluoro-3,5-hexadienyl)cyclohexane carboxylate
760 4-hexylphenyl trans-4-(6-cyano-6-fluoro-3,5-hexadienyl)cyclohexane carboxylate
761 4-heptylphenyl trans-4-(6-cyano-6-fluoro-3,5-hexadienyl)cyclohexane carboxylate 762 trans-4-(4-ethylphenyl)cyclohexyl trans-4-(6-cyano-6-fluoro-3,5-hexadienyl)cyclohexane carboxylate
763 trans-4-(4-propylphenyl)cyclohexyl trans-4-(6-cyano-6-fluoro-3,5-hexadienyl)cyclohexane carboxylate
764 trans-4-(4-butylphenyl)cyclohexyl trans-4-(6-cyano-6-fluoro-3,5-hexadienyl)cyclohexane carboxylate
765 trans-4-(4-pentylphenyl)cyclohexyl trans-4-(6-cyano-6-fluoro-3, 5-hexadienyl)cyclohexane carboxylate
766 trans-4-(4-hexylphenyl)cyclohexyl trans-4-(6-cyano-6-fluoro-3,5-hexadienyl)cyclohexane carboxylate
767 trans-4-(6-cyano-6-fluoro-3,5-hexadienyl)cyclohexyl trans-4-(4-ethylphenyl)cyclohexane carboxylate
768 trans-4-(6-cyano-6-fluoro-3,5-hexadienyl)cyclohexyl trans-4-(4-propylphenyl)cyclohexane carboxylate
769 trans-4-(6-cyano-6-fluoro-3,5-hexadienyl)cyclohexyl trans-4-(4-butylphenyl)cyclohexane carboxylate
770 trans-4-(6-cyano-6-fluoro-3,5-hexadienyl)cyclohexyl trans-4-(4-pentylphenyl)cyclohexane carboxylate
771 trans-4-(6-cyano-6-fluoro-3,5-hexadienyl)cyclohexyl trans-4-(4-hexylphenyl)cyclohexane carboxylate

EXAMPLE 47

Preparation of 1-cyano-1-fluoro-6-(trans-4-(4-ethylphenyl)methoxycyclohexyl)-1,3-hexadiene [Compound expressed by general formula I wherein $R^1$ represents ethyl group, $A^1$ represents 1,4-phenylene, $B^1$ represents methyleneoxy, n1 is 0, n2 is 0, n3 is 1, $R^2$ represents a group expressed by formula III, and X represents fluorine atom (Compound No. 772)]

Subject compound was synthesized by the same procedures as in Example 25 with the exception that 5-(trans-4-(4-ethylphenyl)methoxycyclohexyl)-2-pentene-1-al was used as starting material instead of trans-4-(trans-4-ethylcyclohexyl)cyclohexane carboaldehyde.

By the procedures similar to those described above, the following compounds (Compound Nos. 773 to 788) are synthesized.

773 1-cyano-1-fluoro-6-(trans-4-(4-propylphenyl)methoxycyclohexyl-1,3-hexadiene
774 1-cyano-1-fluoro-6-(trans-4-(4-butylphenyl)methoxycyclohexyl-1,3-hexadiene
775 1-cyano-1-fluoro-6-(trans-4-(4-pentylphenyl)methoxycyclohexyl-1,3-hexadiene
776 1-cyano-1-fluoro-6-(trans-4-(4-heptylphenyl)methoxycyclohexyl-1,3-hexadiene
777 1-cyano-1-fluoro-6-(trans-4-(trans-4-propylcyclohexyl)methoxycyclohexyl)-1,3-hexadiene
778 1-cyano-1-fluoro-6-(trans-4-(trans-4-butylcyclohexyl)methoxycyclohexyl)-1,3-hexadiene
779 1-cyano-1-fluoro-6-(trans-4-(trans-4-pentylcyclohexyl)methoxycyclohexyl)-1,3-hexadiene
780 1-cyano-1-fluoro-6-(trans-4-(trans-4-heptylcyclohexyl)methoxycyclohexyl)-1,3-hexadiene
781 1-cyano-1-fluoro-6-(trans-4-(trans-4-(4-ethylphenyl)cyclohexyl)methoxycyclohexyl)-1,3-hexadiene
782 1-cyano-1-fluoro-6-(trans-4-(trans-4-(4-propylphenyl)cyclohexyl)methoxycyclohexyl)-1,3-hexadiene
783 1-cyano-1-fluoro-6-(trans-4-(trans-4-(4-butylphenyl)cyclohexyl)methoxycyclohexyl)-1,3-hexadiene
784 1-cyano-1-fluoro-6-(trans-4-(trans-4-(4-pentylphenyl)cyclohexyl)methoxycyclohexyl)-1,3-hexadiene
785 1-cyano-1-fluoro-6-(trans-4-(trans-4-(4-ethylphenyl)cyclohexyl)oxymethylcyclohexyl)-1,3-hexadiene
786 1-cyano-1-fluoro-6-(trans-4-(trans-4-(4-propylphenyl)cyclohexyl)oxymethylcyclohexyl)-1,3-hexadiene
787 1-cyano-1-fluoro-6-(trans-4-(trans-4-(4-butylphenyl)cyclohexyl)oxymethylcyclohexyl)-1,3-hexadiene
788 1-cyano-1-fluoro-6-(trans-4-(trans-4-(4-pentylphenyl)cyclohexyl)oxymethylcyclohexyl)-1,3-hexadiene

EXAMPLE 48

Preparation of 1-cyano-1-fluoro-6-(trans-4-(4-(4-ethylphenyl)butyl)cyclohexyl)-1,3-hexadiene [Compound expressed by general formula I wherein $R^1$ represents ethyl group, $A^1$ represents 1,4-phenylene, $B^1$ represents 1,4-butenyl, n1 is 0, n2 is 0, n3 is 1, $R^2$ represents a group expressed by formula III, and X represents fluorine atom (Compound No. 789)]

Subject compound was synthesized by the same procedures as in Example 25 with the exception that 5-(trans-4-(4-(4-ethylphenyl)butyl)cyclohexyl)-2-pentene-1-al was used as starting material instead of trans-4-(trans-4-ethylcyclohexyl)cyclohexane carboaldehyde.

By the procedures similar to those described above, the following compounds (Compound Nos. 790 to 800) are synthesized.

790 1-cyano-1-fluoro-6-(trans-4-(4-(4-propylphenyl)butyl)cyclohexyl)-1,3-hexadiene
791 1-cyano-1-fluoro-6-(trans-4-(4-(4-pentylphenyl)butyl)cyclohexyl)-1,3-hexadiene
792 1-cyano-1-fluoro-6-(trans-4-(4-(4-heptylphenyl)butyl)cyclohexyl)-1,3-hexadiene
793 1-cyano-1-fluoro-6-(trans-4-(trans-4-(4-ethylphenyl)butyl)cyclohexyl)cyclohexyl)- 1,3-hexadiene
794 1-cyano-1-fluoro-6-(trans-4-(trans-4-(4-(4-propylphenyl)butyl)cyclohexyl)cyclohexyl)-1,3-hexadiene
795 1-cyano-1-fluoro-6-(trans-4-(trans-4-(4-(4-pentylphenyl)butyl)cyclohexyl)cyclohexyl)-1,3-hexadiene
796 1-cyano-1-fluoro-6-(trans-4-(trans-4-(4-(4-heptylphenyl)butyl)cyclohexyl)cyclohexyl)-1,3-hexadiene
797 1-cyano-1-fluoro-6-(trans-4-(4-(trans-4-(4-ethylphenyl)cyclohexyl)butyl)cyclohexyl)-1,3-hexadiene
798 1-cyano-1-fluoro-6-(trans-4-(4-(trans-4-(4-propylphenyl)cyclohexyl)butyl)cyclohexyl)-1,3-hexadiene
799 1-cyano-1-fluoro-6-(trans-4-(4-(trans-4-(4-pentylphenyl)cyclohexyl)butyl)cyclohexyl)-1,3-hexadiene
800 1-cyano-1-fluoro-6-(trans-4-(4-(trans-4-(4-hexylphenyl)cyclohexyl)butyl)cyclohexyl)-1,3-hexadiene

EXAMPLE 49

Preparation of 1-cyano-2-(trans-4-(4-cyanophenyl)cyclohexyl)ethene [Compound expressed by general formula I wherein $R^1$ represents cyano group, $A^1$ represents 1,4-phenylene, $B^1$ represents a covalent bond, n1 is 0, n2 is 0, n3 is 0, $R^2$ represents a group expressed by formula II, and X represents hydrogen atom (Compound No. 801)]

Subject compound was synthesized by the same procedures as in Example 1 with the exception that trans-4-(4-cyanophenyl)cyclohexane carboaldehyde was used as starting material instead of trans-4-(trans-4-ethylcyclohexyl)cyclohexane carboaldehyde.

NI 169.2 to 170.0° C.
CN 147.0 to 147.9° C.

By the procedures similar to those described above, the following compounds (Compound Nos. 802 to 820) are synthesized.

802 1-cyano-2-(trans-4-(4-fluorophenyl)cyclohexyl)ethene
903 1-cyano-2-(trans-4-(3,4-difluorophenyl)cyclohexyl)ethene
804 1-cyano-2-(trans-4-(4-trifluoromethylphenyl)cyclohexyl)ethene
805 1-cyano-2-(trans-4-(4-trifluoromethoxyphenyl)cyclohexyl)ethene 806 1-cyano-2-(trans-4-(2-(4-cyanophenyl)ethyl) cyclohexyl)ethene
807 1-cyano-2-(trans-4-(2-(4-fluorophenyl)ethyl) cyclohexyl)ethene
808 1-cyano-2-(trans-4-(2-(3,4-difluorophenyl)ethyl) cyclohexyl)ethene
809 1-cyano-2-(trans-4-(2-(4-trifluoromethylphenyl)ethyl) cyclohexyl)ethene
810 1-cyano-2-(trans-4-(2-(4-trifluoromethoxyphenyl) ethyl)cyclohexyl)ethene
811 1-cyano-2-(trans-4-(trans-4-(4-cyanophenyl) cyclohexyl)cyclohexyl)ethene
812 1-cyano-2-(trans-4-(trans-4-(4-fluorophenyl) cyclohexyl)cyclohexyl)ethene
813 1-cyano-2-(trans-4-(trans-4-(3,4-difluorophenyl) cyclohexyl)cyclohexyl)ethene
814 1-cyano-2-(trans-4-(trans-4-(4-trifluoromethylphenyl) cyclohexyl)cyclohexyl)ethene
815 1-cyano-2-(trans-4-(trans-4-(4-trifluoromethoxyphenyl)cyclohexyl)cyclohexyl)ethene
816 1-cyano-2-(trans-4-(2-(trans-4-(4-cyanophenyl) cyclohexyl)ethyl)cyclohexyl)ethene
817 1-cyano-2-(trans-4-(2-(trans-4-(4-fluorophenyl) cyclohexyl)ethyl)cyclohexyl)ethene
818 1-cyano-2-(trans-4-(2-(trans-4-(3,4-difluorophenyl) cyclohexyl)ethyl)cyclohexyl)ethene
819 1-cyano-2-(trans-4-(2-(trans-4-(4-trifluoromethylphenyl)cyclohexyl)ethyl)cyclohexyl) ethene
820 1-cyano-2-(trans-4-(2-(trans-4-(4-trifluoromethoxyphenyl)cyclohexyl)ethyl)cyclohexyl) ethene

EXAMPLE 50

Preparation of 1-cyano-2-(trans-4-(2E-(trans-4-(4-cyanophenyl)cyclohexyl)ethenyl)cyclohexyl)ethene [Compound expressed by general formula I wherein $R^1$ represents cyano group, $A^1$ represents 1,4-phenylene, $B^1$ represents a covalent bond, $A^2$ represents 1,4-cyclohexylene, $B^2$ represents 1,2-ethenylene, n1 is 0, n2 is 0, n3 is 0, $R^2$ represents a group expressed by formula II, and X represents hydrogen atom (Compound No. 821)]

Subject compound was synthesized by the same procedures as in Example 1 with the exception that trans-4-(2E-(4-cyanophenyl)ethenyl)cyclohexane carboaldehyde was used as starting material instead of trans-4-(trans-4-ethylcyclohexyl)cyclohexane carboaldehyde.

By the procedures similar to those described above, the following compounds (Compound Nos. 822 to 825) are synthesized.
822 1-cyano-2-(trans-4-(2E-(trans-4-(4-fluorophenyl) cyclohexyl)ethenyl)cyclohexyl)ethene
823 1-cyano-2-(trans-4-(2E-(trans-4-(3,4-difluorophenyl) cyclohexyl)ethenyl)cyclohexyl)ethene
824 1-cyano-2-(trans-4-(2E-(trans-4-(4-trifluoromethylphenyl)cyclohexyl)ethenyl)cyclohexyl) ethene
825 1-cyano-2-(trans-4-(2E-(trans-4-(4-trifluoromethoxyphenyl)cyclohexyl)ethenyl)cyclohexyl) ethene

EXAMPLE 51

Preparation of trans-4-(2-cyanoethenyl)cyclohexyl) 4-cyanobenzoate [Compound expressed by general formula I wherein $R^1$ represents cyano group, $A^1$ represents 1,4-phenylene, $B^1$ represents carbonyloxy, n1 is 0, n2 is 0, n3 is 0, $R^2$ represents a group expressed by formula II, and X represents hydrogen atom (Compound No. 826)]

Subject compound was synthesized by the same procedures as in Example 1 with the exception that trans-4-formylcyclohexyl 4-cyanobenzoate was used as starting material instead of trans-4-(trans-4-ethylcyclohexyl) cyclohexane carboaldehyde.

By the procedures similar to those described above, the following compounds (Compound Nos. 827 to 846) are synthesized.
827 trans-4-(2-cyanoethenyl)cyclohexyl 4-fluorobenzoate
828 trans-4-(2-cyanoethenyl)cyclohexyl 3,4-difluorobenzoate
829 trans-4-(2-cyanoethenyl)cyclohexyl 4-trifluoromethyl benzoate
830 trans-4-(2-cyanoethenyl)cyclohexyl 4-trifluoromethoxybenzoate
831 4-cyanophenyl trans-4-(2-cyanoethenyl)cyclohexane carboxylate
832 4-fluorophenyl trans-4-(2-cyanoethenyl)cyclohexane carboxylate
833 3,4-difluorophenyl trans-4-(2-cyanoethenyl) cyclohexane carboxylate
834 4-trifluoromethylphenyl trans-4-(2-cyanoethenyl) cyclohexane carboxylate
835 3-fluoro-4-cyanophenyl trans-4-(2-cyanoethenyl) cyclohexane carboxylate
836 4-trifluoromethoxyphenyl trans-4-(2-cyanoethenyl) cyclohexane carboxylate
837 trans-4-(4-cyanophenyl)cyclohexyl trans-4-(2-cyanoethenyl)cyclohexane carboxylate
838 trans-4-(4-fluorophenyl)cyclohexyl trans-4-(2-cyanoethenyl)cyclohexane carboxylate
839 trans-4-(3,4-difluorophenyl)cyclohexyl trans-4-(2-cyanoethenyl)cyclohexane carboxylate
840 trans-4-(4-trifluoromethylphenyl)cyclohexyl trans-4-(2-cyanoethenyl)cyclohexane carboxylate
841 trans-4-(3-fluoro-4-cyanophenyl)cyclohexyl trans-4-(2-cyanoethenyl)cyclohexane carboxylate
842 trans-4-(2-cyanoethenyl)cyclohexyl trans-4-(4-cyanophenyl)cyclohexane carboxylate
843 trans-4-(2-cyanoethenyl)cyclohexyl trans-4-(4-fluorophenyl)cyclohexane carboxylate
844 trans-4-(2-cyanoethenyl)cyclohexyl trans-4-(3,4-difluorophenyl)cyclohexane carboxylate
845 trans-4-(2-cyanoethenyl)cyclohexyl trans-4-(4-trifluoromethylphenyl)cyclohexane carboxylate
846 trans-4-(2-cyanoethenyl)cyclohexyl trans-4-(3-fluoro-4-cyanophenyl)cyclohexane carboxylate

EXAMPLE 52

Preparation of 1-cyano-2-(trans-4-(4-cyanophenyl) methoxycyclohexyl)ethene [Compound expressed by general formula I wherein $R^1$ represents cyano group, $A^1$ represents 1,4-phenylene, $B^1$ represents methyleneoxy, n1 is 0, n2 is 0, n3 is 0, $R^2$ represents a group expressed by formula II, and X represents hydrogen atom (Compound No. 847)]

Subject compound was synthesized by the same procedures as in Example 1 with the exception that trans-4-(4-cyanophenyl)methoxycyclohexane carboaldehyde was used as starting material instead of trans-4-(trans-4-ethylcyclohexyl)cyclohexane carboaldehyde.

By the procedures similar to those described above, the following compounds (Compound Nos. 848 to 861) are synthesized.
848 1-cyano-2-(trans-4-(4-fluorophenyl) methoxycyclohexyl)ethene
849 1-cyano-2-(trans-4-(3,4-difluorophenyl) methoxycyclohexyl)ethene 850 1-cyano-2-(trans-4-(4-trifluoromethylphenyl) methoxycyclohexyl)ethene
851 1-cyano-2-(trans-4-(4-trifluoromethoxyphenyl) methoxycyclohexyl)ethene
852 1-cyano-2-(trans-4-(trans-4-(4-cyanophenyl) cyclohexyl)methoxycyclohexyl)ethene
853 1-cyano-2-(trans-4-(trans-4-(4-fluorophenyl) cyclohexyl)methoxycyclohexyl)ethene
854 1-cyano-2-(trans-4-(trans-4-(3,4-difluorophenyl) cyclohexyl)methoxycyclohexyl)ethene
855 1-cyano-2-(trans-4-(trans-4-(4-trifluoromethylphenyl) cyclohexyl)methoxycyclohexyl)ethene
856 1-cyano-2-(trans-4-(trans-4-(4-trifluoromethoxyphenyl)cyclohexyl)methoxycyclohexyl) ethene
857 1-cyano-2-(trans-4-(2-(trans-4-(4-cyanophenyl) cyclohexyl)oxymethyl)cyclohexyl)ethene
858 1-cyano-2-(trans-4-(2-(trans-4-(4-fluorophenyl) cyclohexyl)oxymethyl)cyclohexyl)ethene
859 1-cyano-2-(trans-4-(2-(trans-4-(3,4-difluorophenyl) cyclohexyl)oxymethyl)cyclohexyl)ethene
860 1-cyano-2-(trans-4-(2-(trans-4-(4-trifluoromethylphenyl)cyclohexyl)oxymethyl) cyclohexyl)ethene
861 1-cyano-2-(trans-4-(2-(trans-4-(4-trifluoromethoxyphenyl)cyclohexyl)oxymethyl) cyclohexyl)ethene EXAMPLE 53
Preparation of 1-cyano-2-(trans-4-(4-(4-cyanophenyl)butyl) cyclohexyl)ethene [Compound expressed by general formula I wherein $R^1$ represents cyano group, $A^1$ represents 1,4-phenylene, $B^1$ represents 1,4-butylene, n1 is 0, n2 is 0, n3 is 0, $R^2$ represents a group expressed by formula II, and X represents hydrogen atom (Compound No. 862)]

Subject compound was synthesized by the same procedures as in Example 1 with the exception that trans-4-(4-(4-cyanophenyl)butyl)cyclohexane carboaldehyde was used as starting material instead of trans-4-(trans-4-ethylcyclohexyl)cyclohexane carboaldehyde.

By the procedures similar to those described above, the following compounds (Compound Nos. 863 to 876) are synthesized.
863 1-cyano-2-(trans-4-(4-(4-fluorophenyl)butyl) cyclohexyl)ethene
864 1-cyano-2-(trans-4-(4-(3,4-difluorophenyl)butyl) cyclohexyl)ethene
865 1-cyano-2-(trans-4-(4-(4-trifluoromethylphenyl)butyl) cyclohexyl)ethene
866 1-cyano-2-(trans-4-(4-(4-trifluoromethoxyphenyl) butyl)cyclohexyl)ethene
867 1-cyano-2-(trans-4-(trans-4-(4-(4-cyanophenyl)butyl) cyclohexyl)cyclohexyl)ethene
868 1-cyano-2-(trans-4-(trans-4-(4-(4-fluorophenyl)butyl) cyclohexyl)cyclohexyl)ethene
869 1-cyano-2-(trans-4-(trans-4-(4-(3,4-difluorophenyl) butyl)cyclohexyl)cyclohexyl)ethene
870 1-cyano-2-(trans-4-(trans-4-(4-(4-trifluoromethylphenyl)butyl)cyclohexyl)cyclohexyl) ethene
871 1-cyano-2-(trans-4-(trans-4-(4-(4-trifluoromethoxyphenyl)butyl)cyclohexyl)cyclohexyl) ethene
872 1-cyano-2-(trans-4-(4-(trans-4-(4-cyanophenyl) cyclohexyl)butyl)cyclohexyl)ethene
873 1-cyano-2-(trans-4-(4-(trans-4-(4-fluorophenyl) cyclohexyl)butyl)cyclohexyl)ethene
874 1-cyano-2-(trans-4-(4-(trans-4-(3,4-difluorophenyl) cyclohexyl)butyl)cyclohexyl)ethene
875 1-cyano-2-(trans-4-(4-(trans-4-(4-trifluoromethylphenyl)cyclohexyl)butyl)cyclohexyl) ethene
876 1-cyano-2-(trans-4-(4-(trans-4-(4-trifluoromethoxyphenyl)cyclohexyl)butyl)cyclohexyl) ethene EXAMPLE 54
Preparation of 1-cyano-4-(trans-4-(4-cyanophenyl) cyclohexyl)-1-butene [Compound expressed by general formula I wherein $R^1$ represents cyano group, $A^1$ represents 1,4-phenylene, $B^1$ represents a covalent bond, n1 is 0, n2 is 0, n3 is 1, $R^2$ represents a group expressed by formula II, and X represents hydrogen atom (Compound No. 877)]

Subject compound was synthesized by the same procedures as in Example 1 with the exception that 3-(trans-4-(4-cyanophenyl)cyclohexyl propanal was used as starting material instead of trans-4-(trans-4-ethylcyclohexyl) cyclohexane carboaldehyde.

By the procedures similar to those described above, the following compounds (Compound Nos. 878 to 896) are synthesized.
878 1-cyano-4-(trans-4-(4-fluorophenyl)cyclohexyl)-1-butene
879 1-cyano-4-(trans-4-(3,4-difluorophenyl)cyclohexyl)-1-butene
880 1-cyano-4-(trans-4-(4-trifluoromethylphenyl) cyclohexyl)-1-butene
881 1-cyano-4-(trans-4-(4-trifluoromethoxyphenyl) cyclohexyl)-1-butene
882 1-cyano-4-(trans-4-(2-(4-cyanophenyl)ethyl) cyclohexyl)-1 -butene
883 1-cyano-4-(trans-4-(2-(4-fluorophenyl)ethyl) cyclohexyl)-1-butene
884 1-cyano-4-(trans-4-(2-(3,4-difluorophenyl)ethyl) cyclohexyl)-1-butene
885 1-cyano-4-(trans-4-(2-(4-trifluoromethylphenyl)ethyl) cyclohexyl)-1-butene
886 1-cyano-4-(trans-4-(2-(4-trifluoromethoxyphenyl) ethyl)cyclohexyl)-1-butene
887 1-cyano-4-(trans-4-(trans-4-(4-cyanophenyl) cyclohexyl)cyclohexyl)-1-butene
888 1-cyano-4-(trans-4-(trans-4-(4-fluorophenyl) cyclohexyl)cyclohexyl)-1-butene
889 1-cyano-4-(trans-4-(trans-4-(3,4-difluorophenyl) cyclohexyl)cyclohexyl)-1-butene
890 1-cyano-4-(trans-4-(trans-4-(4-trifluoromethylphenyl) cyclohexyl)cyclohexyl)-1-butene
891 1-cyano-4-(trans-4-(trans-4-(4-trifluoromethoxyphenyl)cyclohexyl)cyclohexyl)-1-butene
892 1-cyano-4-(trans-4-(2-(trans-4-(4-cyanophenyl) cyclohexyl)ethyl)cyclohexyl)-1-butene
893 1-cyano-4-(trans-4-(2-(trans-4-(4-fluorophenyl) cyclohexyl)ethyl)cyclohexyl)-1-butene
894 1-cyano-4-(trans-4-(2-(trans-4-(3,4-difluorophenyl) cyclohexyl)ethyl)cyclohexyl)-1-butene
895 1-cyano-4-(trans-4-(2-(trans-4-(4-trifluoromethylphenyl)cyclohexyl)ethyl)cyclohexyl)-1-butene
896 1-cyano-4-(trans-4-(2-(trans-4-(4-trifluoromethoxyphenyl)cyclohexyl)ethyl)cyclohexyl)-1-butene EXAMPLE 55
Preparation of 1-cyano-4-(trans-4-(2E-(trans-4-(4-cyanophenyl)cyclohexyl)ethenyl)cyclohexyl)-1-butene [Compound expressed by general formula I wherein $R^1$ represents cyano group, $A^1$ represents 1,4-phenylene, $B^1$ represents covalent bond, $A^2$ represents 1,4-cyclohexylene, $B^2$ represents 1,2-ethenylene, n1 is 1, n2 is 0, n3 is 1, $R^2$ represents a group expressed by formula II, and X represents hydrogen atom (Compound No. 897)]

Subject compound was synthesized by the same procedures as in Example 1 with the exception that 3-(trans-4-(2E-(4-cyanophenyl)ethenyl)cyclohexyl propanal was used as starting material instead of trans-4-(trans-4-ethylcyclohexyl)cyclohexane carboaldehyde.

By the procedures similar to those described above, the following compounds (Compound Nos. 898 to 901) are synthesized.

898 1-cyano-4-(trans-4-(2E-(trans-4-(4-fluorophenyl)cyclohexyl)ethenyl)cyclohexyl)-1-butene
899 1-cyano-4-(trans-4-(2E-(trans-4-(3,4-difluorophenyl)cyclohexyl)ethenyl)cyclohexyl)-1-butene
900 1-cyano-4-(trans-4-(2E-(trans-4-(4-trifluoromethylphenyl)cyclohexyl)ethenyl)cyclohexyl)-1-butene
901 1-cyano-4-(trans-4-(2E-(trans-4-(4-trifluoromethoxyphenyl)cyclohexyl)ethenyl)cyclohexyl)-1-butene EXAMPLE 56
Preparation of trans-(4-cyano-3-butenyl)cyclohexyl 4-cyanobenzoate [Compound expressed by general formula I wherein $R^1$ represents cyano group, $A^1$ represents 1,4-phenylene, $B^1$ represents carbonyloxy, n1 is 0, n2 is 0, n3 is 1, $R^2$ represents a group expressed by formula II, and X represents hydrogen atom (Compound No. 902)]

Subject compound was synthesized by the same procedures as in Example 1 with the exception that trans-4-(2-formylethyl)cyclohexyl 4-cyanobenzoate was used as starting material instead of trans-4-(trans-4-ethylcyclohexyl)cyclohexane carboaldehyde.

By the procedures similar to those described above, the following compounds (Compound Nos. 903 to 922) are synthesized.

903 trans-4-(4-cyano-3-butenyl)cyclohexyl 4-fluorobenzoate
904 trans-4-(4-cyano-3-butenyl)cyclohexyl 3,4-difluorobenzoate
905 trans-4-(4-cyano-3-butenyl)cyclohexyl 4-trifluoromethylbenzoate
906 trans-4-(4-cyano-3-butenyl)cyclohexyl 4-trifluoromethoxybenzoate
907 4-cyanophenyl trans-4-(4-cyano-3-butenyl)cyclohexane carboxylate
908 4-fluorophenyl trans-4-(4-cyano-3-butenyl)cyclohexane carboxylate
909 3,4-difluorophenyl trans-4-(4-cyano-3-butenyl)cyclohexane carboxylate
910 4-trifluoromethylphenyl trans-4-(4-cyano-3-butenyl)cyclohexane carboxylate
911 3-fluoro-4-cyanophenyl trans-4-(4-cyano-3-butenyl)cyclohexane carboxylate
912 4-trifluoromethoxyphenyl trans-4-(4-cyano-3-butenyl)cyclohexane carboxylate
913 trans-4-(4-cyanophenyl)cyclohexyl trans-4-(4-cyano-3-butenyl)cyclohexane carboxylate
914 trans-4-(4-fluorophenyl)cyclohexyl trans-4-(4-cyano-3-butenyl)cyclohexane carboxylate
915 trans-4-(3,4-difluorophenyl)cyclohexyl trans-4-(4-cyano-3-butenyl)cyclohexane carboxylate
916 trans-4-(4-trifluoromethylphenyl)cyclohexyl trans-4-(4-cyano-3-butenyl)cyclohexane carboxylate
917 trans-4-(3-fluoro-4-cyanophenyl)cyclohexyl trans-4-(4-cyano-3-butenyl)cyclohexane carboxylate
918 trans-4-(4-cyano-3-butenyl)cyclohexyl trans-4-(4-cyanophenyl)cyclohexane carboxylate
919 trans-4-(4-cyano-3-butenyl)cyclohexyl trans-4-(4-fluorophenyl)cyclohexane carboxylate
920 trans-4-(4-cyano-3-butenyl)cyclohexyl trans-4-(3,4-difluorophenyl)cyclohexane carboxylate
921 trans-4-(4-cyano-3-butenyl)cyclohexyl trans-4-(4-trifluoromethylphenyl)cyclohexane carboxylate
922 trans-4-(4-cyano-3-butenyl)cyclohexyl trans-4-(3-fluoro-4-cyanophenyl)cyclohexane carboxylate EXAMPLE 57
Preparation of 1-cyano-4-(trans-4-(4-cyanophenyl)methoxycyclohexyl)-1-butene [Compound expressed by general formula I wherein $R^1$ represents cyano group, $A^1$ represents 1,4-phenylene, $B^1$ represents methyleneoxy, n1 is 0, n2 is 0, n3 is 1, $R^2$ represents a group expressed by formula II, and X represents hydrogen atom (Compound No. 923)]

Subject compound was synthesized by the same procedures as in Example 1 with the exception that 3-trans-4-(4-cyanophenyl)methoxycyclohexyl propanal was used as starting material instead of trans-4-(trans-4-ethylcyclohexyl)cyclohexane carboaldehyde.

By the procedures similar to those described above, the following compounds (Compound Nos. 924 to 937) are synthesized.

924 1-cyano-4-(trans-4-(4-fluorophenyl)methoxycyclohexyl)-1-butene
925 1-cyano-4-(trans-4-(3,4-difluorophenyl)methoxycyclohexyl)-1-butene
926 1-cyano-4-(trans-4-(4-trifluoromethylphenyl)methoxycyclohexyl)-1-butene
927 1-cyano-4-(trans-4-(4-trifluoromethoxyphenyl)methoxycyclohexyl)-1-butene
928 1-cyano-4-(trans-4-(trans-4-(4-cyanophenyl)cyclohexyl)methoxycyclohexyl)-1-butene
929 1-cyano-4-(trans-4-(trans-4-(4-fluorophenyl)cyclohexyl)methoxycyclohexyl)-1-butene
930 1-cyano-4-(trans-4-(trans-4-(3,4-difluorophenyl)cyclohexyl)methoxycyclohexyl)-1-butene
931 1-cyano-4-(trans-4-(trans-4-(4-trifluoromethylphenyl)cyclohexyl)methoxycyclohexyl)-1-butene
932 1-cyano-4-(trans-4-(trans-4-(4-trifluoromethoxyphenyl)cyclohexyl)methoxycyclohexyl)-1-butene
933 1-cyano-4-(trans-4-(2-(trans-4-(4-cyanophenyl)cyclohexyl)oxymethyl)cyclohexyl)-1-butene
934 1-cyano-4-(trans-4-(2-(trans-4-(4-fluorophenyl)cyclohexyl)oxymethyl)cyclohexyl)-1-butene
935 1-cyano-4-(trans-4-(2-(trans-4-(3,4-difluorophenyl)cyclohexyl)oxymethyl)cyclohexyl)-1-butene
936 1-cyano-4-(trans-4-(2-(trans-4-(4-trifluoromethylphenyl)cyclohexyl)oxymethyl)cyclohexyl)-1-butene
937 1-cyano-4-(trans-4-(2-(trans-4-(4-trifluoromethoxyphenyl)cyclohexyl)oxymethyl)cyclohexyl)-1-butene EXAMPLE 58
Preparation of 1-cyano-4-(trans-4-(4-(4-cyanophenyl)butyl)cyclohexyl)-1-butene [Compound expressed by general formula I wherein $R^1$ represents cyano group, $A^1$ represents 1,4-phenylene, $B^1$ represents 1,4-butylene, n1 is 0, n2 is 0, n3 is 1, $R^2$ represents a group expressed by formula II, and X represents hydrogen atom (Compound No. 938)]

Subject compound was synthesized by the same procedures as in Example 1 with the exception that 3-trans-4-(4-

(4-cyanophenyl)butyl)cyclohexyl propanal was used as starting material instead of trans-4-(trans-4-ethylcyclohexyl)cyclohexane carboaldehyde.

By the procedures similar to those described above, the following compounds (Compound Nos. 939 to 952) are synthesized.

939 1-cyano-4-(trans-4-(4-(4-fluorophenyl)butyl) cyclohexyl)-1-butene
940 1-cyano-4-(trans-4-(4-(3,4-difluorophenyl)butyl) cyclohexyl)- 1-butene
941 1-cyano-4-(trans-4-(4-(4-trifluoromethylphenyl)butyl) cyclohexyl)-1-butene
942 1-cyano-4-(trans-4-(4-(4-trifluoromethoxyphenyl) butyl)cyclohexyl)-1-butene
943 1-cyano-4-(trans-4-(trans-4-(4-(4-cyanophenyl)butyl) cyclohexyl)cyclohexyl)-1-butene
944 1-cyano-4-(trans-4-(trans-4-(4-(4-fluorophenyl)butyl) cyclohexyl)cyclohexyl)-1-butene
945 1-cyano-4-(trans-4-(trans-4-(4-(3,4-difluorophenyl) butyl)cyclohexyl)cyclohexyl)-1-butene
946 1-cyano-4-(trans-4-(4-(4-trifluoromethylphenyl)butyl)cyclohexyl)cyclohexyl)-1-butene
947 1-cyano-4-(trans-4-(4-(4-trifluoromethoxyphenyl)butyl)cyclohexyl)cyclohexyl)-1-butene
948 1-cyano-4-(trans-4-(4-(trans-4-(4-cyanophenyl) cyclohexyl)butyl)cyclohexyl)-1-butene
949 1-cyano-4-(trans-4-(4-(trans-4-(4-fluorophenyl) cyclohexyl)butyl)cyclohexyl)-1-butene
950 1-cyano-4-(trans-4-(4-(trans-4-(3,4-difluorophenyl) cyclohexyl)butyl)cyclohexyl)-1-butene
951 1-cyano-4-(trans-4-(4-(trans-4-(4-trifluoromethylphenyl)cyclohexyl)butyl)cyclohexyl)-1-butene
952 1-cyano-4-(trans-4-(4-(trans-4-(4-trifluoromethoxyphenyl)cyclohexyl)butyl)cyclohexyl)-1-butene

EXAMPLE 59

Preparation of 1-cyano-4-(trans-4-(4-cyanophenyl) cyclohexyl)- 1,3-butadiene [Compound expressed by general formula I wherein $R^1$ represents cyano group, $A^1$ represents 1,4-phenylene, $B^1$ represents a covalent bond, n1 is 0, n2 is 0, n3 is 0, $R^2$ represents a group expressed by formula III, and X represents hydrogen atom (Compound No. 953)]

Subject compound was synthesized by the same procedures as in Example 1 with the exception that 3-(trans-4-(4-cyanophenyl)cyclohexyl-2-propene-1-al was used as starting material instead of trans-4-(trans-4-ethylcyclohexyl)cyclohexane carboaldehyde.

By the procedures similar to those described above, the following compounds (Compound Nos. 954 to 972) are synthesized.

954 1-cyano-4-(trans-4-(4-fluorophenyl)cyclohexyl)-1,3-butadiene
955 1-cyano-4-(trans-4-(3,4-difluorophenyl)cyclohexyl)-1,3-butadiene
956 1-cyano-4-(trans-4-(4-trifluoromethylphenyl) cyclohexyl)-1,3-butadiene
957 1-cyano-4-(trans-4-(4-trifluoromethoxyphenyl) cyclohexyl)-1,3-butadiene
958 1-cyano-4-(trans-4-(2-(4-cyanophenyl)ethyl) cyclohexyl)-1,3-butadiene
959 1-cyano-4-(trans-4-(2-(4-fluorophenyl)ethyl) cyclohexyl)-1,3-butadiene
960 1-cyano-4-(trans-4-(2-(3,4-difluorophenyl)ethyl) cyclohexyl)-1,3-butadiene
961 1-cyano-4-(trans-4-(2-(4-trifluoromethylphenyl)ethyl) cyclohexyl)-1,3-butadiene
962 1-cyano-4-(trans-4-(2-(4-trifluoromethoxyphenyl) ethyl)cyclohexyl)-1,3-butadiene
963 1-cyano-4-(trans-4-(trans-4-(4-cyanophenyl) cyclohexyl)cyclohexyl)-1,3-butadiene
964 1-cyano-4-(trans-4-(trans-4-(4-fluorophenyl) cyclohexyl)cyclohexyl)-1,3-butadiene
965 1-cyano-4-(trans-4-(trans-4-(3,4-difluorophenyl) cyclohexyl)cyclohexyl)-1,3-butadiene
966 1-cyano-4-(trans-4-(trans-4-(4-trifluoromethylphenyl) cyclohexyl)cyclohexyl)-1,3-butadiene
967 1-cyano-4-(trans-4-(trans-4-(4-trifluoromethoxyphenyl)cyclohexyl)cyclohexyl)-1,3-butadiene
968 1-cyano-4-(trans-4-(2-(trans-4-(4-cyanophenyl) cyclohexyl)ethyl)cyclohexyl)-1,3-butadiene
969 1-cyano-4-(trans-4-(2-(trans-4-(4-fluorophenyl) cyclohexyl)ethyl)cyclohexyl)-1,3-butadiene
970 1-cyano-4-(trans-4-(2-(trans-4-(3,4-difluorophenyl) cyclohexyl)ethyl)cyclohexyl)-1,3-butadiene
971 1-cyano-4-(trans-4-(2-(trans-4-(4-trifluoromethylphenyl)cyclohexyl)ethyl)cyclohexyl)-1,3-butadiene
972 1-cyano-4-(trans-4-(2-(trans-4-(4-trifluoromethoxyphenyl)cyclohexyl)ethyl)cyclohexyl)-1,3-butadiene

EXAMPLE 60

Preparation of 1-cyano-4-(trans-4-(2E-(trans-4-(4-cyanophenyl)cyclohexyl)ethenyl)cyclohexyl)-1,3-butadiene [Compound expressed by general formula I wherein $R^1$ represents cyano group, $A^1$ represents 1,4-phenylene, $B^1$ represents a covalent bond, $A^2$ represents 1,4-cyclohexylene, $B^2$ represents 1,2-ethenylene, n1 is 1, n2 is 0, n3 is 0, $R^2$ represents a group expressed by formula III, and X represents hydrogen atom (Compound No. 973)]

Subject compound was synthesized by the same procedures as in Example 1 with the exception that 3-(trans-4-(2E-(4-cyanophenyl)ethenyl)cyclohexyl-2-propene-1-al was used as starting material instead of trans-4-(trans-4-ethylcyclohexyl)cyclohexane carboaldehyde.

By the procedures similar to those described above, the following compounds (Compound Nos. 973 to 976) are synthesized.

973 1-cyano-4-(trans-4-(2E-(trans-4-(4-fluorophenyl) cyclohexyl)ethenyl)cyclohexyl)-1,3-butadiene
974 1-cyano-4-(trans-4-(2E-(trans-4-(3,4-difluorophenyl) cyclohexyl)ethenyl)cyclohexyl)-1,3-butadiene
975 1-cyano-4-(trans-4-(2E-(trans-4-(4-trifluoromethylphenyl)cyclohexyl)ethenyl)cyclohexyl)-1,3-butadiene
976 1-cyano-4-(trans-4-(2E-(trans-4-(4-trifluoromethoxyphenyl)cyclohexyl)ethenyl)cyclohexyl)-1,3-butadiene

EXAMPLE 61

Preparation of trans-4-(4-cyano-1,3-butadienyl)cyclohexyl 4-ethylbenzoate [Compound expressed by general formula I wherein $R^1$ represents cyano group, $A^1$ represents 1,4-phenylene, $B^1$ represents carbonyloxy, n1 is 0, n2 is 0, n3 is 0, $R^2$ represents a group expressed by formula III, and X represents hydrogen atom (Compound No. 977)]

Subject compound was synthesized by the same procedures as in Example 1 with the exception that trans-4-(2-formylethyl)cyclohexyl 4-cyano benzoate was used as starting material instead of trans-4-(trans-4-ethylcyclohexyl) cyclohexane carboaldehyde.

By the procedures similar to those described above, the following compounds (Compound Nos. 978 to 997) are synthesized.

978 trans-4-(4-cyano-1,3-butadienyl)cyclohexyl 4-fluorobenzoate
979 trans-4-(4-cyano-1,3-butadienyl)cyclohexyl 3,4-difluorobenzoate
980 trans-4-(4-cyano-1,3-butadienyl)cyclohexyl 4-trifluoromethyl benzoate
981 trans-4-(4-cyano-1,3-butadienyl)cyclohexyl 4-trifluoromethoxybenzoate
982 4-cyanophenyl trans-4-(4-cyano-1,3-butadienyl) cyclohexane carboxylate
983 4-fluorophenyl trans-4-(4-cyano-1,3-butadienyl) cyclohexane carboxylate
984 3,4-difluorophenyl trans-4-(4-cyano-1,3-butadienyl) cyclohexane carboxylate
985 4-trifluoromethylphenyl trans-4-(4-cyano-1,3-butadienyl)cyclohexane carboxylate
986 3-fluoro-4-cyanophenyl trans-4-(4-cyano-1,3-butadienyl)cyclohexane carboxylate
987 4-trifluoromethoxyphenyl trans-4-(4-cyano-1,3-butadienyl)cyclohexane carboxylate
988 trans-4-(4-cyanophenyl)cyclohexyl trans-4-(4-cyano-1,3-butadienyl)cyclohexane carboxylate
989 trans-4-(4-fluorophenyl)cyclohexyl trans-4-(4-cyano-1,3-butadienyl)cyclohexane carboxylate
990 trans-4-(3,4-difluorophenyl)cyclohexyl trans-4-(4-cyano-1,3-butadienyl)cyclohexane carboxylate
991 trans-4-(4-trifluoromethylphenyl)cyclohexyl trans-4-(4-cyano-1,3-butadienyl)cyclohexane carboxylate
992 trans-4-(3-fluoro-4-cyanophenyl)cyclohexyl trans-4-(4-cyano-1,3-butadienyl)cyclohexane carboxylate
993 trans-4-(4-cyano-1,3-butadienyl)cyclohexyl trans-4-(4-cyanophenyl)cyclohexane carboxylate
994 trans-4-(4-cyano-1,3-butadienyl)cyclohexyl trans-4-(4-fluorophenyl)cyclohexane carboxylate
995 trans-4-(4-cyano-1,3-butadienyl)cyclohexyl trans-4-(3,4-difluorophenyl)cyclohexane carboxylate
996 trans-4-(4-cyano-1,3-butadienyl)cyclohexyl trans-4-(4-trifluoromethylphenyl)cyclohexane carboxylate
997 trans-4-(4-cyano-1,3-butadienyl)cyclohexyl trans-4-(3-fluoro-4-cyanophenyl)cyclohexane carboxylate

EXAMPLE 62

Preparation of 1-cyano-4-(trans-4-(4-cyanophenyl) methoxycyclohexyl)-1,3-butadiene [Compound expressed by general formula I wherein $R^1$ represents cyano group, $A^1$ represents 1,4-phenylene, $B^1$ represents methyleneoxy, n1 is 0, n2 is 0, n3 is 0, $R^2$ represents a group expressed by formula III, and X represents hydrogen atom (Compound No. 998)]

Subject compound was synthesized by the same procedures as in Example 1 with the exception that 3-(trans-4-(4-cyanophenyl)methoxycyclohexyl)- 2-propene-1-al was used as starting material instead of trans-4-(trans-4-ethylcyclohexyl)cyclohexane carboaldehyde.

By the procedures similar to those described above, the following compounds (Compound Nos. 999 to 1012) are synthesized.

999 1-cyano-4-(trans-4-(4-fluorophenyl) methoxycyclohexyl)-1,3-butadiene
1000 1-cyano-4-(trans-4-(3,4-difluorophenyl) methoxycyclohexyl)-1,3-butadiene
1001 1-cyano-4-(trans-4-(4-trifluoromethylphenyl) methoxycyclohexyl)-1,3-butadiene
1002 1-cyano-4-(trans-4-(4-trifluoromethoxyphenyl) methoxycyclohexyl)-1,3-butadiene
1003 1-cyano-4-(trans-4-(trans-4-(4-cyanophenyl) cyclohexyl)methoxycyclohexyl)-1,3-butadiene
1004 1-cyano-4-(trans-4-(trans-4-(4-fluorophenyl) cyclohexyl)methoxycyclohexyl)-1,3-butadiene
1005 1-cyano-4-(trans-4-(trans-4-(3,4-difluorophenyl) cyclohexyl)methoxycyclohexyl)-1,3-butadiene
1006 1-cyano-4-(trans-4-(trans-4-(4-trifluoromethylphenyl) cyclohexyl)methoxycyclohexyl)-1,3-butadiene
1007 1-cyano-4-(trans-4-(trans-4-(4-trifluoromethoxyphenyl)cyclohexyl) methoxycyclohexyl)-1,3-butadiene
1008 1-cyano-4-(trans-4-(2-(trans-4-(4-cyanophenyl) cyclohexyl)oxymethyl)cyclohexyl)-1,3-butadiene
1009 1-cyano-4-(trans-4-(2-(trans-4-(4-fluorophenyl) cyclohexyl)oxymethyl)cyclohexyl)-1,3-butadiene
1010 1-cyano-4-(trans-4-(2-(trans-4-(3,4-difluorophenyl) cyclohexyl)oxymethyl)cyclohexyl)-1,3-butadiene
1011 1-cyano-4-(trans-4-(2-(trans-4-(4-trifluoromethylphenyl)cyclohexyl)oxymethyl) cyclohexyl)-1,3-butadiene
1012 1-cyano-4-(trans-4-(2-(trans-4-(4-trifluoromethoxyphenyl)cyclohexyl)oxymethyl) cyclohexyl)-1,3-butadiene

EXAMPLE 63

Preparation of 1-cyano-4-(trans-4-(4-(4-cyanophenyl)butyl) cyclohexyl)-1,3-butadiene [Compound expressed by general formula I wherein $R^1$ represents cyano group, $A^1$ represents 1,4-phenylene, $B^1$ represents 1,4-butylene, n1 is 0, n2 is 0, n3 is 0, $R^2$ represents a group expressed by formula III, and X represents hydrogen atom (Compound No. 1013)]

Subject compound was synthesized by the same procedures as in Example 1 with the exception that 3-(trans-4-(4-(4-cyanophenyl)butyl)cyclohexyl)-2-propene-1-al was used as starting material instead of trans-4-(trans-4-ethylcyclohexyl)cyclohexane carboaldehyde.

By the procedures similar to those described above, the following compounds (Compound Nos. 1014 to 1027) are synthesized.

1014 1-cyano-4-(trans-4-(4-(4-fluorophenyl)butyl) cyclohexyl)-1,3-butadiene
1015 1-cyano-4-(trans-4-(4-(3,4-difluorophenyl)butyl) cyclohexyl)-1,3-butadiene
1016 1-cyano-4-(trans-4-(4-(4-trifluoromethylphenyl)butyl) cyclohexyl)-1,3-butadiene
1017 1-cyano-4-(trans-4-(4-(4-trifluoromethoxyphenyl) butyl)cyclohexyl)-1,3-butadiene
1018 1-cyano-4-(trans-4-(trans-4-(4-(4-cyanophenyl)butyl) cyclohexyl)cyclohexyl)-1,3-butadiene
1019 1-cyano-4-(trans-4-(trans-4-(4-(4-fluorophenyl)butyl) cyclohexyl)cyclohexyl)-1,3-butadiene
1020 1-cyano-4-(trans-4-(trans-4-(4-(3,4-difluorophenyl) butyl)cyclohexyl)cyclohexyl)-1,3-butadiene
1021 1-cyano-4-(trans-4-(trans-4-(4-(4-trifluoromethylphenyl)butyl)cyclohexyl)cyclohexyl)-1,3-butadiene
1022 1-cyano-4-(trans-4-(trans-4-(4-(4-trifluoromethoxyphenyl)butyl)cyclohexyl)cyclohexyl)-1,3-butadiene
1023 1-cyano-4-(trans-4-(4-(trans-4-(4-cyanophenyl) cyclohexyl)butyl)cyclohexyl)-1,3-butadiene
1024 1-cyano-4-(trans-4-(4-(trans-4-(4-fluorophenyl) cyclohexyl)butyl)cyclohexyl)-1,3-butadiene
1025 1-cyano-4-(trans-4-(4-(trans-4-(3,4-difluorophenyl) cyclohexyl)butyl)cyclohexyl)-1,3-butadiene
1026 1-cyano-4-(trans-4-(4-(trans-4-(4-trifluoromethylphenyl)cyclohexyl)butyl)cyclohexyl)-1,3-butadiene 1027 1-cyano-4-(trans-4-(4-(trans-4-(4-trifluoromethoxyphenyl)cyclohexyl)butyl)cyclohexyl)-1,3-butadiene

EXAMPLE 64

Preparation of 1-cyano-6-(trans-4-(4-cyanophenyl)cyclohexyl)-1,3-hexadiene [Compound expressed by general formula I wherein $R^1$ represents cyano group, $A^1$ represents 1,4-phenylene, $B^1$ represents a covalent bond, n1 is 0, n2 is 0, n3 is 1, $R^2$ represents a group expressed by formula III, and X represents hydrogen atom (Compound No. 1028)]

Subject compound was synthesized by the same procedures as in Example 1 with the exception that 5-(trans-4-(4-cyanophenyl)cyclohexyl)-2-pentene-1-al was used as starting material instead of trans-4-(trans-4-ethylcyclohexyl)cyclohexane carboaldehyde.

By the procedures similar to those described above, the following compounds (Compound Nos. 1029 to 1047) are synthesized.

1029 1-cyano-6-(trans-4-(4-fluorophenyl)cyclohexyl)-1,3-hexadiene 1030 1-cyano-6-(trans-4-(3,4-difluorophenyl)cyclohexyl)-1,3-hexadiene 1031 1-cyano-6-(trans-4-(4-trifluoromethylphenyl)cyclohexyl)-1,3-hexadiene 1032 1-cyano-6-(trans-4-(4-trifluoromethoxyphenyl)cyclohexyl)-1,3-hexadiene 1033 1-cyano-6-(trans-4-(2-(4-cyanophenyl)ethyl)cyclohexyl)-1,3-hexadiene 1034 1-cyano-6-(trans-4-(2-(4-fluorophenyl)ethyl)cyclohexyl)-1,3-hexadiene 1035 1-cyano-6-(trans-4-(2-(3,4-difluorophenyl)ethyl)cyclohexyl)-1,3-hexadiene 1036 1-cyano-6-(trans-4-(2-(4-trifluoromethylphenyl)ethyl)cyclohexyl)-1,3-hexadiene 1037 1-cyano-6-(trans-4-(2-(4-trifluoromethoxyphenyl)ethyl)cyclohexyl)-1,3-hexadiene 1038 1-cyano-6-(trans-4-(trans-4-(4-cyanophenyl)cyclohexyl)cyclohexyl)-1,3-hexadiene 1039 1-cyano-6-(trans-4-(trans-4-(4-fluorophenyl)cyclohexyl)cyclohexyl)-1,3-hexadiene 1040 1-cyano-6-(trans-4-(trans-4-(3,4-difluorophenyl)cyclohexyl)cyclohexyl)-1,3-hexadiene 1041 1-cyano-6-(trans-4-(trans-4-(4-trifluoromethylphenyl)cyclohexyl)cyclohexyl)-1,3-hexadiene 1042 1-cyano-6-(trans-4-(trans-4-(4-trifluoromethoxyphenyl)cyclohexyl)cyclohexyl)-1,3-hexadiene 1043 1-cyano-6-(trans-4-(2-(trans-4-(4-cyanophenyl)cyclohexyl)ethyl)cyclohexyl)-1,3-hexadiene 1044 1-cyano-6-(trans-4-(2-(trans-4-(4-fluorophenyl)cyclohexyl)ethyl)cyclohexyl)-1,3-hexadiene 1045 1-cyano-6-(trans-4-(2-(trans-4-(3,4-difluorophenyl)cyclohexyl)ethyl)cyclohexyl)-1,3-hexadiene 1046 1-cyano-6-(trans-4-(2-(trans-4-(4-trifluoromethylphenyl)cyclohexyl)ethyl)cyclohexyl)-1,3-hexadiene 1047 1-cyano-6-(trans-4-(2-(trans-4-(4-trifluoromethoxyphenyl)cyclohexyl)ethyl)cyclohexyl)-1,3-hexadiene

EXAMPLE 65

Preparation of 1-cyano-6-(trans-4-(2E-(trans-4-(4-cyanophenyl)cyclohexyl)ethenyl)cyclohexyl)-1,3-hexadiene [Compound expressed by general formula I wherein $R^1$ represents cyano group, $A^1$ represents 1,4-phenylene, $B^1$ represents a covalent bond, $A^2$ represents 1,4-cyclohexylene, $B^2$ represents 1,2-ethenylene, n1 is 1, n2 is 0, n3 is 1, $R^2$ represents a group expressed by formula III, and X represents hydrogen atom (Compound No. 1048)]

Subject compound was synthesized by the same procedures as in Example 1 with the exception that 5-(trans-4-(2E-(4-cyanophenyl)ethenyl)cyclohexyl)-2-pentene-1-al was used as starting material instead of trans-4-(trans-4-ethylcyclohexyl)cyclohexane carboaldehyde.

By the procedures similar to those described above, the following compounds (Compound Nos. 1049 to 1052) are synthesized.

1049 1-cyano-6-(trans-4-(2E-(trans-4-(4-fluorophenyl)cyclohexyl)ethenyl)cyclohexyl)-1,3-hexadiene 1050 1-cyano-6-(trans-4-(2E-(trans-4-(3,4-difluorophenyl)cyclohexyl)ethenyl)cyclohexyl)-1,3-hexadiene 1051 1-cyano-6-(trans-4-(2E-(trans-4-(4-trifluoromethylphenyl)cyclohexyl)ethenyl)cyclohexyl)-1,3-hexadiene 1052 1-cyano-6-(trans-4-(2E-(trans-4-(4-trifluoromethoxyphenyl)cyclohexyl)ethenyl)cyclohexyl)-1,3-hexadiene

EXAMPLE 66

Preparation of trans-4-(6-cyano-3,5-hexadienyl)cyclohexyl 4-ethyl benzoate [Compound expressed by general formula I wherein $R^1$ represents cyano group, $A^1$ represents 1,4-phenylene, $B^1$ represents carbonyloxy, n1 is 0, n2 is 0, n3 is 1, $R^2$ represents a group expressed by formula III, and X represents hydrogen atom (Compound No. 1053)]

Subject compound was synthesized by the same procedures as in Example 1 with the exception that trans-4-(4-formyl-3-butenyl)cyclohexyl 4-cyanobenzoate was used as starting material instead of trans-4-(trans-4-ethylcyclohexyl)cyclohexane carboaldehyde.

By the procedures similar to those described above, the following compounds (Compound Nos. 1054 to 1073) are synthesized.

1054 trans-4-(6-cyano-3,5-hexadienyl)cyclohexyl 4-fluorobenzoate 1055 trans-4-(6-cyano-3,5-hexadienyl)cyclohexyl 3,4-difluorobenzoate 1056 trans-4-(6-cyano-3,5-hexadienyl)cyclohexyl 4-trifluoromethyl benzoate 1057 trans-4-(6-cyano-3,5-hexadienyl)cyclohexyl 4-trifluoromethoxybenzoate 1058 4-cyanophenyl trans-4-(6-cyano-3,5-hexadienyl)cyclohexane carboxylate 1059 4-fluorophenyl trans-4-(6-cyano-3,5-hexadienyl)cyclohexane carboxylate 1060 3,4-difluorophenyl trans-4-(6-cyano-3,5-hexadienyl)cyclohexane carboxylate 1061 4-trifluoromethylphenyl trans-4-(6-cyano-3,5-hexadienyl)cyclohexane carboxylate 1062 3-fluoro-4-cyanophenyl trans-4-(6-cyano-3,5-hexadienyl)cyclohexane carboxylate 1063 4-trifluoromethoxyphenyl trans-4-(6-cyano-3,5-hexadienyl)cyclohexane carboxylate 1064 trans-4-(4-cyanophenyl)cyclohexyl trans-4-(6-cyano-3,5-hexadienyl)cyclohexane carboxylate 1065 trans-4-(4-fluorophenyl)cyclohexyl trans-4-(6-cyano-3,5-hexadienyl)cyclohexane carboxylate 1066 trans-4-(3,4-difluorophenyl)cyclohexyl trans-4-(6-cyano-3,5-hexadienyl)cyclohexane carboxylate 1067 trans-4-(4-trifluoromethylphenyl)cyclohexyl trans-4-(6-cyano-3,5-hexadienyl)cyclohexane carboxylate 1068 trans-4-(3-fluoro-4-cyanophenyl)cyclohexyl trans-4-(6-cyano-3,5-hexadienyl)cyclohexane carboxylate 1069 trans-4-(6-cyano-3,5-hexadienyl)cyclohexyl trans-4-(4-cyanophenyl)cyclohexane carboxylate 1070 trans-4-(6-cyano-3,5-hexadienyl)cyclohexyl trans-4-(4-fluorophenyl)cyclohexane carboxylate 1071 trans-4-(6-cyano-3,5-hexadienyl)cyclohexyl trans-4-(3,4-difluorophenyl)cyclohexane carboxylate 1072 trans-4-(6-cyano-3,5-hexadienyl)cyclohexyl trans-4-(4-trifluoromethylphenyl)cyclohexane carboxylate 1073 trans-4-(6-cyano-3,5-hexadienyl)cyclohexyl trans-4-(3-fluoro-4-cyanophenyl)cyclohexane carboxylate

EXAMPLE 67

Preparation of 1-cyano-6-(trans-4-(4-cyanophenyl)methoxycyclohexyl)-1,3-hexadiene [Compound expressed by general formula I wherein $R^1$ represents cyano group, $A^1$ represents 1,4-phenylene, $B^1$ represents methyleneoxy, n1 is 0, n2 is 0, n3 is 1, $R^2$ represents a group expressed by formula III, and X represents hydrogen atom (Compound No. 1074)]

Subject compound was synthesized by the same procedures as in Example 1 with the exception that 5-(trans-4-(4-cyanophenyl)methoxycyclohexyl)- 2-pentene-1-al was used as starting material instead of trans-4-(trans-4-ethylcyclohexyl)cyclohexane carboaldehyde.

By the procedures similar to those described above, the following compounds (Compound Nos. 1075 to 1088) are synthesized.

1075 1-cyano-6-(trans-4-(4-fluorophenyl)methoxycyclohexyl)-1,3-hexadiene 1076 1-cyano-6-(trans-4-(3,4-difluorophenyl)methoxycyclohexyl)-1,3-hexadiene 1077 1-cyano-6-(trans-4-(4-trifluoromethylphenyl)methoxycyclohexyl)-1,3-hexadiene 1078 1-cyano-6-(trans-4-(4-trifluoromethoxyphenyl)methoxycyclohexyl)-1,3-hexadiene 1079 1-cyano-6-(trans-4-(trans-4-(4-cyanophenyl)cyclohexyl)methoxycyclohexyl)-1,3-hexadiene 1080 1-cyano-6-(trans-4-(trans-4-(4-fluorophenyl)cyclohexyl)methoxycyclohexyl)-1,3-hexadiene 1081 1-cyano-6-(trans-4-(trans-4-(3,4-difluorophenyl)cyclohexyl)methoxycyclohexyl)-1,3-hexadiene 1082 1-cyano-6-(trans-4-(trans-4-(4-trifluoromethylphenyl)cyclohexyl)methoxycyclohexyl)-1,3-hexadiene 1083 1-cyano-6-(trans-4-(trans-4-(4-trifluoromethoxyphenyl)cyclohexyl)methoxycyclohexyl)-1,3-hexadiene 1084 1-cyano-6-(trans-4-(2-(trans-4-(4-cyanophenyl)cyclohexyl)oxymethyl)cyclohexyl)-1,3-hexadiene 1085 1-cyano-6-(trans-4-(2-(trans-4-(4-fluorophenyl)cyclohexyl)oxymethyl)cyclohexyl)- 1,3-hexadiene 1086 1-cyano-6-(trans-4-(2-(trans-4-(3,4-difluorophenyl)cyclohexyl)oxymethyl)cyclohexyl)-1,3-hexadiene 1087 1-cyano-6-(trans-4-(2-(trans-4-(4-trifluoromethylphenyl)cyclohexyl)oxymethyl)cyclohexyl)-1,3-hexadiene 1088 1-cyano-6-(trans-4-(2-(trans-4-(4-trifluoromethoxyphenyl)cyclohexyl)oxymethyl)cyclohexyl)-1,3-hexadiene

EXAMPLE 68

Preparation of 1-cyano-6-(trans-4-(4-(4-cyanophenyl)butyl)cyclohexyl)-1,3-hexadiene [Compound expressed by general formula I wherein $R^1$ represents cyano group, $A^1$ represents 1,4-phenylene, $B^1$ represents 1,4-butylene, n1 is 0, n2 is 0, n3 is 1, $R^2$ represents a group expressed by formula III, and X represents hydrogen atom (Compound No. 1089)]

Subject compound was synthesized by the same procedures as in Example 1 with the exception that 5-(trans-4-(4-(4-cyanophenyl)butyl)cyclohexyl)-2-pentene-1-al was used as starting material instead of trans-4-(trans-4-ethylcyclohexyl)cyclohexane carboaldehyde.

By the procedures similar to those described above, the following compounds (Compound Nos. 1090 to 1103) are synthesized.

1090 1-cyano-6-(trans-4-(4-(4-fluorophenyl)butyl)cyclohexyl)-1,3-hexadiene 1091 1-cyano-6-(trans-4-(4-(3,4-difluorophenyl)butyl)cyclohexyl)-1,3-hexadiene 1092 1-cyano-6-(trans-4-(4-(4-trifluoromethylphenyl)butyl)cyclohexyl)- 1,3-hexadiene 1093 1-cyano-6-(trans-4-(4-(4-trifluoromethoxyphenyl)butyl)cyclohexyl)-1,3-hexadiene 1094 1-cyano-6-(trans-4-(trans-4-(4-(4-cyanophenyl)butyl)cyclohexyl)cyclohexyl)-1,3-hexadiene 1095 1-cyano-6-(trans-4-(trans-4-(4-(4-fluorophenyl)butyl)cyclohexyl)cyclohexyl)-1,3-hexadiene 1096 1-cyano-6-(trans-4-(trans-4-(4-(3,4-difluorophenyl)butyl)cyclohexyl)cyclohexyl)-1,3-hexadiene 1097 1-cyano-6-(trans-4-(trans-4-(4-(4-trifluoromethylphenyl)butyl)cyclohexyl)cyclohexyl)-1,3-hexadiene 1098 1-cyano-6-(trans-4-(trans-4-(4-(4-trifluoromethoxyphenyl)butyl)cyclohexyl)cyclohexyl)-1,3-hexadiene 1099 1-cyano-6-(trans-4-(4-(trans-4-(4-cyanophenyl)cyclohexyl)butyl)cyclohexyl)-1,3-hexadiene 1100 1-cyano-6-(trans-4-(4-(trans-4-(4-fluorophenyl)cyclohexyl)butyl)cyclohexyl)-1,3-hexadiene 1101 1-cyano-6-(trans-4-(4-(trans-4-(3,4-difluorophenyl)cyclohexyl)butyl)cyclohexyl)-1,3-hexadiene 1102 1-cyano-6-(trans-4-(4-(trans-4-(4-trifluoromethylphenyl)cyclohexyl)butyl)cyclohexyl)-1,3-hexadiene 1103 1-cyano-6-(trans-4-(4-(trans-4-(4-trifluoromethoxyphenyl)cyclohexyl)butyl)cyclohexyl)-1,3-hexadiene

EXAMPLE 69

Preparation of 1-cyano-1-fluoro-2-(trans-4-(4-cyanophenyl)cyclohexyl)ethene [Compound expressed by general formula I wherein $R^1$ represents cyano group, $A^1$ represents 1,4-phenylene, $B^1$ represents a covalent bond, n1 is 0, n2 is 0, n3 is 0, $R^2$ represents a group expressed by formula II, and X represents fluorine atom (Compound No. 1104)]

Subject compound was synthesized by the same procedures as in Example 25 with the exception that trans-4-(4-cyanophenyl)cyclohexane carboaldehyde was used as starting material instead of trans-4-(trans-4-ethylcyclohexyl)cyclohexane carboaldehyde.

By the procedures similar to those described above, the following compounds (Compound Nos. 1105 to 1123) are synthesized.

1105 1-cyano-1-fluoro-2-(trans-4-(4-fluorophenyl)cyclohexyl)ethene 1106 1-cyano-1-fluoro-2-(trans-4-(3,4-difluorophenyl)cyclohexyl)ethene 1107 1-cyano-1-fluoro-2-(trans-4-(4-trifluoromethylphenyl)cyclohexyl)ethene 1108 1-cyano-1-fluoro-2-(trans-4-(4-trifluoromethoxyphenyl)cyclohexyl)ethene 1109 1-cyano-1-fluoro-2-(trans-4-(2-(4-cyanophenyl)ethyl)cyclohexyl)ethene 1110 1-cyano-1-fluoro-2-(trans-4-(2-(4-fluorophenyl)ethyl)cyclohexyl)ethene 1111 1-cyano-1-fluoro-2-(trans-4-(2-(3,4-difluorophenyl)ethyl)cyclohexyl)ethene 1112 1-cyano-1-fluoro-2-(trans-4-(2-(4-trifluoromethylphenyl)ethyl)cyclohexyl)ethene 1113 1-cyano-1-fluoro-2-(trans-4-(2-(4-trifluoromethoxyphenyl)ethyl)cyclohexyl)ethene 1114 1-cyano-1-fluoro-2-(trans-4-(trans-4-(4-cyanophenyl)cyclohexyl)cyclohexyl)ethene 1115 1-cyano-1-fluoro-2-(trans-4-(trans-4-(4-fluorophenyl)cyclohexyl)cyclohexyl)ethene 1116 1-cyano-1-fluoro-2-(trans-4-(trans-4-(3,4-difluorophenyl)cyclohexyl)cyclohexyl)ethene 1117 1-cyano-1-fluoro-2-(trans-4-(trans-4-(4-trifluoromethylphenyl)cyclohexyl)cyclohexyl)ethene 1118 1-cyano-1-fluoro-2-(trans-4-(trans-4-(4-trifluoromethoxyphenyl)cyclohexyl)cyclohexyl)ethene 1119 1-cyano-1-fluoro-2-(trans-4-(2-(trans-4-(4-cyanophenyl)cyclohexyl)ethyl)cyclohexyl)ethene 1120 1-cyano-1-fluoro-2-(trans-4-(2-(trans-4-(4-fluorophenyl)cyclohexyl)ethyl)cyclohexyl)ethene 1121 1-cyano-1-fluoro-2-(trans-4-(2-(trans-4-(3,4-difluorophenyl)cyclohexyl)ethyl)cyclohexyl)ethene 1122 1-cyano-1-fluoro-2-(trans-4-(2-(trans-4-(4-trifluoromethylphenyl)cyclohexyl)ethyl)cyclohexyl)ethene 1123 1-cyano-1-fluoro-2-(trans-4-(2-(trans-4-(4-trifluoromethoxyphenyl)cyclohexyl)ethyl)cyclohexyl)ethene

EXAMPLE 70

Preparation of 1-cyano-1-fluoro-2-(trans-4-(2E-(trans-4-(4-cyanophenyl)cyclohexyl)ethenyl)cyclohexyl)ethene [Compound expressed by general formula I wherein $R^1$ represents cyano group, $A^1$ represents 1,4-phenylene, $B^1$ represents a covalent bond, $A^2$ represents 1,4-cyclohexylene, $B^2$ represents 1,2-ethenylene, n1 is 1, n2 is 0, n3 is 0, $R^2$ represents a group expressed by formula II, and X represents fluorine atom (Compound No. 1124)]

Subject compound was synthesized by the same procedures as in Example 25 with the exception that trans-4-(2E-(4-cyanophenyl)ethenyl)cyclohexane carboaldehyde was used as starting material instead of trans-4-(trans-4-ethylcyclohexyl)cyclohexane carboaldehyde.

By the procedures similar to those described above, the following compounds (Compound Nos. 1125 to 1128) are synthesized.

1125 1-cyano-1-fluoro-2-(trans-4-(2E-(trans-4-(4-fluorophenyl)cyclohexyl)ethenyl)cyclohexyl)ethene 1126 1-cyano-1-fluoro-2-(trans-4-(2E-(trans-4-(3,4-difluorophenyl)cyclohexyl)ethenyl)cyclohexyl)ethene 1127 1-cyano-1-fluoro-2-(trans-4-(2E-(trans-4-(4-trifluoromethylphenyl)cyclohexyl)ethenyl)cyclohexyl)ethene 1128 1-cyano-1-fluoro-2-(trans-4-(2E-(trans-4-(4-trifluoromethoxyphenyl)cyclohexyl)ethenyl)cyclohexyl)ethene

EXAMPLE 71

Preparation of trans-4-(2-cyano-2-fluoroethenyl)cyclohexyl 4-ethylbenzoate [Compound expressed by general formula I wherein $R^1$ represents cyano group, $A^1$ represents 1,4-phenylene, $B^1$ represents carbonyloxy, n1 is 0, n2 is 0, n3 is 0, $R^2$ represents a group expressed by formula II, and X represents fluorine atom (Compound No. 1129)]

Subject compound was synthesized by the same procedures as in Example 25 with the exception that trans-4-formylcyclohexyl 4-cyanobenzoate was used as starting material instead of trans-4-(trans-4-ethylcyclohexyl)cyclohexane carboaldehyde.

By the procedures similar to those described above, the following compounds (Compound Nos. 1130 to 1149) are synthesized.

1130 trans-4-(2-cyano-2-fluoroethenyl)cyclohexyl 4-fluorobenzoate 1131 trans-4-(2-cyano-2-fluoroethenyl)cyclohexyl 3,4-difluorobenzoate 1132 trans-4-(2-cyano-2-fluoroethenyl)cyclohexyl 4-trifluoromethylbenzoate 1133 trans-4-(2-cyano-2-fluoroethenyl)cyclohexyl 4-trifluoromethoxybenzoate 1134 4-cyanophenyl trans-4-(2-cyano-2-fluoroethenyl)cyclohexane carboxylate 1135 4-fluorophenyl trans-4-(2-cyano-2-fluoroethenyl)cyclohexane carboxylate 1136 3,4-difluorophenyl trans-4-(2-cyano-2-fluoroethenyl)cyclohexane carboxylate 1137 4-trifluoromethylphenyl trans-4-(2-cyano-2-fluoroethenyl)cyclohexane carboxylate 1138 3-fluoro-4-cyanophenyl trans-4-(2-cyano-2-fluoroethenyl)cyclohexane carboxylate 1139 4-trifluoromethoxyphenyl trans-4-(2-cyano-2-fluoroethenyl)cyclohexane carboxylate 1140 trans-4-(4-cyanophenyl)cyclohexyl trans-4-(2-cyano-2-fluoroethenyl)cyclohexane carboxylate 1141 trans-4-(4-fluorophenyl)cyclohexyl trans-4-(2-cyano-2-fluoroethenyl)cyclohexane carboxylate 1142 trans-4-(3,4-difluorophenyl)cyclohexyl trans-4-(2-cyano-2-fluoroethenyl)cyclohexane carboxylate 1143 trans-4-(4-trifluoromethylphenyl)cyclohexyl trans-4-(2-cyano-2-fluoroethenyl)cyclohexane carboxylate 1144 trans-4-(3-fluoro-4-cyanophenyl)cyclohexyl trans-4-(2-cyano-2-fluoroethenyl)cyclohexane carboxylate 1145 trans-4-(2-cyano-2-fluoroethenyl)cyclohexyl trans-4-(4-cyanophenyl)cyclohexane carboxylate 1146 trans-4-(2-cyano-2-fluoroethenyl)cyclohexyl trans-4-(4-fluorophenyl)cyclohexane carboxylate 1147 trans-4-(2-cyano-2-fluoroethenyl)cyclohexyl trans-4-(3,4-difluorophenyl)cyclohexane carboxylate 1148 trans-4-(2-cyano-2-fluoroethenyl)cyclohexyl trans-4-(4-trifluoromethylphenyl)cyclohexane carboxylate 1149 trans-4-(2-cyano-2-fluoroethenyl)cyclohexyl trans-4-(3-fluoro-4-cyanophenyl)cyclohexane carboxylate

EXAMPLE 72

Preparation of 1-cyano-1-fluoro-2-(trans-4-(4-cyanophenyl)methoxycyclohexyl)ethene [Compound expressed by general formula I wherein $R^1$ represents cyano group, $A^1$ represents 1,4-phenylene, $B^1$ represents methyleneoxy, n1 is 0, n2 is 0, n3 is 0, $R^2$ represents a group expressed by formula II, and X represents fluorine atom (Compound No. 1150)]

Subject compound was synthesized by the same procedures as in Example 25 with the exception that trans-4-(4-cyanophenyl)methoxycyclohexane carboxylate was used as starting material instead of trans-4-(trans-4-ethylcyclohexyl)cyclohexane carboaldehyde.

By the procedures similar to those described above, the following compounds (Compound Nos. 1151 to 1164) are synthesized.

1151 1-cyano-1-fluoro-2-(trans-4-(4-fluorophenyl)methoxycyclohexyl)ethene 1152 1-cyano-1-fluoro-2-(trans-4-(3,4-difluorophenyl)methoxycyclohexyl)ethene 1153 1-cyano-1-fluoro-2-(trans-4-(4-trifluoromethylphenyl)methoxycyclohexyl)ethene 1154 1-cyano-1-fluoro-2-(trans-4-(4-trifluoromethoxyphenyl)methoxycyclohexyl)ethene 1155 1-cyano-1-fluoro-2-(trans-4-(trans-4-(4-cyanophenyl)cyclohexyl)methoxycyclohexyl)ethene 1156 1-cyano-1-fluoro-2-(trans-4-(trans-4-(4-fluorophenyl)cyclohexyl)methoxycyclohexyl)ethene 1157 1-cyano-1-fluoro-2-(trans-4-(trans-4-(3,4-difluorophenyl)cyclohexyl)methoxycyclohexyl)ethene 1158 1-cyano-1-fluoro-2-(trans-4-(trans-4-(4-trifluoromethylphenyl)cyclohexyl)methoxycyclohexyl)ethene 1159 1-cyano-1-fluoro-2-(trans-4-(trans-4-(4-trifluoromethoxyphenyl)cyclohexyl)methoxycyclohexyl)ethene 1160 1-cyano-1-fluoro-2-(trans-4-(2-(trans-4-(4-cyanophenyl)cyclohexyl)oxymethyl)cyclohexyl)ethene 1161 1-cyano-1-fluoro-2-(trans-4-(2-(trans-4-(4-fluorophenyl)cyclohexyl)oxymethyl)cyclohexyl)ethene 1162 1-cyano-1-fluoro-2-(trans-4-(2-(trans-4-(3,4-difluorophenyl)cyclohexyl)oxymethyl)cyclohexyl)ethene 1163 1-cyano-1-fluoro-2-(trans-4-(2-(trans-4-(4-trifluoromethylphenyl)cyclohexyl)oxymethyl)cyclohexyl)ethene 1164 1-cyano-1-fluoro-2-(trans-4-(2-(trans-4-(4-trifluoromethoxyphenyl)cyclohexyl)oxymethyl)cyclohexyl)ethene

EXAMPLE 73

Preparation of 1-cyano-1-fluoro-2-(trans-4-(4-(4-cyanophenyl)butyl)cyclohexyl)ethene [Compound expressed by general formula I wherein $R^1$ represents cyano group, $A^1$ represents 1,4-phenylene, $B^1$ represents 1,4-butylene, n1 is 0, n2 is 0, n3 is 0, $R^2$ represents a group expressed by formula II, and X represents fluorine atom (Compound No. 1165)]

Subject compound was synthesized by the same procedures as in Example 25 with the exception that trans-4-(4-(4-cyanophenyl)butyl)cyclohexane carboaldehyde was used as starting material instead of trans-4-(trans-4-ethylcyclohexyl)cyclohexane carboaldehyde.

By the procedures similar to those described above, the following compounds (Compound Nos. 1166 to 1179) are synthesized.

1166 1-cyano-1-fluoro-2-(trans-4-(4-(4-fluorophenyl)butyl)cyclohexyl)ethene 1167 1-cyano-1-fluoro-2-(trans-4-(4-(3,4-difluorophenyl)butyl)cyclohexyl)ethene 1168 1-cyano-1-fluoro-2-(trans-4-(4-(4-trifluoromethylphenyl)butyl)cyclohexyl)ethene 1169 1-cyano-1-fluoro-2-(trans-4-(4-(4-trifluoromethoxyphenyl)butyl)cyclohexyl)ethene 1170 1-cyano-1-fluoro-2-(trans-4-(trans-4-(4-(4-cyanophenyl)butyl)cyclohexyl)cyclohexyl)ethene 1171 1-cyano-1-fluoro-2-(trans-4-(trans-4-(4-(4-fluorophenyl)butyl)cyclohexyl)cyclohexyl)ethene 1172 1-cyano-1-fluoro-2-(trans-4-(trans-4-(4-(3,4-difluorophenyl)butyl)cyclohexyl)cyclohexyl)ethene 1173 1-cyano-1-fluoro-2-(trans-4-(trans-4-(4-(4-trifluoromethylphenyl)butyl)cyclohexyl)cyclohexyl)ethene 1174 1-cyano-1-fluoro-2-(trans-4-(trans-4-(4-(4-trifluoromethoxyphenyl)butyl)cyclohexyl)cyclohexyl)ethene 1175 1-cyano-1-fluoro-2-(trans-4-(4-(trans-4-(4-cyanophenyl)cyclohexyl)butyl)cyclohexyl)ethene 1176 1-cyano-1-fluoro-2-(trans-4-(4-(trans-4-(4-fluorophenyl)cyclohexyl)butyl)cyclohexyl)ethene 1177 1-cyano-1-fluoro-2-(trans-4-(4-(trans-4-(3,4-difluorophenyl)cyclohexyl)butyl)cyclohexyl)ethene 1178 1-cyano-1-fluoro-2-(trans-4-(4-(trans-4-(4-trifluoromethylphenyl)cyclohexyl)butyl)cyclohexyl)ethene 1179 1-cyano-1-fluoro-2-(trans-4-(4-(trans-4-(4-trifluoromethoxyphenyl)cyclohexyl)butyl)cyclohexyl)ethene

EXAMPLE 74

Preparation of 1-cyano-1-fluoro-4-(trans-4-(4-cyanophenyl)cyclohexyl)-1-butene [Compound expressed by general formula I wherein $R^1$ represents cyano group, $A^1$ represents 1,4-phenylene, $B^1$ represents a covalent bond, n1 is 0, n2 is 0, n3 is 1, $R^2$ represents a group expressed by formula II, and X represents fluorine atom (Compound No. 1180)]

Subject compound was synthesized by the same procedures as in Example 25 with the exception that 3-(trans-4-(4-cyanophenyl)cyclohexyl)propanal was used as starting material instead of trans-4-(trans-4-ethylcyclohexyl)cyclohexane carboaldehyde.

By the procedures similar to those described above, the following compounds (Compound Nos. 1181 to 1199) are synthesized.

1181 1-cyano-1-fluoro-4-(trans-4-(4-fluorophenyl)cyclohexyl)-1-butene 1182 1-cyano-1-fluoro-4-(trans-4-(3,4-difluorophenyl)cyclohexyl)-1-butene 1183 1-cyano-1-fluoro-4-(trans-4-(4-trifluoromethylphenyl)cyclohexyl)-1-butene 1184 1-cyano-1-fluoro-4-(trans-4-(4-trifluoromethoxyphenyl)cyclohexyl)-1-butene 1185 1-cyano-1-fluoro-4-(trans-4-(2-(4-cyanophenyl)ethyl)cyclohexyl)-1-butene 1186 1-cyano-1-fluoro-4-(trans-4-(2-(4-fluorophenyl)ethyl)cyclohexyl)-1-butene 1187 1-cyano-1-fluoro-4-(trans-4-(2-(3,4-difluorophenyl)ethyl)cyclohexyl)-1-butene 1188 1-cyano-1-fluoro-4-(trans-4-(2-(4-trifluoromethylphenyl)ethyl)cyclohexyl)-1-butene 1189 1-cyano-1-fluoro-4-(trans-4-(2-(4-trifluoromethoxyphenyl)ethyl)cyclohexyl)- 1-butene 1190 1-cyano-1-fluoro-4-(trans-4-(trans-4-(4-cyanophenyl)cyclohexyl)cyclohexyl)-1-butene 1191 1-cyano-1-fluoro-4-(trans-4-(trans-4-(4-fluorophenyl)cyclohexyl)cyclohexyl)-1-butene 1192 1-cyano-1-fluoro-4-(trans-4-(trans-4-(3,4-difluorophenyl)cyclohexyl)cyclohexyl)-1-butene 1193 1-cyano-1-fluoro-4-(trans-4-(trans-4-(4-trifluoromethylphenyl)cyclohexyl)cyclohexyl)-1-butene 1194 1-cyano-1-fluoro-4-(trans-4-(trans-4-(4-trifluoromethoxyphenyl)cyclohexyl)cyclohexyl)-1-butene 1195 1-cyano-1-fluoro-4-(trans-4-(2-(trans-4-(4-cyanophenyl)cyclohexyl)ethyl)cyclohexyl)-1-butene 1196 1-cyano-1-fluoro-4-(trans-4-(2-(trans-4-(4-fluorophenyl)cyclohexyl)ethyl)cyclohexyl)-1-butene 1197 1-cyano-1-fluoro-4-(trans-4-(2-(trans-4-(3,4-difluorophenyl)cyclohexyl)ethyl)cyclohexyl)-1-butene 1198 1-cyano-1-fluoro-4-(trans-4-(2-(trans-4-(4-trifluoromethylphenyl)cyclohexyl)ethyl)cyclohexyl)-1-butene 1199 1-cyano-1-fluoro-4-(trans-4-(2-(trans-4-(4-trifluoromethoxyphenyl)cyclohexyl)ethyl)cyclohexyl)-1-butene

EXAMPLE 75

Preparation of 1-cyano-1-fluoro-4-(trans-4-(2E-(trans-4-(4-cyanophenyl)cyclohexyl)ethenyl)cyclohexyl)-1-butene [Compound expressed by general formula I wherein $R^1$ represents cyano group, $A^1$ represents 1,4-phenylene, $B^1$ represents a covalent bond, $A^2$ represents 1,4-cyclohexylene, $B^2$ represents 2-ethenylene, n1 is 1, n2 is 0, n3 is 1, $R^2$ represents a group expressed by formula II, and X represents fluorine atom (Compound No. 1200)]

Subject compound was synthesized by the same procedures as in Example 25 with the exception that 3-(trans-4-

(2E-(4-cyanophenyl)ethenyl)cyclohexyl)propanal was used as starting material instead of trans-4-(trans-4-ethylcyclohexyl)cyclohexane carboaldehyde.

By the procedures similar to those described above, the following compounds (Compound Nos. 1201 to 1204) are synthesized.

1201 1-cyano-1-fluoro-4-(trans-4-(2E-(trans-4-(4-fluorophenyl)cyclohexyl)ethenyl)cyclohexyl)-1-butene
1202 1-cyano-1-fluoro-4-(trans-4-(2E-(trans-4-(3,4-difluorophenyl)cyclohexyl)ethenyl)cyclohexyl)-1-butene
1203 1-cyano-1-fluoro-4-(trans-4-(2E-(trans-4-(4-trifluoromethylphenyl)cyclohexyl)ethenyl)cyclohexyl)-1-butene
1204 1-cyano-1-fluoro-4-(trans-4-(2E-(trans-4-(4-trifluoromethoxyphenyl)cyclohexyl)ethenyl)cyclohexyl)-1-butene

EXAMPLE 76

Preparation of trans-4-(4-cyano-4-fluoro-3-butenyl)cyclohexyl 4-ethylbenzoate [Compound expressed by general formula I wherein $R^1$ represents cyano group, $A^1$ represents 1,4-phenylene, $B^1$ represents carbonyloxy, n1 is 0, n2 is 0, n3 is 1, $R^2$ represents a group expressed by formula II, and X represents fluorine atom (Compound No. 1205)]

Subject compound was synthesized by the same procedures as in Example 25 with the exception that trans-4-(2-formylethyl)cyclohexyl 4-cyanobenzoate was used as starting material instead of trans-4-(trans-4-ethylcyclohexyl)cyclohexane carboaldehyde.

By the procedures similar to those described above, the following compounds (Compound Nos. 1206 to 1225) are synthesized.

1206 trans-4-(4-cyano-4-fluoro-3-butenyl)cyclohexyl 4-fluorobenzoate
1207 trans-4-(4-cyano-4-fluoro-3-butenyl)cyclohexyl 3,4-difluorobenzoate
1208 trans-4-(4-cyano-4-fluoro-3-butenyl)cyclohexyl 4-trifluoromethylbenzoate
1209 trans-4-(4-cyano-4-fluoro-3-butenyl)cyclohexyl 4-trifluoromethoxybenzoate
1210 4-cyanophenyl trans-4-(4-cyano-4-fluoro-3-butenyl)cyclohexane carboxylate
1211 4-fluorophenyl trans-4-(4-cyano-4-fluoro-3-butenyl)cyclohexane carboxylate
1212 3,4-difluorophenyl trans-4-(4-cyano-4-fluoro-3-butenyl)cyclohexane carboxylate
1213 4-trifluoromethylphenyl trans-4-(4-cyano-4-fluoro-3-butenyl)cyclohexane carboxylate
1214 3-fluoro-4-cyanophenyl trans-4-(4-cyano-4-fluoro-3-butenyl)cyclohexane carboxylate
1215 4-trifluoromethoxyphenyl trans-4-(4-cyano-4-fluoro-3-butenyl)cyclohexane carboxylate
1216 trans-4-(4-cyanophenyl)cyclohexyl trans-4-(4-cyano-4-fluoro-3-butenyl)cyclohexane carboxylate
1217 trans-4-(4-fluorophenyl)cyclohexyl trans-4-(4-cyano-4-fluoro-3-butenyl)cyclohexane carboxylate
1218 trans-4-(3,4-difluorophenyl)cyclohexyl trans-4-(4-cyano-4-fluoro-3-butenyl)cyclohexane carboxylate
1219 trans-4-(4-trifluoromethylphenyl)cyclohexyl trans-4-(4-cyano-4-fluoro-3-butenyl)cyclohexane carboxylate
1220 trans-4-(3-fluoro-4-cyanophenyl)cyclohexyl trans-4-(4-cyano-4-fluoro-3-butenyl)cyclohexane carboxylate
1221 trans-4-(4-cyano-4-fluoro-3-butenyl)cyclohexyl trans-4-(4-cyanophenyl)cyclohexane carboxylate
1222 trans-4-(4-cyano-4-fluoro-3-butenyl)cyclohexyl trans-4-(4-fluorophenyl)cyclohexane carboxylate
1223 trans-4-(4-cyano-4-fluoro-3-butenyl)cyclohexyl trans-4-(3,4-difluorophenyl)cyclohexane carboxylate
1224 trans-4-(4-cyano-4-fluoro-3-butenyl)cyclohexyl trans-4-(4-trifluoromethylphenyl)cyclohexane carboxylate
1225 trans-4-(4-cyano-4-fluoro-3-butenyl)cyclohexyl trans-4-(3-fluoro-4-cyanophenyl)cyclohexane carboxylate

EXAMPLE 77

Preparation of 1-cyano-1-fluoro-4-(trans-4-(4-cyanophenyl)methoxycyclohexyl)-1-butene [Compound expressed by general formula I wherein $R^1$ represents cyano group, $A^1$ represents 1,4-phenylene, $B^1$ represents methyleneoxy, n1 is 0, n2 is 0, n3 is 1, $R^2$ represents a group expressed by formula II, and X represents fluorine atom (Compound No. 1226)]

Subject compound was synthesized by the same procedures as in Example 1 with the exception that 3-(trans-4-(4-cyanophenyl)methoxycyclohexyl)propanal was used as starting material instead of trans-4-(trans-4-ethylcyclohexyl)cyclohexane carboaldehyde.

By the procedures similar to those described above, the following compounds (Compound Nos. 1227 to 1240) are synthesized.

1227 1-cyano-1-fluoro-4-(trans-4-(4-fluorophenyl)methoxycyclohexyl)-1-butene
1228 1-cyano-1-fluoro-4-(trans-4-(3,4-difluorophenyl)methoxycyclohexyl)-1-butene
1229 1-cyano-1-fluoro-4-(trans-4-(4-trifluoromethylphenyl)methoxycyclohexyl)-1-butene
1230 1-cyano-1-fluoro-4-(trans-4-(4-trifluoromethoxyphenyl)methoxycyclohexyl)-1-butene
1231 1-cyano-1-fluoro-4-(trans-4-(trans-4-(4-cyanophenyl)cyclohexyl)methoxycyclohexyl)-1-butene
1232 1-cyano-1-fluoro-4-(trans-4-(trans-4-(4-fluorophenyl)cyclohexyl)methoxycyclohexyl)-1-butene
1233 1-cyano-1-fluoro-4-(trans-4-(trans-4-(3,4-difluorophenyl)cyclohexyl)methoxycyclohexyl)-1-butene
1234 1-cyano-1-fluoro-4-(trans-4-(trans-4-(4-trifluoromethylphenyl)cyclohexyl)methoxycyclohexyl)-1-butene
1235 1-cyano-1-fluoro-4-(trans-4-(trans-4-(4-trifluoromethoxyphenyl)cyclohexyl)methoxycyclohexyl)-1-butene
1236 1-cyano-1-fluoro-4-(trans-4-(2-(trans-4-(4-cyanophenyl)cyclohexyl)oxymethyl)cyclohexyl)-1-butene
1237 1-cyano-1-fluoro-4-(trans-4-(2-(trans-4-(4-fluorophenyl)cyclohexyl)oxymethyl)cyclohexyl)-1-butene
1238 1-cyano-1-fluoro-4-(trans-4-(2-(trans-4-(3,4-difluorophenyl)cyclohexyl)oxymethyl)cyclohexyl)-1-butene
1239 1-cyano-1-fluoro-4-(trans-4-(2-(trans-4-(4-trifluoromethylphenyl)cyclohexyl)oxymethyl)cyclohexyl)-1-butene
1240 1-cyano-1-fluoro-4-(trans-4-(2-(trans-4-(4-trifluoromethoxyphenyl)cyclohexyl)oxymethyl)cyclohexyl)-1-butene

EXAMPLE 78

Preparation of 1-cyano-1-fluoro-4-(trans-4-(4-(4-cyanophenyl)butyl)cyclohexyl)-1-butene [Compound expressed by general formula I wherein $R^1$ represents cyano group, $A^1$ represents 1,4-phenylene, $B^1$ represents 1,4-butylene, n1 is 0, n2 is 0, n3 is 1, $R^2$ represents a group expressed by formula II, and X represents fluorine atom (Compound No. 1241)]

Subject compound was synthesized by the same procedures as in Example 25 with the exception that 3-(trans-4-(4-(4-cyanophenyl)butyl)cyclohexyl)propanal was used as starting material instead of trans-4-(trans-4-ethylcyclohexyl)cyclohexane carboaldehyde.

By the procedures similar to those described above, the following compounds (Compound Nos. 1242 to 1255) are synthesized.

1242 1-cyano-1-fluoro-4-(trans-4-(4-(4-fluorophenyl)butyl)cyclohexyl)-1-butene
1243 1-cyano-1-fluoro-4-(trans-4-(4-(3,4-difluorophenyl)butyl)cyclohexyl)-1-butene
1244 1-cyano-1-fluoro-4-(trans-4-(4-(4-trifluoromethylphenyl)butyl)cyclohexyl)-1-butene
1245 1-cyano-1-fluoro-4-(trans-4-(4-(4-trifluoromethoxyphenyl)butyl)cyclohexyl)-1-butene
1246 1-cyano-1-fluoro-4-(trans-4-(trans-4-(4-(4-cyanophenyl)butyl)cyclohexyl)cyclohexyl)-1-butene
1247 1-cyano-1-fluoro-4-(trans-4-(trans-4-(4-(4-fluorophenyl)butyl)cyclohexyl)cyclohexyl)-1-butene
1248 1-cyano-1-fluoro-4-(trans-4-(trans-4-(4-(3,4-difluorophenyl)butyl)cyclohexyl)cyclohexyl)-1-butene
1249 1-cyano-1-fluoro-4-(trans-4-(trans-4-(4-(4-trifluoromethylphenyl)butyl)cyclohexyl)cyclohexyl)-1-butene
1250 1-cyano-1-fluoro-4-(trans-4-(trans-4-(4-(4-trifluoromethoxyphenyl)butyl)cyclohexyl)cyclohexyl)-1-butene
1251 1-cyano-1-fluoro-4-(trans-4-(4-(trans-4-(4-cyanophenyl)cyclohexyl)butyl)cyclohexyl)-1-butene
1252 1-cyano-1-fluoro-4-(trans-4-(4-(trans-4-(4-fluorophenyl)cyclohexyl)butyl)cyclohexyl)-1-butene
1253 1-cyano-1-fluoro-4-(trans-4-(4-(trans-4-(3,4-difluorophenyl)cyclohexyl)butyl)cyclohexyl)-1-butene
1254 1-cyano-1-fluoro-4-(trans-4-(4-(trans-4-(4-trifluoromethylphenyl)cyclohexyl)butyl)cyclohexyl)-1-butene
1255 1-cyano-1-fluoro-4-(trans-4-(4-(trans-4-(4-trifluoromethoxyphenyl)cyclohexyl)butyl)cyclohexyl)-1-butene

EXAMPLE 79

Preparation of 1-cyano-1-fluoro-4-(trans-4-(4-cyanophenyl)cyclohexyl)-1,3-butadiene [Compound expressed by general formula I wherein $R^1$ represents cyano group, $A^1$ represents 1,4-phenylene, $B^1$ represents a covalent bond, n1 is 0, n2 is 0, n3 is 0, $R^2$ represents a group expressed by formula III, and X represents fluorine atom (Compound No. 1256)]

Subject compound was synthesized by the same procedures as in Example 25 with the exception that 3-(trans-4-(4-cyanophenyl)cyclohexyl)-2-propenal was used as starting material instead of trans-4-(trans-4-ethylcyclohexyl)cyclohexane carboaldehyde.

By the procedures similar to those described above, the following compounds (Compound Nos. 1257 to 1275) are synthesized.

1257 1-cyano-1-fluoro-4-(trans-4-(4-fluorophenyl)cyclohexyl)-1,3-butadiene
1258 1-cyano-1-fluoro-4-(trans-4-(3,4-difluorophenyl)cyclohexyl)-1,3-butadiene
1259 1-cyano-1-fluoro-4-(trans-4-(4-trifluoromethylphenyl)cyclohexyl)-1,3-butadiene
1260 1-cyano-1-fluoro-4-(trans-4-(4-trifluoromethoxyphenyl)cyclohexyl)-1,3-butadiene
1261 1-cyano-1-fluoro-4-(trans-4-(2-(4-cyanophenyl)ethyl)cyclohexyl)-1,3-butadiene
1262 1-cyano-1-fluoro-4-(trans-4-(2-(4-fluorophenyl)ethyl)cyclohexyl)-1,3-butadiene
1263 1-cyano-1-fluoro-4-(trans-4-(2-(3,4-difluorophenyl)ethyl)cyclohexyl)-1,3-butadiene
1264 1-cyano-1-fluoro-4-(trans-4-(2-(4-trifluoromethylphenyl)ethyl)cyclohexyl)-1,3-butadiene
1265 1-cyano-1-fluoro-4-(trans-4-(2-(4-trifluoromethoxyphenyl)ethyl)cyclohexyl)-1,3-butadiene
1266 1-cyano-1-fluoro-4-(trans-4-(trans-4-(4-cyanophenyl)cyclohexyl)cyclohexyl)-1,3-butadiene
1267 1-cyano-1-fluoro-4-(trans-4-(trans-4-(4-fluorophenyl)cyclohexyl)cyclohexyl)-1,3-butadiene
1268 1-cyano-1-fluoro-4-(trans-4-(trans-4-(3,4-difluorophenyl)cyclohexyl)cyclohexyl)-1,3-butadiene
1269 1-cyano-1-fluoro-4-(trans-4-(trans-4-(4-trifluoromethylphenyl)cyclohexyl)cyclohexyl)-1,3-butadiene
1270 1-cyano-1-fluoro-4-(trans-4-(trans-4-(4-trifluoromethoxyphenyl)cyclohexyl)cyclohexyl)-1,3-butadiene
1271 1-cyano-1-fluoro-4-(trans-4-(2-(trans-4-(4-cyanophenyl)cyclohexyl)ethyl)cyclohexyl)-1,3-butadiene
1272 1-cyano-1-fluoro-4-(trans-4-(2-(trans-4-(4-fluorophenyl)cyclohexyl)ethyl)cyclohexyl)-1,3-butadiene
1273 1-cyano-1-fluoro-4-(trans-4-(2-(trans-4-(3,4-difluorophenyl)cyclohexyl)ethyl)cyclohexyl)-1,3-butadiene
1274 1-cyano-1-fluoro-4-(trans-4-(2-(trans-4-(4-trifluoromethylphenyl)cyclohexyl)ethyl)cyclohexyl)-1,3-butadiene
1275 1-cyano-1-fluoro-4-(trans-4-(2-(trans-4-(4-trifluoromethoxyphenyl)cyclohexyl)ethyl)cyclohexyl)-1,3-butadiene

EXAMPLE 80

Preparation of 1-cyano-1-fluoro-4-(trans-4-(2E-(trans-4-(4-cyanophenyl)cyclohexyl)ethenyl)cyclohexyl)-1,3-butadiene [Compound expressed by general formula I wherein $R^1$ represents cyano group, $A^1$ represents 1,4-phenylene, $B^1$ represents a covalent bond, $A^2$ represents 1,4-cyclohexylene, $B^2$ represents 1,2-ethenylene, ni is 1, n2 is 0, n3 is 0, $R^2$ represents a group expressed by formula III, and X represents fluorine atom (Compound No. 1256)]

Subject compound was synthesized by the same procedures as in Example 1 with the exception that 3-(trans-4-(2E-(4-cyanophenyl)ethenyl)cyclohexyl)propenal was used as starting material instead of trans-4-(trans-4-ethylcyclohexyl)cyclohexane carboaldehyde.

By the procedures similar to those described above, the following compounds (Compound Nos. 1277 to 1280) are synthesized.

1277 1-cyano-1-fluoro-4-(trans-4-(2E-(trans-4-(4-fluorophenyl)cyclohexyl)ethenyl)cyclohexyl)-1,3-butadiene
1278 1-cyano-1-fluoro-4-(trans-4-(2E-(trans-4-(3,4-difluorophenyl)cyclohexyl)ethenyl)cyclohexyl)-1,3-butadiene
1279 1-cyano-1-fluoro-4-(trans-4-(2E-(trans-4-(4-trifluoromethylphenyl)cyclohexyl)ethenyl)cyclohexyl)-1,3-butadiene
1280 1-cyano-1-fluoro-4-(trans-4-(2E-(trans-4-(4-trifluoromethoxyphenyl)cyclohexyl)ethenyl)cyclohexyl)-1,3-butadiene

EXAMPLE 81

Preparation of trans-4-(4-cyano-4-fluoro-1,3-butadienyl)cyclohexyl 4-cyanobenzoate [Compound expressed by general formula I wherein $R^1$ represents cyano group, $A^1$ represents 1,4-phenylene, $B^1$ represents carbonyloxy, n1 is 0, n2 is 0, n3 is 0, $R^2$ represents a group expressed by formula III, and X represents fluorine atom (Compound No. 1281)]

Subject compound was synthesized by the same procedures as in Example 1 with the exception that trans-4-(2-formylethenyl)cyclohexyl 4-cyanobenzoate was used as starting material instead of trans-4-(trans-4-ethylcyclohexyl)cyclohexane carboaldehyde.

By the procedures similar to those described above, the following compounds (Compound Nos. 1282 to 1301) are synthesized.

1282 trans-4-(4-cyano-4-fluoro-1,3-butadienyl)cyclohexyl 4-fluorobenzoate
1283 trans-4-(4-cyano-4-fluoro-1,3-butadienyl)cyclohexyl 3,4-difluorobenzoate
1284 trans-4-(4-cyano-4-fluoro-1,3-butadienyl)cyclohexyl 4-trifluoromethylbenzoate
1285 trans-4-(4-cyano-4-fluoro-1,3-butadienyl)cyclohexyl 4-trifluoromethoxybenzoate
1286 4-cyanophenyl trans-4-(4-cyano-4-fluoro-1,3-butadienyl)cyclohexane carboxylate
1287 4-fluorophenyl trans-4-(4-cyano-4-fluoro-1,3-butadienyl)cyclohexane carboxylate
1288 3,4-difluorophenyl trans-4-(4-cyano-4-fluoro-1,3-butadienyl)cyclohexane carboxylate
1289 4-trifluoromethylphenyl trans-4-(4-cyano-4-fluoro-1,3-butadienyl)cyclohexane carboxylate
1290 3-fluoro-4-cyanophenyl trans-4-(4-cyano-4-fluoro-1,3-butadienyl)cyclohexane carboxylate
1291 4-trifluoromethoxyphenyl trans-4-(4-cyano-4-fluoro-1,3-butadienyl)cyclohexane carboxylate
1292 trans-4-(4-cyanophenyl)cyclohexyl trans-4-(4-cyano-4-fluoro-1,3-butadienyl)cyclohexane carboxylate
1293 trans-4-(4-fluorophenyl)cyclohexyl trans-4-(4-cyano-4-fluoro-1,3-butadienyl)cyclohexane carboxylate
1294 trans-4-(3,4-difluorophenyl)cyclohexyl trans-4-(4-cyano-4-fluoro-1,3-butadienyl)cyclohexane carboxylate
1295 trans-4-(4-trifluoromethylphenyl)cyclohexyl trans-4-(4-cyano-4-fluoro-1,3-butadienyl)cyclohexane carboxylate
1296 trans-4-(3-fluoro-4-cyanophenyl)cyclohexyl trans-4-(4-cyano-4-fluoro-1,3-butadienyl)cyclohexane carboxylate
1297 trans-4-(4-cyano-4-fluoro-1,3-butadienyl)cyclohexyl trans-4-(4-cyanophenyl)cyclohexane carboxylate
1298 trans-4-(4-cyano-4-fluoro-1,3-butadienyl)cyclohexyl trans-4-(4-fluorophenyl)cyclohexane carboxylate
1299 trans-4-(4-cyano-4-fluoro-1,3-butadienyl)cyclohexyl trans-4-(3,4-difluorophenyl)cyclohexane carboxylate
1300 trans-4-(4-cyano-4-fluoro-1,3-butadienyl)cyclohexyl trans-4-(4-trifluoromethylphenyl)cyclohexane carboxylate
1301 trans-4-(4-cyano-4-fluoro-1,3-butadienyl)cyclohexyl trans-4-(3-fluoro-4-cyanophenyl)cyclohexane carboxylate

EXAMPLE 82

Preparation of 1-cyano-1-fluoro-4-(trans-4-(4-cyanophenyl)methoxycyclohexyl)-1,3-butadiene [Compound expressed by general formula I wherein $R^1$ represents cyano group, $A^1$ represents 1,4-phenylene, $B^1$ represents methyleneoxy, n1 is 0, n2 is 0, n3 is 0, $R^2$ represents a group expressed by formula III, and X represents fluorine atom (Compound No. 1302)]

Subject compound was synthesized by the same procedures as in Example 1 with the exception that 3-(trans-4-(4-cyanophenyl)methoxycyclohexyl)-2-propene-1-al was used as starting material instead of trans-4-(trans-4-ethylcyclohexyl)cyclohexane carboaldehyde.

By the procedures similar to those described above, the following compounds (Compound Nos. 1303 to 1316) are synthesized.

1303 1-cyano-1-fluoro-4-(trans-4-(4-fluorophenyl)methoxycyclohexyl)-1,3-butadiene
1304 1-cyano-1-fluoro-4-(trans-4-(3,4-difluorophenyl)methoxycyclohexyl)-1,3-butadiene
1305 1-cyano-1-fluoro-4-(trans-4-(4-trifluoromethylphenyl)methoxycyclohexyl)-1,3-butadiene
1306 1-cyano-1-fluoro-4-(trans-4-(4-trifluoromethoxyphenyl)methoxycyclohexyl)-1,3-butadiene
1307 1-cyano-1-fluoro-4-(trans-4-(trans-4-(4-cyanophenyl)cyclohexyl)methoxycyclohexyl)-1,3-butadiene
1308 1-cyano-1-fluoro-4-(trans-4-(trans-4-(4-fluorophenyl)cyclohexyl)methoxycyclohexyl)-1,3-butadiene
1309 1-cyano-1-fluoro-4-(trans-4-(trans-4-(3,4-difluorophenyl)cyclohexyl)methoxycyclohexyl)-1,3-butadiene
1310 1-cyano-1-fluoro-4-(trans-4-(trans-4-(4-trifluoromethylphenyl)cyclohexyl)methoxycyclohexyl)-1,3 -butadiene
1311 1-cyano-1-fluoro-4-(trans-4-(trans-4-(4-trifluoromethoxyphenyl)cyclohexyl)methoxycyclohexyl)-1,3-butadiene
1312 1-cyano-1-fluoro-4-(trans-4-(2-(trans-4-(4-cyanophenyl)cyclohexyl)oxymethyl)cyclohexyl)-1,3-butadiene
1313 1-cyano-1-fluoro-4-(trans-4-(2-(trans-4-(4-fluorophenyl)cyclohexyl)oxymethyl)cyclohexyl)-1,3-butadiene
1314 1-cyano-1-fluoro-4-(trans-4-(2-(trans-4-(3,4-difluorophenyl)cyclohexyl)oxymethyl)cyclohexyl)-1,3-butadiene
1315 1-cyano-1-fluoro-4-(trans-4-(2-(trans-4-(4-trifluoromethylphenyl)cyclohexyl)oxymethyl)cyclohexyl)-1,3-butadiene
1316 1-cyano-1-fluoro-4-(trans-4-(2-(trans-4-(4-trifluoromethoxyphenyl)cyclohexyl)oxymethyl)cyclohexyl)-1,3-butadiene

EXAMPLE 83

Preparation of 1-cyano-1-fluoro-4-(trans-4-(4-(4-cyanophenyl)butyl)cyclohexyl)-1,3-butadiene [Compound expressed by general formula I wherein $R^1$ represents cyano group, $A^1$ represents 1,4-phenylene, $B^1$ represents 1,4-butylene, n1 is 0, n2 is 0, n3 is 0, $R^2$ represents a group expressed by formula III, and X represents fluorine atom (Compound No. 1317)]

Subject compound was synthesized by the same procedures as in Example 1 with the exception that 3-(trans-4-(4-(4-cyanophenyl)butyl)cyclohexyl)-2-propene-1-al was used as starting material instead of trans-4-(trans-4-ethylcyclohexyl)cyclohexane carboaldehyde.

By the procedures similar to those described above, the following compounds (Compound Nos. 1318 to 1331) are synthesized.

1318 1-cyano-1-fluoro-4-(trans-4-(4-(4-fluorophenyl)butyl)cyclohexyl)-1,3-butadiene
1319 1-cyano-1-fluoro-4-(trans-4-(4-(3,4-difluorophenyl)butyl)cyclohexyl)-1,3-butadiene
1320 1-cyano-1-fluoro-4-(trans-4-(4-(4-trifluoromethylphenyl)butyl)cyclohexyl)-1,3-butadiene
1321 1-cyano-1-fluoro-4-(trans-4-(4-(4-trifluoromethoxyphenyl)butyl)cyclohexyl)-1,3-butadiene
1322 1-cyano-1-fluoro-4-(trans-4-(trans-4-(4-(4-cyanophenyl)butyl)cyclohexyl)cyclohexyl)-1,3-butadiene
1323 1-cyano-1-fluoro-4-(trans-4-(trans-4-(4-(4-fluorophenyl)butyl)cyclohexyl)cyclohexyl)-1,3-butadiene 1324 1-cyano-1-fluoro-4-(trans-4-(trans-4-(4-(3,4-difluorophenyl)butyl)cyclohexyl)cyclohexyl)-1,3-butadiene 1325 1-cyano-1-fluoro-4-(trans-4-(trans-4-(4-(4-trifluoromethylphenyl)butyl)cyclohexyl)cyclohexyl)-1,3-butadiene 1326 1-cyano-1-fluoro-4-(trans-4-(trans-4-(4-(4-trifluoromethoxyphenyl)butyl)cyclohexyl)cyclohexyl)-1,3-butadiene 1327 1-cyano-1-fluoro-4-(trans-4-(4-(trans-4-(4-cyanophenyl)cyclohexyl)butyl)cyclohexyl-1,3-butadiene 1328 1-cyano-1-fluoro-4-(trans-4-(4-(trans-4-(4-fluorophenyl)cyclohexyl)butyl)cyclohexyl-1,3-butadiene 1329 1-cyano-1-fluoro-4-(trans-4-(4-(trans-4-(3,4-difluorophenyl)cyclohexyl)butyl)cyclohexyl-1,3-butadiene 1330 1-cyano-1-fluoro-4-(trans-4-(4-(trans-4-(4-trifluoromethylphenyl)cyclohexyl)butyl)cyclohexyl-1,3-butadiene 1331 1-cyano-1-fluoro-4-(trans-4-(4-(trans-4-(4-trifluoromethoxyphenyl)cyclohexyl)butyl)cyclohexyl-1,3-butadiene

EXAMPLE 84

Preparation of 1-cyano-1-fluoro-6-(trans-4-(4-cyanophenyl)cyclohexyl)-1,3-hexadiene [Compound expressed by general formula I wherein $R^1$ represents cyano group, $A^1$ represents 1,4-phenylene, $B^1$ represents a covalent bond, n1 is 0, n2 is 0, n3 is 1, $R^2$ represents a group expressed by formula III, and X represents fluorine atom (Compound No. 1332)]

Subject compound was synthesized by the same procedures as in Example 1 with the exception that 5-(trans-4-(4-cyanophenyl)cyclohexyl)-2-pentene-1-al was used as starting material instead of trans-4-(trans-4-ethylcyclohexyl)cyclohexane carboaldehyde.

By the procedures similar to those described above, the following compounds (Compound Nos. 1333 to 1351) are synthesized.

1333 1-cyano-1-fluoro-6-(trans-4-(4-fluorophenyl)cyclohexyl)-1,3-hexadiene 1334 1-cyano-1-fluoro-6-(trans-4-(3,4-difluorophenyl)cyclohexyl)-1,3-hexadiene 1335 1-cyano-1-fluoro-6-(trans-4-(4-trifluoromethylphenyl)cyclohexyl)-1,3-hexadiene 1336 1-cyano-1-fluoro-6-(trans-4-(4-trifluoromethoxyphenyl)cyclohexyl)-1,3-hexadiene 1337 1-cyano-1-fluoro-6-(trans-4-(2-(4-cyanophenyl)ethyl)cyclohexyl)-1,3-hexadiene 1338 1-cyano-1-fluoro-6-(trans-4-(2-(4-fluorophenyl)ethyl)cyclohexyl)-1,3-hexadiene 1339 1-cyano-1-fluoro-6-(trans-4-(2-(3,4-difluorophenyl)ethyl)cyclohexyl)-1,3-hexadiene 1340 1-cyano-1-fluoro-6-(trans-4-(2-(4-trifluoromethylphenyl)ethyl)cyclohexyl)-1,3-hexadiene 1341 1-cyano-1-fluoro-6-(trans-4-(2-(4-trifluoromethoxyphenyl)ethyl)cyclohexyl)-1,3-hexadiene 1342 1-cyano-1-fluoro-6-(trans-4-(trans-4-(4-cyanophenyl)cyclohexyl)cyclohexyl)-1,3-hexadiene 1343 1-cyano-1-fluoro-6-(trans-4-(trans-4-(4-fluorophenyl)cyclohexyl)cyclohexyl)-1,3-hexadiene 1344 1-cyano-1-fluoro-6-(trans-4-(trans-4-(3,4-difluorophenyl)cyclohexyl)cyclohexyl)-1,3-hexadiene 1345 1-cyano-1-fluoro-6-(trans-4-(trans-4-(4-trifluoromethylphenyl)cyclohexyl)cyclohexyl)-1,3-hexadiene 1346 1-cyano-1-fluoro-6-(trans-4-(trans-4-(4-trifluoromethoxyphenyl)cyclohexyl)cyclohexyl)-1,3-hexadiene 1347 1-cyano-1-fluoro-6-(trans-4-(2-(trans-4-(4-cyanophenyl)cyclohexyl)ethyl)cyclohexyl)-1,3-hexadiene 1348 1-cyano-1-fluoro-6-(trans-4-(2-(trans-4-(4-fluorophenyl)cyclohexyl)ethyl)cyclohexyl)-1,3-hexadiene 1349 1-cyano-1-fluoro-6-(trans-4-(2-(trans-4-(3,4-difluorophenyl)cyclohexyl)ethyl)cyclohexyl)-1,3-hexadiene 1350 1-cyano-1-fluoro-6-(trans-4-(2-(trans-4-(4-trifluoromethylphenyl)cyclohexyl)ethyl)cyclohexyl)-1,3-hexadiene 1351 1-cyano-1-fluoro-6-(trans-4-(2-(trans-4-(4-trifluoromethoxyphenyl)cyclohexyl)ethyl)cyclohexyl)-1,3-hexadiene

EXAMPLE 85

Preparation of 1-cyano-1-fluoro-6-(trans-4-(2E-(trans-4-(4-cyanophenyl)cyclohexyl)ethenyl)cyclohexyl)-1,3-hexadiene [Compound expressed by general formula I wherein $R^1$ represents cyano group, $A^1$ represents 1,4-phenylene, $B^1$ represents a covalent bond, $A^2$ represents 1,4-cyclohexylene, $B^2$ represents 1,2-ethenylene, n1 is 1, n2 is 0, n3 is 1, $R^2$ represents a group expressed by formula III, and X represents fluorine atom (Compound No. 1352)]

Subject compound was synthesized by the same procedures as in Example 1 with the exception that 5-(trans-4-(2E-(4-cyanophenyl)ethenyl)cyclohexyl)-2-pentene-1-al was used as starting material instead of trans-4-(trans-4-ethylcyclohexyl)cyclohexane carboaldehyde.

By the procedures similar to those described above, the following compounds (Compound Nos. 1353 to 1356) are synthesized.

1353 1-cyano-1-fluoro-6-(trans-4-(2E-(trans-4-(4-fluorophenyl)cyclohexyl)ethenyl)cyclohexyl)-1,3-hexadiene 1354 1-cyano-1-fluoro-6-(trans-4-(2E-(trans-4-(3,4-difluorophenyl)cyclohexyl)ethenyl)cyclohexyl)-1,3-hexadiene 1355 1-cyano-1-fluoro-6-(trans-4-(2E-(trans-4-(4-trifluoromethylphenyl)cyclohexyl)ethenyl)cyclohexyl)-1,3-hexadiene 1356 1-cyano-1-fluoro-6-(trans-4-(2E-(trans-4-(4-trifluoromethoxyphenyl)cyclohexyl)ethenyl)cyclohexyl)-1,3-hexadiene

EXAMPLE 86

Preparation of trans-4-(2-cyano-2-fluoro-3,5-hexadienyl)cyclohexyl 4-ethyl benzoate [Compound expressed by general formula I wherein $R^1$ represents cyano group, $A^1$ represents 1,4-phenylene, $B^1$ represents carbonyloxy, n1 is 0, n2 is 0, n3 is 1, $R^2$ represents a group expressed by formula III, and X represents fluorine atom (Compound No. 1357)]

Subject compound was synthesized by the same procedures as in Example 1 with the exception that trans-4-(4-formyl-3-butene-1-yl)cyclohexyl 4-cyanobenzoate was used as starting material instead of trans-4-(trans-4-ethylcyclohexyl)cyclohexane carboaldehyde.

By the procedures similar to those described above, the following compounds (Compound Nos. 1358 to 1377) are synthesized.

1358 trans-4-(6-cyano-6-fluoro-3,5-hexadieneyl)cyclohexyl 4-fluorobenzoate 1359 trans-4-(6-cyano-6-fluoro-3,5-hexadieneyl)cyclohexyl 3,4-difluorobenzoate 1360 trans-4-(6-cyano-6-fluoro-3,5-hexadieneyl)cyclohexyl 4-trifluoromethyl benzoate 1361 trans-4-(6-cyano-6-fluoro-3,5-hexadieneyl)cyclohexyl 4-trifluoromethoxy benzoate 1362 4-cyanophenyl trans-4-(6-cyano-6-fluoro-3,5-hexadienyl)cyclohexane carboxylate 1363 4-fluorophenyl trans-4-(6-cyano-6-fluoro-3,5-hexadienyl)cyclohexane carboxylate 1364 3,4-difluorophenyl trans-4-(6-cyano-6-fluoro-3,5-hexadienyl)cyclohexane carboxylate 1365 4-trifluoromethylphenyl trans-4-(6-cyano-6-fluoro-3,5-hexadienyl)cyclohexane carboxylate 1366 3-fluoro-4-cyanophenyl trans-4-(6-cyano-6-fluoro-3,5-hexadienyl)cyclohexane carboxylate 1367 4-trifluoromethoxyphenyl trans-4-(6-cyano-6-fluoro-3,5-hexadienyl)cyclohexane carboxylate 1368 trans-4-(4-cyanophenyl)cyclohexyl trans-4-(6-cyano-6-fluoro-3,5-hexadienyl)cyclohexane carboxylate 1369 trans-4-(4-fluorophenyl)cyclohexyl trans-4-(6-cyano-6-fluoro-3,5-hexadienyl)cyclohexane carboxylate 1370 trans-4-(3,4-difluorophenyl)cyclohexyl trans-4-(6-cyano-6-fluoro-3,5-hexadienyl)cyclohexane carboxylate 1371 trans-4-(4-trifluoromethylphenyl)cyclohexyl trans-4-(6-cyano-6-fluoro-3,5-hexadienyl)cyclohexane carboxylate 1372 trans-4-(3-fluoro-4-cyanophenyl)cyclohexyl trans-4-(6-cyano-6-fluoro-3,5-hexadienyl)cyclohexane carboxylate 1373 trans-4-(6-cyano-6-fluoro-3,5-hexadienyl)cyclohexyl trans-4-(4-cyanophenyl)cyclohexane carboxylate 1374 trans-4-(6-cyano-6-fluoro-3,5-hexadienyl)cyclohexyl trans-4-(4-fluorophenyl)cyclohexane carboxylate 1375 trans-4-(6-cyano-6-fluoro-3,5-hexadienyl)cyclohexyl trans-4-(3,4-difluorophenyl)cyclohexane carboxylate 1376 trans-4-(6-cyano-6-fluoro-3,5-hexadienyl)cyclohexyl trans-4-(4-trifluoromethylphenyl)cyclohexane carboxylate 1377 trans-4-(6-cyano-6-fluoro-3,5-hexadienyl)cyclohexyl trans-4-(3-fluoro-4-cyanophenyl)cyclohexane carboxylate

EXAMPLE 87

Preparation of 1-cyano-1-fluoro-6-(trans-4-(4-cyanophenyl)methoxycyclohexyl)-1,3-hexadiene [Compound expressed by general formula I wherein $R^1$ represents cyano group, $A^1$ represents 1,4-phenylene, $B^1$ represents methyleneoxy, n1 is 0, n3 is 1, $R^2$ represents a group expressed by formula III, and X represents fluorine atom (Compound No. 1378)]

Subject compound was synthesized by the same procedures as in Example 1 with the exception that 5-(trans-4-(4-cyanophenyl)methoxycyclohexyl)-2-pentene-1-al was used as starting material instead of trans-4-(trans-4-ethylcyclohexyl)cyclohexane carboaldehyde.

By the procedures similar to those described above, the following compounds (Compound Nos. 1379 to 1392) are synthesized.

1379 1-cyano-1-fluoro-6-(trans-4-(4-fluorophenyl)methoxycyclohexyl)-1,3-hexadiene 1380 1-cyano-1-fluoro-6-(trans-4-(3,4-difluorophenyl)methoxycyclohexyl)-1,3-hexadiene 1381 1-cyano-1-fluoro-6-(trans-4-(4-trifluoromethylphenyl)methoxycyclohexyl)-1,3-hexadiene 1382 1-cyano-1-fluoro-6-(trans-4-(4-trifluoromethoxyphenyl)methoxycyclohexyl)-1,3-hexadiene 1383 1-cyano-1-fluoro-6-(trans-4-(trans-4-(4-cyanophenyl)cyclohexyl)methoxycyclohexyl)-1,3-hexadiene 1384 1-cyano-1-fluoro-6-(trans-4-(trans-4-(4-fluorophenyl)cyclohexyl)methoxycyclohexyl)-1,3-hexadiene 1385 1-cyano-1-fluoro-6-(trans-4-(trans-4-(3,4-difluorophenyl)cyclohexyl)methoxycyclohexyl)-1,3-hexadiene 1386 1-cyano-1-fluoro-6-(trans-4-(trans-4-(4-trifluoromethylphenyl)cyclohexyl)methoxycyclohexyl)-1,3-hexadiene 1387 1-cyano-1-fluoro-6-(trans-4-(trans-4-(4-trifluoromethoxyphenyl)cyclohexyl)methoxycyclohexyl)-1,3-hexadiene 1388 1-cyano-1-fluoro-6-(trans-4-(2-(trans-4-(4-cyanophenyl)cyclohexyl)oxymethyl)cyclohexyl)-1,3-hexadiene 1389 1-cyano-1-fluoro-6-(trans-4-(2-(trans-4-(4-fluorophenyl)cyclohexyl)oxymethyl)cyclohexyl)-1,3-hexadiene 1390 1-cyano-1-fluoro-6-(trans-4-(2-(trans-4-(3,4-difluorophenyl)cyclohexyl)oxymethyl)cyclohexyl)-1,3-hexadiene 1391 1-cyano-1-fluoro-6-(trans-4-(2-(trans-4-(4-trifluoromethylphenyl)cyclohexyl)oxymethyl)cyclohexyl)-1,3-hexadiene 1392 1-cyano-1-fluoro-6-(trans-4-(2-(trans-4-(4-trifluoromethoxyphenyl)cyclohexyl)oxymethyl)cyclohexyl)-1,3-hexadiene

EXAMPLE 88

Preparation of 1-cyano-1-fluoro-6-(trans-4-(4-(4-cyanophenyl)butyl)cyclohexyl)-1,3-hexadiene [Compound expressed by general formula I wherein $R^1$ represents cyano group, $A^1$ represents 1,4-phenylene, $B^1$ represents 1,4-butylene, n1 is 0, n2 is 0, n3 is 1, $R^2$ represents a group expressed by formula III, and X represents fluorine atom (Compound No. 1393)]

Subject compound was synthesized by the same procedures as in Example 1 with the exception that 5-(trans-4-(4-(4-cyanophenyl)butyl)cyclohexyl)-2-pentene-1-al was used as starting material instead of trans-4-(trans-4-ethylcyclohexyl)cyclohexane carboaldehyde.

By the procedures similar to those described above, the following compounds (Compound Nos. 1394 to 1407) are synthesized.

1394 1-cyano-1-fluoro-6-(trans-4-(4-(4-fluorophenyl)butyl)cyclohexyl)-1,3-hexadiene 1395 1-cyano-1-fluoro-6-(trans-4-(4-(3,4-difluorophenyl)butyl)cyclohexyl)-1,3-hexadiene 1396 1-cyano-1-fluoro-6-(trans-4-(4-(4-trifluoromethylphenyl)butyl)cyclohexyl)-1,3-hexadiene 1397 1-cyano-1-fluoro-6-(trans-4-(4-(4-trifluoromethoxyphenyl)butyl)cyclohexyl)-1,3-hexadiene 1398 1-cyano-1-fluoro-6-(trans-4-(trans-4-(4-(4-cyanophenyl)butyl)cyclohexyl)cyclohexyl)-1,3-hexadiene 1399 1-cyano-1-fluoro-6-(trans-4-(trans-4-(4-(4-fluorophenyl)butyl)cyclohexyl)cyclohexyl)-1,3-hexadiene 1400 1-cyano-1-fluoro-6-(trans-4-(trans-4-(4-(3,4-difluorophenyl)butyl)cyclohexyl)cyclohexyl)-1,3-hexadiene 1401 1-cyano-1-fluoro-6-(trans-4-(trans-4-(4-(4-trifluoromethylphenyl)butyl)cyclohexyl)cyclohexyl)-1,3-hexadiene 1402 1-cyano-1-fluoro-6-(trans-4-(trans-4-(4-(4-trifluoromethoxyphenyl)butyl)cyclohexyl)cyclohexyl)-1,3-hexadiene 1403 1-cyano-1-fluoro-6-(trans-4-(4-(trans-4-(4-cyanophenyl)cyclohexyl)butyl)cyclohexyl)-1,3-hexadiene 1404 1-cyano-1-fluoro-6-(trans-4-(4-(trans-4-(4-fluorophenyl)cyclohexyl)butyl)cyclohexyl)-1,3-hexadiene 1405 1-cyano-1-fluoro-6-(trans-4-(4-(trans-4-(3,4-difluorophenyl)cyclohexyl)butyl)cyclohexyl)-1,3-hexadiene 1406 1-cyano-1-fluoro-6-(trans-4-(4-(trans-4-(4-trifluoromethylphenyl)cyclohexyl)butyl)cyclohexyl)-1,3-hexadiene 1407 1-cyano-1-fluoro-6-(trans-4-(4-(trans-4-(4-trifluoromethoxyphenyl)cyclohexyl)butyl)cyclohexyl)-1,3-hexadiene Now, examples of compositions in which the compounds of the present invention are used are described.

In the examples, compounds are indicated according to the definition shown in Table 1 in the same way as those described above. Further, "%" indicating the content of each compound means "% by weight" unless otherwise specified.

Data on the properties of liquid crystal compositions are shown by $T_{NI}$ (clearing point), $\eta$ (viscosity at 20° C.), $\Delta n$ (optical anisotropy at 25.0° C.), $\Delta\varepsilon$ (dielectric anisotropy at 25.0° C.), and $V_{th}$ (threshold voltage at 25.0° C.), and further P (twist pitch, at 25.0° C., of the composition obtained by adding 2.0 parts by weight of a chiral agent (CN) expressed by formula (6) below to 100 parts by weight of the composition shown in the corresponding Example) as circumstances require.

(6)

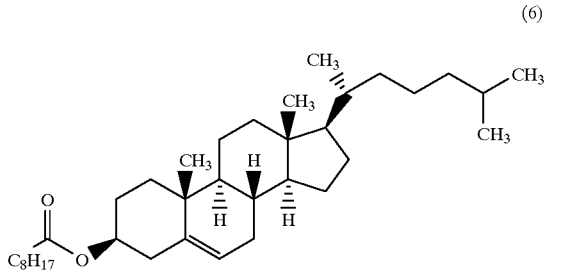

EXAMPLE 89

Use Example 1

Liquid crystal composition comprising the following compounds in the following content was prepared:

| 2-HH—VVC | (No. 201) | 4.0% |
|---|---|---|
| 3-HH—VVC | (No. 202) | 4.0% |
| 5-HH—VVC | (No. 204) | 4.0% |
| 2-BB—C | | 6.0% |
| 2-HB—C | | 10.0% |
| 3-HB—C | | 16.0% |
| 1O1-HH-5 | | 5.0% |
| 2-BTB-1 | | 6.5% |
| 1-BTB-6 | | 13.0% |
| 4-BTB-4 | | 6.5% |
| 3-HHB-1 | | 6.0% |
| 3-HHB—O1 | | 4.0% |
| 3-HHB-3 | | 9.0% |
| 3-H2BTB-2 | | 3.0% |
| 3-H2BTB-3 | | 3.0% |

Properties of this composition were determined and the results were as follows:

$T_{NI}$=78.0 (°C.)

$\eta$=16.2 (mPa.s)

$\Delta n$=0.158

$\Delta\varepsilon$=7.0

$V_{th}$=1.91 (V)

k3/k1=1.3 k3/k2=2.7

EXAMPLE 90

Use Example 2

Liquid crystal composition comprising the following compounds in the following content was prepared:

| 1-BHH—VC | (No. 20) | 9.0% |
|---|---|---|
| 2-HH—VC | (No. 1) | 4.0% |
| 3-HH—VC | (No. 2) | 4.0% |
| 4-HH—VC | (No. 3) | 3.0% |
| 5-HH—VC | (No. 4) | 3.0% |
| 1V2-BEB(F,F)—C | | 5.0% |
| 3-HB—C | | 25.0% |
| 1-BTB-3 | | 5.0% |
| 2-BTB-1 | | 10.0% |
| 3-HH-4 | | 11.0% |
| 3-HHB-1 | | 11.0% |
| 3-H2BTB-4 | | 4.0% |
| 3-HB(F)TG-3 | | 6.0% |

Properties of this composition were determined and the results were as follows:

$T_{NI}$=98.9 (°C.)

$\eta$=28.5 (mPa.s)

$\Delta n$=0.148

$\Delta\varepsilon$=7.8

$V_{th}$=2.15 (V)

EXAMPLE 91

Use Example 3

Liquid crystal composition comprising the following compounds in the following content was prepared:

| 1-BHH—VCF | (No. 421) | 5.0% |
|---|---|---|
| 3-BHH—VCF | (No. 422) | 5.0% |
| 1-BHH—VC | (No. 20) | 4.0% |
| V2-HB—C | | 12.0% |
| 1V2-HB—C | | 12.0% |
| 3-HB—C | | 24.0% |
| 3-HB(F)—C | | 5.0% |
| 2-BTB-1 | | 2.0% |
| 3-HH-4 | | 8.0% |
| 3-HH—VFF | | 6.0% |
| 2-HHB—C | | 3.0% |
| 3-HHB—C | | 6.0% |
| 3-HB(F)TB-2 | | 8.0% |

Properties of this composition were determined and the results were as follows:

$T_{NI}$=95.1 (°C.)

$\eta$=24.7 (mPa.s)

$\Delta n$=0.140

$\Delta\varepsilon$=9.5

$V_{th}$=1.81 (V)

EXAMPLE 92

Use Example 4

Liquid crystal composition comprising the following compounds in the following content was prepared:

| 3-HH—VC | (No. 2) | 15.0% |
|---|---|---|
| 3-HH—VCF | (No. 402) | 8.0% |

-continued

| | |
|---|---|
| 2O1-BEB(F)—C | 5.0% |
| 3O1-BEB(F)—C | 15.0% |
| 4O1-BEB(F)—C | 13.0% |
| 5O1-BEB—(F)—C | 13.0% |
| 3-HHB(F)—C | 15.0% |
| 3-HB(F)TB-4 | 4.0% |
| 3-HHB-1 | 8.0% |
| 3-HHB—O1 | 4.0% |

Properties of this composition were determined and the results were as follows:

$T_{NI}$=89.3 (°C.)
$\eta$=83.5 (mPa.s)
$\Delta n$=0.135
$\Delta \varepsilon$=29.3
$V_{th}$=0.97 (V)

EXAMPLE 93

Use Example 5

Liquid crystal composition comprising the following compounds in the following content was prepared:

| | | |
|---|---|---|
| 3-HH—VC | (No. 2) | 6.0% |
| 5-HH—VC | (No. 4) | 8.0% |
| 5-PyB—F | | 4.0$ |
| 3-PyB(F)—F | | 4.0% |
| 2-BB—C | | 5.0% |
| 4-BB—C | | 4.0% |
| 5-BB—C | | 5.0% |
| 2-PyB-2 | | 2.0% |
| 3-PyB-2 | | 2.0% |
| 4-PyB-2 | | 2.0% |
| 6-PyB—O5 | | 3.0% |
| 6-PyB—O6 | | 3.0% |
| 6-PyB—O7 | | 3.0% |
| 6-PyB—O8 | | 3.0% |
| 3-PyBB—F | | 6.0% |
| 4-PyBB—F | | 6.0% |
| 5-PyBB—F | | 6.0% |
| 2-H2BTB-2 | | 4.0% |
| 2-H2BTB-3 | | 4.0% |
| 2-H2BTB-4 | | 5.0% |
| 3-H2BTB-2 | | 5.0% |
| 3-H2BTB-3 | | 5.0% |
| 3-H2BTB-4 | | 5.0% |

Properties of this composition were determined and the results were as follows:

$T_{NI}$=95.7 (°C.)
$\eta$=40.7 (mPa.s)
$\Delta n$=0.201
$\Delta \varepsilon$=6.7
$V_{th}$=2.24 (V)

EXAMPLE 94

Use Example 6

Liquid crystal composition comprising the following compounds in the following content was prepared:

| | | |
|---|---|---|
| 3-HH—VC | (No. 2) | 10.0% |
| 3-HH—VCF | (No. 402) | 6.0% |
| 4-DB—C | | 10.0% |
| 2-BEB—C | | 12.0% |
| 3-BEB—C | | 4.0% |
| 3-PyB(F)—F | | 6.0% |
| 3-HEB—O4 | | 8.0% |
| 4-HEB—O2 | | 6.0% |
| 5-HEB—O1 | | 6.0% |
| 3-HEB—O2 | | 5.0% |
| 5-HEB—O2 | | 4.0% |
| 5-HEB-5 | | 5.0% |
| 4-HEB-5 | | 5.0% |
| 1O-BEB-2 | | 4.0% |
| 3-HHEBB—C | | 3.0% |
| 3-HBEBB—C | | 3.0% |
| 5-HBEBB—C | | 3.0% |

Properties of this composition were determined and the results were as follows:

$T_{NI}$=79.0 (°C.)
$\eta$=41.8 (mPa.s)
$\Delta n$=0.121
$\Delta \varepsilon$=9.5
$V_{th}$=1.42 (V)

EXAMPLE 95

Use Example 7

Liquid crystal composition comprising the following compounds in the following content was prepared:

| | | |
|---|---|---|
| 3-HH—VCF | (No. 402) | 9.0% |
| 5-HH—VCF | (No. 404) | 9.0% |
| 1-BHH—VCF | (No. 421) | 7.0% |
| 5-HB—C | | 3.0% |
| 1O1-HB—C | | 10.0% |
| 3-HB(F)—C | | 10.0% |
| 2-PyB-2 | | 2.0% |
| 3-PyB-2 | | 2.0% |
| 4-PyB-2 | | 2.0% |
| 1O1-HH-3 | | 7.0% |
| 2-BTB—O1 | | 7.0% |
| 3-HHB—F | | 4.0% |
| 3-HHB—O1 | | 4.0% |
| 3-HHB-3 | | 8.0% |
| 3-H2BTB-2 | | 3.0% |
| 3-H2BTB-3 | | 3.0% |
| 2-PyBH-3 | | 4.0% |
| 3-PyBH-3 | | 3.0% |
| 3-PyBB-2 | | 3.0% |

Properties of this composition were determined and the results were as follows:

$T_{NI}$=91.5 (°C.)
$\eta$=22.2 (mPa.s)
$\Delta n$=0.139
$\Delta \varepsilon$=6.0
$V_{th}$=1.98 (V)

EXAMPLE 96

Use Example 8

Liquid crystal composition comprising the following compounds in the following content was prepared:

| | | |
|---|---|---|
| 3-HH—VVC | (No. 202) | 5.0% |
| 3-H2H—VC | (No. 7) | 9.0% |
| 1-BHH—VVC | (No. 221) | 5.0% |

-continued

| | | |
|---|---|---|
| 5-BH—CV | (No. 13) | 3.0% |
| 3O1-BEB(F)—C | | 12.0% |
| 5O1-BEB(F)—C | | 4.0% |
| 1V2-BEB(F,F)—C | | 10.0% |
| 3-HH-EMe | | 10.0% |
| 3-HB—O2 | | 18.0% |
| 3-HHEB—F | | 3.0% |
| 5-HHEB—F | | 3.0% |
| 3-HBEB—F | | 4.0% |
| 2O1-HBEB(F)—C | | 2.0% |
| 3-HB(F)EB(F)—C | | 2.0% |
| 3-HBEB(F,F)—C | | 2.0% |
| 3-HHB—F | | 4.0% |
| 3-HHB—O1 | | 4.0% |
| 3-HEBEB—F | | 2.0% |
| 3-HeBEB-1 | | 2.0% |

Properties of this composition were determined and the results were as follows:

$T_{NI}$=90.3 (°C.)
$\eta$=41.9 (mPa.s)
$\Delta n$=0.122
$\Delta\varepsilon$=22.7
$V_{th}$=1.12 (V)

EXAMPLE 97

Use Example 9

Liquid crystal composition comprising the following compounds in the following content was prepared:

| | | |
|---|---|---|
| 3-HH—VC | (No. 2) | 8.0% |
| 5-HH—VC | (No. 4) | 4.0% |
| 2O1-BEB(F)—C | | 5.0% |
| 3O1-BEB(F)—C | | 12.0% |
| 5O1-BEB(F)—C | | 4.0% |
| 1V2-BEB(F,F)—C | | 16.0% |
| 3-HB—O2 | | 10.0% |
| 3-HH-4 | | 3.0% |
| 3-HHB—F | | 3.0% |
| 3-HBEB—F | | 4.0% |
| 3-HHEB—F | | 7.0% |
| 5-HHEB—F | | 7.0% |
| 3-H2BTB-2 | | 4.0% |
| 3-H2BTB-3 | | 4.0% |
| 3-H2BTB-4 | | 4.0% |
| 3-HB(F)TB-2 | | 5.0% |

Properties of this composition were determined and the results were as follows:

$T_{NI}$=88.6 (°C.)
$\eta$=44.2 (mPa.s)
$\Delta n$=0.142
$\Delta\varepsilon$=28.3
$V_{th}$=1.01 (V)

EXAMPLE 98

Use Example 10

Liquid crystal composition comprising the following compounds in the following content was prepared:

| | | |
|---|---|---|
| 1-BHH—VC | (No. 20) | 7.0% |
| 1-BHH—VCF | (No. 421) | 4.0% |
| 2-BEB—C | | 12.0% |
| 3-BEB—C | | 4.0% |
| 4-BEB—C | | 6.0% |
| 3-HB—C | | 28.0% |
| 3-HEB—O4 | | 12.0% |
| 4-HEB—O2 | | 8.0% |
| 5-HEB—O1 | | 8.0% |
| 3-HEB—O2 | | 6.0% |
| 5-HEB—O2 | | 5.0% |

Properties of this composition were determined and the results were as follows:

$T_{NI}$=68.7 (°C.)
$\eta$=33.4 (mPa.s)
$\Delta n$=0.119
$\Delta\varepsilon$=10.5
$V_{th}$=1.39 (V)

EXAMPLE 99

Use Example 11

Liquid crystal composition comprising the following

| | | |
|---|---|---|
| 3-HH—VCF | (No. 402) | 4.0% |
| 3-HH—VC | (No. 2) | 13.0% |
| 2-BEB—C | | 10.0% |
| 5-BB—C | | 12.0% |
| 7-BB—C | | 7.0% |
| 1-BTB-3 | | 7.0% |
| 2-BTB-1 | | 10.0% |
| 1O—BEB-2 | | 10.0% |
| 1O—BEB-5 | | 12.0% |
| 3-HHB—F | | 4.0% |
| 3-HHB-1 | | 7.0% |
| 3-HHB—O1 | | 4.0% |

Properties of this composition were determined and the results were as follows:

$T_{NI}$=68.5 (°C.)
$\eta$=23.5 (mPa.s)
$\Delta n$=0.159
$\Delta\varepsilon$=6.7
$V_{th}$=1.80 (V)

EXAMPLE 100

Use Example 12

Liquid crystal composition comprising the following compounds in the following content was prepared:

| | | |
|---|---|---|
| 3-HH—VC | | 15.0% |
| 1V2-BEB(F,F)—C | (No. 2) | 8.0% |
| 3-HB—C | | 18.0% |
| 3-HB—O2 | | 4.0% |
| 3-HH-4 | | 11.0% |
| 3-HH-5 | | 5.0% |
| 5-HH-2 | | 5.0% |
| 3-HHB-1 | | 11.0% |
| 3-HB(F)TB-2 | | 5.0% |
| 3-HB(F)TB-3 | | 5.0% |
| 3-H2BTB-2 | | 5.0% |
| 3-H2BTB-3 | | 4.0% |
| 3-H2BTB-4 | | 4.0% |

Properties of this composition were determined and the results were as follows:

$T_{NI}=101.8$ (°C.)
$\eta=16.2$ (mPa.s)
$\Delta n=0.132$
$\Delta\epsilon=8.9$
$V_{th}=2.08$ (V)
$P=11.6$ ($\mu$m)

EXAMPLE 101

Use Example 13

Liquid crystal composition comprising the following compounds in the following content was prepared:

| | | |
|---|---|---|
| 3-HH—VC | (No. 2) | 20.0% |
| 1V2-BEB(F,F)—C | | 9.0% |
| 3-HB—C | | 6.0% |
| 5-HH—VFF | | 30.0% |
| 3-HH-4 | | 7.0% |
| 2-BTB-1 | | 2.0% |
| 3-HB(F)TB-2 | | 5.0% |
| 3-HB(F)TB-3 | | 5.0% |
| 3-HB(F)TB-4 | | 4.0% |
| 3-H2BTB-2 | | 4.0% |
| 3-H2BTB-3 | | 4.0% |
| 3-H2BTB-4 | | 4.0% |

Properties of this composition were determined and the results were as follows:
$T_{NI}=101.0$ (°C.)
$\eta=14.5$ (mPa.s)
$\Delta n=0.133$
$\Delta\epsilon=8.5$
$V_{th}=2.13$ (V)
$P=10.7$ ($\mu$m)

EXAMPLE 102

Use Example 14

Liquid crystal composition comprising the following compounds in the following content was prepared:

| | | |
|---|---|---|
| 1-BHHVC | (No. 21) | 10.0% |
| 1V2-BEB(F,F)—C | | 8.0% |
| 3-HB—C | | 19.0% |
| 3-HB—O2 | | 11.0% |
| 3-HH-4 | | 11.0% |
| 3-HH-5 | | 5.0% |
| 5-HH-2 | | 5.0% |
| 3-HHB-1 | | 11.0% |
| 3-HB(F)TB-2 | | 4.0% |
| 3-HB(F)TB-3 | | 4.0% |
| 3-H2BTB-2 | | 4.0% |
| 3-H2BTB-3 | | 4.0% |
| 3-H2BTB-4 | | 4.0% |

Properties of this composition were determined and the results were as follows:
$T_{NI}=100.2$ (°C.)
$\eta=17.5$ (mPa.s)
$\Delta n=0.132$
$\Delta\epsilon=8.8$
$V_{th}=2.14$ (V)
$P=11.8$ ($\mu$m)

EXAMPLE 103

Use Example 15

Liquid crystal composition comprising the following compounds in the following content was prepared:

| | | |
|---|---|---|
| 2-HH—VVC | (No. 201) | 3.0% |
| 3-HH—VVC | (No. 202) | 3.0% |
| 5-HH—VVC | (No. 204) | 4.0% |
| 2-HHB(F)—F | | 17.0% |
| 3-HHB(F)—F | | 17.0% |
| 5-HHB(F)—F | | 16.0% |
| 3-H2HB(F)—F | | 5.0% |
| 5-H2HB(F)—F | | 10.0% |
| 2-HBB(F)—F | | 6.0% |
| 3-HBB(F)—F | | 6.0% |
| 5-HBB(F)—F | | 13.0% |

Properties of this composition were determined and the results were as follows:
$T_{NI}=109.7$ (°C.)
$\eta=27.5$ (mPa.s)
$\Delta n=0.104$
$\Delta\epsilon=5.6$
$V_{th}=2.12$ (V)

EXAMPLE 104

Use Example 16

Liquid crystal composition comprising the following compounds in the following content was prepared:

| | | |
|---|---|---|
| 5-BH—VC | (No. 13) | 5.0% |
| 7-HB(F)—F | | 5.0% |
| 5-H2B(F)—F | | 5.0% |
| 3-HB—O2 | | 10.0% |
| 3-HH-4 | | 5.0% |
| 2-HHB(F)—F | | 5.0% |
| 3-HHB(F)—F | | 10.0% |
| 5-HHB(F)—F | | 10.0% |
| 3-H2HB(F)—F | | 5.0% |
| 2-HBB(F)—F | | 3.0% |
| 3-HBB(F)—F | | 3.0% |
| 5-HBB(F)—F | | 6.0% |
| 2-H2BB(F)—F | | 5.0% |
| 3-H2BB(F)—F | | 6.0% |
| 3-HHB-1 | | 8.0% |
| 3-HHB—O1 | | 5.0% |
| 3-HHB-3 | | 4.0% |

Properties of this composition were determined and the results were as follows:
$T_{NI}=86.0$ (°C.)
$\eta=19.1$ (mPa.s)
$\Delta n=0.096$
$\Delta\epsilon=3.5$
$V_{th}=2.69$ (V)

EXAMPLE 105

Use Example 17

Liquid crystal composition comprising the following compounds in the following content was prepared:

| | | |
|---|---|---|
| C—BH—VC | (No. 801) | 3.0% |
| 7-HB(F,F)—F | | 3.0% |
| 3-HB—O2 | | 7.0% |
| 2-HHB(F)—F | | 10.0% |
| 3-HHB(F)—F | | 10.0% |
| 5-HHB(F)—F | | 10.0% |
| 2-HBB(F)—F | | 9.0% |

-continued

| | | |
|---|---|---|
| 3-HBB(F)—F | | 9.0% |
| 5-HBB(F)—F | | 16.0% |
| 2-HBB—F | | 4.0% |
| 3-HBB—F | | 4.0% |
| 3-HBB(F,F)—F | | 5.0% |
| 5-HBB(F,F)—F | | 10.0% |

Properties of this composition were determined and the results were as follows:
$T_{NI}$=86.4 (°C.)
$\eta$=27.9 (mPa.s)
$\Delta n$=0.118
$\Delta\epsilon$=11.9
$V_{th}$=1.79 (V)

EXAMPLE 106

Use Example 18

Liquid crystal composition comprising the following compounds in the following content was prepared:

| | | |
|---|---|---|
| 1-BBH—VCF | (No. 420) | 5.0% |
| 7-HB(F,F)—F | | 4.0% |
| 3-H2HB(F,F)—F | | 12.0% |
| 4-H2HB(F,F)—F | | 10.0% |
| 5-H2HB(F,F)—F | | 10.0% |
| 3-HHB(F,F)—F | | 10.0% |
| 3-HH2B(F,F)—F | | 15.0% |
| 5-HH2B(F,F)—F | | 10.0% |
| 3-HBB(F,F)—F | | 12.0% |
| 5-HBB(F,F)—F | | 12.0% |

Properties of this composition were determined and the results were as follows:
$T_{NI}$=79.8 (°C.)
$\eta$=29.6 (mPa.s)
$\Delta n$=0.094
$\Delta\epsilon$=8.7
$V_{th}$=1.60 (V)

EXAMPLE 107

Use Example 19

Liquid crystal composition comprising the following compounds in the following content was prepared:

| | | |
|---|---|---|
| 3-HH-2VC | (No. 102) | 5.0% |
| 3-HB—CL | | 10.0% |
| 5-HB—CL | | 4.0% |
| 7-HB—CL | | 4.0% |
| 1O1-HH-5 | | 5.0% |
| 2-HBB(F)—F | | 3.0% |
| 3-HBB(F)—F | | 8.0% |
| 5-HBB(F)—F | | 14.0% |
| 4-HHB—CL | | 8.0% |
| 5-HHB—CL | | 8.0% |
| 3-H2HB(F)—CL | | 4.0% |
| 3-HBB(F,F)—F | | 10.0% |
| 5-H2BB(F,F)—F | | 9.0% |
| 3-HB(F)VB-2 | | 4.0% |
| 3-HB(F)VB-3 | | 4.0% |

Properties of this composition were determined and the results were as follows:
$T_{NI}$=92.9 (°C.)
$\eta$=21.6 (mPa.s)
$\Delta n$=0.131
$\Delta\epsilon$=5.0
$V_{th}$=2.34 (V)

EXAMPLE 108

Use Example 20

Liquid crystal composition comprising the following compounds in the following content was prepared:

| | | |
|---|---|---|
| 3-H2H—VC | (No. 7) | 8.0% |
| 3-HHB(F,F)—F | | 9.0% |
| 4-H2HB(F,F)—F | | 8.0% |
| 5-H2HB(F,F)—F | | 8.0% |
| 3-HBB(F,F)—F | | 21.0% |
| 5-HBB(F,F)—F | | 20.0% |
| 3-H2BB(F,F)—F | | 10.0% |
| 5-HHBB(F,F)—F | | 3.0% |
| 3-HH2BB(F,F)—F | | 3.0% |
| 5-HHEBB—F | | 2.0% |
| 1O1-HBBH-4 | | 4.0% |
| 1O1-HBBH-5 | | 4.0% |

Properties of this composition were determined and the results were as follows:
$T_{NI}$=102.6 (°C.)
$\eta$=35.8 (mPa.s)
$\Delta n$=0.119
$\Delta\epsilon$=8.6
$V_{th}$=1.87 (V)

EXAMPLE 109

Use Example 21

Liquid crystal composition comprising the following compounds in the following content was prepared:

| | | |
|---|---|---|
| 2-HH—VC | (No. 1) | 5.0% |
| 3-HH—VC | (No. 2) | 5.0% |
| 5-HB—F | | 12.0% |
| 6-HB—F | | 9.0% |
| 7-HB—F | | 7.0% |
| 2-HHB—OCF3 | | 7.0% |
| 3-HHB—OCF3 | | 11.0% |
| 4-HHB—OCF3 | | 7.0% |
| 5-HHB—OCF3 | | 5.0% |
| 3-HH2B—OCF3 | | 4.0% |
| 5-HH2B—OCF3 | | 4.0% |
| 3-HHB(F,F)—OCF3 | | 5.0% |
| 3-HBB(F)—F | | 10.0% |
| 3-HH2B(F)—F | | 3.0% |
| 3-HB(F)BH-3 | | 3.0% |
| 5-HBBH-3 | | 3.0% |

Properties of this composition were determined and the results were as follows:
$T_{NI}$=90.9 (°C.)
$\eta$=13.7 (mPa.s)
$\Delta n$=0.089
$\Delta\epsilon$=4.6
$V_{th}$=2.42 (V)

EXAMPLE 110

Use Example 22

Liquid crystal composition comprising the following compounds in the following content was prepared:

| | | |
|---|---|---|
| 3-HH—VCF | (No. 402) | 5.0% |
| 5-HH—VCF | (No. 404) | 5.0% |
| 5-H4HB(F,F)—F | | 7.0% |
| 5-H4HB—OCF3 | | 15.0% |
| 3-H4HB(F,F)—CF3 | | 8.0% |
| 5-H4HB(F,F)—CF3 | | 10.0% |
| 3-HB—CL | | 6.0% |
| 5-HB—CL | | 4.0% |
| 4-H2BB(F)—F | | 5.0% |
| 5-HVHB(F,F)—F | | 5.0% |
| 3-HHB—OCF3 | | 5.0% |
| 3-H2HB—OCF3 | | 5.0% |
| V-HHB(F)—F | | 5.0% |
| 3-HChB(F)—F | | 5.0% |
| 5-HHEB—OCF3 | | 2.0% |
| 3-HBEB(F,F)—F | | 5.0% |
| 5-HH—V2F | | 3.0% |

Properties of this composition were determined and the results were as follows:

$T_{NI}$=72.1 (°C.)

η=23.5 (mPa.s)

Δn=0.085

Δ∈=7.7

$V_{th}$=1.84 (V)

INDUSTRIAL APPLICABILITY

According to the present invention, novel liquid crystalline compounds which can impart a large elastic constant ratio to liquid crystal compositions while maintaining excellent characteristics as liquid crystal component, that is, a wide temperature range of liquid crystal, excellent miscibility with other liquid crystals, and a low viscosity; liquid crystal compositions comprising the liquid crystalline compounds; and liquid crystal display devices comprising the composition can be provided.

We claim:

1. An acrylonitrile derivative expressed by general formula I

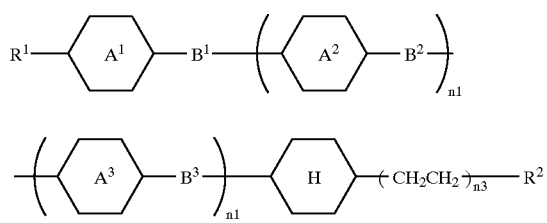

wherein ring $A^1$, ring $A^2$, and Ring $A^3$ independently represent 1,4-phenylene one or two hydrogen atoms of which may be replaced by fluorine atom, 1,4-cyclohexylene, 1,3-dioxane-2,5-diyl, or 1,3-pyrimidine-2,5-diyl, $R^1$ represents cyano group, halogen atom, an alkyl group, an alkoxy group, an alkyl group one or more hydrogen atoms of which are replaced by fluorine atom, an alkoxy group one or more hydrogen atoms of which are replaced by fluorine atom, or an alkoxyalkyl group when the ring $A^1$ represents 1,4-phenylene, but when the ring $A^1$ represents 1,4-cyclohexylene, 1,3-dioxane-2,5-diyl, or 1,3-pyrimidine-2,5-diyl, $R^1$ represents an alkyl group, an alkoxy group, or an alkoxyalkyl group, $B^1$, $B^2$, and $B^3$ represent a covalent bond, ethylene, ethenylene, ethynylene, oxymethylene, carbonyloxy, 1,4-butanediyl, or 1,4-butenediyl, n1, n2, and n3 are independently 0 or 1, $R^2$ represents a group expressed by formula II or formula III

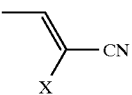

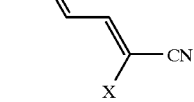

wherein X represents hydrogen atom or fluorine atom, and ring H represents 1,4-cyclohexylene, provided that in no case two or more hetero-rings are included in a molecule at the same time.

2. The acrylonitrile derivative according to claim 1 wherein n1 and n2 are 0.

3. The acrylonitrile derivative according to claim 1 wherein n1 is 0 and n2 is 1.

4. The acrylonitrile derivative according to claim 1 wherein n1 and n2 are 1.

5. The acrylonitrile derivative according to claim 1 wherein $R^1$ is an alkyl group, an alkoxy group, or an alkoxyalkyl group, ring $A^1$, ring $A^2$, and ring $A^3$ represent 1,4-phenylene one or two hydrogen atoms of which may be replaced by fluorine atom, or 1,4-cyclohexylene.

6. The acrylonitrile derivative according to claim 2 wherein $R^1$ represents an alkyl group, an alkoxy group, or an alkoxyalkyl group, and ring A1 represents 1,4-phenylene or 1,4-cyclohexylene.

7. The acrylonitrile derivative according to claim 5 wherein either n1 or n2 is 0, and both $B^2$ and $B^3$ represent a covalent bond.

8. The acrylonitrile derivative according to claim 5 wherein either n1 or n2 is 0, $B^2$ and $B^3$ independently represent a covalent bond or 1,2-ethylene, and $R^2$ represents a group expressed by the formula II.

9. The acrylonitrile derivative according to claim 5 wherein either n1 or n2 is 0, $B^2$ and $B^3$ independently represent a covalent bond or 1,2-ethylene, and $R^2$ represents a group expressed by the formula III.

10. The acrylonitrile derivative according to claim 1 wherein ring $A^1$ represents 1,4-phenylene one or two hydrogen atoms of which may be replaced by fluorine atom, and $R^1$ represents cyano group, halogen atom, an alkyl group one or more hydrogen atoms of which are replaced by fluorine atom, or an alkoxy group one or more hydrogen atoms of which are replaced by fluorine atom.

11. The acrylonitrile derivative according to claim 2 wherein ring $A^1$ represents 1,4-phenylene one or more hydrogen atoms of which may be replaced by fluorine atom, and $R^1$ represents cyano group, halogen atom, an alkyl group one or more hydrogen atoms of which are replaced by fluorine atom, or an alkoxy group one or more hydrogen atoms of which are replaced by fluorine atom.

12. The acrylonitrile derivative according to claim 3 wherein ring $A^1$ represents 1,4-phenylene one or more hydrogen atoms of which may be replaced by fluorine atom, and $R^1$ represents cyano group, halogen atom, an alkyl group one or more hydrogen atoms of which are replaced by fluorine atom, or an alkoxy group one or more hydrogen atoms of which are replaced by fluorine atom.

13. The acrylonitrile derivative according to claim 10 wherein $R^1$ represents cyano group or halogen atom.

14. The acrylonitrile derivative according to claim 10 wherein either n1 or n2 is 0, and both $B^2$ and $B^3$ represent a covalent bond.

15. The acrylonitrile derivative according to claim 13 wherein either n1 or n2 is 0, $B^2$ and $B^3$ represent a covalent bond, and $R^2$ represents a group expressed by the formula II.

16. The acrylonitrile derivative according to claim 13 wherein either n1 or n2 is 0, both $B^2$ and $B^3$ represent a covalent bond, and R2 represents a group expressed by the formula III.

17. A liquid crystal composition comprising two or more components at least one of which is a liquid crystalline compound expressed by the general formula I defined in claim 1.

18. A liquid crystal composition comprising, as a first component, at least one acrylonitrile derivative defined in any one of claims 1 to 16, and comprising, as a second component, at least one compound selected from the group consisting of the compounds expressed by any one of general formulas IV, V, and VI

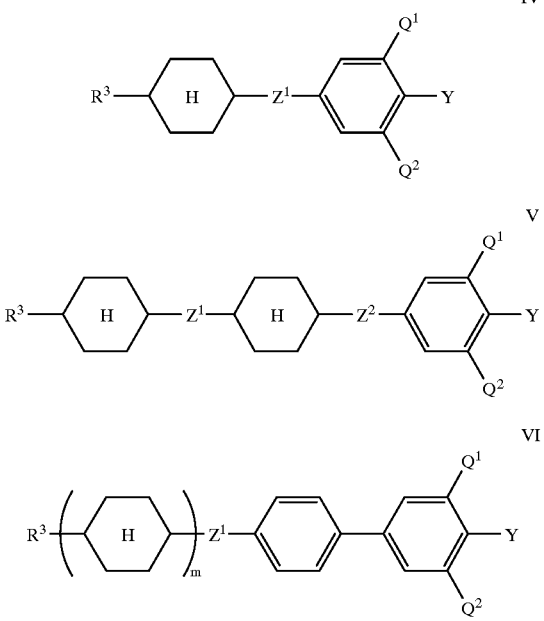

IV

V

VI wherein $R^3$ represents an alkyl group having 1 to 10 carbon atoms, Y represents fluorine atom or chlorine atom, $Q^1$ and $Q^2$ independently represent hydrogen atom or fluorine atom, m is 1 or 2, and $Z^1$ and $Z^2$ independently represent —$CH_2CH_2$— or a covalent bond.

19. A liquid crystal composition comprising, as a first component, at least one acrylonitrile derivative defined in any one of claims 1 to 16, and comprising, as a second component, at least one compound selected from the group consisting of the compounds expressed by any one of general formula VII, VIII, IX, X, and XI

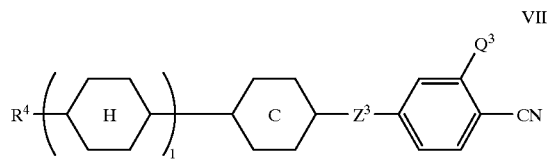

VII wherein $R^4$ represents an alkyl group having 1 to 10 carbon atoms or an alkenyl group having 2 to 10 carbon atoms, any methylene group (—$CH_2$—) in each of the alkyl group and alkenyl group may be replaced by oxygen atom (—O—), but in no case two or more methylene groups are continuously replaced by oxygen group, $Z^3$ represents —$CH_2CH_2$—, —COO—, or a covalent bond, $Q^3$ represents hydrogen atom or fluorine atom, ring C represents 1,4-cyclohexylene, 1,4-phenylene, or 1,3-dioxane-2,5-diyl, and Q is 0 or 1,

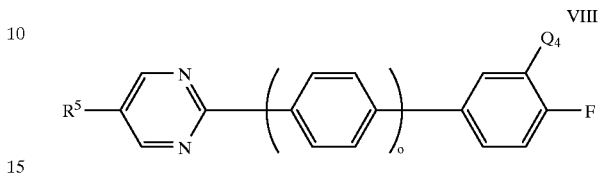

VIII wherein $R^5$ represents an alkyl group having 1 to 10 carbon atoms, $Q^4$ represents hydrogen atom or fluorine atom, and o is 0 or 1,

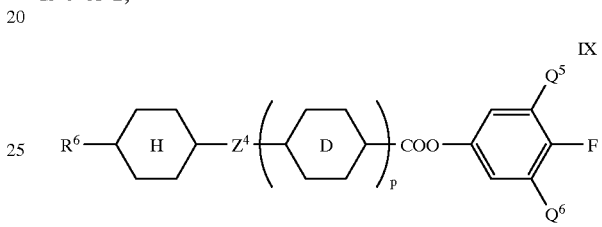

IX wherein $R^6$ represents an alkyl group having 1 to 10 carbon atoms, ring D represents 1,4-cyclohexylene or 1,4-phenylene, $Q^5$ and $Q^6$ represent hydrogen atom or fluorine atom, respectively, $Z^4$ represents —COO— or a covalent bond, and p is 0 or 1,

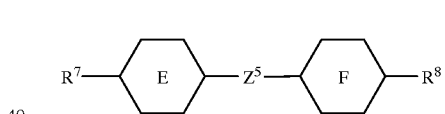

X wherein $R^7$ and $R^8$ independently represent an alkyl group having 1 to 10 carbon atoms or an alkenyl group having 2 to 10 carbon atoms, any methylene group (—$CH_2$—) in each of the alkyl group and alkenyl group may be replaced by oxygen atom, but in no case two or more methylene groups are continuously replaced by oxygen atom, ring E represents 1,4-cyclohexylene, 1,3-pyrimidine-2,5-diyl, or 1,4-phenylene, ring F represents 1,4-cyclohexylene or 1,4-phenylene, and $Z^5$ represents —C≡C—, —COO—, —$CH_2CH_2$—, or a covalent bond

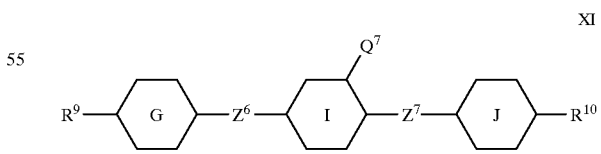

XI wherein $R^9$ represents an an alkyl group or an alkoxy group having 1 to 10 carbon atoms, $R^{10}$ represents an alkyl, an alkoxy, or an alkoxymethyl group having 1 to 10 carbon atoms, ring G represents 1,4-cyclohexylene or 1,3-pyrimidine-2,5-diyl, ring I and ring J independently represent 1,4-cyclohexylene or 1,4-phenylene, $Z^6$ represents —COO—, —$CH_2CH_2$—, or a covalent bond, $Z^7$ represents —C≡C—, —COO—, or a covalent bond, and $Q^7$ represents hydrogen atom or fluorine atom.

20. A liquid crystal display device comprising a liquid crystal composition defined in claim 17.

21. A liquid crystal display device comprising a liquid crystal composition defined in claim 18.

22. A liquid crystal display device comprising a liquid crystal composition defined in claim 19.

23. A liquid crystal composition comprising, as a first component, at least one liquid crystalline compound defined in any one of claims 1 to 16, comprising, as a part of a second component, at least one compound selected from the group consisting of the compounds expressed by any one of the general formulas IV, V, and VI, and comprising, as another part of the second component, at least one compound selected from the group consisting of the compounds expressed by any one of the general formulas VII, VIII, IX, X, and XI

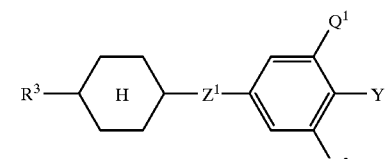

IV

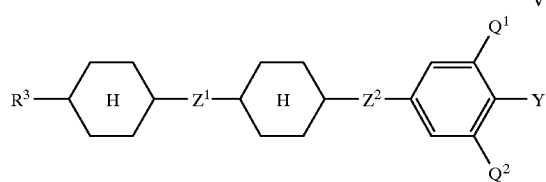

V

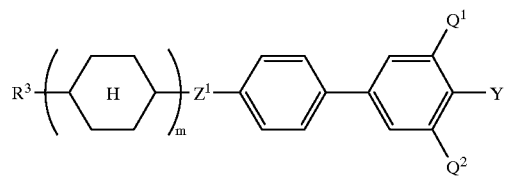

VI wherein $R^3$ represents an alkyl group having 1 to 10 carbon atoms, Y represents fluorine atom or chlorine atom, $Q^1$ and $Q^2$ independently represent hydrogen atom or fluorine atom, m is 1 or 2, and $Z^1$ and $Z^2$ independently represent —CH$_2$CH$_2$— or a covalent bond,

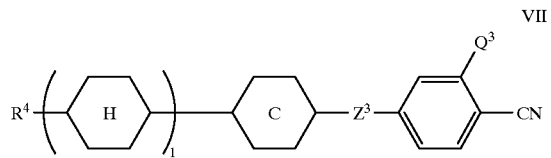

VII wherein $R^4$ represents an alkyl group having 1 to 10 carbon atoms or an alkenyl group having 2 to 10 carbon atoms, any methylene group (—CH$_2$—) in each of the alkyl group and alkenyl group may be replaced by oxygen atom (—O—), but in no case two or more methylene groups are continuously replaced by oxygen group, $Z^3$ represents —CH$_2$CH$_2$—, —COO—, or a covalent bond, $Q^3$ represents hydrogen atom or fluorine atom, ring C represents 1,4-cyclohexylene, 1,4-phenylene, or 1,3-dioxane-2,5-diyl, and l is 0 or 1,

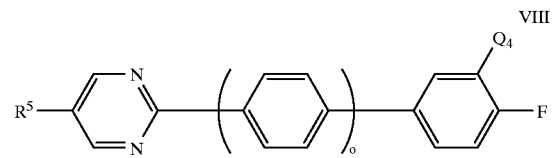

VIII wherein $R^5$ represents an alkyl group having 1 to 10 carbon atoms, $Q^4$ represents hydrogen atom or fluorine atom, and o is 0 or 1,

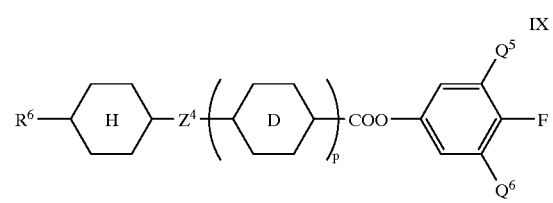

IX wherein $R^6$ represents an alkyl group having 1 to 10 carbon atoms, ring D represents 1,4-cyclohexylene or 1,4-phenylene, $Q^5$ and $Q^6$ represent hydrogen atom or fluorine atom, respectively, $Z^4$ represents —COO— or a covalent bond, and p is 0 or 1,

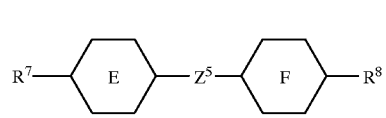

X wherein $R^7$ and $R^8$ independently represent an alkyl group having 1 to 10 carbon atoms or an alkenyl group having 2 to 10 carbon atoms, any methylene group (—CH$_2$—) in each of the alkyl group and alkenyl group may be replaced by oxygen atom, but in no case two or more methylene groups are continuously replaced by oxygen atom, ring E represents 1,4-cyclohexylene, 1,3-pyrimidine-2,5-diyl, or 1,4-phenylene, ring F represents 1,4-cyclohexylene or 1,4-phenylene, and $Z^5$ represents —C≡C—, —COO—, —CH$_2$CH$_2$—, or a covalent bond,

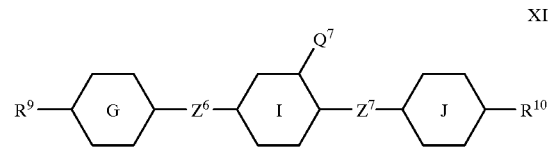

XI wherein $R^9$ represents an alkyl group or an alkoxy group having 1 to 10 carbon atoms, $R^{10}$ represents an alkyl, an alkoxy, or an alkoxymethyl group having 1 to 10 carbon atoms, ring G represents 1,4-cyclohexylene or 1,3-pyrimidine-2,5-diyl, ring I and ring J independently represent 1,4-cyclohexylene or 1,4-phenylene, $Z^6$ represents —COO—, CH$_2$CH$_2$, or a covalent bond, $Z^7$ represents —C≡C—, —COO—, or a covalent bond, and $Q^7$ represents hydrogen atom or fluorine atom.

24. A liquid crystal display device comprising a liquid crystal composition defined in claim 23.

* * * * *